United States Patent
Griffioen et al.

(10) Patent No.: US 9,750,745 B2
(45) Date of Patent: Sep. 5, 2017

(54) 2,7-DIAZASPIRO[3.5]NONANE COMPOUNDS

(71) Applicant: REMYND NV, Heverlee (BE)

(72) Inventors: Gerard Griffioen, Linden (BE); Bart De Taeye, Kessel-Lo (BE); Katrien Princen, Heverlee (BE); Koen De Witte, Ukkel (BE); Emilie Blanche, Heverlee (BE); Hasane Ratni, Habsheim (FR); Mark Rogers-Evans, Bottmingen (CH)

(73) Assignee: REMYND NV, Heverlee (BE)

( * ) Notice: Subject to any disclaimer, the term of this patent is extended or adjusted under 35 U.S.C. 154(b) by 0 days.

(21) Appl. No.: 15/433,164

(22) Filed: Feb. 15, 2017

(65) Prior Publication Data

US 2017/0157137 A1 Jun. 8, 2017

Related U.S. Application Data

(63) Continuation of application No. 15/121,790, filed as application No. PCT/EP2015/055494 on Mar. 17, 2015.

(30) Foreign Application Priority Data

Mar. 17, 2014 (EP) .................................... 14160344

(51) Int. Cl.
*A61K 31/5377* (2006.01)
*A61K 31/435* (2006.01)
*A61K 31/444* (2006.01)

(52) U.S. Cl.
CPC ........ *A61K 31/5377* (2013.01); *A61K 31/435* (2013.01); *A61K 31/444* (2013.01)

(58) Field of Classification Search
CPC .................................................... C07D 471/10
USPC .................................................... 546/16, 160
See application file for complete search history.

(56) References Cited

U.S. PATENT DOCUMENTS

| 8,609,680 B2 | 12/2013 | Bhattacharya et al. |
| 2008/0070888 A1 | 3/2008 | McKittrick et al. |
| 2011/0230461 A1 | 9/2011 | Bhattacharya et al. |
| 2014/0080756 A1 | 3/2014 | Bhattacharya et al. |
| 2015/0099734 A1 | 4/2015 | Hunziker et al. |

FOREIGN PATENT DOCUMENTS

| CN | 102939290 A | 2/2013 |
| WO | 2008033447 A1 | 3/2008 |
| WO | 2011114271 A1 | 9/2011 |
| WO | 2013186159 A1 | 12/2013 |

OTHER PUBLICATIONS

PCT International Search Report and Written Opinion dated May 12, 2015 for PCT International Patent Application No. PCT/EP2015/055494, 8 pages.
Database Registry [Online] Chemical Abstracts Service, Dec. 26, 2007, XP002725585, 4 pages.
PCT Notification Concerning Transmittal of International Preliminary Report on Patentability and Written Opinion of the International Searching Authority, date of issuance Sep. 29, 2016 in connection with PCT International Patent Application No. PCT/EP2015/055494, 6 pages.
Tong L et al., entitled "Expansion of SAR studies on triaryl bis-sulfone cannabinoid CB2 receptor ligands," Bioorganic & Medicinal Chemistry Letters 20 (2010) 6785-6789.

*Primary Examiner* — Kristin Vajda
(74) *Attorney, Agent, or Firm* — Amster, Rothstein & Ebenstein LLP

(57) ABSTRACT

The present invention relates to a compound of formula (I) or a stereoisomer, enantiomer, racemic, or tautomer thereof, Formula (I), wherein $R^1$, $R^3$, $R^4$, $L^1$, $L^2$, $L^3$, $L^4$, and n, have the same meaning as that defined in the claims and the description. The present invention also relates to compositions, in particular pharmaceuticals, comprising such compounds, and to uses of such compounds and compositions for the prevention and/or treatment of metabolic disorders and/or neurodegenerative diseases, and/or protein misfolding disorders.

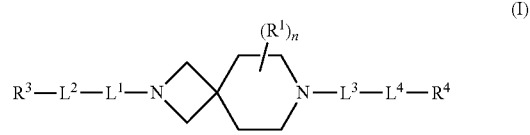

12 Claims, 1 Drawing Sheet

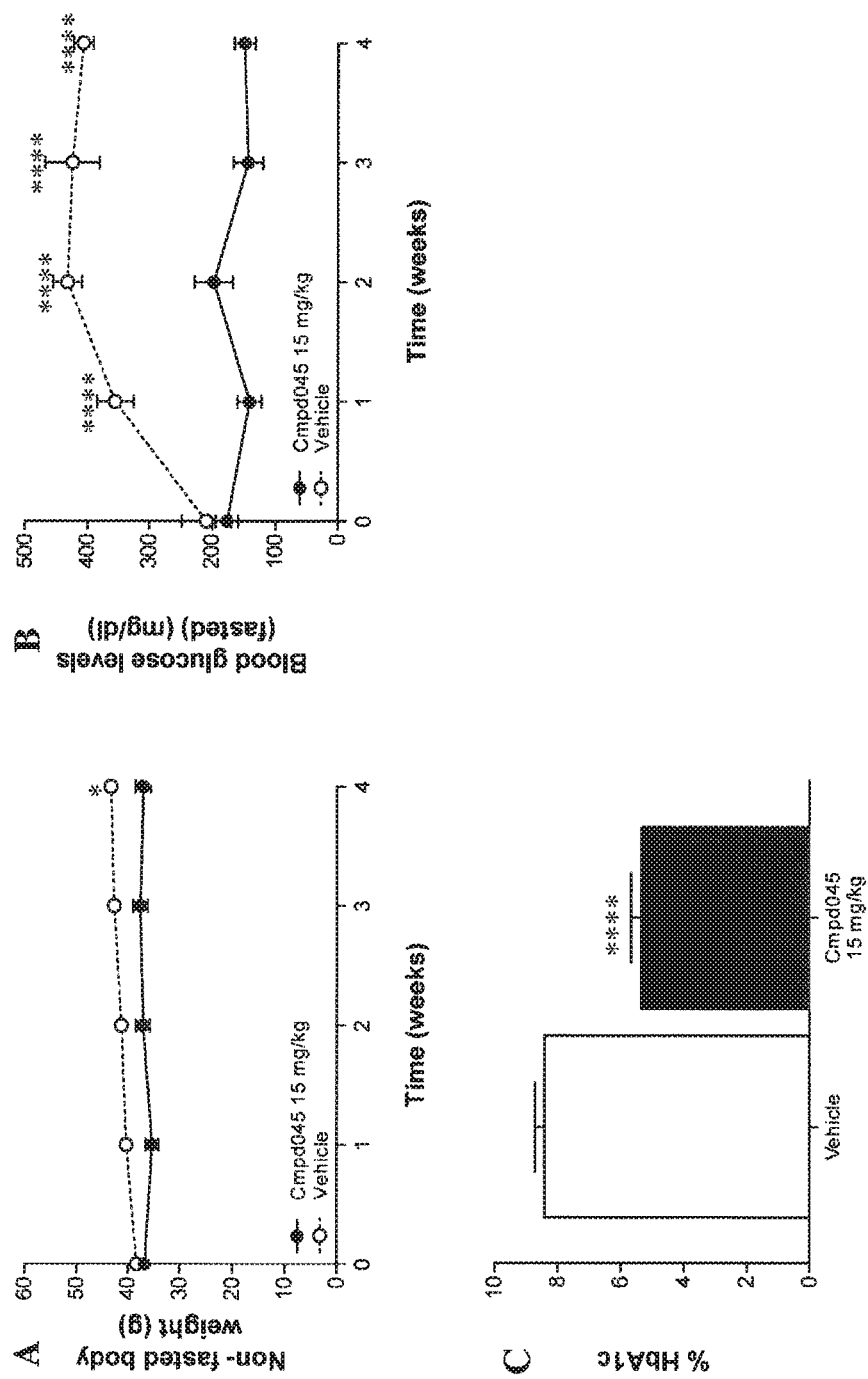

2,7-DIAZASPIRO[3.5]NONANE COMPOUNDS

CROSS-REFERENCE TO RELATED APPLICATIONS

This application is a continuation of U.S. patent application Ser. No. 15/121,790, filed Aug. 26, 2016, which is the U.S. national stage of PCT Application No. PCT/EP2015/055494, filed Mar. 17, 2015, which claims priority to European Patent Application No. 14160344.9, filed Mar. 17, 2014, the contents of which are incorporated herein by reference in their entirety.

FIELD OF THE INVENTION

The present invention relates to 2,7-diazaspiro[3.5] nonane derivative compounds, or pharmaceutically acceptable salts thereof as defined herein, that are useful for treating diseases related to protein misfolding and in particular neurodegenerative diseases or diabetes.

BACKGROUND OF THE INVENTION

Several human disorders referred to as aryloidoses entail the accumulation and/or aggregation of misfolded proteins as a pathological characteristic and are therefore also referred to as protein-misfolding diseases. Most notably, Alzheimer's disease, Parkinson's disease and type 2 diabetes are common diseases which involve aberrant aggregation of aryloid-β (Aβ) and tau, alpha-synuclcin and Islet Amyloid Polypeptide Precursor (IAPP), respectively. [*Misfolded Proteins in Alzheimer's Disease and Type II Diabetes*, DeToma et al, 2012. *Chem. Soc. Rev.,* 608-621]

The process or processes which lead to protein misfolding and aggregation is/are generally believed to be cytotoxic and as such may contribute to degeneration or failure of target cells such as neurons in the case of brain disorders such as Alzheimer's and Parkinson's disease or beta-cell function in the case of type 2 diabetes. Although neurodegenerative diseases such as Alzheimer's disease and Parkinson's disease and metabolic disorders such as type 2 diabetes affect different tissues (respectively brain and pancreas), they have been shown to share similar risk factors [Janson J, Laedtke T, Parisi J E, O'Brien P, Petersen R C, Butler P C. *Diabetes.* 2004; 53:474-481]. Also the mechanism underlying the protein aggregation itself, despite the fact that it involves different proteins across different indications, has common denominators. [*Common Structure of Soluble Amyloid Oligomers Implies Common Mechanism of Pathogenesis*; Rakez Kayed1, Elizabeth Head2, Jennifer L. Thompson1, Theresa M. McIntire3, Saskia C. Milton1, Carl W. Cotman2, Charles G. Glabe1; *Science* 18 Apr. 2003: Vol. 300 no 5618 pp. 486-489:]. These observed mechanistic commonalties between protein misfolding disorders indicate that therapeutic interventions aimed to preserve cellular integrity are expected to be efficacious over a variety of disorders which involve protein aggregation. However, the precise mechanism as to the pathways and processes involved in cellular degeneration and protein aggregation is/are still highly elusive. Therefore, in the absence of detailed mechanistic insights as to the molecular mechanism involved, the use of phenotypic assays to identify small molecules which preserve cellular integrity in cellular and animal models of aryloidosis is relevant to find effective treatments for pathients suffering aryloidoses such as Alzheimer's, Parkinson's disease and diabetes. Importantly, such treatments will alter fundamentally the course of the disease as these preserve cellular integrity of the target cells such as neurons and beta-cells and thus are expected to be disease-modifying. As such these treatments are not merely reducing temporarily disease symptoms and therefore address an important current medical need. To date, beyond diet management, medication for type 2 diabetes is focused on minimizing diabetic complications using oral hypoglycemic agents and at a later stage of the disease, insulin replacement therapy. These medications belong to four main classes:

Sulfonylureas stimulate insulin release by pancreatic β-cells. They are cheap and show little side effect, but they induce weight gain and risk of hypoglycemia and are thought to precipitate failure of insulin-producing β-cells Biguanides (of which metformin is the reference) decrease insulin resistance and triglyceride levels. They are however inducing gastrointestinal problems and are counter-indicated for people with kidney disease or heart problems.

Alpha-glucosidase inhibitors reduce glucose absorbance by small intestine. It is however an expensive treatment with inconvenient dosing, which can induce gastrointestinal problems.

Thiazolidinediones reduce insulin resistance by activating PPAR-γ in fat and muscle. They are however expensive and associated with weight gain, increased risk of hart failure, anemia and edema.

GLP-1 analogues stimulate insulin release by pancreatic β-cells in a glucose-dependent manner, inhibit glucagon release by α-cells and slow down gastric emptying. They are expensive, need to be injected and lead to nausea.

DPP-4 inhibitors increase endogenous GLP-1 levels and exert effects similar to GLP-1 analogues. There are suggestions of an increased risk of pancreatitis and pancreatic cancer associated with the use of these drugs.

SGLT-2 inhibitors increase glucose clearance through the kidney/urine. Of this class, canagliflozin recently entered the market but is associated with side effects such as an increased desire to urinate and also associated with higher risk of vaginal yeast infections and urinary tract infections.

Regarding neurodegenerative diseases, treatments are focused on delaying the onset, or reduce the existing symptoms. For example, cholinesterase inhibitors and/or Memantine are given to Alzheimer's pathients to delay the onset of cognitive symptoms. Levodopa is given to Parkinson's pathients to temporarily diminish motor symptoms.

There is therefore a great need for treatments which preserve and/or refunctionalize cells affected in aryloidoses to prevent the development of associated symptoms in pathients.

SUMMARY OF THE INVENTION

According to a first aspect of the present invention, a compound of formula (I); or a stereoisomer, enantiomer, racemic, or tautomer thereof is provided,

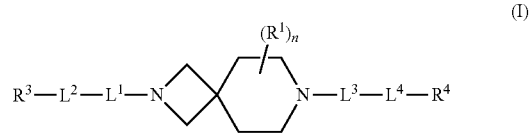

wherein, n is an integer selected from 0, 1, 2 or 3;

$R^1$ is selected from the group consisting of $C_{1-6}$alkyl, halo, halo$C_{1-6}$alkyl, and halo$C_{1-6}$alkyloxy;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$;

$L^1$ is selected from the group consisting of —$SO_2$—, —CO—,

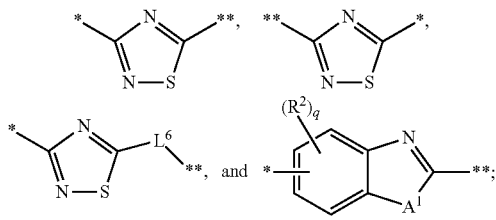

wherein * represents where $L^1$ is bound to $L^2$; and ** represents where $L^1$ is bound to the azetidine ring; and wherein, $A^1$ is S or O;

q is an integer selected from 0, 1, 2, or 3, $L^6$ is —CO— or —$SO_2$—;

each $R^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heteroaryl, hydroxyl, $SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$; wherein two $R^2$ together with the atom to which they are attached can form a saturated or unsaturated 5-, 6-, or 7-membered ring; and wherein at least one carbon atom or heteroatom of said ring, $C_{6-12}$aryl, $C_{3-8}$cycloalkyl, heterocyclyl, heteroaryl can be oxidized to form at least one C=O, C=S, N=O, N=S, S=O or $S(O)_2$;

$R^4$ is selected from the group consisting $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$;

$L^2$ is a single bond or a group of formula (i);

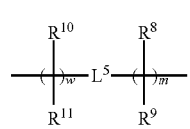

(i)

wherein the left side of the group of formula (i) is attached to $R^3$ and the right side thereof is attached to the nitrogen atom of the azetidine ring; and wherein, m is an integer selected from 0, 1, 2, or 3;

w is an integer selected from 0, 1, 2 or 3;

$L^5$ is a single bond, or is selected from the group consisting of —O—, and —$NR^{12}$—;

$R^8$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;

$R^9$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;

or $R^8$ and $R^9$ together with the carbon atom to which they are attached from a saturated or unsaturated 3-, 4-, 5-, 6- or 7-membered ring;

$R^{10}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;

$R^{11}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;

or $R^{10}$ and $R^{11}$ together with the carbon atom to which they are attached from a saturated or unsaturated 3-, 4-, 5-, 6- or 7-membered ring;

$R^{12}$ is selected from the group consisting of hydrogen, and $C_{1-6}$alkyl;

$L^3$ is selected from the group consisting of —$SO_2$—, —$PO_4$—, and —$PO_3$—;

$L^4$ is a single bond or is selected from the group consisting of —($CR^{15}R^{16}$)—, —O—, and —$NR^{17}$—; wherein t is an integer selected from 1, 2 or 3;

$R^{15}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;

$R^{16}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;

or $R^{15}$ and $R^{16}$ together with the carbon atom to which they are attached form a saturated or unsaturated 3-, 4-, 5-, 6- or 7-membcrod ring;

$R^{17}$ is selected from the group consisting of hydrogen, and $C_{1-6}$alkyl;

wherein at least one of $L^3$, $L^4$ is not a single bond; and wherein when $L^4$ is a single bond, $R^4$ is not methyl;

each $R^{18}$ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$ alkyl, heterocyclyl, heteroaryl, heterocyclyl$C_{1-6}$alkyl, heteroaryl$C_{1-6}$alkyl, and cyano$C_{1-6}$ alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$ alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{19}$ is independently selected from the group consisting of hydrogen, $C_{1-6}$alkyl, $C_{2-6}$alkenyl, $C_{2-6}$alkynyl. $C_{6-11}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, hetrocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$ alkyl, and heteroaryl$C_{1-6}$ alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteoaryl, heterocyclyl$C_{1-6}$alkyl, or heteroaryl$C_{1-6}$alkyl can be oxidized to form at least one C=O, C=S, N=O, N=S, S=O or $S(O)_2$;

each $R^{21}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$ alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

or wherein $R^{20}$ and $R^{21}$ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or $S(O)_2$;

each $R^{22}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heteorcyclyl$C_{1-6}$alkyl, and heteroaryl$C_{1-6}$ alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

each $R^{23}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heteorcyclyl, heteroaryl, heterocyclyl$C_{1-6}$alkyl, and heteroaryl$C_{1-6}$ alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$ alkyl, heterocyclyl, heteroaryl, heterocyclyl$C_{1-6}$alkyl, and heteroaryl$C_{1-6}$alkyl can be oxidized to form at least one C=O, C=S, N=O, N=S, S=O or $S(O)_2$;

each $R^{24}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$ alkylene*, and heteroarylene$C_{1-6}$alkylene*; wherein * represents where $R^{24}$ is bound to CO;

wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, C=S, N=O, N=S, S=O or $S(O)_2$;

each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl, heteroaryl$C_{1-6}$ alkyl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$; wherein two $Z^1$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$ alkyl can be oxidized to form at least one C=O, C=S, N=O, N=S, S=O or $S(O)_2$;

each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$ alkyl, heterocyclyl, heterocyclyl$C_{1-6}$alkyl, heteroaryl, heteroaryl$C_{1-6}$alkyl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}C(O)NR^{20}R^{21}$, —$NR^{23}S(O)_2R^{22}$, and $NR^{23}C(O)NR^{20}R^{21}$; wherein two $Z^2$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteoaryl$C_{1-6}$ alkyl can be oxidized to form at least one C=O, C=S, N=O, N=S, S=O or $S(O)_2$;

with the proviso that said compound is not
N-(1-methylethyl)-7-(phenylsulfonyl)-2,7-diazaspiro[3.5]nonane-2-carboxamide,
N-(3-fluorophenyl)-7-(phenylsulfonyl)-2,7-diazaspiro[3.5]nonane-2-carboxamide,
N-phenyl-7-(phenylsulfonyl)$_{2,7}$-diazaspiro[3.5]nonane-2-carboxamide,
N-(4-methoxyphenyl)-7-(phenylsulfonyl)-2,7-diazaspiro[3.5]nonane-2-carboxamide,
(1H-benzotriazol-5-yl)-{7-[2-(3-chloro-phenyl)-ethanesulfonyl]-2,7-diaza-spiro[3.5]non-2-yl}-methanone,
N-4-methoxyphenyl)-7-(methylsulfonyl)-2,7-diazaspiro[3.5]nonane-2-carboxamide,
N-(3-cyanophenyl)-7-(methylsulfonyl)-2,7-diazaspiro[3.5]nonane-2-carboxamide,
7-(methylsulfonyl)-N-phenyl-2,7-diazaspiro[3.5]nonane-2-carboxamide,
N-(3-fluorophenyl)-7-(methylsulfonyl)-2,7-diazaspiro[3.5]nonane-2-carboxamide,
or a solvate, hydrate, pharmaceutically acceptable salt or prodrug thereof.

According to a second aspect, the present invention also encompasses a pharmaceutical composition comprising one or more pharmaceutically excipients and a therapeutically effective amount of a compound according to the first aspect of the invention or a therapeutically effective amount of a compound selected from the group consisting of N-(1-methylethyl)-7-phenylsulfonyl)-2,7-diazaspiro[3.5]nonane-2-carboxamide, N-(3-fluorophenyl)-7-(phenylsulfonyl)-2,7-diazaspiro[3.5]nonane-2-carboxamide, N-phenyl-7-(phenylsulfonyl)-2,7-diazaspiro[3.5]nonane-2-carboxamide, N-(4-methoxyphenyl)-7-(phenylsulfonyl)-2,7-diazaspiro[3.5]nonane-2-carboxamide, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, and N-(3-fluorophenyl)-7-(methylsulfonyl)-2,7-diazaspiro[3.5]nonane-2-carboxamide, or a solvate, hydrate, or pharmaceutically acceptable salt thereof.

According to a third aspect, the present invention also encompasses a compound according to the first aspect of the invention, or a compound selected from the group consisting of N-(1-methylethyl)-7-(phenylsulfonyl)-2,7-diazaspiro[3.5]nonane-2-carboxamide, N-(3-fluorophenyl)-7-(phenylsulfonyl)-2,7-diazaspiro[3.5]nonane-2-carboxamide, N-phenyl-7-(phenylsulfonyl)-2,7-diazaspiro[3.5]nonane-2-carboxamide, N-4-methoxyphenyl)-7-(phenylsulfonyl)-2,7-diazaspiro[3.5]nonane-2-carboxamide, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, and N-(3-fluorophenyl)-7-(methylsulfonyl-2,7-diazaspiro[3.5]nonane-2-carboxamide, or a solvate, hydrate, or pharmaceutically acceptable salt thereof, or pharmaceutically acceptable salt thereof; or a pharmaceutical composition according to the second aspect of the invention, for use as a medicament.

According to a fourth aspect, the present invention also encompasses a compound according to the first aspect of the invention, or a compound selected from the group consisting of N-(1-methylethyl)-7-(phenylsulfonyl)-2,7-diazaspiro[3.5]nonane-2-carboxamide, N-(3-fluorophenyl)-7-(phenylsulfonyl)-2,7-diazaspiro[3.5]nonane-2-carboxamide, N-phenyl-7-(phenylsulfonyl)-2,7-diazaspiro[3.5]nonane-2-carboxamide, N-(4-methoxyphenyl)-7-(phenylsulfonyl)-2,7-diazaspiro[3.5]nonane-2-carboxamide, (1H-benzotriazol-5-yl)-{7-[2-(3-chloro-phenyl)-ethanesulfonyl]-2,7-diazaspiro[3.5]non-2-yl}-methanone, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, and N-(3-fluorophenyl)-7-(methylsulfonyl)-2,7-diazaspiro[3.5]nonane-2-carboxamide, or a solvate, hydrate, or pharmaceutically acceptable salt thereof; or a pharmaceutical composition according to the second aspect of the invention, for use as a medicine for the prevention and/or treatment of metabolic disorders and/or neurodegenerative diseases.

According to a fifth aspect, the present invention also encompasses a compound according to the first aspect of the invention, or a compound selected from the group consisting of N-(1-methylethyl)-7-(phenylsulfonyl)-2,7-diazaspiro[3.5]nonane-2-carboxamide, N-(3-fluorophenyl)-7-(phenylsulfonyl)-2,7-diazaspiro[3.5]nonane-2-carboxamide, N-phenyl-7-(phenylsulfonyl)-2,7-diazaspiro[3.5]nonane-2-carboxamide, N-(4-methoxyphenyl)-7-(phenylsulfonyl)-2,7-diazaspiro[3.5]nonane-2-carboxamide, (1H-benzotriazol-5-yl)-{7-[2-(3-chloro-phenyl)-ethanesulfonyl]-2,7-diazaspiro[3.5]non-2-yl}-methanone, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, and N-(3-fluorophenyl)-7-(methylsulfonyl)-2,7-diazaspiro[3.5]nonane-2-carboxamide, or a solvate, hydrate, or pharmaceutically acceptable salt thereof; or a pharmaceutical composition according to the second aspect of the invention, for use as a medicine for the prevention and/or treatment of protein misfolding disorders.

According to a sixth aspect, the present invention also encompasses a compound according to the first aspect of the invention, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide, N-phenyl-7-(phenylsulfonyl)-2,7-diazaspiro[3.5]nonane-2-carboxamide, N-4 methoxyphenyl)-7-(phenylsulfonyl)-2,7-diazaspiro[3.5]nonane-2-carboxamide, (1H-benzotriazol-5-yl)-{7-[2-(3-chloro-phenyl)-ethanesulfonyl]-2,7-diaza-spiro[3.5]non-2-yl}-methanone, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, and N-(3-fluorophenyl)-7-(methylsulfonyl)-2,7-diazaspiro[3.5]nonane-2-carboxamide, or a solvate, hydrate, or pharmaceutically acceptable salt thereof, or pharmaceutically acceptable salt thereof; or a pharmaceutical composition according to the second aspect of the invention, for use as a medicine for the prevention and/or treatment of diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension.

The present invention also encompasses method for the preparation of the compounds according to the first aspect of the invention.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The independent and dependent claims set out particular and preferred features of the invention. Features from the dependent claims may be combined with features of the independent or other dependent claims as appropriate.

BRIEF DESCRIPTION OF THE FIGURES

FIG. 1 represents in Section (A) a graph plotting the non-fasted body weight of db/db mice treated with compound 45 (Cmpd045) of the invention, as a function of duration of treatment in weeks. Section (B) is a graph plotting the blood glucose levels of fasted db/db mice treated with compound Cmpd045 of the invention, as a function of duration of treatment in weeks. Section (C) is a graph plotting the % HbA1c levels of db/db mice treated with compound Cmpd045 for 4 weeks.

DETAILED DESCRIPTION OF THE INVENTION

Before the present invention is described, it is to be understood that this invention is not limited to particular processes, methods, and compounds described, as such processes, methods, and compounds may, of course, vary. It is also to be understood that the terminology used herein is not intended to be limiting, since the scope of the present invention will be limited only by the appended claims.

When describing the compounds and processes of the invention, the terms used are to be construed in accordance with the following definitions, unless a context dictates otherwise.

As used in the specification and the appended claims, the singular forms "a", "an," and "the" include both singular and plural referents unless the context clearly dictates otherwise. By way of example, "a compound" means one compound or more than one compound.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Unless otherwise defined, all terms used in disclosing the invention, including technical and scientific terms, have the meaning as commonly understood by one of ordinary skill in the art to which this invention belongs.

By means of further guidance, definitions for the terms used in the description are included to better appreciate the teaching of the present invention.

When describing the present invention, the terms used are to be construed in accordance with the following definitions, unless a context dictates otherwise.

The terms described above and others used in the specification are well understood to those in the art.

Whenever the term "substituted" is used herein, it is meant to indicate that one or more hydrogen atoms on the atom indicated in the expression using "substituted" is replaced with a selection from the indicated group, provided that the indicated atom's normal valence is not exceeded, and that the substitution results in a chemically stable compound, i.e. a compound that is sufficiently robust to survive isolation from a reaction mixture.

Where groups can be substituted, such groups may be substituted with one or more, and preferably one, two or three substituents. Preferred substituents may be selected from but not limited to, for example, the group comprising halo, hydroxyl, $C_{1-6}$alkyl, $C_{1-6}$alkoxy, halo$C_{1-6}$alkyl, halo$C_{1-6}$alkyloxy, $C_{3-12}$cycloalkyl, $C_{6-12}$aryl, $C_{6-12}$aryl$C_{1-6}$alkyl, heterocyclyl, heteroaryl, $C_{1-6}$alkylthio, cyano, amino, nitro, carboxyl, aminocarbonyl, hydroxycarbonyl$C_{1-6}$alkyl, $C_{1-6}$alkyloxycarbonyl, mono- or di$C_{1-6}$alkylamino, mono- or di$C_{1-6}$alkylaminocarbonyl, $C_{1-6}$alkylcarbonyl, —S(O)$C_{1-6}$alkyl, —S(O)$_2C_{1-6}$alkyl, $C_{1-6}$alkylcarbonylamino, and mono- or di-$C_{1-6}$alkylaminocarbonyl$C_{1-6}$alkyl.

The terminology regarding a chemical group "wherein at least one carbon atom or heteroatom of said group can be oxidized to form at least one C=O, C=S, N=O, N=S, S=O or S(O)$_2$" as used herein, refers to a group where two or more hydrogen atoms on a carbon atom or heteroatom of said group are taken together to form C=O, C=S, N=O, N=S, S=O or S(O)$_2$. As an example, the terminology "an alkyl wherein a carbon atom or heteroatom of said alkyl can oxidized to form a C=O, C=S. N=O, N=S, S=O or S(O)$_2$", includes among other examples CH$_3$—C(O)—CH$_2$—, CH$_3$—C(O)—, CH$_3$—C(S)—CH$_2$— and (CH$_3$)$_2$—CH$_2$—C(O)—CH$_2$—CH$_2$—. For example, the terminology "a 5-, 6-, or 7-membered heterocyclyl wherein a carbon atom or heteroatom of said heterocyclyl can be oxidized to form a C=O, C=S, N=O, N=S, S=O or S(O)$_2$", includes among other examples 6-oxo-1H-pyridin-3-yl, 2-oxo-1H-pyridin-4-yl, 6-thioxo-1H-pyridin-3-yl and 2-thioxo-1H-pyridin-4-yl.

The term "halo" or "halogen" as a group or part of a group is generic for fluoro, chloro, bromo, iodo.

The term "amino" refers to the group —NH$_2$.

The term "hydroxyl" or "hydroxy" as used herein refers to the group —OH.

The term "thiol" or "sulfuhydryl" refers to the group —SH.

The term "oxo" as used herein refers to the group =O.

The term "nitro" as used herein refers to the group —NO$_2$.

The term "cyano" as used herein refers to the group —CN.

The term "carboxy" or "carboxyl" or "hydroxycarbonyl" as used herein refers to the group —CO$_2$H.

The term "aminocarbonyl" as used herein refers to the group —CO—NH$_2$.

The term "alkyl" by itself or as part of another substituent refers to a hydrocarbyl group of formula $C_nH_{2n+1}$ wherein n is a number greater than or equal to 1. Alkyl groups may be linear or branched and may be substituted as indicated herein. Generally, alkyl groups of this invention comprise from 1 to 6 carbon atoms, preferably from 1 to 5 carbon atoms, preferably from 1 to 4 carbon atoms, more preferably from 1 to 3 carbon atoms, still more preferably 1 to 2 carbon atoms. When a subscript is used herein following a carbon atom, the subscript refers to the number of carbon atoms that the named group may contain. For example, the term "$C_{1-6}$alkyl", as a group or part of a group, refers to a hydrocarbyl group of formula —$C_nH_{2n+1}$ wherein n is a number ranging from 1 to 6. Thus, for example, "$C_{1-6}$alkyl" includes all linear or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers. For example, "$C_{1-5}$alkyl" includes all includes all linear or branched alkyl groups with between 1 and 5 carbon atoms, and thus includes methyl, ethyl, n-propyl, i-propyl, butyl and its isomers (e.g. n-butyl, i-butyl and t-butyl); pentyl and its isomers. For example, "$C_{1-4}$alkyl" includes all linear or branched alkyl groups with between 1 and 4 carbon atoms, and thus includes methyl, ethyl, n-propyl, i-propyl, butyl and its isomers (e.g. n-butyl, i-butyl and t-butyl). For example "$C_{1-3}$alkyl" includes all linear or branched alkyl groups with between 1 and 3 carbon atoms, and thus includes methyl, ethyl, n-propyl, i-propyl. A "substituted $C_{1-6}$alkyl" refers to a $C_{1-6}$alkyl group substituted with one or more substituent(s) (for example 1 to 3 substituent(s), for example 1, 2, or 3 substituent(s)) at any available point of attachment.

When the suffix "ene" is used in conjunction with an alkyl group, i.e. "alkylene", this is intended to mean the alkyl group as defined herein having two single bonds as points of attachment to other groups. As used herein, the term "$C_{1-6}$alkylene", by itself or as part of another substituent, refers to $C_{1-6}$alkyl groups that are divalent, i.e., with two single bonds for attachment to two other groups. Alkylene groups may be linear or branched and may be substituted as indicated herein. Non-limiting examples of alkylene groups include methylene (—$CH_2$—), ethylene (—$CH_2$—$CH_2$—), methylmethylene (—$CH(CH_3)$—), 1-methyl-ethylene (—$CH(CH_3)$—$CH_2$—), n-propylene (—$CH_2$—$CH_2$—$CH_2$—), 2-methylpropylene (—$CH_2$—$CH(CH_3)$—$CH_2$—), 3-methylpropylene (—$CH_2$—$CH_2$—$CH(CH_3)$—), n-butylene (—$CH_2$—$CH_2$—$CH_2$—$CH_2$—), 2-methylbutylene (—$CH_2$—$CH(CH_3)$—$CH_2$—$CH_2$—), 4-methylbutylene (—$CH_2$—$CH_2$—$CH_2$—$CH(CH_3)$—), pentylene and its chain isomers, hexylene and its chain isomers.

When the term "alkyl" is used as a suffix following another term, as in "hydroxyalkyl," this is intended to refer to an alkyl group, as defined above, being substituted with one or two (preferably one) substituent(s) selected from the other, specifically-named group, also as defined herein. The term "hydroxy$C_{1-6}$alkyl" therefore refers to a —$R^a$—OH group wherein $R^a$ is $C_{1-6}$alkylene as defined herein.

The term "halo$C_{1-6}$alkyl" as a group or part of a group, refers to a $C_{1-6}$alkyl group having the meaning as defined above wherein one, two, or three hydrogen atoms are each replaced with a halogen as defined herein. Non-limiting examples of such halo$C_{1-6}$alkyl groups include chloromethyl, 1-bromoethyl, fluoromethyl, difluoromethyl, trifluoromethyl, 1,1,1-trifluoromethyl and the like.

The term "$C_{1-6}$alkoxy" or "$C_{1-6}$alkyloxy", as a group or part of a group, refers to a group having the formula —$OR^b$ wherein $R^b$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "halo$C_{1-6}$alkoxy", as a group or part of a group, refers to a group of formula —O—$R^c$, wherein $R^c$ is halo $C_{1-6}$alkyl as defined herein. Non-limiting examples of suitable halo$C_{1-6}$alkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The term "alkenyl" as a group or part of a group, refers to an unsaturated hydrocarbyl group, which may be linear, or branched, comprising one or more carbon-carbon double bonds. When a subscript is used herein following a carbon atom, the subscript refers to the number of carbon atoms that the named group my contain. For example, the term "$C_{2-6}$alkenyl" refers to an unsaturated hydrocarbyl group, which may be linear, or branched comprising one or more carbon-carbon double bonds and comprising from 2 to 6 carbon atoms. For example, $C_{2-4}$alkenyl includes all linear, or branched alkenyl groups having 2 to 4 carbon atoms. Examples of $C_{2-6}$alkenyl groups are ethenyl, 2-prophenyl, 2-butenyl, 3-butenyl, 2-pentenyl and its isomers, 2-hexenyl and its isomers, 2,4-pentadienyl, and the like.

Where alkenyl groups as defined herein are divalent groups having single bonds for attachment to two other groups, they are termed "alkenylene". As used herein, the term "$C_{2-6}$alkenylene", by itself or as part of another substituent, refers to $C_{2-6}$alkenyl groups that are divalent, i.e., with two single bonds for attachment to two other groups.

The term "$C_{2-6}$alkenyloxy", as a group or part of a group, refers to a group having the formula —$OR^d$ wherein $R^d$ is $C_{2-6}$alkenyl as defined herein above.

The term "alkynyl" by itself or as part of another substituent, refers to an unsaturated hydrocarbyl group, which may be linear, or branched, comprising one or more carbon-carbon triple bonds. When a subscript is used herein following a carbon atom, the subscript refers to the number of carbon atoms that the named group may contain. For example, the term "$C_{2-6}$alkynyl" refers to an unsaturated hydrocarbyl group, which may be linear, or branched comprising one or more carbon-carbon triple bonds and comprising from 2 to 6 carbon atoms. For example, $C_{2-4}$alkynyl includes all linear, or branched alkynyl groups having 2 to 4 carbon atoms. Non limiting examples of $C_{2-6}$alkynyl groups include ethynyl, 2-propynyl, 2-butynyl, 3-butynyl, 2-pentynyl and its chain isomers, 2-hexynyl and its chain isomers, and the like.

Where alkynyl groups as defined herein are divalent groups having single bonds for attachment to two other groups, they are termed "alkynylene". As used herein, the term "$C_{2-6}$alkynylene", by itself or as part of another substituent, refers to $C_{2-6}$alkynyl groups that are divalent, i.e., with two single bonds for attachment to two other groups.

The term "$C_{2-6}$alkynyloxy", as a group or part of a group, refers to a group having the formula —$OR^e$ wherein $R_c$ is $C_{2-6}$alkynyl as defined herein above.

The term "cycloalkyl", as a group or part of a group, refers to a cyclic alkyl group, that is a monovalent, saturated, hydrocarbyl group having 1 or more cyclic structure, and comprising from 3 to 12 carbon atoms, more preferably from 3 to 9 carbon atoms, more preferably from 3 to 7 carbon atoms; more preferably from 3 to 6 carbon atoms. Cycloalkyl includes all saturated hydrocarbon groups containing 1 or more rings, including monocyclic or bicyclic groups. The further rings of multi-ring cycloalkyls may be either fused, bridged and/or joined through one or more spiro atoms. When a subscript is used herein following a carbon atom, the subscript refers to the number of carbon atoms that the named group may contain. For example, the term "$C_{3-8}$cycloalkyl", a cyclic alkyl group comprising from 3 to 8 carbon atoms. For example, the term "$C_{3-6}$cycloalkyl", a cyclic alkyl group comprising from 3 to 6 carbon atoms. Examples of $C_{3-12}$cycloalkyl groups include but are not limited to cyclopropyl, cyclobutyl, cyclopentyl, cyclohexyl, cycloheptyl, cyclooctyl, bicycle[2.2.1]heptan-2-yl, (1S,4R)-norbornan-2-yl, (1R,4R)-norbornan-2-yl, (1S,4S)-norbornan-2-yl, (1R,4S)-norbornan-2-yl.

When the suffix "ene" is used in conjunction with a cycloalkyl group, i.e. cycloalkylene, this is intended to mean the cycloalkyl group as defined herein having two single bonds as points of attachment to other groups. Non-limiting examples of "$C_{3-8}$cycloalkylene" include 1,2-cyclopropylene, 1,1-cyclopropylene, 1,1-cyclobutylene, 1,2-cyclobutylene, 1,3-cyclopentylene, 1,1-cyclopentylene, and 1,4-cyclohexylene.

Where an alkylene or cycloalkylene group is present, connectivity to the molecular structure of which it forms part may be through a common carbon atom or different carbon atom. To illustrate this applying the asterisk nomenclature of this invention, a $C_3$alkylene group may be for example *—CH$_2$—CH$_2$CH$_2$—*, *—CH(—CH$_2$CH$_3$)—* or *—CH$_2$CH(—CH$_3$)—*. Likewise a $C_3$cycloalkylene group may be

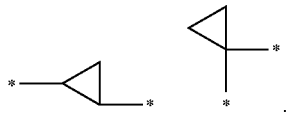

The term "$C_{6-12}$cycloalkyloxy", as a group or part of a group, refers to a group having the formula —OR$^f$ wherein $R_f$ is $C_{3-12}$cycloalkyl as defined herein above.

The term "$C_{6-12}$aryl", as a group or part of a group, refers to a polyunsaturated, aromatic hydrocarbyl group having a single ring (i.e. phenyl) or multiple aromatic rings fused together (e.g. naphthyl), or linked covalently, typically containing 6 to 12 atoms; preferably 6 to 10, wherein at least one ring is aromatic. The aromatic ring may optionally include one to two additional rings (either cycloalkyl, heterocyclyl or heteroaryl) fused thereto. Examples of suitable aryl include $C_{6-10}$aryl, more preferably $C_{6-8}$aryl, Non-limiting examples of $C_{6-12}$aryl comprise phenyl; biphenylyl; biphenylenyl; or 1- or 2-naphthanelyl; 1-, 2-, 3-, 4-, 5- or 6-tetralinyl (also known as "1,2,3,4-tetrahydronaphthalene); 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl; 1,2,3,4-tetrahydronaphthyl; and 1,4-dihydronaphthyl; 1-, 2-, 3-, 4- or 5-pyrenyl. A "substituted $C_{6-12}$aryl" refers to a $C_{6-12}$aryl group having one or more substituent(s) (for example 1, 2 or 3 substituent(s), or 1 to 2 substituent(s)), at any available point of attachment.

As used herein, the term "spiro atom" refers to the atom that connects two cyclic structures in a spiro compound. Non limiting examples of spiro atoms include quaternary carbon atoms. As used herein, the term "spiro compound" refers to a bicyclic compound wherein the two rings are connected through one atom.

When the suffix "ene" is used in conjunction with an aryl group; i.e. arylene, this is intended to mean the aryl group as defined herein having two single bonds as points of attachment to other groups. Suitable "$C_{6-12}$arylene" groups include 1,4-phenylene, 1,2-phenylene, 1,3-phenylene, biphenylylene, naphthylene, indenylene, 1-, 2-, 5- or 6-tetralinylene, and the like. Where a carbon atom in an aryl group is replaced with a heteroatom, the resultant ring is referred to herein as a heteroaryl ring.

The term "$C_{6-12}$aryloxy", as a group or part of a group, refers to a group having the formula —OR$^8$ wherein $R^8$ is $C_{6-12}$aryl as defined herein above.

The term "$C_{6-12}$arylC$_{1-6}$alkyl", as a group or part of a group, means a $C_{1-6}$alkyl as defined herein, wherein at least one hydrogen atom is replaced by at least one $C_{6-12}$aryl as defined herein. Non-limiting examples of $C_{6-12}$arylC$_{1-6}$alkyl group include benzyl, phenethyl, dibenzylmethyl, methylphenylmethyl, 3-(2-naphthyl)-butyl, and the like.

The term "$C_{6-12}$arylC$_{1-6}$alkylC$_{6-12}$aryl", as a group or part of a group, means a $C_{6-12}$aryl, wherein at least one hydrogen atom is replaced by at least one $C_{6-12}$arylC$_{1-6}$alkyl as defined herein.

The term "$C_{6-12}$aryleneC$_{1-6}$alkylene", as a group or part of a group, refers to a group having the formula —R$^h$—R$^a$— wherein R$^h$ is $C_{6-12}$arylene as defined herein and R$^a$ is $C_{1-6}$alkylene as defined herein.

The term "$C_{6-12}$arylC$_{1-6}$alkyloxy", as a group or part of a group, refers to a group having the formula —O—R$^a$—R$^g$ wherein R$^g$ is $C_{6-12}$aryl, and R$^a$ is $C_{1-6}$alkylene as defined herein above.

The terms "heterocyclyl" or "heterocycloalkyl" or "heterocyclo", as a group or part of a group, refer to non-aromatic, fully saturated or partially unsaturated cyclic groups (for example, 3 to 7 member monocyclic, 7 to 11 member bicyclic, or comprising a total of 3 to 10 ring atoms) which have at least one heteroatom in at least one carbon atom-containing ring; wherein said ring may be fused to an aryl, cycloalkyl, heteroaryl or heterocyclyl ring. Each ring of the heterocyclyl group containing a heteroatom may have 1, 2, 3 or 4 heteroatoms selected from N, O and/or S, where the N and S heteroatoms may optionally be oxidized and the N heteroatoms may optionally be quaternized; and wherein at least one carbon atom of heterocyclyl can be oxidized to form at least one C=O. The heterocyclic group may be attached at any heteroatom or carbon atom of the ring or ring system, where valence allows. The rings of multi-ring heterocycles may be fused, bridged and/or joined through one or more spiro atoms.

Non limiting exemplary heterocyclic groups include aziridinyl, oxiranyl, thiiranyl, piperidinyl, azetidinyl, oxetanyl, pyrrolidinyl, thietanyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, chromanyl (also known as 3,4-dihydrobenzo[b]pyranyl), 2H-pyrrolyl, 1-pyrrolinyl, 2-pyrrolinyl, 3-pyrrolinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioxoimidazolidinyl, 2-oxopiperidinyl, 2-oxopyrrolidinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl. The term "aziridinyl" as used herein includes aziridin-1-yl and aziridin-2-yl. The term "oxyranyl" as used herein includes oxyranyl-2-yl. The term "thiiranyl" as used herein includes thiiran-2-yl. The term "azetidinyl" as used herein includes azetidin-1-yl, azetidin-2-yl and azetidin-3-yl. The term "oxetanyl" as used herein includes oxetan-2-yl and oxetan-3-yl. The term "thietanyl" as used herein includes thietan-2-yl and thietan-3-yl. The term "pyrrolidinyl" as used herein includes pyrrolidin-1-yl, pyrrolidin-2-yl and pyrrolidin-3-yl. The term "tetrahydrofuranyl" as used herein includes tetrahydrofuran-2-yl and tetrahydrofuran-3-yl. The term "tetrahydrothiophenyl" as used herein includes tetrahydrothiophen-2-yl and tetrahydrothiophen-3-yl. The term "succinimidyl" as used herein includes succinimid-1-yl and succininmid-3-yl. The term "dihydropyrrolyl" as used herein includes 2,3-dihydropyrrol-1-yl, 2,3-dihydro-1H-pyrrol-2-yl, 2,3-dihydro-H-pyrrol-3-yl, 2,5-dihydropyrrol-1-yl, 2,5-dihydro-1H-pyrrol-3-yl and 2,5-dihydropyrrol-5-yl. The term "2H-pyrrolyl" as used herein includes 2H-pyrrol-2-yl, 2H-pyrrol-3-yl, 2H-pyrrol-4-yl and 2H-pyrrol-5-yl. The term "3H-pyrrolyl" as used herein includes 3H-pyrrol-2-yl, 3H-pyrrol-3-yl, 3H-pyrrol-4-yl and 3H-pyrrol-5-yl. The term "dihydrofuranyl" as used herein includes 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,5-dihydrofuran-4-yl and 2,5-dihydrofuran-5-yl. The term "dihydrothiophenyl" as used herein includes 2,3-dihydrothiophen-2-yl, 2,3-dihydrothiophen-3-yl, 2,3-dihydrothiophen-4-yl, 2,3-dihydrothiophen-5-yl, 2,5-dihydrothiophen-2-yl, 2,5-dihydrothiophen-3-yl, 2,5-dihydrothiophen-4-yl and 2,5-dihydrothiophen-5-yl. The term "imidazolidinyl" as used herein includes imidazolidin-1-yl, imidazolidin-2-yl and imidazolidin-4-yl. The term "pyrazolidinyl" as used herein includes pyrazolidin-1-yl, pyrazolidin-3-yl and pyrazolidin-4-yl. The term "imidazolinyl" as used herein includes imidazolin-1-yl, imidazolin-2-yl, imidazolin-4-yl and imidazolin-5-yl. The term "pyrazolinyl" as used herein includes 1-pyrazolin-3-yl, 1-pyrazolin-4-yl, 2-pyrazolin-1-yl, 2-pyrazolin-3-yl, 2-pyrazolin-4-yl, 2-pyrazolin-5-yl, 3-pyrazolin-1-yl, 3-pyrazolin-2-yl, 3-pyrazolin-3-yl, 3-pyrazolin-4-yl and 3-pyrazolin-5-yl. The term "dioxolanyl" also known as "1,3-dioxolanyl" as used herein includes dioxolan-2-yl, dioxolan-4-yl and dioxolan-5-yl. The term "dioxolyl" also known as "1,3-dioxolyl" as used herein includes dioxol-2-yl, dioxol-4-yl and dioxol-5-yl. The term "oxazolidinyl" as used herein includes oxazolidin-2-yl, oxazolidin-3-yl, oxazolidin-4-yl and oxazolidin-5-yl. The term "isoxazolidinyl" as used herein includes isoxazolidin-2-yl, isoxazolidin-3-yl, isoxazolidin-4-yl and isoxazolidin-5-yl. The term "oxazolinyl" as used herein includes 2-oxazolinyl-2-yl, 2-oxazolinyl-4-yl, 2-oxazolinyl-5-yl, 3-oxazolinyl-2-yl, 3-oxazolinyl-4-yl, 3-oxazolinyl-5-yl, 4-oxazolinyl-2-yl, 4-oxazolinyl-3-yl, 4-oxazolinyl-4-yl and 4-oxazolinyl-5-yl. The term "isoxazolinyl" as used herein includes 2-isoxazolinyl-3-yl, 2-isoxazolinyl-4-yl, 2-isoxazolinyl-5-yl, 3-isoxazolinyl-3-yl, 3-isoxazolinyl-4-yl, 3-isoxazolinyl-5-yl, 4-isoxazolinyl-2-yl, 4-isoxazolinyl-3-yl, 4-isoxazolinyl-4-yl and 4-isoxazolinyl-5-yl. The term "thiazolidinyl" as used herein includes thiazolidin-2-yl, thiazolidin-3-yl, thiazolidin-4-yl and thiazolidin-5-yl. The term "isothiazolidinyl" as used herein includes isothiazolidin-2-yl, isothiazolidin-3-yl, isothiazolidin-4-yl and isothiazolidin-5-yl. The term "thiazolinyl" as used herein includes 2-thiazolinyl-2-yl, 2-thiazolinyl-4-yl, 2-thiazolinyl-5-yl, 3-thiazolinyl-2-yl, 3-thiazolinyl-4-yl, 3-thiazolinyl-5-yl, 4-thiazolinyl-2-yl, 4-thiazolinyl-3-yl, 4-thiazolinyl-4-yl and 4-thiazolinyl-5-yl. The term "isothiazolinyl" as used herein includes 2-isothiazolinyl-3-yl, 2-isothiazolinyl-4-yl, 2-isothiazolinyl-5-yl, 3-isothiazolinyl-3-yl, 3-isothiazolinyl-4-yl, 3-isothiazolinyl-5-yl, 4-isothiazolinyl-2-yl, 4-isothiazolinyl-3-yl, 4-isothiazolinyl-4-yl and 4-isothiazolinyl-5-yl. The term "piperidyl" also known as "piperidinyl" as used herein includes piperid-1-yl, piperid-2-yl, piperid-3-yl and piperid-4-yl. The term "dihydropyridinyl" as used herein includes 1,2-dihydropyridin-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,4-dihydropyridin-1-yl, 1,4-dihydropyridin-2-yl, 1,4-dihydropyridin-3-yl, 1,4-dihydropyridin-4-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 3,4-dihydropyridin-2-yl, 3,4-dihydropyridin-3-yl, 3,4-dihydropyridin-4-yl, 3,4-dihydropyridin-5-yl and 3,4-dihydropyridin-6-yl. The term "tetrahydropyridinyl" as used herein includes 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl, 1,2,3,4-tetrahydropyridin-5-yl, 1,2,3,4-tetrahydropyridin-6-yl, 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl, 1,2,3,6-tetrahydropyridin-6-yl, 2,3,4,5-tetrahydropyridin-2-yl, 2,3,4,5-tetrahydropyridin-3-yl, 2,3,4,5-tetrahydropyridin-3-yl, 2,3,4,5-tetrahydropyridin-4-yl, 2,3,4,5-tetrahydropyridin-5-yl and 2,3,4,5-tetrahydropyridin-6-yl. The term "tetrahydropyranyl" also known as "oxanyl" or "tetrahydro-2H-pyranyl", as used herein includes tetrahydropyran-2-yl, tetrahydropyran-3-yl and tetrahydropyran-4-yl. The term "2H-pyranyl" as used herein includes 2H-pyran-2-yl, 2H-pyran-3-yl, 2H-pyran-4-yl, 2H-pyran-5-yl and 2H-pyran-6-yl. The term "4H-pyranyl" as used herein includes 4H-pyran-2-yl, 4H-pyran-3-yl and 4H-pyran-4-yl. The term "3,4-dihydro-2H-pyranyl" as used herein includes 3,4-dihydro-2H-pyran-2-yl, 3,4-dihydro-2H-pyran-3-yl, 3,4-dihydro-2H-pyran-4-yl, 3,4-dihydro-2H-pyran-5-yl and 3,4-dihydro-2H-pyran-6-yl. The term "3,6-dihydro-2H-pyranyl" as used herein includes 3,6-dihydro-2H-pyran-2-yl, 3,6-dihydro-2H-pyran-3-yl, 3,6-dihydro-2H-pyran-4-yl, 3,6-dihydro-2H-pyran-5-yl and 3,6-dihydro-2H-pyran-6-yl. The term "tetrahydrodthiophenyl", as used herein includes tetrahydrothiophen-2-yl, tetrahydrothiophenyl-3-yl and tetrahydrothiophenyl-4-yl. The term "2H-thiopyranyl" as used herein includes 2H-thiopyran-2-yl, 2H-thiopyran-3-yl, 2H-thiopyran-4-yl, 2H-thiopyran-5-yl and 2H-thiopyran-6-yl. The term "4H-thiopyranyl" as used herein includes 4H-thiopyran-2-yl, 4H-thiopyran-3-yl and 4H-thiopyran-4-yl. The term "3,4-dihydro-2H-thiopyranyl" as used herein includes 3,4-dihydro-2H-thiopyran-2-yl, 3,4-dihydro-2H-thiopyran-3-yl, 3,4-dihydro-2H-thiopyran-4-yl, 3,4-dihydro-2H-thiopyran-5-yl and 3,4-dihydro-2H-thiopyran-6-yl. The term "3,6-dihydro-2H-thiopyranyl" as used herein includes 3,6-dihydro-2H-thiopyran-2-yl, 3,6-dihydro-2H-thiopyran-3-yl, 3,6-dihydro-2H-thiopyran-4-yl, 3,6-dihydro-2H-thiopyran-5-yl and 3,6-dihydro-2H-thiopyran-6-yl. The term "piperazinyl" also known as "piperazidinyl" as used herein includes piperazin-1-yl and piperazin-2-yl. The term "morpholinyl" as used herein includes morpholin-2-yl, morpholin-3-yl and morpholin-4-yl. The term "thiomorpholinyl" as used herein includes thiomorpholin-2-yl, thiomorpholin-3-yl and thiomorpholin-4-yl. The term "dioxanyl" as used herein includes 1,2-dioxan-3-yl, 1,2-dioxan-4-yl, 1,3-dioxan-2-yl, 1,3-dioxan-4-yl, 1,3-dioxan-5-yl and 1,4-dioxan-2-yl. The term "dithianyl" as used herein includes 1,2-dithian-3-yl, 1,2-dithia-4-yl, 1,3-dithian-2-yl, 1,3-dithian-4-yl, 1,3-dithian-5-yl and 1,4-dithian-2-yl. The term "oxathianyl" as used herein includes oxathian-2-yl and oxathian-3-yl. The term "trioxanyl" as used herein includes 1,2,3-trioxan-1-yl, 1,2,3-trioxay-5-yl, 1,2,4-trioxay-3-yl, 1,2,4-trioxay-5-yl, 1,2,4-trioxay-6-yl and 1,3,4-trioxay-2-yl. The term "azepanyl" as used herein includes azepan-1-yl, azepan-2-yl, azepan-1-yl, azepan-3-yl and azepan-4-yl. The term "homopiperazinyl" as used herein includes homopiperazin-1-yl, homopiperazin-2-yl, homopiperazin-3-yl and homopiperazin-4-yl. The term "indolinyl" as used herein includes indolin-1-yl, indolin-2-yl, indolin-3-yl, indolin-4-yl, indolin-5-yl, indolin-6-yl, and indolin-7-yl. The term "quinolizinyl" as used herein includes quinolizidin-1-yl, quinolizidin-2-yl, quinolizidin-3-yl and quinolizidin-4-yl. The term "isoindolinyl" as used herein includes isoindolin-1-yl, isoindolin-2-yl, isoindolin-3-yl, isoindolin-4-yl, isoindolin-5-yl, isoindolin-6-yl, and isoindolin-7-yl. The term "3H-indolyl" as used herein includes 3H-indol-2-yl, 3H-indol-3-yl, 3H-indol-4-yl, 3H-indol-5-yl, 3H-indol-6-yl, and 3H-indol-7-yl. The term "quinolizinyl" as used herein includes quinolizidin-1-yl, quinolizidin-2-yl, quinolizidin-3-yl and quinolizidin-4-yl. The term "quinolizinyl" as used herein includes quinolizidin-1-yl, quinolizidin-2-yl, quinolizidin-3-yl and quinolizidin-4-yl. The term "tetrahydroquinolinyl" as used herein includes tetrahydroquinolin-1-yl, tetrahydroquinolin-2-yl, tetrahydroquinolin-3-yl, tetrahydroquinolin-4-yl, tetrahydroquinolin-5-yl, tetrahydroquinolin-6-yl, tetrahydroquinolin-7-yl and tetrahydroquinolin-8-yl. The term "tetrahydroisoquinolinyl" as used herein includes tetrahydroisoquinolin-1-yl, tetrahydroisoquinolin-2-yl, tetrahydroisoquinolin-3-yl tetrahydroisoquinolin-4-yl, tetrahydroisoquinolin-5-yl, tetrahydroisoquinolin-6-yl, tetrahydroisoquinolin-7-yl and tetrahydroisoquinolin-8-yl. The term "chromanyl" as used herein includes chroman-2-yl, chroman-3-yl, chroman-4-yl, chroman-5-yl, chroman-6-yl, chroman-7-yl and chroman-8-yl. The term "1H-pyrrolizine" as used herein includes 1H-pyrrolizin-1-yl, 1H-pyrrolizin-2-yl, 1H-pyrrolizin-3-yl, 1H-pyrrolizin-5-yl, 1H-pyrrolizin-6-yl and 1H-pyrrolizin-7-yl. The term "3H-pyrrolizine" as used herein includes 3H-pyrrolizin-1-yl, 3H-pyrrolizin-2-yl, 3H-pyrrolizin-3-yl, 3H-pyrrolizin-5-yl, 3H-pyrrolizin-6-yl and 3H-pyrrolizin-7-yl.

When the suffix "ene" is used in conjunction with a heterocyclyl group; i.e. "heterocyclylene", this is intended to mean the heterocyclyl group as defined herein having two single bonds as points of attachment to other groups.

The term "heterocyclyloxy", as a group or part of a group, refers to a group having the formula —O—$R^i$ wherein $R^i$ is heterocyclyl as defined herein above.

The term "heterocyclyl$C_{1-6}$alkyloxy", as a group or part of a group, refers to a group having the formula —O—$R^a$—$R^i$ wherein $R^i$ is heterocyclyl, and $R^a$ is $C_{1-6}$alkylene as defined herein above.

The term "heterocyclyl$C_{1-6}$alkyl", as a group or part of a group, means a $C_{1-6}$alkyl as defined herein, wherein at least one hydrogen atom is replaced by at least one heterocyclyl as defined herein.

The term "heterocyclylene$C_{1-6}$alkylene", as a group or part of a group, refers to a group having the formula —$R^j$—$R^a$— wherein $R^j$ is heterocyclylene as defined herein and $R^a$ is $C_{1-6}$alkylene as defined herein.

The term "heteroaryl" as a group or pert of a group, refers but is not limited to 5 to 12 carbon-atom aromatic rings or ring systems containing 1 or 2 rings which can be fused together or linked covalently, typically containing 5 to 6 atoms; at least one of which is aromatic in which one or more carbon atoms in one or more of these rings can be replaced by N, O and/or S atoms where the N and S heteroatoms may optionally be oxidized and the N heteroatoms may optionally be quaternized, and wherein at least one carbon atom of said heteroaryl can be oxidized to form at least one C=O, Such rings nay be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, imidazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, thienopyridinyl, purinyl, imidazo[1,2-a]pyridinyl, 6-oxo-pyridazin-1(6H)-yl, 2-oxopyridin-(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolyl, quinoxalinyl; preferably said heteroaryl group is selected from the group consisting of pyridyl, 1,3-benzodioxolyl, benzo[d]oxazol-2(3H)-one, 2,3-dihydro-benzofuranyl, pyrazinyl, pyrazolyl, pyrrolyl, isoxazolyl, thiophenyl, imidazolyl benzimidazolyl, pyrimidinyl, triazolyl and thiazolyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxaryl-2-yl, oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl) as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl" as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, -indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-imidazol-1-yl, 1H-imidazol-3-yl, 1H-imidazol-4-yl, 1H-imidazol-5-yl, 1H-imidazol-6-yl, 1H-imidazol-7-yl, 2H-imidazol-2-yl, 2H-imidazol-3-yl, 2H-imidazol-4-yl, 2H-imidazol-5-yl, 2H-imidazol-6-yl, and 2H-imidazol-7-yl. The term "benzimidazmlyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzisoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzoisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol-4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein, includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quinazolin-4-yl, quinazolin-5-yl, quinazolin-6-yl, quinazolin-7-yl and quinazolin-8-yl. The term "quinoxalinyl" as used herein includes quinoxalin-2-yl, quinoxalin-5-yl, and quinoxalin-6-yl.

When the suffix "ene" is used in conjunction with a heteroaryl group; i.e. "heteroarylene", this is intended to mean the heteroaryl group as defined herein having two single bonds as points of attachment to other groups.

The term "heteroaryloxy", as a group or part of a group, refers to a group having the formula —O—$R^k$ wherein $R^k$ is heteroaryl as defined herein above.

The term "heteroaryl$C_{1-6}$alkyl", as a group or part of a group, means a $C_{1-6}$alkyl as defined herein, wherein at least one hydrogen atom is replaced by at least one heteroaryl as defined herein.

The term "heteroaryl$C_{1-6}$alkyloxy", as a group or part of a group, refers to a group having the formula —O—$R^a$—$R^k$ wherein $R^k$ is heteroaryl, and $R^a$ is $C_{1-6}$alkylene as defined herein above.

The term "heteroarylene$C_{1-6}$alkylene", as a group or part of a group, refers to a group having the formula —$R^m$—

$R^a$— wherein $R^m$ is heteroarylene as defined herein and $R^a$ is $C_{1-6}$alkylene as defined herein.

The term "cyano$C_{1-6}$alkyl" as a group or part of a group, refers to a $C_{1-6}$alkyl group having the meaning as defined above wherein at least one hydrogen atom is replaced with at least one cyano group as defined herein.

Non-limiting examples of such cyano$C_{1-6}$alkyl groups include cyanomethyl, 1-cyanoethyl, 1-cyanopropyl and the like.

The term "cyano$C_{1-6}$alkyloxy", as a group or part of a group, refers to a group having the formula —O—$R^n$ wherein $R^n$ is cyano$C_{1-6}$alkyl as defined herein above.

The term "$C_{1-6}$alkylthio", as a group or part of a group, refers to a group having the formula —S—$R^b$ wherein $R^b$ is $C_{1-6}$alkyl as defined herein above. Non-limiting examples of $C_{1-6}$alkylthio groups include methylthio (—SCH$_3$), ethylthio (—SCH$_2$CH$_3$), n-propylthio, isopropylthio, n-butylthio, isobutylthio, sec-butylthio, tert-butylthio and the like.

The term "$C_{2-6}$alkenylthio", as a group or part of a group, refers to a group having the formula —S—$R^d$ wherein $R^d$ is $C_{2-6}$alkenyl as defined herein above.

The term "$C_{2-6}$alkynylthio", as a group or part of a group, refers to a group having the formula —S—$R^e$ wherein $R^e$ is $C_{2-6}$alkynyl as defined herein above.

The term "$C_{6-12}$arylthio", as a group or part of a group, refers to a group having the formula —S—$R^g$ wherein $R^g$ is $C_{6-12}$aryl as defined herein above.

The term "$C_{3-12}$cycloalkylthio", as a group or pert of a group, refers to a group having the formula —S—$R^f$ wherein $R^f$ is $C_{3-12}$cycloalkyl as defined herein above.

The term "$C_{6-12}$aryl$C_{1-6}$ alkylthio", as a group or part of a group, refers to a group having the formula —S—$R^a$—$R^g$ wherein $R^a$ is $C_{1-6}$alkylene and $R^g$ is $C_{6-12}$aryl as defined herein above.

The term "heterocyclylthio", as a group or part of a group, refers to a group having the formula —S—$R^i$ wherein $R^i$ is heterocyclyl as defined herein above.

The term "heteroarylthio", as a group or part of a group, refers to a group having the formula —S—$R^k$ wherein $R^k$ is heteroaryl as defined herein above.

The term "heterocyclyl$C_{1-6}$alkylthio", as a group or part of a group, refers to a group having the formula —S—$R^a$—$R^i$ wherein $R^a$ is $C_{1-6}$alkylene and $R^i$ is heterocyclyl as defined herein above.

The term "heteroaryl$C_{1-6}$alkylthio", as a group or part of a group, refers to a group having the formula —S—$R^a$—$R^k$ wherein $R^a$ is $C_{1-6}$alkylene and $R^k$ is heteroaryl as defined herein above.

The term "cyano$C_{1-6}$alkylthio", as a group or part of a group, refers to a group having the formula —S—$R^n$ wherein $R^n$ is cyano$C_{1-6}$alkyl as defined herein above.

The term "mono- or di-$C_{6-12}$alkylamino", as a group or part of a group, refers to a group of formula —N($R^o$)($R^p$) wherein $R^o$ and $R^p$ are each independently selected from hydrogen, or $C_{1-6}$alkyl, wherein at least one of $R^o$ or $R^p$ is $C_{1-6}$alkyl. Thus, alkylamino include mono-alkyl amino group (e.g. mono-$C_{1-6}$alkylamino group such as methylamino and ethylamino), and di-alkylamino group (e.g. di-$C_{1-6}$alkylamino group such as dimethylamino and diethylamino). Non-limiting examples of suitable mono- or di-$C_{1-6}$alkylamino groups include n-propylamino, isopropylamino, n-butylamino, i-butylamino, sec-butylamino, r-butylamino, pentylamino, n-hexylamino, di-n-propylamino, di-i-propylamino, ethylmethylamino, methyl-n-propylamino, methyl-i-propylamino, n-butylmethylamino, i-butylmethylamino, t-butylmethylamino, ethyl-n-propylamino, ethyl-i-propylamino, n-butylethylamino, i-butylethylamino, t-butylethylamino, di-n-butylamino, di-i-butylamino, methylpentylamino, methylhexylamino, ethylpentylamino, ethylhexylamino, propylpentylamino, propylhexylamino, and the like.

The term "mono- or di-$C_{6-12}$arylamino", as a group or part of a group, refers to a group of formula —N($R^q$)($R^r$) wherein $R^q$ and $R^r$ are each independently selected from hydrogen, $C_{6-12}$aryl, or $C_{1-6}$alkyl, wherein at least one of $R^q$ or $R^r$ is $C_{6-12}$aryl.

The term "mono- or di-$C_{3-8}$cycloalkylamino", as a group or part of a group, refers to a group of formula —N($R^s$)($R^t$) wherein $R^s$ and $R^t$ are each independently selected from hydrogen, $C_{3-8}$cycloalkyl, or $C_{1-6}$alkyl, wherein at least one of $R^s$ or $R^t$ is $C_{3-8}$cycloalkyl.

The term "amino$C_{1-6}$alkyl", as a group or part of a group, refers to a group of formula —$R^a$—N$R^o R^p$ wherein $R^a$ is $C_{1-6}$alkylene, $R^o$ is hydrogen or $C_{1-6}$alkyl as defined herein, and $R^p$ is hydrogen or $C_{1-6}$alkyl as defined herein.

The term "mono- or di-heteroarylamino", as a group or part of a group, refers to a group of formula —N($R^u$)($R^v$) wherein $R^u$ and $R^v$ are each independently selected from hydrogen, heteroaryl, or $C_{1-6}$alkyl, wherein at least one of $R^u$ or $R^v$ is heteroaryl as defined herein.

The term "mono- or di-heterocyclylamino", as a group or part of a group, refers to a group of formula —N($R^w$)($R^x$) wherein $R^w$ and $R^x$ are each independently selected from hydrogen, heterocyclyl, or $C_{1-6}$alkyl, wherein at least one of $R^w$ or $R^x$ is heterocyclyl as defined herein.

The term "hydroxycarbonyl$C_{1-6}$alkyl", as a group or part of a group, refers to a group of formula —$R^a$—COOH, wherein $R^a$ is $C_{1-6}$alkylene as defined herein.

The term "$C_{1-6}$alkyloxycarbonyl", as a group or part of a group, refers to a group of formula —COO—$R^b$, wherein $R^b$ is $C_{1-6}$alkyl as defined herein.

The term "mono- or di$C_{1-6}$alkylaminocarbonyl", as a group or part of a group, refers to a group of formula —CONR$^o R^p$ wherein $R^o R^p$ are each independently selected from hydrogen, or $C_{1-6}$alkyl, wherein at least one of $R^o$ or $R^p$ is $C_{1-6}$alkyl.

The term "$C_{1-6}$alkylcarbonyl", as a group or part of a group, refers to a group of formula —CO—$R^b$, wherein $R^b$ is $C_{1-6}$alkyl as defined herein.

The term "$C_{1-6}$alkylcarbonylamino", as a group or part of a group, refers to a group of formula —NR$^o$—CO—$R^b$, wherein $R^o$ is selected from hydrogen, or $C_{1-6}$alkyl and $R^b$ is $C_{1-6}$alkyl as defined herein.

The term "mono or di-$C_{1-6}$alkylaminocarbonyl$C_{1-6}$alkyl", as a group or part of a group, refers to a group of formula —$R^a$—CONR$^o R^p$ wherein $R^o R^p$ are each independently selected from hydrogen, or $C_{1-6}$alkyl, wherein at least one of $R^o$ or $R^p$ is $C_{1-6}$alkyl, and $R^a$ is $C_{1-6}$alkylene as defined herein.

The term "leaving group" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I).

Whenever used in the present invention the term "compounds of the invention" or a similar term is meant to include the compounds of general formula (I) and any subgroup thereof. This term also refers to the compounds as depicted in Table 1 and their derivatives, N-oxides, salts, solvates, hydrates, stereoisomeric forms, racemic mixtures, tautomeric forms, optical isomers, analogues, pro-drugs, esters and metabolites, as well as their quaternized nitrogen analogues. The N-oxide forms of said compounds are meant to comprise compounds wherein one or several nitrogen atoms are oxidized to the so-called N-oxide.

Preferred statements (features) and embodiments of the compounds and processes of this invention are now set forth. Each statements and embodiments of the invention so defined may be combined with any other statement and/or embodiments unless clearly indicated to the contrary. In particular, any feature indicated as being preferred or advantageous may be combined with any other feature or features indicated as being preferred or advantageous.

Numbered statements of this invention are:
1. A compound of formula (I) or a stereoisomer, enantiomer, racemic, or tautomer thereof,

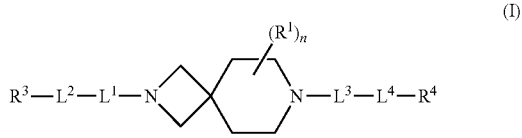
(I)

wherein,
n is an integer selected from 0, 1, 2 or 3;
$R^1$ is selected from the group consisting of $C_{1-6}$alkyl, halo, halo$C_{1-6}$alkyl, and halo$C_{1-6}$alkyloxy;
$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$;
$L^1$ is selected from the group consisting of —$SO_2$—, —CO—,

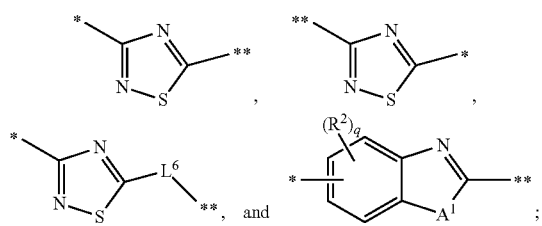

wherein * represents where $L^1$ is bound to $L^2$; and ** represents where $L^1$ is bound to the azetidine ring; and wherein,
$A^1$ is S or O;
q is an integer selected from 0, 1, 2, or 3;
$L^6$ is —CO— or —$SO_2$—,
each $R^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heteroaryl, hydroxyl, $SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$; wherein two $R^2$ together with the atom to which they are attached can form a saturated or unsaturated 5-, 6-, or 7-membered ring; and wherein at least one carbon atom or heteroatom of said ring, $C_{6-12}$aryl, $C_{3-8}$cycloalkyl, heterocyclyl, heteroaryl can be oxidized to form at least one C=O, C=S, N=O, N=S, S=O or $S(O)_2$;
$R^4$ is selected from the group consisting $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$;
$L^2$ is a single bond or a group of formula (i);

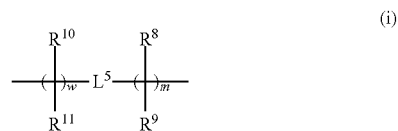
(i)

wherein the left side of the group of formula (i) is attached to $R^3$ and the right side thereof is attached to the nitrogen atom of the azetidine ring; and wherein,
m is an integer selected from 0, 1, 2, or 3;
w is an integer selected from 0, 1, 2 or 3;
$L^5$ is a single bond, or is selected from the group consisting of —O—, and —$NR^{12}$—;
$R^8$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;
$R^9$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;
or $R^8$ and $R^9$ together with the carbon atom to which they are attached from a saturated or unsaturated 3-, 4-, 5-, 6- or 7-membered ring;
$R^{10}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;
$R^{11}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;
or $R^{10}$ and $R^{11}$ together with the carbon atom to which they are attached from a saturated or unsaturated 3-, 4-, 5-, 6- or 7-membered ring;
$R^{12}$ is selected from the group consisting of hydrogen, and $C_{1-6}$alkyl;
$L^3$ is selected from the group consisting of —$SO_2$—, —$PO_4$—, and —$PO_3$—;
$L^4$ is a single bond or is selected from the group consisting of —$(CR^{15}R^{16})_t$—, —O—, and —$NR^{17}$—; wherein,
t is an integer selected from 1, 2 or 3;
$R^{15}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;
$R^{16}$ is selected from the group consisting of hydrogen, $C_{1-6}$alkyl, halo, hydroxyl, —$OR^{18}$, —$SR^{19}$, halo$C_{1-6}$alkyl, and halo$C_{1-6}$alkyloxy;
or $R^{15}$ and $R^{16}$ together with the carbon atom to which they are attached form a saturated or unsaturated 3-, 4-, 5-, 6- or 7-membered ring;
$R^{17}$ is selected from the group consisting of hydrogen, and $C_{1-6}$alkyl;
wherein at least one of $L^3$, $L^4$ is not a single bond; and wherein when $L^4$ is a single bond, $R^4$ is not methyl;

each $R^{18}$ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroeryl$C_{1-6}$alkyl, and cyano$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{19}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteoroaryl$C_{1-6}$alkyl, or cyano$C_{1-6}$alkyl can be oxidized to form at least one C=O, C=S, N=O, N=S, S=O or $S(O)_2$;

each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$ alkyl, can be oxidized to form at least one C=O, C=S, N=O, N=S, S=O or $S(O)_2$;

each $R^{21}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl heterocyclyl, heteroaryl, heterocyclyl$C_{1-6}$alkyl, and heteroaryl$C_{1-6}$ alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

or wherein $R^{20}$ and $R^{21}$ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or $S(O)_2$;

each $R^{22}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$ alkyl can be oxidized to form at least one C=O, C=S, N=O, N=S, S=O or $S(O)_2$;

each $R^{23}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl can be oxidized to form at least one C=O, C=S, N=O, N=S, S=O or $S(O)_2$;

each $R^{24}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroaylene, heterocyclylene$C_{1-6}$alkylene*, and heteroarylene$C_{1-6}$alkylene*; wherein * represents where $R^{24}$ is bound to CO;

wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heteroyclylene$C_{1-6}$alkene, or heteroarylene$C_{1-6}$alkylene can be oxidized to form at least one C=O, C=S, N=O, N=S, S=O or $S(O)_2$;

each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl, heteroaryl$C_{1-6}$alkyl, hydroxyl, —$SR^{19}$, cyano, amino, —$NR^{20}R^{21}$, —$CO_2R^2$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$; wherein two $Z^1$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$-aryl, $C_{6-12}$aryl$C_{6-12}$alkyl, heterocyclyl, heterocyclyl$C_{1-6}$alkyl, heteroaryl or heteroaryl $C_{1-6}$alkyl can be oxidized to form at least one C=O, C=S, N=O, N=S, S=O or $S(O)_2$;

each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl, heteroaryl$C_{1-6}$ alkyl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}C(O)NR^{20}R^{21}$, —$NR^{23}S(O)_2R^{22}$, and $NR^{23}C(O)NR^{20}R^{21}$; wherein two $Z^2$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl $C_{1-6}$alkyl can be oxidized to form at least one C=O, C=S, N=O, N=S, S=O or $S(O)_2$;

with the proviso that said compound is not

N-(1-methylethyl)-7-(phenylsulfonyl)-2,7-diazaspiro[3.5]nonane-2-carboxamide (CAS-959528-45-1), N-(3-fluorophenyl)-7-(phenylsulfonyl)-2,7-diazaspiro[3.5]nonane-2-carboxamide, (CAS-959495-39-7), N-phenyl-7-(phenylsulfonyl)-2,7-diazaspiro[3.5]nonane-2-carboxamide, (CAS-959490-58-5), N-(4-methoxyphenyl)-7-(phenylsulfonyl)-2,7-diazaspiro[3.5]nonane-2-carboxamide, (CAS-959481-84-6), (1H-benzotriazol-5-yl)-{7-[2-(3-chloro-phenyl)-ethanesulfonyl]-2,7-diaza-spiro[3.5]non-2-yl}-methanone, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, N-(3-fluorophenyl)-7-(methylsulfonyl)-2,7-diazaspiro[3.5]nonane-2-carboxamide, or a solvate, hydrate, pharmaceutically acceptable salt or prodrug thereof.

2. The compound according to statement 1, having structural formula (IA)

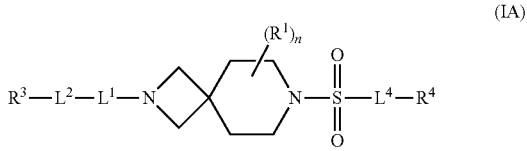

wherein $L^1$, $L^2$, $L^4$, n, $R^1$, $R^3$, and $R^4$ have the same meaning as that defined in statement 1.

3. The compound according to statements 1 or 2, having structural formula or (IB)

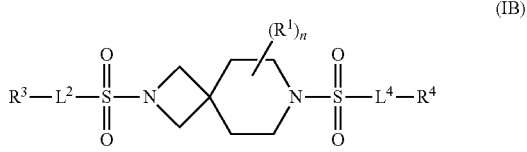

wherein, $L^2$, $L^4$, n, $R^1$, $R^3$, and $R^4$ have the same meaning as that defined in statements 1 or 2.

4. The compound according to any one of statements 1 to 3, wherein m is an integer selected from 0, 1, or 2.

5. The compound according to any one of statements 1 to 4, wherein m is an integer selected from 0, or 1.

6. The compound according to any one of statements 1 to 5, wherein m is an integer selected from 1.

7. The compound according to any one of statements 1 to 6, wherein $R^8$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo $C_{1-6}$alkyloxy.

8. The compound according to any one of statements 1 to 7, wherein $R^8$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.

9. The compound according to any one of statements 1 to 8, wherein $R^8$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.

10. The compound according to any one of statements 1 to statement 9, wherein $R^8$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.

11. The compound according to any one of statements 1 to 10, wherein $R^8$ is selected from the group consisting of hydrogen, $C_{1-6}$alkyl, halo, halo$C_{1-6}$alkyl, and halo$C_{1-6}$alkyloxy.

12. The compound according to any one of statements 1 to 11, wherein $R^9$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclythio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo $C_{1-6}$alkyloxy.

13. The compound according to any one of statements 1 to 12, wherein $R^9$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.

14. The compound according to any one of statements 1 to 132, wherein $R^9$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.

15. The compound according to any one of statements 1 to 14, wherein $R^9$ is selected from the group consisting of hydrogen, $C_{1-6}$alkyl, halo, halo$C_{1-6}$alkyl, and halo$C_{1-6}$alkyloxy.

16. The compound according to any one of statements 1 to 15, wherein $R^8$ and $R^9$ together with the carbon atom to which they are attached form a saturated or unsaturated 3-, 4-, or 5-membered ring.

17. The compound according to any one of statements 1 to 16, wherein $R^8$ and $R^9$ together with the carbon atom to which they are attached form a $C_{3-7}$cycloalkyl or a $C_{5-7}$cycloalkylene.

18. The compound according to any one of statements 1 to 17, wherein $R^8$ and $R^9$ together with the carbon atom to which they are attached form a $C_{3-6}$cycloalkyl or a $C_{5-6}$cycloalkylene.

19. The compound according to any one of statements 1 to 18, wherein $R^8$ and $R^9$ together with the carbon atom to which they are attached form a $C_{3-6}$cycloalkyl.

20. The compound according to any one of statements 1 to 19, wherein $R^8$ and $R^9$ together with the carbon atom to which they are attached form a $C_{3-5}$cycloalkyl.

21. The compound according to any one of statements 1 to 20, wherein $L^5$ is a single bond, or is selected from the group consisting of —O—, —NH—, and —N($C_{1-6}$alkyl)-.

22. The compound according to any one of statements 1 to 21, wherein $L^5$ is a single bond, or is selected from the group consisting of —O—, and —NH—.

23. The compound according to any one of statements 1 to 22, wherein $L^5$ is a single bond.

24. The compound according to any one of statements 1 to 23, wherein $L^5$ is —NH—.

25. The compound according to any one of statements 1 to 24, wherein w is an integer selected from 0, 1, or 2.

26. The compound according to any one of statements 1 to 25, wherein w is an integer selected from 0, or 1.

27. The compound according to any one of statements 1 to 26, wherein w is 0.

28. The compound according to any one of statements 1 to 27, wherein $R^{10}$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$ alkyloxy, cyanoC$_{1-6}$alkyloxy, thiol, C$_{1-6}$alkylthio, C$_{2-6}$alkenylthio, C$_{2-6}$alkynylthio, C$_{6-12}$arylthio, C$_{3-8}$cycloalkylthio, C$_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, haloC$_{1-6}$alkyl, and halo C$_{1-6}$alkyloxy.

29. The compound according to any one of statements 1 to 28, wherein R$^{10}$ is selected from the group consisting of hydrogen, C$_{1-6}$alkyl, halo, hydroxyl, C$_{1-6}$alkyloxy, C$_{6-12}$aryloxy, C$_{3-12}$cycloalkyloxy, thiol, C$_{1-6}$alkylthio, C$_{6-12}$arylthio, C$_{3-8}$cycloalkylthio, haloC$_{1-6}$alkyl, and haloC$_{1-6}$alkyloxy.

30. The compound according to any one of statements 1 to 29, wherein R$^{10}$ is selected from the group consisting of hydrogen, C$_{1-6}$alkyl, halo, hydroxyl, C$_{1-6}$alkyloxy, thiol, C$_{1-6}$alkylthio, haloC$_{1-6}$alkyl, and haloC$_{1-6}$alkyloxy.

31. The compound according to any one of statements 1 to 30, wherein R$^{10}$ is selected from the group consisting of hydrogen, C$_{1-6}$alkyl, halo, haloC$_{1-6}$alkyl, and haloC$_{1-6}$alkyloxy.

32. The compound according to any one of statements 1 to 31, wherein R$^{11}$ is selected from the group consisting of hydrogen, C$_{1-6}$alkyl, halo, hydroxyl, C$_{1-6}$alkyloxy, C$_{2-6}$alkenyloxy, C$_{2-6}$alkynyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{2-6}$alkenylthio, C$_{2-6}$alkynylthio, C$_{6-12}$arylthio, C$_{1-6}$cycloalkylthio, C$_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, haloC$_{1-6}$alkyl, and halo C$_{1-6}$alkyloxy.

33. The compound according to any one of statements 1 to 32, wherein R$^{11}$ is selected from the group consisting of hydrogen, C$_{1-6}$alkyl, halo, hydroxyl, C$_{1-6}$alkyloxy, C$_{6-12}$aryloxy, C$_{3-12}$cycloalkyloxy, thiol, C$_{1-6}$alkylthio, C$_{6-12}$arylthio, C$_{3-8}$cycloalkylthio, haloC$_{1-6}$alkyl, and haloC$_{1-6}$alkyloxy.

34. The compound according to any one of statements 1 to 33, wherein R$^{11}$ is selected from the group consisting of hydrogen, C$_{1-6}$alkyl, halo, hydroxyl, C$_{1-6}$alkyloxy, thiol, C$_{1-6}$alkylthio, haloC$_{1-6}$alkyl, and haloC$_{1-6}$alkyloxy.

35. The compound according to any one of statements 1 to 34, wherein R$^{11}$ is selected from the group consisting of hydrogen, C$_{1-6}$alkyl, halo, haloC$_{1-6}$alkyl, and haloC$_{1-6}$alkyloxy.

36. The compound according to any one of statements 1 to 35, wherein R$^{10}$ and R$^{11}$ together with the carbon atom to which they are attached form a C$_{3-7}$cycloalkyl or a C$_{5-7}$cycloalkylene.

37. The compound according to any one of statements 1 to 36, wherein R$^{10}$ and R$^{11}$ together with the carbon atom to which they are attached form a C$_{3-6}$cycloalkyl or a C$_{5-6}$cycloalkylene.

38. The compound according to any one of statements 1 to 37, wherein R$^{10}$ and R$^{11}$ together with the carbon atom to which they are attached form a C$_{3-6}$cycloalkyl.

39. The compound according to any one of statements 1 to 38, wherein R$^{10}$ and R$^{11}$ together with the carbon atom to which they are attached form a C$_{3-8}$cycloalkyl 40. The compound according to any one of statements 1 to 39, having structural formula (IC)

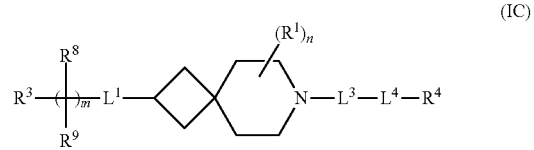

(IC)

wherein, L$^1$, L$^3$, L$^4$, m, n, R$^1$, R$^3$, R$^4$, R$^8$ and R$^9$ have the same meaning as that defined in any one of statements 1 to 39.

41. The compound according to any one of statements 1 to 40, wherein L$^2$ is a single bond.

42. The compound according to any one of statements 1 to 41, having structural formula (ID)

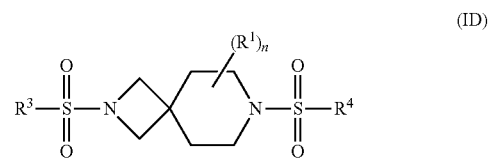

(ID)

wherein, n, R$^1$, R$^3$, and R$^4$ have the same meaning as that defined in any one of statements 1 to 41.

43. The compound according to any one of statements 1 to 42, wherein R$^3$ is selected from the group consisting of C$_{6-12}$aryl, hydrogen, C$_{1-6}$alkyl, C$_{3-12}$cycloalkyl, heterocyclyl, heteroaryl, C$_{6-12}$arylC$_{1-6}$alkyl, C$_{6-12}$arylC$_{1-6}$alkylC$_{6-12}$aryl, halo, hydroxyl, C$_{1-6}$alkyloxy, C$_{2-6}$alkenyloxy, C$_{2-6}$alkynyloxy, C$_{6-12}$alkyloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{2-6}$alkenylthio, C$_{2-6}$alkynylthio, C$_{6-12}$arylthio, C$_{3-8}$cycloalkylthio, C$_{6-12}$arylC$_{1-6}$alkylthio, heterocyclythio, heteroarylthio, heterocyclylC$_{1-6}$alkylthio, heteroarylC$_{1-6}$alkylthio, cyanoC$_{1-6}$alkylthio, haloC$_{1-6}$alkyl, haloC$_{1-6}$alkyloxy, amino, C$_{1-6}$alkylamino, C$_{2-6}$alkenylamino, C$_{2-6}$alkynylamino, C$_{6-12}$arylamino, C$_{3-8}$cycloalkylamino, C$_{6-12}$arylC$_{1-6}$alkylamino, heterocyclylamino, heteroarylamino, heterocyclylC$_{1-6}$alkylamino, heteroarylC$_{1-6}$alkylamino, di-C$_{1-6}$alkylamino, di-C$_{2-6}$alkenylamino, di-C$_{2-6}$alkynylamino, di-C$_{6-12}$arylamino, di-C$_{3-8}$-cycloalkylamino, di-C$_{6-12}$arylC$_{1-6}$alkylamino, di-heterocyclylamino, di-heteroarylamino, di-heterocyclylC$_{1-6}$alkylamino, di-heteroaryl C$_{1-6}$alkylamino, and cyano; wherein said C$_{6-12}$aryl, C$_{1-6}$alkyl, C$_{3-12}$cycloalkyl, heterocyclyl, heteroaryl, C$_{6-12}$arylC$_{1-6}$alkyl, C$_{6-12}$arylC$_{1-6}$alkylC$_{6-12}$aryl, C$_{1-6}$alkyloxy, C$_{2-6}$alkenyloxy, C$_{2-6}$alkynyloxy, C$_{6-12}$alkyloxy, C$_{3-8}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, C$_{1-6}$alkylthio, C$_{2-6}$alkenylthio, C$_{2-6}$alkynylthio, C$_{6-12}$arylthio, C$_{3-8}$cycloalkylthio, C$_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, haloC$_{1-6}$alkyl, haloC$_{1-6}$alkyloxy, C$_{1-6}$alkytamino, C$_{2-6}$alkenylamino, C$_{2-6}$alkynylamino, C$_{6-12}$arylamino, C$_{1-6}$cycloalkylamino, C$_{6-12}$arylC$_{1-6}$alkylamino, heterocyclylamino, heteroarylamino, heterocyclylC$_{1-6}$alkylamino, heteroarylC$_{1-6}$alkylamino, di-C$_{1-6}$alkylamino, di-C$_{2-6}$alkenylamino, di-C$_{2-6}$alkynylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, or di-heteroarylC$_{1-6}$alkylamino can be unsubstituted or substituted with 1, 2, or 3 Z$^1$.

44. The compound according to any one of statements 1 to 43, wherein R$^3$ is selected from the group consisting of C$_{6-12}$aryl, hydrogen, C$_{1-6}$alkyl, C$_{3-12}$cycloalkyl, heterocyclyl, heteroaryl, C$_{6-12}$arylC$_{1-6}$alkyl, C$_{6-12}$arylC$_{1-6}$alkylC$_{6-12}$aryl, halo, hydroxyl, C$_{1-6}$alkyloxy, C$_{6-12}$aryloxy, C$_{3-12}$cycloalkyloxy, C$_{6-12}$arylC$_{1-6}$alkyloxy, heterocyclyloxy, heteroaryloxy, hcerocyclylC$_{1-6}$alkyloxy, heteroarylC$_{1-6}$alkyloxy, cyanoC$_{1-6}$alkyloxy, thiol, C$_{1-6}$alkylthio, haloC$_{1-6}$alkyl, haloC$_{1-6}$alkyloxy, amino, C$_{1-6}$alkylamino, C$_{6-12}$arylamino, C$_{3-8}$cycloalkylamino, C$_{6-12}$arylC$_{1-6}$alkylamino, diC$_{1-6}$alkylamino, diC$_{6-12}$arylamino, di-C$_{3-8}$cycloalkylamino, di-C$_{6-12}$arylC$_{1-6}$alkylamino, and cyano; and wherein said C$_{6-12}$aryl, C$_{1-6}$alkyl, C$_{3-12}$cycloalkyl, heterocyclyl, heteroaryl, C$_{6-12}$arylC$_{1-6}$alkyl, C$_{6-12}$arylC$_{1-6}$alkylC$_{6-12}$aryl, C$_{1-6}$alkyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, C$_{1-6}$alkylthio, haloC$_{1-6}$alkyl, haloC$_{1-6}$alkyloxy, C$_{1-6}$alkylamino, C$_{6-12}$arylamino, C$_{3-8}$cycloalkylamino, C$_{6-12}$arylC$_{1-6}$alkylamino, di-C$_{1-6}$alkylamino, di-C$_{6-12}$arylamino, di-C$_{3-8}$cycloalkylamino, or di-C$_{6-12}$arylC$_{1-6}$alkylamino can be unsubstituted or substituted with 1, 2, or 3 Z$^1$.

45. The compound according to any one of statements 1 to 44, wherein R$^3$ is selected from the group consisting of C$_{6-12}$aryl, hydrogen, C$_{1-6}$alkyl, C$_{3-12}$cycloalkyl, heterocyclyl, heteroaryl, halo, hydroxyl, C$_{1-6}$alkyloxy, thiol, C$_{1-6}$alkylthio, haloC$_{1-6}$alkyl, haloC$_{1-6}$alkyloxy, amino, C$_{1-6}$alkylamino, C$_{6-12}$arylamino, C$_{3-8}$cycloalkylamino, di-C$_{1-6}$alkylamino, di-C$_{6-12}$arylamino, di-C$_{3-8}$cycloalkylamino, and cyano; and wherein said C$_{6-12}$aryl, C$_{1-6}$alkyl, C$_{3-12}$cycloalkyl, heterocyclyl, heteroaryl, C$_{1-6}$alkyloxy, C$_{1-6}$alkylthio, haloC$_{1-6}$alkyl, haloC$_{1-6}$alkyloxy, C$_{1-6}$alkylamino, C$_{6-12}$arylamino, C$_{3-8}$cycloalkylamino, di-C$_{1-6}$alkylamino, di-C$_{6-12}$arylamino, or di-C$_{3-8}$cycloalkylamino can be unsubstituted or substituted with 1, 2, or 3 Z$^1$.

46. The compound according to any one of statements 1 to 45, wherein R$^3$ is selected from the group consisting of C$_{6-12}$aryl, hydrogen, C$_{1-6}$alkyl, C$_{3-12}$cycloalkyl, heterocyclyl, heteroaryl, halo, hydroxyl, C$_{1-6}$alkyloxy, thiol, C$_{1-6}$alkylthio, haloC$_{1-6}$alkyl, haloC$_{1-6}$alkyloxy, and cyano; and wherein said C$_{6-12}$aryl, C$_{1-6}$alkyl, C$_{3-12}$cycloalkyl, heterocyclyl, heteroaryl, C$_{1-6}$alkyloxy, C$_{1-6}$alkylthio, haloC$_{1-6}$alkyl, or haloC$_{1-6}$alkyloxy can be unsubstituted or substituted with 1, 2, or 3 Z$^1$.

47. The compound according to any one of statements 1 to 46, wherein R$^3$ is selected from the group consisting of C$_{6-12}$aryl, hydrogen, C$_{1-6}$alkyl, C$_{3-12}$cycloalkyl, heterocyclyl, heteroaryl, halo, hydroxyl, C$_{1-6}$alkyloxy, haloC$_{1-6}$alkyl, and cyano; and wherein said C$_{6-12}$aryl, C$_{1-6}$alkyl, C$_{3-12}$cycloalkyl, heterocyclyl, heteroaryl, C$_{1-6}$alkyloxy, or haloC$_{1-6}$alkyl, can be unsubstituted or substituted 1, 2, or 3 Z$^1$.

48. The compound according to any one of statements 1 to 47, having structural formula (IE)

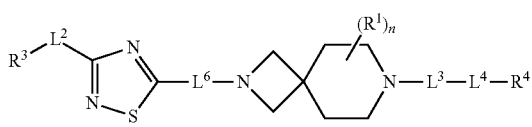

(IE)

wherein, n, L$^1$, L$^3$, L$^4$, R$^1$, R$^3$, R$^4$, and L$^6$, have the same meaning as defined in any one of statements 1 to 47.

49. The compound according to any one of statements 1 to 48, having structural formula (IF)

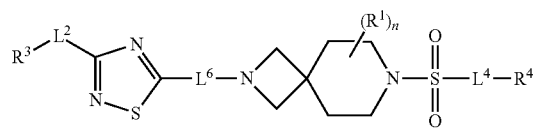

(IF)

wherein, n, L$^1$, L$^4$, R$^1$, R$^3$, R$^4$, and L$^6$, have the same meaning as defined in any one of statements 1 to 48.

50. The compound according to any one of statements 1 to 49, wherein q is an integer selected from 0, 1, or 2.

51. The compound according to any one of statements 1 to 5, wherein q integer selected from 0, or 1.

52. The compound according to any one of statements 1 to 51, wherein q is 0.

53. The compound according to any one of statements 1 to 52, wherein each R$^2$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, heterocyclyl, heteroaryl, hydroxyl, C$_{1-6}$alkyloxy, C$_{6-12}$aryloxy, heterocyclyloxy, heteroaryloxy, cyanoC$_{1-6}$alkyloxy, thiol, C$_{1-6}$alkylthio, cyano, amino, C$_{1-6}$alkylamino, C$_{6-12}$arylamino, C$_{3-8}$cycloalkylamino, di-C$_{1-6}$alkylamino, di-C$_{6-12}$arylamino, di-C$_{3-8}$cycloalkylamino, —CO$_2$H, —CO$_2$C$_{1-6}$alkyl, —CO$_2$C$_{6-12}$aryl, —CO$_2$C$_{3-8}$cycloalkyl, —C(O)NH$_2$, —C(O)NHC$_{1-6}$alkyl, —C(O)NHC$_{6-12}$aryl, —C(O)NHC$_{3-8}$cycloalkyl, —COH, —C(O)C$_{1-6}$alkyl, —C(O)C$_{6-12}$aryl, —C(O)C$_{3-8}$cycloalkyl, —S(O)$_2$OH, —S(O)$_2$C$_{1-6}$alkyl, —S(O)$_2$C$_{6-12}$aryl, —S(O)$_2$C$_{3-8}$cycloalkyl, —S(O)$_2$NH$_2$, —S(O)$_2$NHC$_{1-6}$alkyl, —S(O)$_2$NHC$_{6-12}$aryl, —S(O)$_2$NHC$_{3-8}$cycloalkyl, nitro, —NHC(O)H, —NHC(O)C$_{1-6}$alkyl, —NHC(O)C$_{6-12}$aryl, —NHC(O)C$_{3-8}$cycloalkyl, —N(C$_{1-6}$alkyl)C(O)H, —N(C$_{1-6}$alkyl)C(O)C$_{1-6}$alkyl, —N(C$_{1-6}$alkyl)C(O)C$_{6-12}$aryl, —N(C$_{1-6}$alkyl)C(O)C$_{3-8}$cycloalkyl, —NHS(O)$_2$H, —NHS(O)$_2$OH, —NHS(O)$_2$C$_{1-6}$alkyl, —NHS(O$_2$C$_{6-12}$aryl, —NHS(O)$_2$C$_{3-8}$cycloalkyl, —NC$_{1-6}$alkylS(O)$_2$H, —NC$_{1-6}$alkylS(O)$_2$OH, —NC$_{1-6}$alkylS(O)$_2$C$_{1-6}$alkyl, —NC$_{1-6}$alkylS(O)$_2$C$_{6-12}$aryl, and —NC$_{1-6}$alkylS(O)$_2$C$_{3-8}$cycloalkyl; and wherein at least one carbon atom or heteroatom of said C$_{1-6}$alkyl, C$_{6-12}$aryl, C$_{3-12}$cycloalkyl, heterocyclyl, heteroaryl can be oxidized to form at least one C=O, or N=O.

54. The compound according to any one of statements 1 to 53, wherein each R$^2$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, heterocyclyl, heteroaryl, hydroxyl, C$_{1-6}$alkyloxy, C$_{6-12}$aryloxy, cyanoC$_{1-6}$alkyloxy, thiol, C$_{1-6}$alkylthio, cyano, amino, C$_{1-6}$alkylamino, C$_{6-12}$arylamino, di-C$_{1-6}$alkylamino, di-C$_{6-12}$arylamino, —CO$_2$H, —CO$_2$C$_{1-6}$alkyl, —CO$_2$C$_{6-12}$aryl, —C(O)NH$_2$, —C(O)NHC$_{1-6}$alkyl, —C(O)NHC$_{6-12}$aryl, —COH, —C(O)C$_{1-6}$alkyl, —C(O)C$_{6-12}$aryl, —S(O)$_2$OH, —S(O)$_2$C$_{1-6}$alkyl, —S(O)$_2$C$_{6-12}$aryl, —S(O)$_2$NH$_2$, —S(O)$_2$NHC$_{1-6}$alkyl, —S(O)$_2$NHC$_{6-12}$aryl, nitro, —NHC(O)H, —NHC(O)C$_{1-6}$alkyl, —NHC(O)C$_{6-12}$aryl, —NHS(O)$_2$C$_{1-6}$alkyl, —NHS(O)$_2$C$_{6-12}$aryl, —NC$_{1-6}$alkylS(O)$_2$H, —NC$_{1-6}$alkylS(O)$_2$OH, —NC$_{1-6}$alkylS(O)$_2$C$_{1-6}$alkyl, and —NC$_{1-6}$alkylS(O)$_2$C$_{6-12}$aryl; and wherein at least one carbon atom or het-

33 eroatom of said $C_{1-6}$alkyl, $C_{6-12}$aryl, $C_{3-12}$cycloalkyl, heterocyclyl, heteroaryl can be oxidized to form at least one C=O, or N=O.

55. The compound according to any one of statements 1 to 54, wherein each $R^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, heterocyclyl, heteroaryl, hydroxyl, $C_{1-6}$alkyloxy, cyano $C_{1-6}$alkyloxy, thiol, $C_{1-6}$alkylthio, cyano, amino, $C_{1-6}$alkylamino, di-$C_{1-6}$alkylamino, —$CO_2H$, —$CO_2$ $C_{1-6}$alkyl, —C(O)$NH_2$, —C(O)NH$C_{1-6}$alkyl, —COH, —C(O)$C_{1-6}$alkyl, —NHC(O)H, —NHC(O)$C_{1-6}$alkyl, —N($C_{1-6}$alkyl)C(O)H, and —N($C_{1-6}$alkyl)C(O)$C_{1-6}$alkyl; and wherein at least one carbon atom of said $C_{1-6}$alkyl, $C_{6-12}$aryl, $C_{3-12}$cycloalkyl, heterocyclyl, heteroaryl can be oxidized to form at least one C=O.

56. The compound according to any one of statements 1 to 55, wherein each $R^2$ is independently selected from the group consisting of halo, hydrogen, $C_{1-6}$alkyl, halo$C_{1-6}$alkyl, halo$C_{1-6}$alkyloxy, $C_{6-12}$aryl, heterocyclyl, heteroaryl, hydroxyl, $C_{1-6}$alkyloxy, cyano$C_{1-6}$alkyloxy, thiol, $C_{1-6}$alkylthio, cyano, amino, $C_{1-6}$alkylamino, di-$C_{1-6}$alkylamino, —C(O)$C_{1-6}$alkyl, —NHC(O)$C_{1-6}$alkyl, and —N($C_{1-6}$alkyl)C(O)$C_{1-6}$alkyl; and wherein at least one carbon atom of said $C_{1-6}$alkyl, $C_{6-12}$aryl, heterocyclyl, heteroaryl can be oxidized to form at least one C=O.

57. The compound according to any one of statements 1 to 56, wherein each $R^2$ is independently selected from the group consisting of halo, hydrogen, $C_{1-6}$alkyl, halo$C_{1-6}$alkyl, halo$C_{1-6}$alkyloxy, $C_{6-12}$aryl, heterocyclyl, heteroaryl, hydroxyl, $C_{1-6}$alkyloxy, thiol, $C_{1-6}$alkylthio, cyano, amino, $C_{1-6}$alkylamino, and di-$C_{1-6}$alkylamino; and wherein at least one carbon atom of said $C_{1-6}$alkyl, $C_{6-12}$aryl, heterocyclyl, heteroaryl can be oxidized to form at least one C=O.

58. The compound according to any one of statements 1 to 57, wherein two $R^2$ together with the atom to which they are attached form a 5-, or 6-membered ring; and wherein at least one carbon atom of said ring can be oxidized to form at least one C=O.

59. The compound according to any one of statements 1 to 58, wherein $L^1$ is —$SO_2$—.

60. The compound according to any one of statements 1 to 58, wherein $L^1$ is CO.

61. The compound according to any one of statements 1 to 58 wherein $L^1$ is

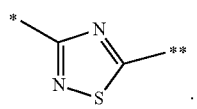

62. The compound according to any one of statements 1 to 58, wherein $L^1$ is

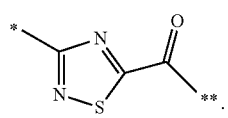

63. The compound according to any one of statements 1 to 62, wherein $L^1$ is

34

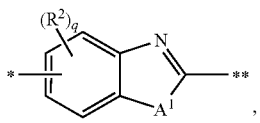

preferably wherein $A^1$ is S, preferably wherein q is 0.

64. The compound according to any one of statements 1 to 63, wherein $L^2$ is a single bond.

65. The compound according to any one of statements 1 to 64, wherein $L^2$ is

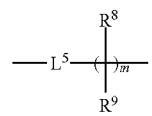

66. The compound according to any one of statements 1 to 65, wherein $L^2$ is $L^5$ and is selected from the group consisting of —O—, and —$NR^{12}$—.

67. The compound according to any one of statements 1 to 66, wherein $L^2$ is

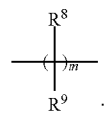

68. The compound according to any one of statements 1 to 67, wherein $L^3$ is —$SO_2$—.

69. The compound according to any one of statements 1 to 68, wherein $L^4$ is a single bond or is selected from the group consisting of —(C$R^{15}R^{16}$)$_t$—, —O—, —NH—, and —N($C_{1-6}$alkyl)-.

70. The compound according to any one of statements 1 to 69, wherein $L^4$ is a single bond.

71. The compound according to any one of statements 1 to 70, wherein $L^4$ is —(C$R^{15}R^{16}$)$_t$—, preferably wherein t is an integer selected from 1, or 2, for example 1.

72. The compound according to any one of statements 1 to 71, wherein $R^{15}$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo $C_{1-6}$alkyloxy.

73. The compound according to any one of statements 1 to 72, wherein $R^{15}$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.

74. The compound according to any one of statements 1 to 73, wherein $R^{15}$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.

75. The compound according to any one of statements 1 to 74, wherein $R^{15}$ is selected from the group consisting of hydrogen, $C_{1-6}$alkyl, halo, hydroxyl, $C_{1-6}$alkyloxy, thiol, $C_{1-6}$alkythio, haloC$_{1-6}$alkyl, and haloC$_{1-6}$alkyloxy.

76. The compound according to any one of statements 1 to 75, wherein $R^{15}$ is selected from the group consisting of hydrogen, $C_{1-6}$alkyl, halo, haloC$_{1-6}$alkyl, and haloC$_{1-6}$alkyloxy.

77. The compound according to any one of statements 1 to 76, wherein $R^{16}$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, haloC$_{1-6}$alkyl, and halo C$_{1-6}$alkyloxy.

78. The compound according to any one of statements 1 to 77, wherein $R^{16}$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, haloC$_{1-6}$alkyl, and haloC$_{1-6}$alkyloxy.

79. The compound according to any one of statements 1 to 78, wherein $R^{16}$ is selected from the group consisting of hydrogen, $C_{1-6}$alkyl, halo, hydroxyl, $C_{1-6}$alkyloxy, thiol, $C_{1-6}$alkylthio, haloC$_{1-6}$alkyl, and haloC$_{1-6}$alkyloxy.

80. The compound according to any one of statements 1 to 79, wherein $R^{16}$ is selected from the group consisting of hydrogen, $C_{1-6}$alkyl, halo, haloC$_{1-6}$alkyl, and haloC$_{1-6}$alkyloxy.

81. The compound according to any one of statements 1 to 80, wherein $R^{15}$ and $R^{16}$ together with the carbon atom to which they are attached form $C_{3-6}$cycloalkyl or $C_{5-6}$cycloalkenyl.

82. The compound according to any one of statements 1 to 81, wherein $R^{15}$ and $R^{16}$ together with the carbon atom to which they are attached form a $C_{3-5}$cycloalkyl.

83. The compound according to any one of statements 1 to 82, wherein $R^4$ is selected from the group consisting of $C_{6-12}$aryl, hydrogen, $C_{1-6}$alkyl, $C_{3-12}$cycloalkyl, heterocyclyl, heteroaryl, $C_{6-12}$arylC$_{1-6}$alkyl, $C_{6-12}$arylC$_{1-6}$alkylC$_{6-12}$aryl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkthio, $C_{6-12}$arylC$_{1-6}$alkylthio, heterocyclylthio, heteroarylthio, heterocyclylC$_{1-6}$alkylthio, heteroaylC$_{1-6}$alkylthio, cyanoC$_{1-6}$alkylthio, haloC$_{1-6}$alkyl, haloC$_{1-6}$alkyloxy, amino, $C_{1-6}$alkylamino, $C_{2-6}$alkenylamino, $C_{2-6}$alkynylamino, $C_{6-12}$arylamino, $C_{3-8}$cycloalkylamino, $C_{6-12}$arylC$_{1-6}$alkylamino, heterocyclylamino, heteroarylamino, heterocyclylC$_{1-6}$alkylamino, heteroarylC$_{1-6}$alkylamino, di-C$_{1-6}$alkylamino, di-C$_{2-6}$alkenylamino, di-C$_{2-6}$alkynylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, di-heteroaryl C$_{1-6}$alkylamino, and cyano; and wherein said $C_{6-12}$aryl, $C_{1-6}$alkyl, $C_{3-12}$cycloalkyl, heterocyclyl, heteroaryl, $C_{6-12}$arylC$_{1-6}$alkyl, $C_{6-12}$arylC$_{1-6}$alkylC$_{6-12}$aryl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$arylC$_{1-6}$alkyloxy, heterocyclyloxy, heteroaryloxy, heterocyclylC$_{1-6}$alkyloxy, heteroarylC$_{1-6}$ alkyloxy, cyanoC$_{1-6}$alkyloxy, $C_{1-6}$alkylthio, $C_{2-6}$alkenylthio, $C_{2-6}$alkynylthio, $C_{6-12}$arylthio, $C_{3-8}$cycloalkylthio, $C_{6-12}$arylC$_{1-6}$alkylthio, heterocyclylthio, heteroarylthio, heterocyclylC$_{1-6}$alkylthio, heteroaryl $C_{1-6}$alkylthio, cyanoC$_{1-6}$alkylthio, haloC$_{1-6}$alkyl, halo $C_{1-6}$alkyloxy, $C_{1-6}$alkylamino, $C_{2-6}$alkenylamino, $C_{2-6}$alkynylamino, $C_{6-12}$arylamino, $C_{3-8}$cycloalkylamino, $C_{6-12}$arylC$_{1-6}$alkylamino, heterocyclylamino, heteroarylamino, heterocyclylC$_{1-6}$alkylamino, heteroarylC$_{1-6}$alkylamino, di-C$_{1-6}$alkylamino, di-C$_{2-6}$alkenylamino, di-C$_{2-6}$alkynylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, or di-heteroarylC$_{1-6}$alkylamino can be unsubstituted or substituted with 1, 2, or 3 $Z^2$.

84. The compound according to any one of statements 1 to 83, wherein $R^4$ is selected from the group consisting of $C_{6-12}$aryl, hydrogen, $C_{1-6}$alkyl, $C_{3-12}$cycloalkyl, heterocyclyl, heteroaryl, $C_{6-12}$arylC$_{1-6}$alkyl, $C_{6-12}$arylC$_{1-6}$ alkylC$_{6-12}$ aryl, halo, hydroxyl, $C_{1-6}$alkyloxy, $C_{6-12}$aryloxy, $C_{3-12}$cycloalkyloxy, $C_{6-12}$arylC$_{1-6}$alkyloxy, heterocyclyloxy, heteroaryloxy, heterocyclyl$_{1-6}$alkyloxy, heteroarylC$_{1-6}$alkyloxy, cyanoC$_{1-6}$alkyloxy, thiol, $C_{1-6}$alkylthio, haloC$_{1-6}$alkyl, haloC$_{1-6}$alkyloxy, amino, $C_{1-6}$alkylamino, $C_{6-12}$arylamino, $C_{3-8}$cycloalkylamino, $C_{6-12}$arylC$_{1-6}$alkylamino, di-C$_{1-6}$akylamino, di-C$_{6-12}$arylamino, di-C$_{3-8}$cycloalkylamino, di-C$_{6-12}$arylC$_{1-6}$alkylamino, and cyano; and wherein said $C_{6-12}$aryl, $C_{1-6}$alkyl, $C_{3-12}$cycloalkyl, heterocyclyl, heteroaryl, $C_{6-12}$arylC$_{1-6}$alkyl, $C_{6-12}$arylC$_{1-6}$alkylC$_{6-12}$aryl, $C_{1-6}$alkyloxy, $C_{6-12}$aryloxy, $C_{3-12}$cycloalkyloxy, $C_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, $C_{1-6}$alkylthio, haloC$_{1-6}$alkyl, haloC$_{1-6}$alkyloxy, $C_{1-6}$alkylamino, $C_{6-12}$arylamino, $C_{3-8}$cycloalkylamino, $C_{6-12}$arylC$_{1-6}$alkylamino, di-C$_{1-6}$alkylamino, di-C$_{6-12}$arylamino, di-C$_{3-8}$cycloalkylamino, or di-C$_{6-12}$arylC$_{1-6}$alkylamino can be unsubstituted or substituted with 1, 2, or 3 $Z^2$.

85. The compound according to any one of statements 1 to 84, wherein $R^4$ is selected from the group consisting of $C_{6-12}$aryl, hydrogen, $C_{1-6}$alkyl, $C_{3-12}$cycloalkyl, heterocyclyl, heteroaryl halo, hydroxyl, $C_{1-6}$alkyloxy, thiol, $C_{1-6}$alkylthio, haloC$_{1-6}$alkyl, haloC$_{1-6}$alkyloxy, amino, $C_{1-6}$alkylamino, $C_{6-12}$arylamino, $C_{3-8}$cycloalkylamino, di-C$_{1-6}$alkylamino, di-C$_{6-12}$arylamino, di-C$_{3-8}$cycloalkylamino, and cyano; and wherein said $C_{6-12}$aryl, $C_{1-6}$alkyl, $C_{3-12}$cycloalkyl, heterocyclyl, heteroaryl, $C_{1-6}$alkyloxy, $C_{1-6}$alkylthio, haloC$_{1-6}$alkyl, haloC$_{1-6}$alkyloxy, $C_{1-6}$alkylamino, $C_{6-12}$arylamino, $C_{3-8}$cycloalkylamino, di-C$_{1-6}$alkylamino, di-C$_{6-12}$arylamino, or di-C$_{3-8}$cycloalkylamino can be unsubstituted or substituted with 1, 2, or 3 $Z^2$.

86. The compound according to any one of statements 1 to 85, wherein $R^4$ is selected from the group consisting of $C_{6-12}$aryl, hydrogen, $C_{1-6}$alkyl, $C_{3-12}$cycloalkyl, heterocyclyl, heteroaryl, halo, hydroxyl, $C_{1-6}$alkyloxy, thiol, $C_{1-6}$alkylthio, haloC$_{1-6}$alkyl, haloC$_{1-6}$alkyloxy, and cyano; and wherein said $C_{6-12}$aryl, $C_{1-6}$alkyl, $C_{3-12}$cycloalkyl, heterocyclyl, heteroaryl, $C_{1-6}$alkyloxy, $C_{1-6}$alkylthio, haloC$_{1-6}$alkyl, or haloC$_{1-6}$alkyloxy can be unsubstituted or substituted with 1, 2, or 3 $Z^2$.

87. The compound according to any one of statements 1 to 86, wherein $R^4$ is selected from the group consisting of $C_{6-12}$aryl, hydrogen, $C_{1-6}$alkyl, $C_{3-12}$cycloalkyl, heterocyclyl, heteroaryl, halo, hydroxyl, $C_{1-6}$alkyloxy, haloC$_{1-6}$ alkyl, and cyano; and wherein said $C_{6-12}$aryl, $C_{1-6}$alkyl, $C_{3-12}$cycloalkyl, heterocyclyl, heteroaryl, $C_{1-6}$alkyloxy, or halo$C_{1-6}$alkyl, can be unsubstituted or substituted 1, 2, or 3 $Z^2$.

88. The compound according to any one of statements 1 to 87, wherein n is an integer selected from 0 or 1.

89. The compound according to any one of statements 1 to 88, wherein $R^1$ is selected from the group consisting of $C_{1-6}$alkyl, and halo.

90. The compound according to any one of statements 1 to 89, wherein $R^1$ is $C_{1-6}$alkyl.

91. The compound according to any one of statements 1 to 90, wherein n is 0.

92. The compound according to any one of statements 1 to 91, wherein each $R^{18}$ independently selected from $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl, can be oxidized to form at least one C=O, or S(O)$_2$.

93. The compound according to any one of statements 1 to 92, wherein each $R^{18}$ is independently selected from $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl, can be oxidized to form at least one C=O.

94. The compound according to any one of statements 1 to 93, wherein each $R^{18}$ is independently selected from $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl, can be oxidized to form at least one C=O;

95. The compound according to any one of statements 1 to 94, wherein each $R^{18}$ is independently selected from $C_{1-6}$alkyl, $C_{6-12}$aryl, $C_{3-8}$cycloalkyl, heterocyclyl, heteroaryl, and cyano$C_{1-6}$alkyl; and wherein at least one carbon atom of said $C_{1-6}$alkyl, $C_{6-12}$aryl, $C_{3-8}$cycloalkyl, heterocyclyl, heteroaryl, or cyano$C_{1-6}$alkyl, can be oxidized to form at least one C=O.

96. The compound according to any one of statements 1 to 95, wherein each $R^{18}$ is independently selected from $C_{1-6}$alkyl, heterocyclyl, heteroaryl, and cyano$C_{1-6}$alkyl; and wherein at least one carbon atom of said $C_{1-6}$alkyl, $C_{3-8}$cycloalkyl, heterocyclyl, heteroaryl, or cyano$C_{1-6}$alkyl can be oxidized to form at least one C=O.

97. The compound according to any one of statements 1 to 96, wherein each $R^{18}$ is independently selected from $C_{1-6}$alkyl, heterocyclyl, heteroaryl, and cyano$C_{1-6}$alkyl.

98. The compound according to any one of statements 1 to 97, wherein $R^{18}$ is independently selected from hydrogen, $C_{1-6}$alkyl, $C_{2-4}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl, can be oxidized to form at least one C=O, or S(O)$_2$.

99. The compound according to any one of statements 1 to 98, wherein $R^{19}$ is independently selected from hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$ alkyl, or cyano$C_{1-6}$alkyl can be oxidized to form at least one C=O.

100. The compound according to any one of statements 1 to 99, wherein $R^{19}$ is independently selected from hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$ alkyl, and cyano$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O.

101. The compound according to any one of statements 1 to 100, wherein $R^{19}$ is independently selected from hydrogen, $C_{1-6}$alkyl, $C_{6-12}$aryl, $C_{3-8}$cycloalkyl, heterocyclyl, heteroaryl, and cyano$C_{1-6}$alkyl; and wherein at least one carbon atom of said $C_{1-6}$alkyl, $C_{6-12}$aryl, $C_{3-8}$cycloalkyl, heterocyclyl, heteroaryl, or cyano$C_{1-6}$alkyl can be oxidized to form at least one C=O.

102. The compound according to any one of statements 1 to 101, wherein $R^{19}$ is independently selected from hydrogen, $C_{1-6}$alkyl, heterocyclyl, heteroaryl, and cyano$C_{1-6}$alkyl; and wherein at least one carbon atom of said $C_{1-6}$alkyl, $C_{3-8}$cycloalkyl, heterocyclyl, heteroaryl, or cyano$C_{1-6}$alkyl can be oxidized to form at least one C=O.

103. The compound according to any one of statements 1 to 102, wherein $R^{19}$ is independently selected from hydrogen, $C_{1-6}$alkyl, heterocyclyl, heteroaryl, and cyano$C_{1-6}$ alkyl.

104. The compound according to any one of statements 1 to 103, wherein each $R^{20}$ is independently selected from hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, or S(O)$_2$.

105. The compound according to any one of statements 1 to 104, wherein each $R^{20}$ is independently selected from hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O.

106. The compound according to any one of statements 1 to 105, wherein each $R^{20}$ is independently selected from hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, or heterocyclyl$C_{1-6}$alkyl, heteroaryl$C_{1-6}$alkyl can be oxidized to form at least one C=O.

107. The compound according to any one of statements 1 to 106, wherein each $R^{20}$ is independently selected from hydrogen, $C_{1-6}$alkyl, $C_{6-12}$aryl, $C_{3-8}$cycloalkyl, heterocyclyl, and heteroaryl; and wherein at least one carbon atom of said $C_{1-6}$alkyl, $C_{6-12}$aryl, $C_{3-8}$cycloalkyl, heterocyclyl, or heteroaryl can be oxidized to form at least one C=O.

108. The compound according to any one of statements 1 to 107, wherein each $R^{20}$ is independently selected from hydrogen, $C_{1-6}$alkyl, heterocyclyl, and heteroaryl; and wherein at least one carbon atom of said $C_{1-6}$alkyl, $C_{3-8}$cycloalkyl, heterocyclyl, or heteroaryl can be oxidized to form at least one C=O.

109. The compound according to any one of statements 1 to 108, wherein each $R^{20}$ is independently selected from hydrogen, $C_{1-6}$alkyl, heterocyclyl, heteroaryl, and cyano$C_{1-6}$alkyl.

110. The compound according to any one of statements 1 to 119, wherein each $R^{21}$ is independently selected from hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl heteroaryl, heterocyclyl$C_{1-6}$alkyl, or heteroaryl$C_{1-6}$alkyl can be oxidized to form at least one C=O, or $S(O)_2$.

111. The compound according to any one of statements 1 to 110, wherein each $R^{21}$ is independently selected from hydrogen, $C_{1-6}$alkyl, $C_{2-6}$alkenyl, $C_{2-6}$alkynyl, $C_{6-12}$aryl, $C_{3-8}$cycloallkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O.

112. The compound according to any one of statements 1 to 111, wherein each $R^{21}$ is independently selected from hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, or heterocyclyl$C_{1-6}$alkyl, heteroaryl$C_{1-6}$alkyl can be oxidized to form at least one C=O.

113. The compound according to any one of statements 1 to 112, wherein each $R^{21}$ is independently selected from hydrogen, $C_{1-6}$alkyl, $C_{6-12}$aryl, $C_{3-8}$cycloalkyl, heterocyclyl, and heteroaryl; and wherein at least one carbon atom of said $C_{1-6}$alkyl, $C_{6-12}$aryl, $C_{3-8}$cycloalkyl, heterocyclyl, or heteroaryl can be oxidized to form at least one C=O.

114. The compound according to any one of statements 1 to 113, wherein each $R^{21}$ is independently selected from hydrogen, $C_{1-6}$alkyl, heterocyclyl, and heteroaryl; and wherein at least one carbon atom of said $C_{1-6}$alkyl, $C_{3-8}$cycloalkyl, heterocyclyl, or heteroaryl can be oxidized to form at least one C=O.

115. The compound according to any one of statements 1 to 114, wherein each $R^{21}$ is independently selected from hydrogen, $C_{1-6}$alkyl, heterocyclyl, heteroaryl, and cyano$C_{1-6}$alkyl.

116. The compound according to any one of statements 1 to 115, wherein $R^{20}$ and $R^{21}$ together with the nitrogen atom to which they are attached form a 5-, or 6-membered heterocyclyl; and wherein at least one carbon atom or heteroatom of said heterocyclyl can be oxidized to form at least one C=O, or N=O.

117. The compound according to any one of statements 1 to 116, wherein $R^{20}$ and $R^{21}$ together with the nitrogen atom to which they are attached form a 5-membered heterocyclyl; and wherein at least one carbon atom of said heterocyclyl can be oxidized to form at least one C=O.

118. The compound according to any one of statements 1 to 117, wherein each R is independently selected from hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, or $S(O)_2$.

119. The compound according to any one of statements 1 to 118, wherein each $R^{22}$ is independently selected from hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O.

120. The compound according to any one of statements 1 to 119, wherein each $R^{22}$ is independently selected from hydrogen, hydroxyl, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, or heterocyclyl$C_{1-6}$alkyl, heteroaryl$C_{1-6}$alkyl can be oxidized to form at least one C=O.

121. The compound according to any one of statements 1 to 120, wherein each $R^{22}$ is independently selected from hydrogen, hydroxyl, $C_{1-6}$alkyl, $C_{6-12}$aryl, $C_{3-8}$cycloalkyl, heterocyclyl, and heteroaryl; and wherein at least one carbon atom of said $C_{1-6}$alkyl, $C_{6-12}$aryl, $C_{3-8}$cycloalkyl, heterocyclyl, or heteroaryl can be oxidized to form at least one C=O.

122. The compound according to any one of statements 1 to 121, wherein each $R^{22}$ is independently selected from hydrogen, hydroxyl, $C_{1-6}$alkyl, heterocyclyl, and heteroaryl; and wherein at least one carbon atom of said $C_{1-6}$alkyl, $C_{3-8}$cycloalkyl, heterocyclyl, or heteroaryl can be oxidized to form at least one C=O.

123. The compound according to any one of statements 1 to 122, wherein each $R^{22}$ is independently selected from hydrogen, hydroxyl, $C_{1-6}$alkyl, heterocyclyl, and heteroaryl.

124. The compound according to any one of statements 1 to 123, wherein each $R^{23}$ is independently selected from hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, or $S(O)_2$.

125. The compound according to any one of statements 1 to 124, wherein each $R^{23}$ is independently selected from hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O.

126. The compound according to any one of statements 1 to 125, wherein each $R^{23}$ is independently selected from hydrogen, $C_{1-6}$alkyl, $C_{6-12}$aryl, $C_{3-8}$cycloalkyl, $C_{6-12}$aryl$C_{1-6}$ alkyl, heterocyclyl, heteroaryl, heterocyclyl$C_{1-6}$, and heteroaryl$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, or heterocyclyl$C_{1-6}$alkyl, heteroaryl$C_{1-6}$alkyl can be oxidized to form at least one C=O.

127. The compound according to any one of statements 1 to 126, wherein each $R^{23}$ is independently selected from hydrogen, $C_{1-6}$alkyl, $C_{6-12}$aryl, $C_{3-8}$cycloalkyl, heterocyclyl, and heteroaryl; and wherein at least one carbon atom of said $C_{1-6}$alkyl, $C_{6-12}$aryl, $C_{3-8}$cycloalkyl, heterocyclyl, or heteroaryl can be oxidized to form at least one C=O.

128. The compound according to any one of statements 1 to 127, wherein each $R^{23}$ is independently selected from hydrogen, $C_{1-6}$alkyl, heterocyclyl, and heteroaryl, and wherein at least one carbon atom of said $C_{1-6}$alkyl, $C_{3-8}$cycloalkyl, heterocyclyl, or heteroaryl can be oxidized to form at least one C=O.

129. The compound according to any one of statements 1 to 128, wherein each $R^{23}$ is independently selected from hydrogen, $C_{1-6}$alkyl, heterocyclyl, heteroaryl, and cyano$C_{1-6}$alkyl.

130. The compound according to any one of statements 1 to 129, wherein each $R^{24}$ is independently selected from $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, and heteroarylene$C_{1-6}$alkylene; and wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, or S(O)$_2$.

131. The compound according to any one of statements 1 to 130, wherein $R^{24}$ is independently selected from $C_{1-6}$alkylene, $C_{6-12}$arylene, and $C_{3-8}$cycloalkylene; and wherein at least one carbon atom of said $C_{1-6}$alkylene, $C_{6-12}$arylene, $C_{3-8}$cycloalkylene, can be oxidized to form at least one C=O.

132. The compound according to any one of statements 1 to 131, wherein each $R^{24}$ is independently selected from $C_{1-6}$alkylene, and $C_{3-8}$cycloalkylene; and wherein at least one carbon atom of said $C_{1-6}$alkylene, $C_{3-8}$cycloalkylene can be oxidized to form at least one C=O.

133. The compound according to any one of statements 1 to 132, wherein each $R^{24}$ is independently selected from $C_{1-6}$alkylene, and $C_{3-8}$cycloalkylene; and wherein at least one carbon atom of said $C_{1-6}$alkylene, $C_{3-8}$cycloalkylene can be oxidized to form at least one C=O.

134. The compound according to any one of statements 1 to 133, wherein each $R^{24}$ is $C_{1-6}$alkylene.

135. The compound according to any one of statements 1 to 134, wherein each $R^{24}$ is $C_{1-4}$alkylene.

136. The compound according to any one of statements 1 to 135, wherein each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkythio, heterocyclylthio, heteroarylthio, heterocyclyl$C_{1-6}$alkylthio, heteroaryl$C_{6-12}$alkylthio, cyano$C_{1-6}$alkylthio, cyano, amino, $C_{1-6}$alkylamino, $C_{2-6}$alkenylamino, $C_{2-6}$alkynylamino, $C_{6-12}$arylamino, $C_{3-8}$cycloalkylamino, $C_{6-12}$aryl$C_{1-6}$alkylamino, heterocyclylamino, heteroarylamino, heterocyclyl$C_{1-6}$alkylamino, heteroaryl$C_{1-6}$alkylamino, di-$C_{1-6}$alkylamino, di-$C_{2-6}$alkenylamino, di-$C_{2-6}$alkynylamino, di-$C_{6-12}$arylamino, di-$C_{3-8}$cycloalkylamino, di-$C_{6-12}$aryl$C_{1-6}$alkylamino, di-heterocyclylamino, di-heteroarylamino, di-heterocyclyl$C_{1-6}$alkylamino, di-heteroaryl$C_{1-6}$alkylamino, $CO_2H$, $CO_2C_{1-6}$alkyl, $CO_2C_{2-6}$ alkenyl, $CO_2C_{2-6}$alkynyl, $CO_2C_{6-12}$aryl, $CO_2C_{3-8}$cycloalkyl, $CO_2C_{6-12}$aryl$C_{1-6}$alkyl, $CO_2$heterocyclyl, $CO_2$heteroaryl, $CO_2$heterocyclyl$C_{1-6}$alkyl, $CO_2$heteroaryl$C_{1-6}$alkyl, C(O)NH$_2$, C(O)NH$C_{1-6}$alkyl, C(O)NH$C_{2-6}$alkenyl, C(O)NH$C_{2-6}$alkynyl, C(O)NH$C_{6-12}$ aryl, C(O)NH$C_{3-8}$cycloalkyl, C(O)NH($C_{6-12}$aryl$C_{1-6}$ alkyl), C(O)NH-heterocyclyl, C(O)NH-heteroaryl, C(O)NH(heterocyclyl$C_{1-6}$alkyl), C(O)NH(heteroaryl$C_{1-6}$ alkyl), COH, C(O)$C_{1-6}$alkyl, C(O)$C_{2-6}$alkenyl, C(O)$C_{2-6}$ alkynyl, C(O)$C_{6-12}$aryl, C(O)$C_{3-8}$cycloalkyl, C(O)heterocyclyl, C(O)heteroaryl, S(O)OH, S(O)$C_{1-6}$alkyl, S(O) $C_{2-6}$alkynyl, S(O)$C_{2-6}$alkynyl, S(O)$C_{6-12}$aryl, —S(O) $C_{3-8}$cycloalkyl, S(O)heterocyclyl, S(O)heteroaryl, S(O)$_2$ OH, S(O)$_2C_{1-6}$alkyl, S(O)$_2C_{2-6}$alkenyl, S(O)$_2C_{2-6}$alkynyl, S(O)$_2C_{6-12}$aryl, S(O)$_2C_{3-8}$cycloalkyl, S(O)$_2C_{6-12}$aryl$C_{1-6}$alkyl, S(O)$_2$heterocyclyl, S(O)$_2$heteroaryl, S(O)$_2$heterocyclyl$C_{1-6}$alkyl, S(O)$_2$heteroaryl$C_{1-6}$alkyl, S(O)$_2$NH$_2$, S(O)$_2$NH$C_{1-6}$alkyl, S(O)$_2$NH$C_{2-6}$alkenyl, S(O)$_2$NH$C_{2-6}$alkynyl, S(O)$_2$NH$C_{6-12}$aryl, S(O)$_2$NH$C_{3-8}$cycloalkyl, S(O)$_2$NH($C_{6-12}$aryl$C_{1-6}$alkyl), S(O)$_2$NHheterocyclyl, S(O)$_2$NHheteroaryl, S(O)$_2$NH(heterocycyl$C_{1-6}$alkyl), S(O)$_2$NH(heteroaryl$C_{1-6}$alkyl), nitro, NHC(O)H, NHC(O)$C_{1-6}$alkyl, NHC(O)$C_{2-6}$alkenyl, NHC(O)$C_{2-6}$ alkynyl, NHC(O)$C_{6-12}$aryl, NHC(O)$C_{3-8}$cycloalkyl, NHC(O)heterocyclyl, NHC(O)heteroaryl, N($C_{1-6}$alkyl)C(O)H, N($C_{1-6}$alkyl)C(O)$C_{1-6}$alkyl, N($C_{1-6}$alkyl)C(O)$C_{6-12}$aryl, N($C_{1-6}$alkyl)C(O)$C_{3-8}$cycloalkyl, N($C_{1-6}$alkyl)C(O)heterocycyl, N($C_{1-6}$alkyl)C(O)heteroaryl, $C_{1-6}$alkylene-C(O)NH$_2$, $C_{1-6}$alkylene-C(O)NH$C_{1-6}$alkyl, $C_{1-6}$alkyleneC(O)NH$C_{2-6}$alkenyl, $C_{1-6}$alkyeneC(O)NH$C_{2-6}$alkynyl, $C_{1-6}$alkyleneC(O)NH$C_{6-12}$aryl, $C_{1-6}$alkyleneC(O)NH$C_{3-8}$cycloalkyl, $C_{1-6}$alkyleneC(O)NH$C_{6-12}$aryl$C_{1-6}$alkyl, $C_{1-6}$alkyleneC(O)NH-heterocyclyl, $C_{1-6}$alkyleneC(O)NH-heteroaryl, $C_{1-6}$alkyleneC(O)NH-heterocyclyl$C_{1-6}$alkyl, $C_{1-6}$alkylene-C(O)NH-heteroaryl$C_{1-6}$alkyl, NHS (O)$_2$H, NHS(O)$_2$OH, —NHS(O)$_2C_{1-6}$alkyl, —NHS (O)$_2C_{2-6}$alkenyl, NHS(O)$_2C_{2-6}$alkynyl, NHS(O)$_2C_{6-12}$ aryl, NHS(O)$_2C_{3-8}$cycloalkyl, NHS(O)$_2C_{6-12}$aryl$C_{1-6}$alkyl, NHS(O)$_2$heterocyclyl, NHS(O)$_2$heteroaryl, NHS (O)$_2$heterocyclyl$C_{1-6}$alkyl, NHS(O)$_2$heteroaryl$C_{1-6}$alkyl, N$C_{1-6}$alkylS(O)$_2$H, N$C_{1-6}$alkylS(O)$_2$OH, N$C_{1-6}$alkyl S(O)$_2C_{1-6}$alkyl, N$C_{1-6}$alkylS(O)$_2C_{2-6}$alkenyl, N$C_{1-6}$ alkylS(O)$_2C_{1-6}$alkynyl, N$C_{1-6}$alkylS(O)$_2C_{6-12}$aryl, N$C_{1-6}$ alkylS(O)$_2C_{3-8}$cycloalkyl, N$C_{1-6}$alkylS(O)$_2C_{6-12}$aryl$C_{1-6}$ alkyl, N$C_{1-6}$alkylS(O)$_2$heterocyclyl, N$C_{1-6}$alkylS(O)$_2$heteroaryl, N$C_{1-6}$alkylS(O)$_2$heterocycyl$C_{1-6}$alkyl, N$C_{1-6}$ alkylS(O)$_2$heterocyclyl$C_{1-6}$alkyl, NHC(O)NH$_2$, NHC(O) NH$C_{1-6}$alkyl, NHC(O)NH$C_{2-6}$alkenyl, NHC(O)NH$C_{2-6}$ alkynyl, NHC(O)NHC$_{6-12}$aryl, NHC(O)NHC$_{3-8}$cycloalkyl, NHC(O)NHC$_{6-12}$arylC$_{1-6}$alkyl, NHC(O)NH-heterocyclyl, NHC(O)NH-heteroaryl, NHC(O)NHheterocyclylC$_{1-6}$alkyl, NHC(O)NHheteroarylC$_{1-6}$alkyl, NHC(O)NC$_{1-6}$alkylC$_{1-6}$alkyl, NHC(O)NC$_{1-6}$alkylC$_{6-12}$aryl, NC$_{1-6}$alkylC(O)NHC$_{1-6}$alkyl, NC$_{1-6}$alkylC(O)NHC$_{2-6}$alkenyl, NC$_{1-6}$alkylC(O)NHC$_{2-6}$alkynyl, NC$_{1-6}$alkylC(O)NHC$_{6-12}$aryl, NC$_{1-6}$-alkylC(O)NHC$_{3-8}$cycloalkyl, NC$_{1-6}$alkylC(O)NHC$_{6-12}$arylC$_{1-6}$alkyl, NC$_{1-6}$alkylC(O)NH-heterocyclyl, NC$_{1-6}$alkylC(O)NH-heteroaryl, NC$_{1-6}$alkylC(O)NHheterocyclylC$_{1-6}$alkyl, and NC$_{1-6}$alkylC(O)NHheteroarylC$_{1-6}$alkyl; and wherein at least one carbon atom or heteroatom of said C$_{1-6}$alkyl, C$_{3-12}$cycloalkyl, C$_{6-12}$aryl, C$_{6-12}$arylC$_{1-6}$alkyl, heterocycyl, heterocyclylC$_{1-6}$alkyl, heteroaryl or heteroarylC$_{1-6}$alkyl can be oxidized to form at least one C=O, or N=O.

137. The compound according to any one of statements 1 to 136, wherein each Z$^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{6-12}$aryl, heterocyclyl, heterocyclylC$_{1-6}$alkyl, heteroaryl, heteroarylC$_{1-6}$alkyl, hydroxyl, C$_{1-6}$alkyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{6-12}$arylthio, C$_{3-8}$cycloalkylthio, C$_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, cyano, amino, C$_{1-6}$alkylamino, C$_{6-12}$arylamino, C$_{3-8}$cycloalkylamino, C$_{6-12}$arylC$_{1-6}$alkylamino, heterocyclylamino, heteroarylamino, heterocyclylC$_{1-6}$alkylamino, heteroarylC$_{1-6}$alkylamino, di-C$_{1-6}$alkylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, di-heteroarylC$_{1-6}$alkylamino, CO$_2$H, CO$_2$C$_{1-6}$alkyl, CO$_2$C$_{6-12}$aryl, CO$_2$C$_{3-8}$cycloalkyl, CO$_2$heterocyclyl, CO$_2$heteroaryl, C(O)NH$_2$, C(O)NHC$_{1-6}$alkyl, C(O)NHC$_{6-12}$aryl, C(O)NHC$_{3-8}$cycloalkyl, C(O)NH-heterocyclyl, C(O)NH-heteroaryl, COH, C(O)C$_{1-6}$alkyl, C(O)C$_{6-12}$aryl, C(O)C$_{3-8}$cycloalkyl, C(O)heterocyclyl, C(O)heteroaryl, S(O)OH, S(O)C$_{1-6}$alkyl, S(O)C$_{6-12}$aryl, S(O)C$_{3-8}$cycloalkyl, S(O)heterocyclyl, S(O)heteroaryl, S(O)$_2$OH, S(O)$_2$C$_{1-6}$alkyl, S(O)$_2$C$_{6-12}$aryl, S(O)$_2$C$_{3-8}$cycloalkyl, S(O)$_2$heterocyclyl, S(O)$_2$heteroaryl S(O)$_2$NH$_2$, S(O)$_2$NHC$_{1-6}$alkyl, S(O)$_2$NHC$_{6-12}$aryl, S(O)$_2$NHC$_{3-8}$cycloalkyl, S(O)$_2$NHheterocyclyl, —S(O)$_2$NHheteroaryl, nitro, NHC(O)H, NHC(O)C$_{1-6}$alkyl, NHC(O)C$_{6-12}$aryl, NHC(O)C$_{3-8}$cycloalkyl, NHC(O)heterocyclyl, NHC(O)heteroaryl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, N(C$_{1-6}$alkyl)C(O)heterocyclyl, N(C$_{1-6}$alkyl)C(O)heteroaryl, C$_{1-6}$alkyleneC(O)NH$_2$, C$_{1-6}$alkyleneC(O)NHC$_{1-6}$alkyl, C$_{1-6}$alkyleneC(O)NHC$_{6-12}$aryl, C$_{1-6}$alkyleneC(O)NHC$_{3-8}$cycloalkyl, C$_{1-6}$alkyleneC(O)NH-heterocyclyl, C$_{1-6}$alkyleneC(O)NH-heteroaryl, NHS(O)$_2$H, NHS(O)$_2$OH, NHS(O)$_2$C$_{1-6}$alkyl, NHS(O)$_2$C$_{6-12}$aryl, NHS(O)$_2$C$_{3-8}$cycloalkyl, NHS(O)heterocyclyl, NHS(O)$_2$heteroaryl, NC$_{1-6}$alkylS(O)$_2$H, NC$_{1-6}$alkylS(O)$_2$OH, NC$_{1-6}$alkylS(O)$_2$C$_{1-6}$alkyl, NC$_{1-6}$alkylS(O)$_2$C$_{6-12}$aryl, NC$_{1-6}$alkylS(O)$_2$C$_{3-8}$cycloalkyl, NC$_{1-6}$alkylS(O)$_2$heterocyclyl, NC$_{1-6}$alkylS(O)$_2$heteroaryl, NHC(O)NH$_2$, NHC(O)NHC$_{1-6}$alkyl, NHC(O)NHC$_{6-12}$aryl, NHC(O)NHC$_{3-8}$cycloalkyl, NHC(O)NHC$_{6-12}$arylC$_{1-6}$alkyl, NHC(O)NH-heterocyclyl, NHC(O)NH-heteroaryl, NC$_{1-6}$alkylC(O)NHC$_{1-6}$alkyl, NC$_{1-6}$alkylC(O)NHC$_{6-12}$aryl, NC$_{1-6}$alkylC(O)NHC$_{3-8}$cycloalkyl, NC$_{1-6}$alkylC(O)NH-heterocyclyl, and NC$_{1-6}$alkylC(O)NH-heteroaryl; and wherein at least one carbon atom or heteroatom of said C$_{1-6}$alkyl, C$_{3-8}$cycloalkyl, C$_{6-12}$aryl, C$_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O, or N=O.

138. The compound according to any one of statements 1 to 137, wherein each Z$^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{6-12}$aryl, heterocyclyl, heterocyclylC$_{1-6}$alkyl, heteroaryl, heteoarylC$_{1-6}$alkyl, hydroxyl, C$_{1-6}$alkyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{6-12}$arylthio, C$_{3-8}$cycloalkylthio, cyano, amino, C$_{1-6}$alkylamino, C$_{6-12}$arylamino, C$_{3-8}$cycloalkylamino, C$_{6-12}$arylC$_{1-6}$alkylamino, heterocyclylamino, heteroarylamino, heterocyclylC$_{1-6}$alkylamino, heteroarylC$_{1-6}$ alkylamino, di-C$_{1-6}$alkylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, di-heteroarylC$_{1-6}$alkylamino, CO$_2$H, CO$_2$C$_{1-6}$alkyl, CO$_2$C$_{6-12}$aryl, CO$_2$C$_{3-8}$cycloalkyl, CO$_2$heteroaryl, C(O)NH$_2$, C(O)NHC$_{1-6}$ alkyl, C(O)NHC$_{6-12}$aryl, C(O)NHC$_{3-8}$cycloalkyl, C(O)NH-heterocyclyl, C(O)NH-heteroaryl, COH, C(O)C$_{1-6}$alkyl, C(O)C$_{6-12}$aryl, C(O)C$_{3-8}$cycloalkyl, C(O)heterocyclyl, C(O)heteroaryl, S(O)$_2$OH, S(O)$_2$C$_{1-6}$alkyl, S(O)$_2$C$_{6-12}$aryl, S(O)$_2$C$_{3-8}$cycloalkyl, S(O)$_2$heterocyclyl, S(O)$_2$heteroaryl, S(O)$_2$NH$_2$, S(O)$_2$NHC$_{1-6}$alkyl, S(O)$_2$NHC$_{6-12}$aryl, S(O)$_2$NHC$_{3-8}$cycloalkyl, S(O)$_2$NHheterocyclyl, S(O)$_2$NHheteroaryl, nitro, NHC(O)H, NHC(O)C$_{1-6}$alkyl, NHC(O)C$_{6-12}$aryl, NHC(O)C$_{3-8}$cycloalkyl, NHC(O)heterocyclyl, NHC(O)heteroaryl, —N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, N(C$_{1-6}$alkyl)C(O)heterocyclyl, N(C$_{1-6}$alkyl)C(O)heteroaryl, C$_{1-6}$alkyleneC(O)NH$_2$, C$_{1-6}$alkyleneC(O)NHC$_{1-6}$alkyl, C$_{1-6}$alkyleneC(O)NHC$_{6-12}$aryl, C$_{1-6}$alkyleneC(O)NHC$_{3-8}$cycloalkyl, C$_{1-6}$alkyleneC(O)NH-heterocyclyl, C$_{1-6}$alkyleneC(O)NH-heteroaryl, NHS(O)$_2$H, NHS(O)$_2$OH, NHS(O)$_2$C$_{1-6}$alkyl, NHS(O)$_2$C$_{6-12}$aryl, NHS(O)$_2$C$_{3-8}$cycloalkyl, NHS(O)heterocyclyl, NHS(O)$_2$heteroaryl, —NC$_{1-6}$alkylS(O)$_2$H, NC$_{1-6}$alkylS(O)$_2$OH, NC$_{1-6}$alkylS(O)$_2$C$_{1-6}$alkyl, NC$_{1-6}$alkylS(O)$_2$C$_{6-12}$aryl, NC$_{1-6}$alkylS(O)$_2$C$_{3-8}$cycloalkyl, NC$_{1-6}$alkylS(O)$_2$heterocyclyl, and NC$_{1-6}$alkylS(O)$_2$heteroaryl; and wherein at least one carbon atom or heteroatom of said C$_{1-6}$alkyl, C$_{3-8}$cycloalkyl, C$_{6-12}$aryl, C$_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O, or N=O.

139. The compound according to any one of statements 1 to 138, wherein each Z$^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{6-12}$aryl, heterocyclyl, heterocyclylC$_{1-6}$alkyl, heteroaryl, heteroarylC$_{1-6}$alkyl, hydroxyl, C$_{1-6}$alkyloxy, C$_{6-12}$aryloxy, heterocyclyloxy, heteroaryloxy, cyanoC$_{1-6}$alkyloxy, thiol, C$_{1-6}$alkylthio, cyano, amino, C$_{1-6}$alkylamino, C$_{6-12}$arylamino, C$_{3-8}$cycloalkylamino, di-C$_{1-6}$alkylamino, di-C$_{6-12}$arylamino, di-C$_{3-8}$cycloalkylamino, CO$_2$H, CO$_2$C$_{1-6}$alkyl, CO$_2$C$_{6-12}$aryl, CO$_2$C$_{3-8}$cycloalkyl, C(O)NH$_2$, C(O)NHC$_{1-6}$alkyl, C(O)NHC$_{6-12}$aryl, C(O)NHC$_{3-8}$cycloalkyl, COH, C(O)C$_{1-6}$alkyl, C(O)C$_{6-12}$aryl, C(O)C$_{3-8}$cycloalkyl, S(O)$_2$OH, S(O)$_2$C$_{1-6}$alkyl, S(O)$_2$ $C_{6-12}$aryl, $S(O)_2C_{3-8}$cycloalkyl, $S(O)_2NH_2$, $S(O)_2NHC_{1-6}$alkyl, $S(O)_2NHC_{6-12}$aryl, $S(O)_2NHC_{3-8}$cycloalkyl, nitro, NHC(O)H, NHC(O)C$_{1-6}$alkyl, NHC(O)C$_{6-12}$aryl, NHC(O)C$_{3-8}$cycloalkyl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, NHS(O)$_2$H, NHS(O)$_2$OH, NHS(O)$_2$C$_{1-6}$alkyl, NHS(O)$_2$C$_{6-12}$aryl, NHS(O)$_2$C$_{3-8}$cycloalkyl, NC$_{1-6}$alkylS(O)$_2$H, NC$_{1-6}$alkylS(O)$_2$OH, NC$_{1-6}$alkylS(O)$_2$C$_{1-6}$alkyl, NC$_{1-6}$alkylS(O)$_2$C$_{6-12}$aryl, and NC$_{1-6}$alkylS(O)$_2$C$_{3-8}$cycloalkyl; and wherein at least one carbon atom or heteroatom of said C$_{1-6}$alkyl, C$_{3-12}$cycloalkyl, C$_{6-12}$aryl, C$_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O, or N=O.

140. The compound according to any one of statements 1 to 139, wherein each $Z^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkyC$_{6-12}$aryl, heterocyclyl, heterocyclylC$_{1-6}$alkyl, heteroaryl, heteroaylC$_{1-6}$alkyl, hydroxyl, C$_{1-6}$alkyloxy, C$_{6-12}$aryloxy, cyanoC$_{1-6}$alkyloxy, thiol, C$_{1-6}$alkylthio, cyano, amino, C$_{1-6}$alkylamino, C$_{6-12}$arylamino, di-C$_{1-6}$alkylamino, di-C$_{6-12}$arylamino, CO$_2$H, CO$_2$C$_{1-6}$alkyl, CO$_2$C$_{6-12}$aryl, C(O)NH$_2$, C(O)NHC$_{1-6}$alkyl, C(O)NHC$_{6-12}$aryl, COH, C(O)C$_{1-6}$alkyl, C(O)C$_{6-12}$aryl, S(O)$_2$OH, S(O)$_2$C$_{1-6}$alkyl, S(O)$_2$C$_{6-12}$aryl, S(O)$_2$NH$_2$, S(O)$_2$NHC$_{1-6}$alkyl, S(O)$_2$NHC$_{6-12}$aryl, nitro, NHC(O)H, NHC(O)C$_{1-6}$alkyl, NHC(O)C$_{6-12}$aryl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, NHS(O)$_2$H, NHS(O)$_2$OH, NHS(O)$_2$C$_{1-6}$alkyl, NHS(O)$_2$C$_{6-12}$aryl, NC$_{1-6}$alkylS(O)$_2$H, NC$_{1-6}$alkylS(O)$_2$OH, NC$_{1-6}$alkylS(O)$_2$C$_{1-6}$alkyl, and NC$_{1-6}$alkylS(O)$_2$C$_{6-12}$aryl; and wherein at least one carbon atom or heteroatom of said C$_{1-6}$alkyl, C$_{3-12}$cycloalkyl, C$_{6-12}$aryl, C$_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O, or N=O.

141. The compound according to any one of statements 1 to 140, wherein each $Z^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{1-6}$alkylC$_{6-12}$aryl, C$_{6-12}$aryl, heterocyclyl, heterocyclylC$_{1-6}$alkyl, heteroaryl, heteroarylC$_{1-6}$alkyl, hydroxyl, C$_{1-6}$alkyloxy, cyanoC$_{1-6}$alkyloxy, thiol, C$_{1-6}$alkylthio, cyano, amino, C$_{1-6}$alkylamino, di-C$_{1-6}$alkylamino, CO$_2$H, CO$_2$C$_{1-6}$alkyl, C(O)NH$_2$, C(O)NHC$_{1-6}$alkyl, COH, C(O)C$_{1-6}$alkyl, NHC(O)H, NHC(O)C$_{1-6}$alkyl, N(C$_{1-6}$alkyl)C(O)H, and N(C$_{1-6}$alkyl)C(O)C$_{1-6}$alkyl; and wherein at least one carbon atom of said C$_{1-6}$alkyl, C$_{3-12}$cycloalkyl, C$_{6-12}$aryl, C$_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O.

142. The compound according to any one of statements 1 to 141, wherein each $Z^1$ is independently selected from the group consisting of halo, hydrogen, C$_{1-6}$alkyl, haloC$_{1-6}$alkyl, haloC$_{1-6}$alkyloxy, C$_{6-12}$aryl, C$_{1-6}$alkylC$_{6-12}$aryl, heterocyclyl, heterocyclylC$_{1-6}$alkyl, heteroaryl, hydroxyl, heteroarylC$_{1-6}$alkyl, C$_{1-6}$alkyloxy, cyanoC$_{1-6}$alkyloxy, thiol, C$_{1-6}$alkythio, cyano, amino, C$_{1-6}$alkylamino, di-C$_{1-6}$alkylamino, C(O)C$_{1-6}$alkyl, NHC(O)C$_{1-6}$alkyl, and N(C$_{1-6}$alkyl)C(O)C$_{1-6}$alkyl; and wherein at least one carbon atom of said C$_{1-6}$alkyl, C$_{6-12}$aryl, C$_{6-12}$arylC$_{1-6}$ alkyl, heterocyclyl, heterocyclylC$_{1-6}$alkyl, heteroaryl or heteroarylC$_{1-6}$alkyl can be oxidized to form at least one C=O.

143. The compound according to any one of statements 1 to 142, wherein each $Z^1$ is independently selected from the group consisting of halo, hydrogen, C$_{1-6}$alkyl, haloC$_{1-6}$alkyl, haloC$_{1-6}$alkyloxy, C$_{6-12}$aryl, heterocyclyl, heteroaryl, hydroxyl, C$_{1-6}$alkyloxy, thiol, C$_{1-6}$alkylthio, cyano, amino, C$_{1-6}$alkylamino, and di-C$_{1-6}$alkylamino; and wherein at least one carbon atom of said C$_{1-6}$alkyl, C$_{6-12}$aryl, heterocyclyl, heteroaryl can be oxidized to form at least one C=O.

144. The compound according to any one of statements 1 to 143, wherein two $Z^1$ together with the atom to which they are attached form a 5-, or 6-membered ring; and wherein at least one carbon atom of said ring can be oxidized to form at least one C=O.

145. The compound according to any one of statements 1 to 144, wherein each $Z^2$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{1-6}$aryl, heterocyclyl, heterocyclylC$_{1-6}$alkyl, heteroaryl, heteroarylC$_{1-6}$alkyl, hydroxyl, C$_{1-6}$alkyloxy, C$_{2-6}$alkenyloxy, C$_{2-6}$alkynyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{2-6}$alkenylthio, C$_{2-6}$alkynylthio, C$_{6-12}$arylthio, C$_{3-8}$cycloalkylthio, C$_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, cyano, amino, C$_{1-6}$alkylamino, C$_{2-6}$alkenylamino, C$_{2-6}$alkynylamino, C$_{6-12}$arylamino, C$_{3-8}$cycloalkylamino, C$_{6-12}$arylC$_{1-6}$alkylamino, heterocyclylamino, heteroarylanmino, heterocyclylC$_{1-6}$alkylamino, heteroarylC$_{1-6}$alkylamino, di-C$_{1-6}$alkylamino, di-C$_{2-6}$alkenylamino, di-C$_{2-6}$alkynylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, di-heteroarylC$_{1-6}$alkylamino, CO$_2$H, CO$_2$C$_{1-6}$alkyl, CO$_2$C$_{2-6}$alkenyl, CO$_2$C$_{2-6}$alkynyl, CO$_2$C$_{6-12}$aryl, —CO$_2$C$_{3-8}$cycloalkyl, CO$_2$C$_{6-12}$arylC$_{1-6}$alkyl, CO$_2$heterocyclyl, CO$_2$heteroaryl, CO$_2$heterocyclylC$_{1-6}$alkyl, CO$_2$heteroarylC$_{1-6}$alkyl, C(O)NH$_2$, C(O)NHC$_{1-6}$alkyl, —C(O)NHC$_{2-6}$alkenyl, C(O)NHC$_{2-6}$alkynyl, C(O)NHC$_{6-12}$aryl, C(O)NHC$_{3-8}$cycloalkyl, C(O)NH(C$_{6-12}$arylC$_{1-6}$alkyl), C(O)NH-heterocyclyl, C(O)NH-heteroaryl, C(O)NH(heterocyclylC$_{1-6}$alkyl) C(O)NH(heteroarylC$_{1-6}$alkyl), COH, C(O)C$_{1-6}$alkyl, C(O)C$_{2-6}$alkenyl, C(O)C$_{2-6}$alkynyl, C(O)C$_{6-12}$aryl, C(O)C$_{3-8}$cycloalkyl, C(O)heterocyclyl, C(O)heteroaryl, S(O)OH, S(O)C$_{1-6}$alkyl, S(O)C$_{2-6}$alkenyl, S(O)C$_{2-6}$alkynyl, S(O)C$_{6-12}$aryl, S(O)C$_{3-8}$cycloalkyl, S(O)heterocyclyl, S(O)heteroaryl, S(O)$_2$OH, S(O)$_2$C$_{1-6}$alkyl, S(O)$_2$C$_{2-6}$alkenyl, S(O)$_2$C$_{2-6}$alkynyl, S(O)$_2$C$_{6-12}$aryl, S(O)$_2$C$_{3-8}$cycloalkyl, S(O)$_2$C$_{6-12}$arylC$_{1-6}$alkyl, S(O)$_2$heterocyclyl, S(O)$_2$heteroaryl, S(O)$_2$heterocyclylC$_{1-6}$alkyl, S(O)$_2$heteroarylC$_{1-6}$alkyl, S(O)$_2$NH$_2$, S(O)$_2$NHC$_{1-6}$alkyl, S(O)$_2$NHC$_{2-6}$alkenyl, S(O)$_2$NHC$_{2-6}$alkynyl, S(O)$_2$NHC$_{6-12}$aryl, S(O)$_2$NHC$_{3-8}$cycloalkyl, S(O)$_2$NH(C$_{6-12}$arylC$_{1-6}$alkyl), S(O)$_2$NHheterocyclyl, S(O)$_2$NHheteroaryl, S(O)$_2$NH(heterocyclylC$_{1-6}$alkyl), S(O)$_2$NH(heteroarylC$_{1-6}$alkyl), nitro, NHC(O)H, NHC(O)C$_{1-6}$alkyl, NHC(O)C$_{2-6}$alkenyl, NHC(O)C$_{2-6}$alkynyl, NHC(O)C$_{6-12}$aryl, NHC(O)C$_{3-8}$cycloalkyl, NHC(O)heterocycyl, NHC(O)heteroaryl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, N(C$_{1-6}$alkyl)C(O)heterocyclyl, N(C$_{1-6}$alkyl)C(O)heteroaryl, C$_{1-6}$alkylene-C(O)NH$_2$, C$_{1-6}$alkylene-C(O)NHC$_{1-6}$alkyl, C$_{1-6}$alkylene-C(O)NHC$_{2-6}$alkenyl, C$_{1-6}$alkylene-C(O)NHC$_{2-6}$alkynyl, C$_{1-6}$alkylene-C(O)NHC$_{6-12}$aryl, C$_{1-6}$alkyl-C(O)NHC$_{3-8}$cycloalkyl, C$_{1-6}$alkylene-C(O)NHC$_{6-12}$arylC$_{1-6}$alkyl, $C_{1-6}$alkylene-C(O)NH-heterocyclyl, $C_{1-6}$alkylene-C(O)NH-heteroaryl, $C_{1-6}$alkylene-C(O)NH-heterocyclyC$_{1-6}$alkyl, $C_{1-6}$alkylene-C(O)NH-heteroarylC$_{1-6}$alkyl, —NHS(O)$_2$H, NHS(O)$_2$OH, NHS(O)$_2$C$_{1-6}$alkyl, NHS(O)$_2$C$_{2-6}$alkenyl, NHS(O)$_2$C$_{2-6}$alkynyl, NHS(O)$_2$C$_{6-12}$aryl, NHS(O)$_2$C$_{1-6}$ cycloalkyl, NHS(O)$_2$C$_{6-12}$arylC$_{1-6}$alkyl, NHS(O)$_2$heterocyclyl, NHS(O)$_2$heteroaryl, NHS(O)$_2$heterocyclylC$_{1-6}$ alkyl, NHS(O)$_2$heteroarylC$_{1-6}$alkyl, NC$_{1-6}$alkylS(O)$_2$H, NC$_{1-6}$alkylS(O)$_2$OH, NC$_{1-6}$alkylS(O)$_2$C$_{1-6}$alkyl, NC$_{1-6}$ alkylS(O)$_2$C$_{2-6}$alkenyl, NC$_{1-6}$alkylS(O)$_2$C$_{2-6}$alkynyl, NC$_{1-6}$alkylS(O)$_2$C$_{6-12}$aryl, NC$_{1-6}$alkylS(O)$_2$C$_{3-8}$cycloalkyl, NC$_{1-6}$alkylS(O)$_2$C$_{6-12}$arylC$_{1-6}$alkyl, NC$_{1-6}$alkylS(O)$_2$heterocyclyl, NC$_{1-6}$alkylS(O)$_2$heteroaryl, NC$_{1-6}$alkylS(O)$_2$heterocyclylC$_{1-6}$alkyl, NC$_{1-6}$alkylS(O)$_2$heteroarylC$_{1-6}$alkyl, NHC(O)NH$_2$, NHC(O)NHC$_{1-6}$alkyl, NHC(O)NHC$_{2-6}$alkenyl, NHC(O)NHC$_{2-6}$alkynyl, NHC(O)NHC$_{6-12}$aryl, NHC(O)NHC$_{3-8}$cycloalkyl, NHC(O)NHC$_{6-12}$arylC$_{1-6}$alkyl, NHC(O)NH-heterocyclyl, NHC(O)NH-heteroaryl, NHC(O)NHheterocycylC$_{1-6}$alkyl, NHC(O)NHheteroarylC$_{1-6}$alkyl, NHC(O)NC$_{1-6}$alkylC$_{1-6}$alkyl, NHC(O)NC$_{1-6}$alkylC$_{6-12}$aryl, NC$_{1-6}$alkylC(O)NHC$_{1-6}$alkyl, NC$_{1-6}$alkylC(O)NHC$_{2-6}$alkenyl, NC$_{1-6}$alkylC(O)NHC$_{2-6}$alkynyl, NC$_{1-6}$alkylC(O)NHC$_{6-12}$aryl, NC$_{1-6}$alkylC(O)NHC$_{3-8}$cycloalkyl, NC$_{1-6}$alkylC(O)NHC$_{6-12}$arylC$_{1-6}$alkyl, NC$_{1-6}$alkylC(O)NH-heterocyclyl, NC$_{1-6}$alkylC(O)NH-heteroaryl, NC$_{1-6}$alkylC(O)NHheterocyclylC$_{1-6}$alkyl, and NC$_{1-6}$alkylC(O)NHheteroaryl C$_{1-6}$alkyl; and wherein at least one carbon atom or heteroatom of said $C_{1-6}$alkyl, $C_{3-12}$cycloalkyl, $C_{6-12}$aryl, $C_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O, or N=O.

146. The compound according to any one of statements 1 to 145, wherein each $Z^2$ is independently selected from the group consisting of halo, hydrogen, $C_{1-6}$alkyl, haloC$_{1-6}$alkyl, haloC$_{1-6}$alkyloxy, $C_{3-12}$cycloalkyl, $C_{6-12}$aryl, $C_{1-6}$alkylC$_{6-12}$aryl, heterocyclyl, heterocyclylC$_{1-6}$alkyl, heteroaryl, heteroarylC$_{1-6}$alkyl, hydroxyl, $C_{1-6}$alkyloxy, $C_{2-6}$alkenyloxy, $C_{2-6}$alkynyloxy, $C_{6-12}$alkyloxy, $C_{3-12}$cycloalkyloxy, $C_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, cyano, amino, $C_{1-6}$alkylamino, $C_{2-6}$alkenylamino, $C_{2-6}$alkynylamino, $C_{6-12}$arylamino, $C_{3-8}$cycloalkylamino, $C_{6-12}$arylC$_{1-6}$ alkylamino, heterocyclylamino, heteroarylamino, heterocyclylC$_{1-6}$alkylamino, heteroarylC$_{1-6}$alkylamino, di-C$_{1-6}$alkylamino, di-C$_{2-6}$alkenylamino, di-C$_{2-6}$alkynylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, di-heteroaryl C$_{1-6}$alkylamino, CO$_2$H, —CO$_2$C$_{1-6}$alkyl, CO$_2$C$_{6-12}$aryl, CO$_2$C$_{3-8}$cycloalkyl, CO$_2$heterocyclyl, CO$_2$heteroaryl, C(O)NH$_2$, C(O)NHC$_{1-6}$alkyl, C(O)NHC$_{6-12}$aryl, C(O)NHC$_{3-8}$cycloalkyl, C(O)NH-heterocyclyl, C(O)NH-heteroaryl, COH, C(O)C$_{1-6}$alkyl, C(O)C$_{6-12}$aryl, C(O)C$_{3-8}$cycloalkyl, C(O)heterocyclyl, C(O)heteroaryl, S(O)OH, S(O)C$_{1-6}$alkyl, S(O)C$_{6-12}$aryl, S(O)C$_{3-8}$cycloalkyl, S(O)heterocyclyl, S(O)heteroaryl, S(O)$_2$OH, S(O)$_2$C$_{1-6}$alkyl, S(O)$_2$C$_{6-12}$aryl, S(O)$_2$C$_{3-8}$cycloalkyl, S(O)$_2$heterocyclyl, S(O)$_2$heteroaryl, S(O)$_2$NH$_2$, S(O)$_2$NHC$_{1-6}$alkyl, S(O)$_2$NHC$_{6-12}$aryl, S(O)$_2$NHC$_{3-8}$cycloalkyl, S(O)$_2$NHheterocyclyl, S(O)$_2$NHheteroaryl, nitro, NHC(O)H, NHC(O)C$_{1-6}$alkyl, NHC(O)C$_{6-12}$aryl, NHC(O)C$_{3-8}$cycloalkyl, NHC(O)heterocyclyl, NHC(O)heteroaryl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, N(C$_{1-6}$alkyl)C(O)heterocyclyl, N(C$_{1-6}$alkyl)C(O)heteroaryl, $C_{1-6}$alkylene-C(O)NH$_2$, $C_{1-6}$alkyleneC(O)NHC$_{1-6}$alkyl, $C_{1-6}$alkyleneC(O)NHC$_{6-12}$aryl, $C_{1-6}$alkyleneC(O)NHC$_{3-8}$cycloalkyl, $C_{1-6}$alkyleneC(O)NH-heterocyclyl, $C_{1-6}$alkyleneC(O)NH-heteroaryl, NHS(O)$_2$H, NHS(O)$_2$OH, NHS(O)$_2$C$_{1-6}$alkyl, NHS(O)$_2$C$_{6-12}$aryl, NHS(O)$_2$C$_{3-8}$cycloalkyl, NHS(O)$_2$heterocyclyl, NHS(O)$_2$heteroaryl, NC$_{1-6}$alkylS(O)$_2$H, NC$_{1-6}$alkylS(O)$_2$OH, NC$_{1-6}$alkylS(O)$_2$C$_{1-6}$alkyl, NC$_{1-6}$alkylS(O)$_2$C$_{6-12}$aryl, NC$_{1-6}$alkylS(O)$_2$C$_{3-8}$cycloalkyl, NC$_{1-6}$alkylS(O)$_2$heterocyclyl, NC$_{1-6}$alkylS(O)$_2$heteroaryl, NHC(O)NH$_2$, NHC(O)NHC$_{1-6}$alkyl, NHC(O)NHC$_{6-12}$aryl, NHC(O)NHC$_{3-8}$cycloalkyl, NHC(O)NHC$_{6-12}$arylC$_{1-6}$alkyl, NHC(O)NH-heterocyclyl, NHC(O)NH-heteroaryl, NC$_{1-6}$alkylC(O)NHC$_{1-6}$alkyl, NC$_{1-6}$alkylC(O)NHC$_{6-12}$aryl, NC$_{1-6}$alkylC(O)NHC$_{3-8}$cycloalkyl, NC$_{1-6}$alkylC(O)NH-heterocyclyl, and NC$_{1-6}$alkylC(O)NH-heteroaryl; and wherein at least one carbon atom or heteroatom of said $C_{1-6}$alkyl, $C_{3-12}$cycloalkyl, $C_{6-12}$aryl, $C_{6-12}$arylC$_{1-6}$alkyl, heterocyclyl, heterocyclylC$_{1-6}$alkyl, heteroaryl or heteroarylC$_{1-6}$alkyl can be oxidized to form at least one C=O, or N=O.

147. The compound according to any one of statements 1 to 146, wherein each $Z^2$ is independently selected from the group consisting of halo, hydrogen, $C_{1-6}$alkyl, halo $C_{1-6}$alkyl, haloC$_{1-6}$alkyloxy, $C_{3-12}$cycloalkyl, $C_{6-12}$aryl, $C_{1-6}$alkylC$_{6-12}$aryl, heteroarylC$_{1-6}$alkyl, heterocyclyl, heterocyclylC$_{1-6}$alkyl, heteroaryl, heteroarylC$_{1-6}$alkyl, hydroxyl, $C_{1-6}$alkyloxy, $C_{6-12}$aryloxy, $C_{3-12}$cycloalkyloxy, $C_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, $C_{1-6}$alkylthio, $C_{6-12}$arylthio, $C_{3-8}$cycloalkylthio, $C_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkythio, cyano, amino, $C_{1-6}$alkylamino, $C_{6-12}$arylamino, $C_{3-8}$cycloalkylamino, $C_{6-12}$arylC$_{1-6}$alkylamino, heterocyclylamino, heteroarylamino, heterocyclylC$_{1-6}$alkylamino, heteroarylC$_{1-6}$alkylamino, di-C$_{1-6}$alkylamino, di-C$_{6-12}$arylamino, di-C$_{3-8}$cycloalkylamino, di-C$_{6-12}$arylC$_{1-6}$alkylamino, di-heterocyclylamino, di-heteroarylamino, di-heterocyclylC$_{1-6}$alkylamino, di-heteroarylC$_{1-6}$alkylamino, CO$_2$H, CO$_2$C$_{1-6}$alkyl, CO$_2$C$_{6-12}$aryl, CO$_2$C$_{3-8}$cycloalkyl, CO$_2$heterocyclyl, CO$_2$heteroaryl, C(O)NH$_2$, C(O)NHC$_{1-6}$alkyl, C(O)NHC$_{6-12}$aryl, C(O)NHC$_{3-8}$cycloalkyl, C(O)NH-heterocyclyl, C(O)NH-heteroaryl, COH, C(O)C$_{1-6}$alkyl, C(O)C$_{6-12}$aryl, C(O)C$_{3-8}$cycloalkyl, C(O)heterocyclyl, C(O)heteroaryl, S(O)$_2$OH, S(O)$_2$C$_{1-6}$alkyl, S(O)$_2$C$_{6-12}$aryl, S(O)$_2$C$_{3-8}$cycloalkyl, S(O)heterocyclyl, S(O)heteroaryl, S(O)$_2$NH$_2$, S(O)$_2$NHC$_{1-6}$alkyl, S(O)$_2$NHC$_{6-12}$aryl, S(O)$_2$NHC$_{3-8}$cycloalkyl, S(O)$_2$NHheterocyclyl, S(O)$_2$NHheteroaryl, nitro, NHC(O)H, NHC(O)C$_{1-6}$alkyl, NHC(O)C$_{6-12}$aryl, NHC(O)C$_{3-8}$cycloalkyl, NHC(O)heterocyclyl, NHC(O)heteroaryl, N(C$_{1-6}$alkyl)C(O)H, N(C$_{1-6}$alkyl)C(O)C$_{1-6}$alkyl, —N(C$_{1-6}$alkyl)C(O)C$_{6-12}$aryl, N(C$_{1-6}$alkyl)C(O)C$_{3-8}$cycloalkyl, N(C$_{1-6}$alkyl)C(O)heterocyclyl, N(C$_{1-6}$alkyl)C(O)heteroaryl, $C_{1-6}$alkylene-C(O)NH$_2$, $C_{1-6}$alkyleneC(O)NHC$_{1-6}$alkyl, $C_{1-6}$alkyleneC(O)NHC$_{6-12}$aryl, $C_{1-6}$alkyleneC(O)NHC$_{3-8}$cycloalkyl, $C_{1-6}$alkyleneC(O)NH-heterocyclyl, $C_{1-6}$alkyleneC(O)NH-heteroaryl, NHS(O)$_2$H, NHS(O)$_2$OH, NHS(O)$_2$C$_{1-6}$alkyl, NHS(O)$_2$C$_{6-12}$aryl, NHS(O)$_2$C$_{3-8}$cycloalkyl, NHS(O)$_2$heterocyclyl, NHS(O)$_2$heteroaryl, NC$_{1-6}$alkylS(O)$_2$H, NC$_{1-6}$alkylS(O)$_2$OH, NC$_{1-6}$alkylS(O)$_2$C$_{1-6}$alkyl, N $C_{1-6}$alkylS(O)$_2C_{6-12}$aryl, $NC_{1-6}$alkylS(O)$_2C_{3-8}$cycloalkyl, $NC_{1-6}$alkylS(O)$_2$heterocyclyl, and $NC_{1-6}$alkylS(O)$_2$heteroaryl; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized to form at least one C=O, or N=O.

148. The compound according to any one of statements 1 to 147, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heteroaryl$C_{1-6}$alkyl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{6-12}$arylthio, $C_{3-8}$cycloalkylthio, cyano, amino, $C_{1-6}$alkylamino, $C_{6-12}$arylamino, $C_{3-8}$cycloalkylamino, $C_{6-12}$aryl$C_{1-6}$alkylamino, heterocyclylamino, heteroarylamino, heterocyclyl$C_{1-6}$alkylamino, heteroaryl$C_{1-6}$alkylamino, di-$C_{1-6}$alkylamino, di-$C_{6-12}$arylamino, di-$C_{3-8}$cycloalkylamino, di-$C_{6-12}$aryl$C_{1-6}$alkylamino, di-heterocyclylamino, di-heteroarylamino, di-heterocyclyl$C_{1-6}$alkylamino, di-heteroaryl$C_{1-6}$alkylamino, CO$_2$H, CO$_2C_{1-6}$alkyl, CO$_2C_{6-12}$aryl, CO$_2C_{3-8}$cycloalkyl, CO$_2$heterocyclyl, CO$_2$heteroaryl, C(O)NH$_2$, C(O)NHC$_{1-6}$alkyl, C(O)NHC$_{6-12}$aryl, C(O)NHC$_{3-8}$cycloalkyl, C(O)NH-heterocyclyl, C(O)NH-heteroaryl, COH, C(O)C$_{1-6}$alkyl, C(O)C$_{6-12}$aryl, C(O)C$_{3-8}$cycloalkyl, C(O)heterocyclyl, C(O)heteroaryl, S(O)$_2$OH, S(O)$_2C_{1-6}$alkyl, S(O)$_2C_{6-12}$aryl, S(O)$_2C_{3-8}$cycloalkyl, S(O)$_2$heterocyclyl, S(O)$_2$heteroaryl, S(O)$_2$NH$_2$, S(O)$_2$NHC$_{1-6}$alkyl, S(O)$_2$NHC$_{6-12}$aryl, S(O)$_2$NHC$_{3-8}$cycloalkyl, S(O)$_2$NHheterocyclyl, S(O)$_2$NHheteroaryl, nitro, NHC(O)H, NHC(O)C$_{1-6}$alkyl, NHC(O)C$_{6-12}$aryl, NHC(O)C$_{3-8}$cycloalkyl, NHC(O)heterocyclyl, NHC(O)heteroaryl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, N(C$_{1-6}$alkyl)C(O)heterocyclyl, N(C$_{1-6}$alkyl)C(O)heteroaryl, NHS(O)$_2$H, NHS(O)$_2$OH, NHS(O)$_2C_{1-6}$alkyl, NHS(O)$_2C_{6-12}$aryl, NHS(O)$_2C_{3-8}$cycloalkyl, NHS(O)$_2$heterocyclyl, NHS(O)$_2$heteroaryl, NC$_{1-6}$alkylS(O)$_2$H, NC$_{1-6}$alkylS(O)$_2$OH, NC$_{1-6}$alkylS(O)$_2C_{1-6}$alkyl, NC$_{1-6}$alkylS(O)$_2C_{6-12}$aryl, NC$_{1-6}$alkylS(O)$_2C_{3-8}$cycloalkyl, NC$_{1-6}$alkylS(O)$_2$heterocyclyl, and NC$_{1-6}$alkylS(O)$_2$heteroaryl; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized so form at least one C=O, or N=O.

149. The compound according to any one of statements 1 to 148, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heteroaryl$C_{1-6}$alkyl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, heterocyclyloxy, heteroaryloxy, cyano$C_{1-6}$alkyloxy, thiol, $C_{1-6}$alkylthio, cyano, amino, $C_{1-6}$alkylamino, $C_{6-12}$arylamino, $C_{3-8}$cycloalkylamino, di-$C_{1-6}$alkylamino, di-$C_{6-12}$arylamino, di-$C_{3-8}$cycloalkylamino, CO$_2$H, CO$_2C_{1-6}$alkyl, CO$_2C_{6-12}$aryl, CO$_2C_{3-8}$cycloalkyl, C(O)NH$_2$, C(O)NHC$_{1-6}$alkyl, C(O)NHC$_{6-12}$aryl, C(O)NHC$_{3-8}$cycloalkyl, COH, C(O)C$_{1-6}$alkyl, C(O)C$_{6-12}$aryl, C(O)C$_{3-8}$cycloalkyl, S(O)$_2$OH, S(O)$_2C_{1-6}$alkyl, S(O)$_2C_{6-12}$aryl, S(O)$_2C_{3-8}$cycloalkyl, S(O)$_2$NH$_2$, S(O)$_2$NHC$_{1-6}$alkyl, S(O)$_2$NHC$_{6-12}$aryl, S(O)$_2$ NHC$_{3-8}$cycloalkyl, nitro, NHC(O)H, NHC(O)C$_{1-6}$alkyl, NHC(O)C$_{6-12}$aryl, NHC(O)C$_{3-8}$cycloalkyl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, N(C$_{1-6}$alkyl)C(O)C$_{3-8}$cycloalkyl, NHS(O)$_2$H, NHS(O)$_2$OH, NHS(O)$_2C_{1-6}$alkyl, NHS(O)$_2C_{6-12}$aryl, NHS(O)$_2C_{3-8}$cycloalkyl, NC$_{1-6}$alkylS(O)$_2$H, NC$_{1-6}$alkylS(O)$_2$OH, NC$_{1-6}$alkylS(O)$_2C_{1-6}$alkyl, NC$_{1-6}$alkylS(O)$_2C_{6-12}$aryl, and NC$_{1-6}$alkylS(O)$_2C_{3-8}$cycloalkyl; and wherein at least one carbon atom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized to form at least one C=O.

150. The compound according to any one of statements 1 to 149, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heteroaryl$C_{1-6}$alkyl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, cyano$C_{1-6}$alkyloxy, thiol, $C_{1-6}$alkylthio, cyano, amino, $C_{1-6}$alkylamino, $C_{6-12}$arylamino, di-$C_{1-6}$alkylamino, di-$C_{6-12}$arylamino, CO$_2$H, CO$_2C_{1-6}$alkyl, CO$_2C_{6-12}$aryl, C(O)NH$_2$, C(O)NHC$_{1-6}$alkyl, C(O)NHC$_{6-12}$aryl, COH, C(O)C$_{1-6}$alkyl, C(O)C$_{6-12}$aryl, S(O)$_2$OH, S(O)$_2C_{1-6}$alkyl, S(O)$_2C_{6-12}$aryl, S(O)$_2$NH$_2$, S(O)$_2$NHC$_{1-6}$alkyl, —S(O)$_2$NHC$_{6-12}$aryl, nitro, NHC(O)H, NHC(O)C$_{1-6}$alkyl, NHC(O)C$_{6-12}$aryl, N(C$_{1-6}$alkyl)C(O)H, N(C$_{1-6}$alkyl)C(O)C$_{1-6}$alkyl, N(C$_{1-6}$alkyl)C(O)C$_{6-12}$aryl, NHS(O)$_2$H, NHS(O)$_2$OH, NHS(O)$_2C_{1-6}$alkyl, NHS(O)$_2C_{6-12}$aryl, NC$_{1-6}$alkylS(O)$_2$H, NC$_{1-6}$alkylS(O)$_2$OH, NC$_{1-6}$alkylS(O)$_2C_{1-6}$alkyl, and NC$_{1-6}$alkylS(O)$_2C_{6-12}$aryl; and wherein at least one carbon atom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized to form at least one C=O.

151. The compound according to any one of statements 1 to 150, wherein each $Z^2$ is independently selected from the group consisting of halo, hydrogen, $C_{1-6}$alkyl, $C_{1-6}$alkyl$C_{6-12}$aryl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heteroaryl$C_{1-6}$alkyl, heterocyclyl, heteroaryl, heterocyclyl$C_{1-6}$alkyl, hydroxyl, heteroaryl$C_{1-6}$alkyl, $C_{1-6}$alkyloxy, cyano$C_{1-6}$alkyloxy, thiol, $C_{1-6}$alkylthio, cyano, amino, $C_{1-6}$alkylamino, di-$C_{1-6}$alkylamino, CO$_2$H, CO$_2C_{1-6}$alkyl, C(O)NH$_2$, C(O)NHC$_{1-6}$alkyl, COH, C(O)C$_{1-6}$alkyl, NHC(O)H, NHC(O)C$_{1-6}$alkyl, N(C$_{1-6}$alkyl)C(O)H, and N(C$_{1-6}$alkyl)C(O)C$_{1-6}$alkyl; and wherein at least one carbon atom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized to form at least one C=O.

152. The compound according to any one of statements 1 to 151, wherein each $Z^2$ is independently selected from the group consisting of halo, hydrogen, $C_{1-6}$alkyl, halo$C_{1-6}$alkyl, halo$C_{1-6}$alkyloxy, $C_{6-12}$aryl, $C_{1-6}$alkyl$C_{6-12}$aryl, heterocyclyl, heteroaryl, hydroxyl, $C_{1-6}$alkyloxy, cyano$C_{1-6}$alkyloxy, thiol, $C_{1-6}$alkylthio, cyano, amino, $C_{1-6}$alkylamino, di-$C_{1-6}$alkylamino, C(O)$C_{1-6}$alkyl, NHC(O)C$_{1-6}$alkyl, N(C$_{1-6}$alkyl)C(O)C$_{1-6}$alkyl.

153. The compound according to any one of statements 1 to 152, wherein two $Z^2$ together with the atom to which they are attached form a 5-, or 6-membered ring; and wherein at least one carbon atom of said ring can be oxidized to form at least one C=O.

154. The compound according to any one of statements 1 to 153, wherein, n is 0, $R^3$ is selected from the group consisting of $C_{6-12}$aryl, hydrogen, $C_{1-6}$alkyl, $C_{3-12}$cycloalkyl, heterocyclyl, heteroaryl, and halo; wherein said $C_{6-12}$aryl, $C_{1-6}$alkyl, $C_{3-12}$cycloalkyl, heterocyclyl, heteroaryl, can be unsubstituted or substituted with one or more $Z^1$;

$L^1$ is selected from the group consisting of —SO$_2$—, —CO—,

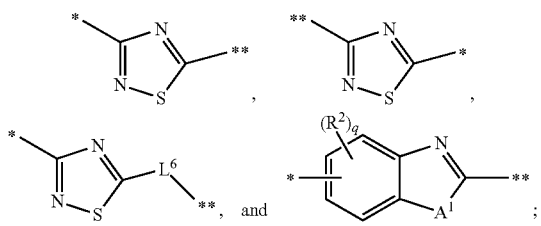

wherein * represents where $L^1$ is bound to $L^2$; and ** represents where $L^1$ is bound to the azetidine ring; and wherein, $A^1$ is S:

q is 0;

$L^6$ is —CO— or —SO$_2$—;

$R^4$ is selected from the group consisting $C_{6-12}$aryl, hydrogen, $C_{1-6}$alkyl, $C_{3-12}$cycloalkyl, heterocyclyl, heteroaryl, halo, hydroxyl, and cyano; and wherein said $C_{6-12}$aryl, $C_{1-6}$alkyl, $C_{3-12}$cycloalkyl, heterocyclyl, heteroaryl, can be unsubstituted or substituted with one or more $Z^2$;

$L^2$ is a single bond or a group of formula (i);

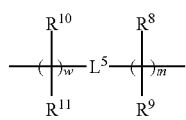 (i)

wherein the left side of the group of formula (i) is attached to $R^3$ and the right side thereof is attached to the nitrogen atom of the azetidine ring; and wherein, m is an integer selected from 0, 1;

w is an integer selected from 0, 1;

$L^5$ is a single bond, or is selected from the group consisting of —O—, and —NR$^{12}$—;

$R^8$ is selected from the group consisting of hydrogen, $C_{1-6}$alkyl, and hydroxyl;

$R^9$ is selected from the group consisting of hydrogen, $C_{1-6}$alkyl, and hydroxyl;

or $R^8$ and $R^9$ together with the carbon atom to which they are attached from a saturated or 3-, 4-, 5-, or 6-carbons membered ring;

$R^{10}$ is selected from the group consisting of hydrogen, $C_{1-6}$alkyl, and hydroxyl;

$R^{11}$ is selected from the group consisting of hydrogen, $C_{1-6}$alkyl, and hydroxyl;

or $R^{10}$ and $R^{11}$ together with the carbon atom to which they are attached from a saturated 3-, 4-, 5-, or 6-carbons membered ring;

$R^{12}$ is hydrogen;

$L^3$ is —SO$_2$—;

$L^4$ is a single bond or is —(CR$^{15}$R$^{16}$)$_t$—; wherein, t is an integer selected from 1, or 2;

$R^{15}$ is hydrogen, or $C_{1-6}$alkyl;

$R^{16}$ is hydrogen, or $C_{1-6}$alkyl;

or $R^{15}$ and $R^{16}$ together with the carbon atom to which they are attached form a saturated 3-, 4-, 5-, or 6-carbons membered ring;

wherein at least one of $L^3$, $L^4$ is not a single bond; and wherein when $L^4$ is a single bond, $R^4$ is not methyl;

each $Z^1$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —SR$^{19}$, cyano, amino, —NR$^{20}$R$^{21}$, —CO$_2$R$^{22}$, —C(O)NR$^{20}$R$^{21}$, —C(O)R$^{22}$, —S(O)$_2$R$^{22}$, —SO$_2$NR$^{20}$R$^{21}$, nitro, and —NR$^{23}$C(O)R$^{22}$; wherein two $Z^1$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O;

each $Z^2$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —SR$^{19}$, cyano, amino, —NR$^{20}$R$^{21}$, —CO$_2$R$^{22}$, —C(O)NR$^{20}$R$^{21}$, —C(O)R$^{22}$, —S(O)$_2$R$^{22}$, —SO$_2$NR$^{20}$R$^{21}$, and —NR$_{23}$C(O)R$^{22}$; wherein two $Z^2$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O;

each $R^{18}$ is independently selected from the group consisting of $C_{1-6}$alkyl, $C_{6-12}$aryl, $C_{3-8}$cycloalkyl, heterocyclyl, and heteroaryl;

each $R^{19}$ is independently selected from the group consisting of hydrogen, $C_{1-6}$alkyl, $C_{6-12}$aryl, $C_{3-8}$cycloalkyl, hetrocyclyl, heteroayl, and heteroaryl$C_{1-6}$alkyl; and;

each $R^{20}$ is independently selected from the group consisting of hydrogen, $C_{1-6}$alkyl, $C_{6-12}$aryl, $C_{3-8}$cycloalkyl, heterocyclyl, and heteroaryl;

each $R^{21}$ is independently selected from the group consisting of hydrogen, $C_{1-6}$alkyl, $C_{6-12}$aryl, $C_{3-8}$cycloalkyl, heterocyclyl, and heteroaryl;

or wherein $R^{20}$ and $R^{21}$ together with the nitrogen atom to which they are attached form a 5-, 6-, or 7-membered heterocyclyl;

each $R^{22}$ is independently selected from the group consisting of hydrogen, hydroxyl, $C_{1-6}$alkyl, $C_{6-12}$aryl, $C_{3-8}$cycloalkyl, heterocyclyl, and heteroaryl;

each $R^{23}$ is independently selected from the group consisting of hydrogen, $C_{1-6}$alkyl, $C_{6-12}$aryl, $C_{3-8}$cycloalkyl, heterocyclyl, and heteroaryl.

155. The compound according to any one of statements 1 to 154, wherein, n is 0;

$R^3$ is selected from the group consisting of $C_{6-12}$aryl, hydrogen, $C_{1-6}$alkyl, $C_{3-12}$cycloalkyl, heterocyclyl, heteroaryl, and halo; wherein said $C_{6-12}$aryl, $C_{1-6}$alkyl, $C_{3-12}$cycloalkyl, heterocyclyl, heteroaryl, can be unsubstituted or substituted with one, two or three $Z^1$;

$L^1$ is selected from the group consisting of —SO$_2$—, —CO—,

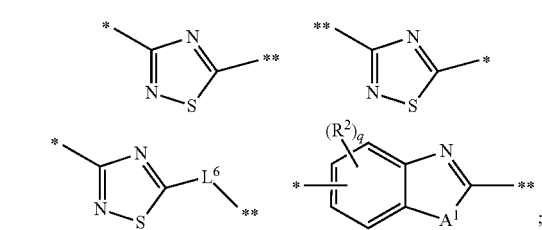

wherein * represents where $L^1$ is bound to $L^2$; and ** represents where $L^1$ is bound to the azetidine ring; and wherein,
$A^1$ is S;
q is 0;
L is —CO— or —SO$_2$—,
$R^4$ is selected from the group consisting $C_{6-12}$aryl, hydrogen, $C_{1-6}$alkyl, $C_{3-12}$cycloalkyl, heterocyclyl, heteroaryl, halo, hydroxyl, and cyano; and wherein said $C_{6-12}$aryl, $C_{1-6}$alkyl, $C_{3-12}$cycloalkyl, heterocyclyl, heteroaryl can be unsubstituted or substituted with one or more $Z^2$;
$L^2$ is a single bond or a group of formula (i);

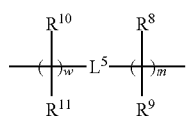
(i)

wherein the left side of the group of formula (i) is attached to $R^3$ and the right side thereof is attached to the nitrogen atom of the azetidine ring; and wherein,
m is an integer selected from 0, or 1;
w is an integer selected from 0, or 1;
$L^5$ is a single bond, or is selected from the group consisting of —O—, and —NR$^{12}$—;
$R^8$ is selected from the group consisting of hydrogen, $C_{1-6}$alkyl, and hydroxyl;
$R^9$ is selected from the group consisting of hydrogen, $C_{1-6}$alkyl, and hydroxyl;
or $R^8$ and $R^9$ together with the carbon atom to which they are attached from a saturated or 3-, 4-, or 5-carbon membered ring;
$R^{10}$ is selected from the group consisting of hydrogen, $C_{1-4}$alkyl, and hydroxyl;
$R^{11}$ is selected from the group consisting of hydrogen, $C_{1-4}$alkyl, and hydroxyl;
or $R^{10}$ and $R^{11}$ together with the carbon atom to which they are attached from a saturated 3-, 4-, or 5-carbons membered ring;
$R^{12}$ is hydrogen;
$L^3$ is —SO$_2$—;
$L^4$ is a single bond or is —(CR$^{15}$R$^{16}$)$_t$—; wherein;
t is an integer selected from 1, or 2;
$R^{15}$ is hydrogen, or $C_{1-4}$alkyl;
$R^{16}$ is hydrogen, or $C_{1-4}$alkyl;
or $R^{15}$ and $R^{16}$ together with the carbon atom to which they are attached form a saturated 3-, 4-, or 5-carbons membered ring;
wherein at least one of $L^3$, $L^4$ is not a single bond; and wherein when $L^4$ is a single bond, $R^4$ is not methyl;
each $Z^1$ is independently selected from the group consisting of haloC$_{1-6}$alkyloxy, —OR$^{18}$, halo, hydrogen, $C_{1-6}$alkyl, haloC$_{1-6}$alkyl, $C_{3-8}$cycloalkyl, $C_{6-12}$aryl, heterocyclyl, heteroaryl, hydroxyl, and cyano; wherein two $Z^1$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O;
each $Z^2$ is independently selected from the group consisting of haloC$_{1-6}$alkyloxy, —OR$^{18}$, halo, hydrogen, $C_{1-6}$alkyl, haloC$_{1-6}$alkyl, $C_{3-12}$cycloalkyl, $C_{6-12}$aryl, heterocyclyl, heteroaryl, hydroxyl, —SR$^{19}$, cyano, —CO$_2$R$^{22}$, —S(O)$_2$R$^{22}$, and —NR$^{23}$C(O)R$^{22}$; wherein two $Z^2$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O;
each $R^{18}$ is independently selected from the group consisting of $C_{1-6}$alkyl, and $C_{6-12}$aryl;
each $R^{19}$ is independently selected from the group consisting of hydrogen, $C_{1-6}$alkyl, and $C_{6-12}$aryl;
each $R^{22}$ is independently selected from the group consisting of hydrogen, hydroxyl, $C_{1-6}$alkyl, and $C_{6-12}$aryl;
each $R^{23}$ is independently selected from the group consisting of hydrogen, $C_{1-6}$alkyl, $C_{6-12}$aryl, and $C_{3-8}$cycloalkyl.

156. The compound according to any one of statements 1 to 155, wherein, n is 0;
$R^3$ is selected from the group consisting of $C_{6-12}$aryl, hydrogen, $C_{1-6}$alkyl, $C_{3-12}$cycloalkyl, heterocyclyl, heteroaryl, and halo; wherein said $C_{6-12}$aryl, $C_{1-6}$alkyl, $C_{3-12}$cycloalkyl, heterocyclyl, heteroaryl can be unsubstituted or substituted with one, two or three $Z^1$;
$L^1$ is selected from the group consisting of —SO$_2$—, —CO—,

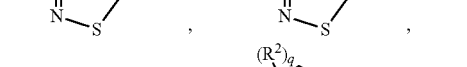

wherein * represents where $L^1$ is bound to $L^2$; and ** represents where $L^1$ is bound to the azetidine ring; and wherein,
$A^1$ is S;
q is 0;
$L^6$ is —CO— or —SO$_2$—;
$R^4$ is selected from the group consisting $C_{6-12}$aryl, hydrogen, $C_{1-6}$alkyl, $C_{3-12}$cycloalkyl, heterocyclyl, and heteroaryl; and wherein said $C_{6-12}$aryl, $C_{1-6}$alkyl, $C_{3-12}$cycloalkyl, heterocyclyl, heteroaryl can be unsubstituted or substituted with one, two or three $Z^2$;
$L^2$ is a single bond or a group of formula (i);

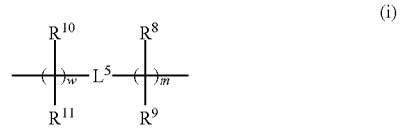
(i)

wherein the left side of the group of formula (i) is attached to $R^3$ and the right side thereof is attached to the nitrogen atom of the azetidine ring; and wherein,
m is 0, or 1;
w is 0, or 1;
$L^5$ is a single bond, or is selected from the group consisting of —O—, and —NH—;
$R^8$ is selected from the group consisting of hydrogen, $C_{1-3}$alkyl, and hydroxyl;
$R^9$ is selected from the group consisting of hydrogen, $C_{1-3}$alkyl, and hydroxyl;

or R$^8$ and R$^9$ together with the carbon atom to which they are attached from a saturated or 3-, 4-, or 5-carbons membered ring;
R$^{10}$ is selected from the group consisting of hydrogen, C$_{1-3}$alkyl, and hydroxyl;
R$^{11}$ is selected from the group consisting of hydrogen, C$_{1-3}$alkyl, and hydroxyl;
or R$^{10}$ and R$^{11}$ together with the carbon atom to which they are attached from a saturated 3-, 4-, or 5-carbons membered ring;
L$^3$ is —SO$_2$—;
L$^4$ is a single bond or is —(CR$^{15}$R$^{16}$)$_t$—; wherein, t is an integer selected from 1, or 2;
R$^{15}$ is hydrogen, or C$_{1-2}$alkyl;
R$^{16}$ is hydrogen, or C$_{1-2}$alkyl;
or R$^{15}$ and R$^{16}$ together with the carbon atom to which they are attached form a saturated 3-, 4-, or 5-carbons membered ring;
wherein at least one of L$^3$, L$^4$ is not a single bond; and wherein when L$^4$ is a single bond, R$^4$ is not methyl;
each Z$^1$ is independently selected from the group consisting of haloC$_{1-6}$alkyloxy, —OR$^{18}$, halo, hydrogen, C$_{1-6}$alkyl, haloC$_{1-6}$alkyl, and cyano; wherein two Z$^1$ together with the atom to which they are attached can form a saturated or unsaturated 5-, or 6-membered ring;
each Z$^2$ is independently selected from the group consisting of haloC$_{1-6}$alkyloxy, —OR$^{18}$, halo, hydrogen, C$_{1-6}$alkyl, haloC$_{1-6}$alkyl, C$_{3-12}$cycloalkyl, —SR$^{19}$, cyano, —CO$_2$R$^{22}$, —S(O)$_2$R$^{22}$, and —NR$^{23}$C(O)R$^{22}$; wherein two Z$^2$ together with the atom to which they are attached can form a saturated or unsaturated 5-, or 6-membered ring;
each R$^{18}$ is independently selected from the group consisting of C$_{1-4}$alkyl, and phenyl;
each R$^{19}$ is independently selected from the group consisting of hydrogen, C$_{1-4}$alkyl, and phenyl;
each R$^{22}$ is independently selected from the group consisting of hydrogen, hydroxyl, and C$_{1-4}$alkyl;
each R$^{23}$ is independently selected from the group consisting of hydrogen, and C$_{1-4}$alkyl.

157. The compound according to any one of statements 1 to 156, wherein the group heteroaryl is selected from a group comprising 5 to 12 carbon-atom aromatic rings or ring systems containing 1 or 2 rings which can be fused together or linked covalently, typically containing 5 to 6 atoms; at least one of which is aromatic in which one or more carbon atoms in one or more of these rings can be replaced by N, O and/or S atoms where the N and S heteroatoms may optionally be oxidized and the N heteroatoms may optionally be quaternized, wherein said rings may be fused to an aryl, cycloalkyl, heteroaryl or heterocyclyl ring; and wherein at least one carbon atom of said heteroaryl can be oxidized to form at least one C=O.

158. The compound according to any one of statements 1 to 157, wherein the group heteroaryl is selected from the group comprising pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, imidazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl; and wherein at least one carbon atom of said heteroaryl can be oxidized to form at least one C=O.

159. The compound according to any one of statements 1 to 158, wherein the group heteroaryl is selected from the group comprising pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, indolizinyl, isoindolyl, benzofuranyl, isobenzofuranyl, benzothiophenyl, isobenzothiophenyl, imidazolyl, benzimidazolyl, 1,3-benzoxazolyl, 1,2-benzisoxazolyl, 2,1-benzisoxazolyl, 1,3-benzothiazolyl, 12-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, purinyl, 1,3-benzodioxolyl; and wherein at least one carbon atom of said heteroaryl can be oxidized to form at least one C=O.

160. The compound according to any one of statements 1 to 159, wherein said heteroaryl group is selected from the group consisting of pyridyl, 1,3-benzodioxolyl, benzo[d]oxaol-2(3H)-one, 2,3-dihydro-benzofuranyl, pyrazinyl, pyrazolyl, pyrrolyl, isoxazolyl, thiophenyl imidazolyl, benzimidazolyl, pyrimidinyl, triazolyl and thiazolyl; and wherein at least one carbon atom of said heteroaryl can be oxidized to form at least one C=O.

161. The compound according to any one of statements 1 to 160, wherein the group heterocyclyl is selected from the group comprising non-aromatic, fully saturated or partially unsaturated cyclic groups which have at least one heteroatom in at least one carbon atom-containing ring; preferably the group heterocyclyl is selected comprising non-aromatic, fully saturated or partially unsaturated cyclic groups which have at least one heteroatom in at least one carbon atom-containing ring, wherein said ring may be fused to an aryl, cycloalkyl, heteroaryl or heterocyclyl ring; wherein each ring of the heterocyclyl group containing a heteroatom may have 1, 2, 3 or 4 heteroatoms selected from N, O and/or S, where the N and S heteroatoms may optionally be oxidized and the N heteroatoms may optionally be quaternized; and wherein at least one carbon atom of heterocyclyl can be oxidized to form at least one C=O.

162. The compound according to any one of statements 1 to 161, wherein the group heterocyclyl is selected from the group comprising aziridinyl, oxiranyl, thiiranyl, piperidinyl, azetidinyl, oxetanyl, pyrrolidinyl, thietanyl, 2-imidazolinyl, pyrazolidinyl imidazolidinyl, isoxazolinyl, oxazolidinyl, isoxazolidinyl, thiazolidinyl, isothiazolidinyl, piperidinyl, chromanyl, succinimidyl, 3H-indolyl, indolinyl, isoindolinyl, 2H-pyrrolyl, 1-pyrrolinyl, 2-pyrrolinyl, 3-pyrrolinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioxoimidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl; and wherein at least one carbon atom of heterocyclyl can be oxidized to form at least one C=O.

163. The compound according to any one of statements 1 to 162, wherein said compound is selected from the group consisting of 2,7-Bis((4-methoxyphenyl)sulfonyl)-2,7-diazaspiro[3.5]nonane; 2-((4-Fluorophenyl)sulfonyl)-7-((4-methoxyphenyl)sulfonyl)-2,7-diazaspiro[3.5]nonane; 2-((4-(Difluoromethoxy)phenyl)sulfonyl)-7-((4-methoxyphenyl)sulfonyl)-2,7-diazaspiro[3.5]nonane; 7-((4-Methoxyphenyl)sulfonyl)-2-((4-propoxyphenyl)sulfonyl)-2,7-diazaspiro[3.5]nonane; 2-((4-Chlorophenyl)sulfonyl)-7-((4-methoxyphenyl)sulfonyl)-2,7-diazaspiro[3.5]nonane; 2-(4-Fluorophenyl) 1-(7-((4-methoxyphenyl)sulfonyl)-2,7-diazaspiro[3.5]nonan-2-yl)ethanone; (4-Chlorophenyl)(7-((4-methoxyphenyl)sulfonyl)-2,7-diazaspiro[3.5]nonan-2-yl)methanone; (3,4-Difluorophenyl)7-((4-methoxyphenyl)sulfonyl)-2,7-diazaspiro[3.5]nonan-2-yl)methanone; (4-Fluorophenyl)(7-((4-methoxyphenyl)sulfonyl)-2,7-diazaspiro[3.5]nonan-2-yl)methanone; 1-(7-((4-Methoxyphenyl)sulfonyl)-2,7-diazaspiro[3.5]nonan-2-yl)-2-phenylethanone; 1-(7-((4-Methoxyphenyl)sulfonyl)-2,7-diazaspiro[3.5]nonan-2-yl)-2-phenylbutan-1-one; 4,4,4-Trifluoro-1-(7-((4-methoxyphenyl)sulfonyl)-2,7-diazaspiro[3.5]nonan-2-yl)butan-1-one; 1-(7-((4-Methoxyphenyl)sulfonyl)-2,7-diazaspiro[3.5]nonan-2-yl)-2-methyl-2-phenylpropan-1-one; (7-((4-Methoxyphenyl)sulfonyl)-2,7-diazaspiro[3.5]nonan-2-yl(1-phenylcyclopropyl)methanone; 3-(4-Fluorophenyl)-1-(7-((4-methoxyphenyl)sulfonyl)-2,7-diazaspiro[3.5]nonan-2-yl)propan-1-one; 2-(3-Methoxyphenyl)-1-(7-((4-methoxyphenyl)sulfonyl)-2,7-diazaspiro[3.5]nonan-2-yl)-2-methylpropan-1-one; 1-(7-((4-Methoxyphenyl)sulfonyl)-2,7-diazaspiro[3.5]nonan-2-yl)$_2$-methyl-2-(pyridin-3-ylmethoxy)propan-1-one; 2-Hydroxy-1-(7-((4-methoxyphenyl)sulfonyl)-2,7-diazaspiro[3.5]nonan-2-yl)-2-(pyridin-2-yl)propan-1-one; 2-(4-Methoxyphenyl)-1-(7-((4-methoxyphenyl)sulfonyl)-2,7-diazaspiro[3.5]nonan-2-yl)propan-1-one; 1-(7-((4-Methoxyphenyl)sulfonyl)-2,7-diazaspiro[3.5]nonan-2-yl)-2-methyl-2-(o-tolyl)propan-1-one; Chroman-4-yl(7-((4-methoxyphenyl)sulfonyl)-2,7-diazaspiro[3.5]nonan-2-yl)methanone; (S)-2-(4-Fluorophenyl)-1-(7-((4-methoxyphenyl)sulfonyl)-2,7-diazaspiro[3.5]nonan-2-yl-3-methylbutan-1-one; 2-(2-Methoxyphenyl)-1-(7-((4-methoxyphenyl)sulfonyl)-2,7-diazaspiro[3.5]nonan-2-yl)propan-1-one; 2-(2-Methoxyphenyl)-1-(7-((4-methoxyphenyl)sulfonyl)-2,7-diazaspiro[3.5]nonan-2-yl)-2-methylpropan-1-one; (7-((4-Methoxyphenyl)sulfonyl)-2,7-diazaspiro[3.5]nonan-2-yl)(1,2,3,4-tetrahydronaphthalen-1-yl)methanone; 2-(4-Chlorophenyl)-1-(7-((4-methoxyphenyl)sulfonyl)-2,7-diazaspiro[3.5]nonan-2-yl)propan-1-one; 2-(4-Chlorophenyl)-1-(7-((4-methoxyphenyl)sulfonyl)-2,7-diazaspiro[3.5]nonan-2-yl)-2-methylpropan-1-one; (7-((4-Methoxyphenyl)sulfonyl)-2,7-diazaspiro[3.5]nonan-2-yl)(1-phenylcyclopentyl)methanone; 2-(3,5-Difluorophenyl)-1-(7-((4-methoxyphenyl)sulfonyl)-2,7-diazaspiro[3.5]nonan-2-yl)propan-1-one; 2-(3-Chlorophenyl)-1-(7-((4-methoxyphenyl)sulfonyl)-2,7-diazaspiro[3.5]nonan-2-yl)-2-methylpropan-1-one; 5-(7-((4-Methoxyphenyl)sulfonyl)-2,7-diazaspiro[3.5]nonan-2-yl)-3-(2,2,2-trifluoroethyl)-1,2,4-thiadiazol; 3-(4-Chlorobenzyl)-5-(7-((4-methoxyphenyl)sulfonyl)-2,7-diazaspiro[3.5]nonan-2-yl)-1,2,4-thiadiazole; 3-(3,4-Difluorobenzyl)-5-(7-((4-methoxyphenyl)sulfonyl)-2,7-diazaspiro[3.5]nonan-2-yl)-1,2,4-thiadiazole; 3-Cyclopropyl-5-(7-((4-methoxyphenyl)sulfonyl)-2,7-diazaspiro[3.5]nonan-2-yl)-1,2,4-thiadiazole; 3-Butyl-5-(7-((4-methoxyphenyl)sulfonyl)-2,7-diazaspiro[3.5]nonan-2-yl)-1,2,4-thiadiazole; 5-(7-((4 Methoxyphenyl)sulfonyl)-2,7-diazaspiro[3.5]nonan-2-yl)-3-(3-(trifluoromethyl)benzyl)-1,2,4-thiadiazole; 3-(4-Methoxyphenyl)-5-(7-((4-methoxyphenyl)sulfonyl)-2,7-diazaspiro[3.5]nonan-2-yl)-1,2,4-thiadiazole; 5-(7-((4-Methoxyphenyl)sulfonyl)-2,7-diazaspiro[3.5]nonan-2-yl)-3-(pyrazin-2-yl)-1,2,4-thiadiazole; 3-(4-Chlorophenyl)-5-(7-((4-methoxyphenyl)sulfonyl)-2,7-diazaspiro[3.5]nonan-2-yl)-1,2,4-thiadiazole; 3-(1-(4-Fluorophenyl)cyclopropyl)-5-(7-((4-methoxyphenyl)sulfonyl)-2,7-diazaspiro[3.5]nonan-2-yl)-1,2,4-thiadiazole; 3-(4-Fluorobenzyl)-5-(7-((4-(methylthio)phenyl)sulfonyl)-2,7-diazaspiro[3.5]nonan-2-yl)-1,2,4-thiadiazole; 7-((4-(Difluoromethoxy)phenyl)sulfonyl)-2-((4-ethoxyphenyl)sulfonyl)-2,7-diazaspiro[3.5]nonane; 2-((4-Chlorophenyl)sulfonyl)-7-((4-(difluoromethoxy)phenyl)sulfonyl)-2,7-diazaspiro[3.5]nonane; 7-((4-(Difluoromethoxy)phenyl)sulfonyl)-2-((4-fluorophenyl)sulfonyl)-2,7-diazaspiro[3.5]nonane; 7-((4-(Difluoromethoxy)phenyl)sulfonyl)-2-((4-methoxyphenyl)sulfonyl)-2,7-diazaspiro[3.5]nonane; 7-((4-Ethoxyphenyl)sulfonyl)-2-((4-methoxyphenyl)sulfonyl)-2,7-diazaspiro[3.5]nonane; 7-((4-Chlorophenyl)sulfonyl)-2-((4-methoxyphenyl)sulfonyl)-2,7-diazaspiro[3.5]nonane; 2,7-Bis((4-(difluoromethoxy)phenyl)sulfonyl)-2,7-diazaspiro[3.5]nonane; 2-((4-(Difluoromethoxy)phenyl)sulfonyl)-7-((4-ethoxyphenyl)sulfonyl)-2,7-diazaspiro[3.5]nonane; 7-((4-Chlorophenyl)sulfonyl)-2-((4-(difluoromethoxy)phenyl)sulfonyl)-2,7-diazaspiro[3.5]nonane; 2-((4-(Difluoromethoxy)phenyl)sulfonyl)-7-((4-fluorophenyl)sulfonyl)-2,7-diazaspiro[3.5]nonane; 6-Chloro-2-(7-((4-methoxyphenyl)sulfonyl)-2,7-diazaspiro[3.5]nonan-2-yl)benzo[d]thiazole; 6-Chloro-2-(7-((4-ethoxyphenyl)sulfonyl)-2,7-diazaspiro[3.5]nonan-2-yl)benzo[d]thiazole; 6-Chloro-2-(7-((4-(difluoromethoxy)phenyl)sulfonyl)-2,7-diazaspiro[3.5]nonane-2-yl)benzo[d]thiazole; 6-Chloro-2-(7-((4-(methylthio)phenyl)sulfonyl)-2,7-diazaspiro[3.5]nonane-2-yl)benzo[d]thiazole; 3-(1-(4-Fluorophenyl)ethyl)-5-(7-((4-methoxyphenyl)sulfonyl)-2,7-diazaspiro[3.5]nonan-2-yl)-1,2,4-thiadiazole; 3-(4-Fluorobenzyl)-5-(7-((4-methoxyphenyl)sulfonyl)-2,7-diazaspiro[3.5]nonan-2-yl)-1,2,4-thiadiazole; N-(4-((2-(3-(4-fluorobenzyl)-1,2,4-thiadiazol-5-yl)-2,7-diazaspiro[3.5]nonan-7-yl)sulfonyl)phenyl)acetamide; 3-(4-Fluorobenzyl)-5-(7-((4-(methylsulfonyl)phenyl)sulfonyl)-2,7-diazaspiro[3.5]nonan-2-yl)-1,2,4-thiadiazole; 5-(7-((4-Difluorophenyl)sulfonyl)-2,7-diazaspiro[3.5]nonan-2-yl)-3-(4-fluorobenzyl)-1,2,4-thiadiazole; 5-(7-((3,4-Dimethoxyphenyl)sulfonyl)-2,7-diazaspiro[3.5]nonan-2-yl)-3-(4-fluorobenzyl)-1,2,4-thiadiazole; 3-(4-Fluorobenzyl)-5-(7-((2-methoxy-5-methylphenyl)sulfonyl)-2,7-diazaspiro[3.5]nonan-2-yl)-1,2,4-thiadiazole; 5-(7-((5-Chloro-2-methoxyphenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-(trifluoromethyl)phenyl)sulfonyl)-2,7-diazaspiro[3.5]

nonan-2-yl)-1,2,4-thiadiazole; 3-(4-Fluorobenzyl)-5-(7-((4-(trifluoromethyl)phenyl)sulfonyl)-2,7-diazaspiro[3.5]nonan-2-yl)-1,2,4-thiadiazole; 3-(4-Fluorobenzyl)-5-(7-(m-tolylsulfonyl)-2,7-diazaspiro[3.5]nonan-2-yl)-1,2,4-thiadiazole; 3-(4-Fluorobenzyl)-5-(7-((2-fluorophenyl)sulfonyl)-2,7-diazaspiro[3.5]nonan-2-yl)-1,2,4-thiadiazole; 5-(7-((4-Ethylphenyl)sulfonyl)-2,7-diazaspiro[3.5]nonan-2-yl)-3-(4-fluorobenzyl)-1,2,4-thiadiazole; 3-(4-Fluorobenzyl)-5-(7-(o-tolylsulfonyl)-2,7-diazaspiro[3.5]nonan-2-yl)-1,2,4-thiadiazole; 5-(7-((4-(Tert-butyl)phenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-fluorophenyl)sulfonyl)-2,7-diazaspiro[3.5]nonan-2-yl)-1,2,4-thiadiazole; 5-(7-((2,5-Dimethoxyphenyl)sulfonyl)-2,7-diazaspiro[3.5]nonan-2-yl)-3-(4-fluorobenzyl)-1,2,4-thiadiazole; 5-(7-((2,5-Difluorophenyl)sulfonyl)-2,7-diazaspiro[3.5]nonan-2-yl)-3-(4-fluorobenzyl)-1,4-thiadiazole; 5-(7-((2,6-Difluorophenyl)sulfonyl)-2,7-diazaspiro[3.5]nonan-2-yl)-3-(4-fluorobenzyl)-1,2,4-thiadiazole; 5-(7-((3,4-Difluorophenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-methoxyphenyl)sulfonyl)-2,7-diazaspiro[3.5]nonan-2-yl)-1,2,4-thiadiazole; 5-(7-((5-Fluoro-2-methylphenyl)sulfonyl)-2,7-diazaspiro[3.5]nonan-2-yl)-3-(4-fluorobenzyl)-1,2,4-thiadiazole; 2-Ethoxy-5-((2-(3-(4-fluorobenzyl)-1,2,4-thiadiazol-5-yl)-2,7-diazaspiro[3.5]nonan-7-yl)sulfonyl)benzonitrile; 3-(4-Fluorobenzyl)-5-(7-((4-methoxy-3-(fluoromethyl)phenyl)sulfonyl)-2,7-diazaspiro[3.5]nonan-2-yl)-1,2,4-thiadiazole; 3-(4-Fluorobenzyl)-5-(7-((2-methoxyphenyl)sulfonyl)-2,7-diazaspiro[3.5]nonan-2-yl)-1,2,4-thiadiazole; 5-(7-((3-Chloro-4-methoxyphenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-(methylsulfonyl)phenyl)sulfonyl)-2,7-diazaspiro[3.5]nonan-2-yl)-1,2,4-thiadiazole; 5-(7-((3-Difluorophenyl)sulfonyl)-2,7-diazaspiro[3.5]nonan-2-yl)-3-(4-fluorobenzyl)-1,2,4-thiadiazole; Methyl 3-((2-(3-(4-fluorobenzyl)-1,2,4-thiadiazol-5-yl)-2,7-diazaspiro[3.5]nonan-7-sulfonyl)benzoate; 5-(7-((4-(Difluoromethoxy)phenyl)sulfonyl)-2,7-diazaspiro[3.5]nonan-2-yl)-3-(4-fluorobenzyl)-1,2,4-thiadiazole; 5-(7-((5-Fluoro-2-methoxyphenyl)sulfonyl)-2,7-diazaspiro[3.5]nonan-2-yl)-3-(4-fluorobenzyl)-1,2,4-thiadiazole; 5-(7-((4-Ethoxy-3-methylphenyl)sulfonyl)-2,7-diazaspiro[3.5]nonan-2-yl)-3-(4-fluorobenzyl)-1,2,4-thiadiazole; 3-(4-Fluorobenzyl)-5-(7-((4-methoxy-3-methylphenyl)sulfonyl)-2,7-diazaspiro[3.5]nonan-2-yl)-1,2,4-thiadiazole; 3-(4-Fluorobenzyl)-5-(7-(pyridin-3-ylsulfonyl)-2,7-diazaspiro[3.5]nonan-2-yl)-1,2,4-thiadiazole; 3-(4-Fluorobenzyl)-5-(7-((1-methyl-1H-pyrazol-4-yl)sulfonyl)-2,7-diazaspiro[3.5]nonan-2-yl)-1,2,4-thiadiazole; 4-((2-(3-(4-Fluorobenzyl)-1,2,4-thiadiazol-5-yl)-2,7-diazaspiro[3.5]nonan-7-yl)sulfonyl)-3,5-dimethylisoxazole; 3-(4-Fluorobenzyl)-5-(7-(thiophen-2-ylsulfonyl)-2,7-diazaspiro[3.5]nonan-2-yl)-1,2,4-thiadiazole; 5-(7-((5-Chlorothiophen-2-yl)sulfonyl)-2,7-diazaspiro[3.5]nonan-2-yl)-3-(4-fluorobenzyl)-1,2,4-thiadiazole, 3-(4-Fluorobenzyl)-5-(7-(thiophen-3-ylsulfonyl)-2,7-diazaspiro[3.5]nonan-2-yl)-1,2,4-thiadiazole; 3-(4-Fluorobenzyl)-5-(7-((5-methylthiophen-2-yl)sulfonyl)-2,7-diazaspiro[3.5]nonan-2-yl)-1,2,4-thiadiazole; 3-(4-Fluorobenzyl)-5-(7-((3,3,3-trifluoropropyl)sulfonyl)-2,7-diazaspiro[3.5]nonan-2-yl)-1,2,4-thiadiazole; 5-(7-(((Cyclohexylmethyl)sulfonyl)-2,7-diazaspiro[3.5]nonan-2-yl)-3-(4-fluorobenzyl)-1,2,4-thiadiazole; 4-((2-(3-(4-Fluorobenzyl)-1,2,4-thiadiazol-5-yl)-2,7-diazaspiro[3.5]nonan-7-yl)sulfonyl)morpholine; and a solvate, hydrate, pharmaceutically acceptable salt thereof.

164. A pharmaceutical composition comprising one or more pharmaceutically excipients and a therapeutically effective amount of a compound according to any one of statements 1 to 163, or a therapeutically effective amount of a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof.

165. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide N-(4-methoxyphenyl)-7-(phenylsulfonyl)-2,7-diazaspiro[3.5]nonane-2-carboxamide; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicament.

166. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diazaspiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof or a pharmaceutical composition according to statement 164, for use as a medicine for the prevention and/or treatment of metabolic disorders and/or neurodegenerative diseases and/or protein misfolding disorders.

167. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-melhoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof or a pharmaceutical composition according to statement 164, for use as a medicine for the prevention and/or treatment of diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension.

168. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicine for the prevention and/or treatment of diabetes mellitus, Parkinson's disease and/or Alzheimer's disease.

169. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicine for the prevention and/or treatment of diabetes mellitus type 1, diabetes mellitus type 2, Parkinson's disease and/or Alzheimer's disease.

170. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicine for the prevention and/or treatment of type-2 diabetes, Parkinson's disease and/or Alzheimer's disease.

171. A compound according to any one of statements 1 to 163, or a compound selected from the group consisting of N-(1-methylsulfonyl)-7-(phenylsulfonyl)-2,7-diazaspiro[3.5]nonan-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicine for the prevention and/or treatment of diabetes mellitus.

172. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diazaspiro[3.5]nonane-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxainide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicine for the prevention and/or treatment of Parkinson's disease.

173. A compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, for use as a medicine for the prevention and/or treatment of protein misfolding disorders.

174. A method of treatment of metabolic disorders and/or neurodegenerative diseases and/or protein misfolding disorders, comprising administering an effective amount of a compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaz-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164.

175. A method of prevention and/or of treatment of diabetes mellitus. Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension, comprising administering to a subject in need thereof an effective amount of a compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164.

176. A method of prevention and/or of treatment of diabetes mellitus, Parkinson's disease and/or Alzheimer's disease, comprising administering an effective amount of a compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, to a subject in need thereof.

177. A method of prevention and/or of treatment of diabetes mellitus type 1, diabetes mellitus type 2, Parkinson's disease and/or Alzheimer's disease, comprising administering an effective amount of a compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorphenyl)-7-(methylsulfonyl)-2,7-diazaspiro[3.5]nonane-2-carboxamide, and a solvate, hydrate, or pharmaceutically acceptable salt thereof or a pharmaceutical composition according to statement 164, to a subject in need thereof.

178. A method of prevention and/or of treatment of diabetes mellitus type 2, Parkinson's disease and/or Alzheimer's disease, comprising administering an effective amount of a compound according to any one of statements 1 to 163, or a compound selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide; (1H-benzotriazol-5-yl)-{7-[2-(3-chloro-phenyl)-ethanesulfonyl]-2,7-diaza-spiro[3.5]non-2-yl}-methanone; N-(4-methoxyphenyl)-7-(methylsulfonyl)-2,7-diazaspiro[3.5]nonane-2-carboxamide; N-(3-cyanophenyl)-7-(methylsulfonyl)-2,7-diazaspiro[3.5]nonane-2-carboxamide; 7-(methylsulfonyl)-N-phenyl-2,7-diazaspiro[3.5]nonane-2-carboxamide; N-(3-fluorophenyl)-7-(methylsulfonyl)-2,7-diazaspiro[3.5]nonane-2-carboxamide, and a solvate, hydrate, or pharmaceutically acceptable salt thereof, or a pharmaceutical composition according to statement 164, to a subject in need thereof.

According to an embodiment, the present invention provides compounds of formula (I), and any subgroup thereof such as (IA), (IB), (IC), (ID), (IE), (IF), wherein, n is an integer selected from 0, 1, 2 or 3; preferably n is 0, 1 or 2; more preferably n is 0 or 1; yet more preferably n is 0;

$R^1$ is selected from the group consisting of $C_{1-6}$alkyl, halo, halo$C_{1-6}$alkyl, and halo$C_{1-6}$ alkyloxy; preferably $R^1$ is selected from the group consisting of $C_{1-6}$alkyl, halo, and halo$C_{1-6}$alkyl; preferably $R^1$ is $C_{1-6}$alkyl, or halo; preferably $R^1$ is $C_{1-6}$alkyl;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$; preferably $R^3$ is selected from the group consisting of $C_{6-12}$aryl, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$; preferably $R^3$ is selected from the group consisting of $C_{6-12}$aryl, hydrogen, $C_{1-6}$alkyl, $C_{3-12}$cycloalkyl, heterocyclyl, heteroaryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, can be unsubstituted or substituted with one or more $Z^1$; preferably $R^3$ is selected from the group consisting of $C_{6-12}$aryl, $C_{1-6}$alkyl, $C_{3-12}$cycloalkyl, heterocyclyl, heteroaryl, halo, hydroxyl, —$OR^{18}$, halo$C_{1-6}$alkyl, halo$C_{1-6}$alkyloxy, and cyano; wherein said $C_{6-12}$aryl, $C_{1-6}$alkyl, $C_{3-12}$cycloalkyl, heterocyclyl, heteroaryl, can be unsubstituted or substituted with one, two or three $Z^1$; preferably $R^3$ is selected from the group consisting of $C_{6-12}$aryl, $C_{1-6}$alkyl, $C_{3-12}$cycloalkyl, heterocyclyl, heteroaryl, halo, —$OR^{18}$, halo$C_{1-6}$alkyl, and halo$C_{1-6}$alkyloxy; wherein said $C_{6-12}$aryl, $C_{1-6}$alkyl, $C_{3-12}$cycloalkyl, heterocyclyl, heteroaryl, can be unsubstituted or substituted with one, two or three $Z^1$; preferably $R^3$ is selected from the group consisting of $C_{6-12}$aryl, $C_{1-6}$alkyl, $C_{3-6}$cycloalkyl, heteroaryl, halo, and halo$C_{1-6}$alkyl; wherein said $C_{6-12}$aryl, $C_{1-6}$alkyl, $C_{3-12}$cycloalkyl, heterocyclyl, heteroaryl can be unsubstituted or substituted with one, two or three $Z^1$;

$L^1$ is selected from the group consisting of —$SO_2$—, —CO—,

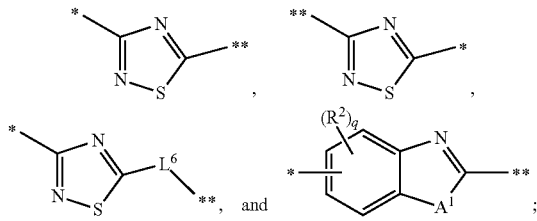

preferably $L^1$ is selected from the group consisting of —$SO_2$—, —CO—

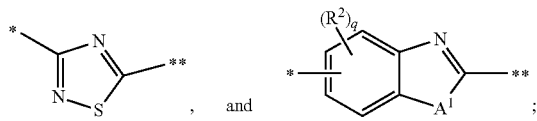

wherein * represents where $L^1$ is bound to $L^2$; and ** represents where $L^1$ is bound to the azetidine ring; and wherein, $A^1$ is S or O; preferably $A^1$ is S;

$L^6$ is —CO— or —$SO_2$—, q is an integer selected from 0, 1, 2, or 3; preferably q is selected from 0, 1, or 2; preferably q is selected from 0, or 1; preferably q is 0;

each $R^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heteroaryl, hydroxyl, $SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$; wherein two $R^2$ together with the atom to which they are attached can form a saturated or unsaturated 5-, 6-, or 7-membered ring; and wherein at least one carbon atom or heteroatom of said ring, $C_{6-12}$aryl, $C_{3-8}$cycloalkyl, heterocyclyl, heteroaryl can be oxidized to form at least one C=O, C=S, N=O, N=S, S=O or $S(O)_2$; preferably each $R^2$ is independently selected from the group consisting of halo$C_{1-6}$alkyloxy, —$OR^{18}$, halo, hydrogen, $C_{1-6}$alkyl, and halo$C_{1-6}$alkyl; preferably each $R^2$ is independently selected from the group consisting of halo, hydrogen, $C_{1-6}$alkyl, and halo$C_{1-6}$alkyl; preferably each $R^2$ is independently hydrogen, or $C_{1-6}$alkyl; preferably each $R^2$ is independently hydrogen;

$R^4$ is selected from the group consisting $C_{6-12}$aryl, hydrogen, $C_{1-6}$alkyl, $C_{3-12}$cycloalkyl, heterocyclyl, heteroayl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano, and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$, preferably $R^4$ is selected from the group consisting $C_{6-12}$aryl, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$; preferably $R^4$ is selected from the group consisting $C_{6-12}$aryl, $C_{1-6}$alkyl, $C_{3-12}$cycloalkyl, heterocyclyl, heteroaryl, halo, hydroxyl, —$OR^{18}$, —$SR^{19}$, halo $C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, can be unsubstituted or substituted with one or more $Z^2$; preferably $R^4$ is selected from the group consisting $C_{6-12}$aryl, $C_{1-6}$alkyl, $C_{3-12}$cycloalkyl, heterocyclyl, heteroaryl, halo, hydroxyl, halo $C_{1-6}$alkyl, and halo$C_{1-6}$alkyloxy; and wherein said $C_{6-12}$aryl, $C_{1-6}$alkyl, $C_{3-12}$cycloalkyl, heterocyclyl, heteroaryl can be unsubstituted or substituted with one, two or three $Z^2$; preferably $R^4$ is selected from the group consisting $C_{6-12}$aryl, $C_{1-6}$alkyl, $C_{3-12}$cycloalkyl, heterocyclyl, and heteroaryl; and wherein said $C_{6-12}$aryl, $C_{1-6}$alkyl, $C_{3-12}$cycloalkyl, heterocyclyl, heteroaryl can be unsubstituted or substituted with one, two or three $Z^1$;

$L^2$ is a single bond or a group of formula (i);

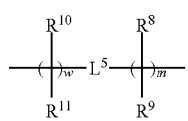

(i)

wherein the left side of the group of formula (i) is attached to $R^3$ and the right side thereof is attached to the nitrogen atom of the azetidine ring; and wherein, m is an integer selected from 0, 1, 2, or 3; preferably m is an integer selected from 0, 1, or 2; preferably m is an integer selected from 0, or 1;

w is an integer selected from 0, 1, 2 or 3; preferably n is selected from 0, 1, or 2; preferably n is selected from 0, or 1:

$L^5$ is a single bond, or is selected from the group consisting of —O—, and —$NR^{12}$—; preferably $L^5$ is a single bond, or is —O—;

$R^8$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy; preferably $R^8$ is selected from the group consisting of hydrogen, $C_{1-6}$alkyl, hydroxyl, halo$C_{1-6}$alkyl, and halo$C_{1-6}$alkyloxy; preferably $R^8$ is selected from the group consisting of hydrogen, $C_{1-6}$alkyl, hydroxyl; preferably $R^8$ is selected from the group consisting of hydrogen, $C_{1-4}$alkyl, and hydroxyl;

$R^9$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy; preferably $R^9$ is selected from the group consisting of hydrogen, $C_{1-6}$alkyl, hydroxyl, halo$C_{1-6}$alkyl, and halo$C_{1-6}$alkyloxy; preferably $R^9$ is selected from the group consisting of hydrogen, $C_{1-6}$alkyl, hydroxyl; preferably $R^9$ is selected from the group consisting of hydrogen, $C_{1-4}$alkyl, and hydroxyl;

or $R^8$ and $R^9$ together with the carbon atom to which they are attached from a saturated or unsaturated 3-, 4-, 5-, 6- or 7-membered ring; preferably $R^8$ and $R^9$ together with the carbon atom to which they are attached from a saturated 3-, 4-, 5-, or 6-membered ring; preferably $R^8$ and $R^9$ together with the carbon atom to which they are attached from a $C_{3-6}$cycloalkyl ring; preferably $R^8$ and $R^9$ together with the carbon atom to which they are attached from a $C_{3-5}$cycloalkyl ring;

$R^{10}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy; preferably $R^{10}$ is selected from the group consisting of hydrogen, $C_{1-6}$alkyl, hydroxyl, halo$C_{1-6}$alkyl, and halo$C_{1-6}$alkyloxy; preferably $R^{10}$ is selected from the group consisting of hydrogen, $C_{1-6}$alkyl, hydroxyl; preferably $R^{10}$ is selected from the group consisting of hydrogen, $C_{1-6}$alkyl, and hydroxyl;

$R^{11}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy; preferably $R^{11}$ is selected from the group consisting of hydrogen, $C_{1-6}$alkyl, hydroxyl, halo$C_{1-6}$alkyl, and halo$C_{1-6}$alkyloxy; preferably $R^{11}$ is selected from the group consisting of hydrogen, $C_{1-6}$alkyl, and hydroxyl; preferably $R^{11}$ is selected from the group consisting of hydrogen, $C_{1-4}$alkyl, and hydroxyl;

or $R^{10}$ and $R^{11}$ together with the carbon atom to which they are attached from a saturated or unsaturated 3-, 4-, 5-, 6- or 7-membered ring; preferably $R^{10}$ and $R^{11}$ together with the carbon atom to which they are attached from a saturated 3-, 4-, 5-, or 6-membered ring; preferably $R^{10}$ and $R^{11}$ together with the carbon atom to which they are attached from a $C_{3-6}$cycloalkyl ring; preferably $R^{10}$ and $R^{11}$ together with the carbon atom to which they are attached from a $C_{3-5}$cycloalkyl ring;

$R^{12}$ is selected from the group consisting of hydrogen, and $C_{1-6}$alkyl; preferably $R^{12}$ is hydrogen;

$L^3$ is selected from the group consisting of —$SO_2$—, —$PO_4$—, and —$PO_3$—; preferably $L^3$ is selected from the group consisting of —$SO_2$—, and —$PO_4$—; preferably $L^3$ is —$SO_2$—;

$L^4$ is a single bond or is selected from the group consisting of —$(CR^{15}R^{16})_t$—, —O—, and —$NR^{17}$—; preferably $L^4$ is a single bond or is —$(CR^{15}R^{16})_t$—; preferably $L^4$ is a single bond or is $C_{1-6}$alkylene; preferably $L^4$ is a single bond or is $C_{1-4}$alkylene; preferably $L^4$ is a single bond or is $C_{1-2}$alkylene; wherein, t is an integer selected from 1, 2 or 3, preferably t is 1 or 2;

$R^{15}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy; preferably $R^{15}$ is hydrogen, or $C_{1-6}$alkyl; preferably $R^{15}$ is hydrogen, or $C_{1-4}$alkyl, preferably $R^{15}$ is hydrogen, or $C_{1-2}$alkyl;

$R^{16}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy; preferably $R^{16}$ is hydrogen, or $C_{1-6}$alkyl; preferably $R^{16}$ is hydrogen, or $C_{1-4}$alkyl; preferably $R^{16}$ is hydrogen, or $C_{1-2}$alkyl;

or $R^{15}$ and $R^{16}$ together with the carbon atom to which they are attached form a saturated or unsaturated 3-, 4-, 5-, 6- or 7-membered ring; preferably $R^{15}$ and $R^{16}$ together with the carbon atom to which they are attached from a saturated 3-, 4-, 5-, or 6-membered ring; preferably $R^{15}$ and $R^{16}$ together with the carbon atom to which they are attached from a $C_{3-6}$cycloalkyl ring; preferably $R^{15}$ and $R^{16}$ together with the carbon atom to which they are attached from a $C_{3-8}$cycloalkyl ring;

$R^{17}$ is selected from the group consisting of hydrogen, and $C_{1-6}$alkyl; preferably $R^{17}$ is hydrogen;

wherein at least one of $L^3$, $L^4$ is not a single bond; and wherein when $L^4$ is a single bond, $R^4$ is not methyl;

each $R^{18}$ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyanoC$_{1-6}$alkyl can be oxidized to form at least one C=O, C=S, N=O, N=S, S=O or S(O)$_2$; preferably each R$^{18}$ is independently selected from the group consisting of C$_{1-6}$alkyl, C$_{6-12}$aryl, C$_{3-8}$cycloalkyl, heterocyclyl, and heteroaryl; wherein at least one carbon atom or heteroatom of said C$_{1-6}$alkyl, C$_{6-12}$aryl, C$_{3-8}$cycloalkyl, heterocyclyl, heteroayl can be oxidized to form at least one C=O, C=S, N=O, N=S, S=O or S(O)$_2$; preferably each R$^{18}$ is independently selected from the group consisting of C$_{1-6}$alkyl, C$_{6-12}$aryl, and C$_{3-8}$cycloalkyl; wherein at least one carbon atom or heteroatom of said C$_{1-6}$alkyl, C$_{6-12}$aryl, C$_{3-8}$cycloalkyl, can be oxidized to form at least one C=O, C=S, N=O, N=S, S=O or S(O)$_2$; preferably each R$^{18}$ is independently selected from C$_{1-6}$alkyl or C$_{6-12}$aryl; preferably each R$^{18}$ is independently C$_{1-6}$alkyl;

each R$^{19}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, heteroarylC$_{1-6}$alkyl, and cyanoC$_{1-6}$alkyl; wherein at least one carbon atom or heteroatom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, heteroarylC$_{1-6}$alkyl, or cyanoC$_{1-6}$alkyl can be oxidized to form at least one C=O, C=S, N=O, N=S, S=O or S(O)$_2$; preferably each R$^{19}$ is independently selected from the group consisting of hydrogen, C$_{1-6}$alkyl, C$_{6-12}$aryl, C$_{3-8}$cycloalkyl, heterocyclyl, and heteroaryl; wherein at least one carbon atom or heteroatom of said C$_{1-6}$alkyl, C$_{6-12}$aryl, C$_{3-8}$cycloalkyl, heterocyclyl, heteroaryl can be oxidized to form at least one C=O; preferably each R$^{19}$ is independently selected from the group consisting of hydrogen, C$_{1-6}$alkyl, C$_{6-12}$aryl, C$_{3-8}$cycloalkyl; wherein at least one carbon atom or heteroatom of said C$_{1-6}$alkyl, C$_{6-12}$aryl, C$_{3-8}$cycloalkyl, can be oxidized to form at least one C=O; preferably each R$^{19}$ is independently hydrogen, or C$_{1-6}$alkyl;

each R$^{20}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; wherein at least one carbon atom or heteroatom of said C$_{1-6}$alkyl, C$_{2-6}$alkynyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O, C=S, N=O, N=S, S=O or S(O)$_2$; preferably each R$^{20}$ is independently selected from the group consisting of hydrogen, C$_{1-6}$alkyl, C$_{6-12}$aryl, C$_{3-8}$cycloalkyl, heterocyclyl, heteroaryl; wherein at least one carbon atom or heteroatom of said C$_{1-6}$alkyl, C$_{6-12}$aryl, C$_{3-8}$cycloalkyl, heterocyclyl, heteroaryl can be oxidized to form at least one C=O; preferably each R$^{20}$ is independently selected from the group consisting of hydrogen, C$_{1-6}$alkyl, C$_{6-12}$aryl, C$_{3-8}$cycloalkyl; wherein at least one carbon atom or heteroatom of said C$_{1-6}$alkyl, C$_{6-12}$aryl, C$_{3-8}$cycloalkyl, can be oxidized to form at least one C=O; preferably each R$^{20}$ is independently hydrogen, or C$_{1-6}$alkyl;

each R$^{21}$ is independently selected from the group consisting of hydrogen, C$_{1-6}$alkyl, C$_{2-6}$alkenyl, C$_{2-4}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; wherein at least one carbon atom or heteroatom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O, C=S, N=O, N=S, S=O or S(O)$_2$; preferably each R$^{21}$ is independently selected from the group consisting of hydrogen, C$_{1-6}$alkyl, C$_{6-12}$aryl, C$_{3-8}$cycloalkyl, heterocyclyl, heteroaryl; wherein at least one carbon atom or heteroatom of said C$_{1-6}$alkyl, C$_{6-12}$aryl, C$_{3-8}$cycloalkyl, heterocyclyl, heteroaryl can be oxidized to form at least one C=O; preferably each R$^{21}$ is independently selected from the group consisting of hydrogen, C$_{1-6}$alkyl, C$_{6-12}$aryl, C$_{3-8}$cycloalkyl; wherein at least one carbon atom or heteroatom of said C$_{1-6}$alkyl, C$_{6-12}$aryl, C$_{3-8}$cycloalkyl, can be oxidized to form at least one C=O; preferably each R$^{21}$ is independently hydrogen, or C$_{1-6}$alkyl;

or wherein R$^{20}$ and R$^{21}$ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or S(O)$_2$; preferably R$^{20}$ and R$^{21}$ together with the nitrogen atom to which they are attached form a 5-, or 6-membered heterocyclyl; and wherein at least one carbon atom or heteroatom of said heterocyclyl can be oxidized to form at least one C=O, each R$^{22}$ is independently selected from the group consisting of hydrogen, hydroxyl, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; wherein at least one carbon atom or heteroatom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O, C=S, N=O, N=S, S=O or S(O)$_2$; preferably each R$^{22}$ is independently selected from the group consisting of hydrogen, hydroxyl, C$_{1-6}$alkyl, C$_{6-12}$aryl, C$_{3-8}$cycloalkyl, heterocyclyl, heteroaryl; wherein at least one carbon atom or heteroatom of said C$_{1-6}$alkyl, C$_{6-12}$aryl, C$_{3-8}$cycloalkyl, heterocyclyl, heteroaryl can be oxidized to form at least one C=O; preferably each R$^{22}$ is independently selected from the group consisting of hydrogen, hydroxyl, C$_{1-6}$alkyl, C$_{6-12}$aryl, C$_{3-8}$cycloalkyl; wherein at least one carbon atom or heteroatom of said C$_{1-6}$alkyl, C$_{6-12}$aryl, C$_{3-8}$cycloalkyl, can be oxidized to form at least one C=O; preferably each R$^{22}$ is independently selected from the group consisting of hydrogen, hydroxyl, and C$_{1-6}$alkyl;

each R$^{23}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; wherein at least one carbon atom or heteroatom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O, C=S, N=O, N=S, S=O or S(O)$_2$; preferably each R$^{23}$ is independently selected from the group consisting of hydrogen, C$_{1-6}$alkyl, C$_{6-12}$aryl, C$_{3-8}$cycloalkyl, heterocyclyl, heteroaryl; wherein at least one carbon atom or heteroatom of said C$_{1-6}$alkyl, C$_{6-12}$aryl, C$_{3-8}$cycloalkyl, heterocyclyl, heteroaryl can be oxidized to form at least one C=O; preferably each R$^{23}$ is independently selected from the group consisting of hydrogen, C$_{1-6}$alkyl, C$_{6-12}$aryl, C$_{3-8}$cycloalkyl; wherein at least one carbon atom or heteroatom of said C$_{1-6}$alkyl, C$_{6-12}$aryl, C$_{3-8}$cycloalkyl, can be oxidized to form at least one C=O; preferably each R$^{23}$ is independently hydrogen, or C$_{1-6}$alkyl;

each $R^{24}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene$C_{1-6}$alkylene*; wherein * represents where $R^{24}$ is bound to CO; wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, C=S, N=O, N=S, S=O or S(O)$_2$; preferably each $R^{24}$ is independently selected from the group consisting of $C_{1-6}$alkylene, $C_{6-12}$arylene, $C_{3-8}$cycloalkylene, heterocyclylene, heteroarylene; wherein at least one carbon atom or heteroatom of said $C_{1-6}$alkylene, $C_{6-12}$arylene, $C_{3-8}$cycloalkylene, heterocyclylene, heteroarylene can be oxidized to form at least one C=O; preferably each $R^{24}$ is independently selected from the group consisting of $C_{1-6}$alkylene, $C_{6-12}$arylene, $C_{3-8}$cycloalkylene; wherein at least one carbon atom or heteroatom of said $C_{1-6}$alkylene, $C_{6-12}$arylene, $C_{3-8}$cycloalkylene, can be oxidized to form at least one C=O; preferably each $R^{24}$ is independently $C_{1-6}$alkylene;

each $Z^1$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl, heteroaryl$C_{1-6}$alkyl, hydroxyl, —SR$^{19}$, cyano, amino, —NR$^{20}$R$^{21}$, —CO$_2$R$^{22}$, —C(O)NR$^{20}$R$^{21}$, —C(O)R$^{22}$, —S(O)R$^{22}$, —S(O)$_2$R$^{22}$, —SO$_2$NR$^{20}$R$^{21}$, nitro, —NR$^{23}$C(O)R$^{22}$, —R$^{24}$—C(O)NR$^{20}$R$^{21}$, —NR$^{23}$S(O)$_2$R$^{22}$, and —NR$^{23}$C(O)NR$^{20}$R$^{21}$; wherein two $Z^1$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl $C_{1-6}$alkyl can be oxidized to form at least one C=O, C=S, N=O, N=S, S=O or S(O)$_2$; preferably each $Z^1$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —SR$^{19}$, cyano, amino, —NR$^{20}$R$^{21}$, —CO$_2$R$^{22}$, —C(O)NR$^{20}$R$^{21}$, —S(O)$_2$R$^{22}$, —SO$_2$NR$^{20}$R$^{21}$, nitro, —NR$^{23}$C(O)R$^{22}$, —NR$^{23}$S(O)$_2$R$^{22}$, and —NR$^{23}$C(O)NR$^{20}$R$^{21}$; wherein two $Z^1$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O; preferably each $Z^1$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, hydroxyl, —SR$^{19}$, cyano, amino; preferably each $Z^1$ is independently selected from the group consisting of halo$C_{1-6}$alkyloxy, halo, hydrogen, $C_{1-6}$alkyl, halo$C_{1-6}$alkyl, hydroxyl, cyano, amino;

each $Z^2$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, $C_{6-12}$aryl $C_{1-6}$alkyl, heterocyclyl, heterocyclyl$C_{1-6}$alkyl, heteroaryl, heteroaryl$C_{1-6}$alkyl, hydroxyl, —SR$^{19}$, cyano, amino, —NR$^{20}$R$^{21}$, —CO$_2$R$^{22}$, —C(O)NR$^{20}$R$^{21}$, —C(O)R$^{22}$, —S(O)R$^{22}$, —S(O)$_2$R$^{22}$, —SO$_2$NR$^{20}$R$^{21}$, nitro, —NR$^{23}$C(O)R$^{22}$, —R$^{24}$C(O)NR$^{20}$R$^{21}$, —NR$^{23}$S(O)$_2$R$^{22}$, and NR$^{23}$C(O)NR$^{20}$R$^{21}$; wherein two $Z^2$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl $C_{1-6}$alkyl can be oxidized to form at least one C=O, C=S, N=O, N=S, S=O or S(O)$_2$; preferably each $Z^2$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —SR$^{19}$, cyano, amino, —NR$^{20}$R$^{21}$, —CO$_2$R$^{22}$, —C(O)NR$^{20}$R$^{21}$, —C(O)R$^{22}$, —S(O)R$^{22}$, —S(O)$_2$R$^{22}$, —SO$_2$NR$^{20}$R$^{21}$, nitro, —NR$^{23}$C(O)R$^{22}$, —R$^{24}$C(O)NR$^{20}$R$^{21}$, —NR$^{23}$S(O)$_2$R$^{22}$, and NR$^{23}$C(O)NR$^{20}$R$^{21}$; wherein two $Z^2$ together with the atom to which they are attached can form a saturated or unsaturated 5-, or 6-membered ring; and wherein at least one carbon atom or heteroatom of said $C_{1-6}$alkyl, $C_{6-12}$cycloalkyl, $C_{6-12}$aryl, heterocyclyl, heteroaryl can be oxidized to form at least one C=O; preferably each $Z^2$ is independently selected from the group consisting of halo $C_{1-6}$alkyloxy, —OR$^{18}$, halo, hydrogen, $C_{1-6}$alkyl, halo $C_{1-6}$alkyl, $C_{3-12}$cycloalkyl, $C_{6-12}$aryl, hydroxyl, —SR$^{19}$, cyano, amino, —NR$^{20}$R$^{20}$, —CO$_2$R$^{22}$, —C(O)NR$^{20}$R$^{21}$, —C(O)R$^{22}$, —S(O)R$^{22}$, —S(O)$_2$R$^{22}$, —SO$_2$NR$^{20}$R$^{21}$, nitro, and —NR$^{23}$C(O)R$^{22}$; preferably each $Z^2$ is independently selected from the group consisting of halo $C_{1-6}$alkyloxy, —OR$^{18}$, halo, hydrogen, $C_{1-6}$alkyl, halo $C_{1-6}$alkyl, $C_{3-12}$cycloalkyl, $C_{6-12}$aryl, hydroxyl, —SR$^{19}$, cyano, amino, —COR$_2$R$^{22}$, —S(O)R$^{22}$, and —NR$^{23}$C(O) R$^{22}$; preferably each $Z^2$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, hydroxyl, —SR$^{19}$, cyano, —CO$_2$R$^{22}$, —S(O)$_2$R$^{22}$, and —NR$^{23}$C(O)R$^{22}$;

with the proviso that said compound is not
N-(1-methylethyl)-7-(phenylsulfonyl)-2,7-diazaspiro[3.5]nonane-2-carboxamide
N-(3-fluorophenyl)-7-(phenylsulfonyl)-2,7-diazaspiro[3.5]nonane-2-carboxamide,
N-phenyl-7-(phenylsulfonyl)-2,7-diazaspiro[3.5]nonane-2-carboxamide,
N-(4-methoxyphenyl)-7-(phenylsulfonyl)-2,7-diazaspiro[3.5]nonane-2-carboxamide,
(1H-benzotriazol-5-yl)-{7-[2-(3-chloro-phenyl)-ethanesulfonyl]-2,7-diaza-spiro[3.5]non-2-yl}-methanone,
N-(4-methoxyphenyl)-7-(methylsulfonyl)-2,7-diazaspiro[3.5]nonane-2-carboxamide,
N-(3-cyanophenyl)-7-(methylsulfonyl)-2,7-diazaspiro[3.5]nonane-2-carboxamide,
7-(methylsulfonyl)-N-phenyl-2,7-diazaspiro[3.5]nonane-2-carboxamide,
N-(3-fluorophenyl)-7-(methylsulfonyl)-2,7-diazaspiro[3.5]nonane-2-carboxamide,
or a solvate, hydrate, pharmaceutically acceptable salt or prodrug thereof.

According to an embodiment, the present invention encompasses compounds of formula (I), and any subgroup thereof such as (IA), (IB), (IC), (ID), (IE), (IF), wherein,
n is 0, 1 or 2; more preferably n is 0 or 1; yet more preferably n is 0;
$R^1$ is selected from the group consisting of $C_{1-6}$alkyl, halo, and halo$C_{1-6}$alkyl; preferably $R^1$ is $C_{1-6}$alkyl, or halo; preferably $R^1$ is $C_{1-6}$alkyl;
$R^3$ is selected from the group consisting of $C_{6-12}$aryl, $C_{1-6}$alkyl, $C_{3-12}$cycloalkyl, heterocyclyl, heteroaryl, $C_{6-12}$arylC$_{1-6}$alkyl, $C_{6-12}$arylC$_{1-6}$ alkylC$_{6-12}$aryl, halo, hydroxyl, —OR$^{18}$, —SR$^{19}$, haloC$_{1-6}$alkyl, haloC$_{1-6}$alkyloxy, amino, —NR$^{20}$R$^{21}$, and cyano; wherein said $C_{6-12}$aryl, $C_{1-6}$alkyl, $C_{3-12}$cycloalkyl, heterocyclyl, heteroaryl, $C_{6-12}$arylC$_{1-6}$alkyl, or $C_{6-12}$arylC$_{1-6}$alkyl $C_{6-12}$aryl can be unsubstituted or substituted with one or more Z$^1$; preferably R$^3$ is selected from the group consisting of $C_{6-12}$aryl, hydrogen, $C_{1-6}$alkyl, $C_{3-12}$cycloalkyl, heterocyclyl, heteroaryl, halo, hydroxyl, —OR$^{18}$, —SR$^{19}$, haloC$_{1-6}$alkyl, haloC$_{1-6}$alkyloxy, amino, —NR$^{20}$R$^{21}$, and cyano; wherein said $C_{6-12}$aryl, $C_{1-6}$alkyl, $C_{3-12}$cycloalkyl, heterocyclyl, heteroaryl can be unsubstituted or substituted with one or more Z$^1$; preferably R$^3$ is selected from the group consisting of $C_{6-12}$aryl, $C_{1-6}$alkyl, $C_{3-12}$cycloalkyl, heterocyclyl, heteroaryl, halo, hydroxyl, —OR$^{18}$, haloC$_{1-6}$alkyl, haloC$_{1-6}$alkyloxy, and cyano; wherein said $C_{6-12}$aryl, $C_{1-6}$alkyl, $C_{3-12}$cycloalkyl, heterocyclyl, heteroaryl, can be unsubstituted or substituted with one, two or three Z$^1$; preferably R$^3$ is selected from the group consisting of $C_{6-12}$aryl, $C_{1-6}$alkyl, $C_{3-12}$cycloalkyl, heterocyclyl, heteroaryl, halo, —OR$^{18}$, halo$C_{1-6}$alkyl, and haloC$_{1-6}$alkyloxy; wherein said $C_{6-12}$aryl, $C_{1-6}$alkyl, $C_{3-12}$cycloalkyl, heterocyclyl, heteroaryl can be unsubstituted or substituted with one, two or three Z$^1$; preferably R$^3$ is selected from the group consisting of $C_{6-12}$aryl, $C_{1-6}$alkyl, $C_{3-6}$cycloalkyl, heterocyclyl, heteroaryl, halo, haloC$_{1-6}$alkyl; wherein said $C_{6-12}$aryl, $C_{1-6}$alkyl, $C_{3-12}$cycloalkyl, heterocyclyl, heteroaryl can be unsubstituted or substituted with one, two or three Z$^1$;

L$^1$ is selected from the group consisting of —SO$_2$—, —CO—,

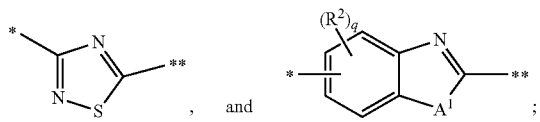

, and

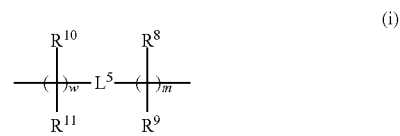

;

wherein * represents where L$^1$ is bound to L$^2$; and ** represents where L$^1$ is bound to the azetidine ring; and wherein, A$^1$ is S;

q is selected from 0, 1, or 2; preferably q is selected from 0, or 1; preferably q is 0;

each R$^2$ is independently selected from the group consisting of haloC$_{1-6}$alkyloxy, —OR$^{18}$, halo, hydrogen, $C_{1-6}$alkyl, haloC$_{1-6}$alkyl; preferably each R$^2$ is independently selected from the group consisting of halo, hydrogen, $C_{1-6}$alkyl, haloC$_{1-6}$alkyl; preferably each R$^2$ is independently hydrogen, or $C_{1-6}$alkyl; preferably each R$^2$ is independently hydrogen;

R$^4$ is selected from the group consisting $C_{6-12}$aryl, $C_{1-6}$alkyl, $C_{3-12}$cycloalkyl, heterocyclyl, heteroaryl, $C_{6-12}$aryl $C_{1-6}$alkyl, $C_{6-12}$arylC$_{1-6}$alkylC$_{6-12}$aryl, halo, hydroxyl, —OR$^{18}$, —SR$^{19}$, haloC$_{1-6}$alkyl, haloC$_{1-6}$alkyloxy, amino, —NR$^{20}$R$^{21}$, and cyano; and wherein said $C_{6-12}$aryl, $C_{1-6}$alkyl, $C_{3-12}$cycloalkyl, heterocyclyl, heteroaryl, $C_{6-12}$arylC$_{1-6}$alkyl, or $C_{6-12}$arylC$_{1-6}$alkylC$_{6-12}$aryl can be unsubstituted or substituted with one or more Z$^2$;

preferably R$^4$ is selected from the group consisting $C_{6-12}$aryl, $C_{1-6}$alkyl, $C_{3-12}$cycloalkyl, heterocyclyl, heteroaryl, halo, hydroxyl, —OR$^{18}$, —SR$^{19}$, haloC$_{1-6}$alkyl, haloC$_{1-6}$alkyloxy, amino, —NR$^{20}$R$^{21}$, and cyano; and wherein said $C_{6-12}$aryl, $C_{1-6}$alkyl, $C_{3-12}$cycloalkyl, heterocyclyl, heteroaryl, can be unsubstituted or substituted with one or more Z$^2$; preferably R$^4$ is selected from the group consisting $C_{6-12}$aryl, $C_{1-6}$alkyl, $C_{3-12}$cycloalkyl, heterocyclyl, heteroaryl, halo, hydroxyl, haloC$_{1-6}$alkyl, haloC$_{1-6}$alkyloxy; and wherein said $C_{6-12}$aryl, $C_{1-6}$alkyl, $C_{3-12}$cycloalkyl, heterocyclyl, heteroaryl, can be unsubstituted or substituted with one, two or three Z$^3$; preferably R$^4$ is selected from the group consisting $C_{6-12}$aryl, $C_{1-6}$alkyl, $C_{3-12}$cycloalkyl, heterocyclyl, heteroaryl; and wherein said $C_{6-12}$aryl, $C_{1-6}$alkyl, $C_{3-12}$cycloalkyl, heterocyclyl, heteroaryl, can be unsubstituted or substituted with one, two or three Z$^2$;

L$^2$ is a single bond or a group of formula (i);

$$\begin{array}{c}\text{(i)}\end{array}$$

wherein the left side of the group of formula (i) is attached to R$^3$ and the right side thereof is attached to the nitrogen atom of the azetidine ring; and wherein, m is an integer selected from 0, 1, or 2; preferably m is an integer selected from 0, or 1;

n is selected from 0, 1, or 2; preferably n is selected from 0, or 1;

L$^1$ is a single bond, or is —O—;

R$^8$ is selected from the group consisting of hydrogen, $C_{1-6}$alkyl, hydroxyl, haloC$_{1-6}$alkyl, and haloC$_{1-6}$alkyloxy; preferably R$^8$ is selected from the group consisting of hydrogen, $C_{1-6}$alkyl, hydroxyl; preferably R$^8$ is selected from the group consisting of hydrogen, $C_{1-4}$alkyl, and hydroxyl;

R$^9$ is selected from the group consisting of hydrogen, $C_{1-6}$alkyl, hydroxyl, haloC$_{1-6}$alkyl, and haloC$_{1-6}$alkyloxy; preferably R$^9$ is selected from the group consisting of hydrogen, $C_{1-6}$alkyl, hydroxyl; preferably R$^9$ is selected from the group consisting of hydrogen, $C_{1-4}$alkyl, and hydroxyl;

or R$^8$ and R$^9$ together with the carbon atom to which they are attached from a saturated 3-, 4-, 5-, or 6-membered ring; preferably R$^8$ and R$^9$ together with the carbon atom to which they are attached from a $C_{3-6}$cycloalkyl ring; preferably R$^8$ and R$^9$ together with the carbon atom to which they are attached from a $C_{3-5}$cycloalkyl ring;

R$^{10}$ is selected from the group consisting of hydrogen, $C_{1-6}$alkyl, hydroxyl, haloC$_{1-6}$alkyl, and haloC$_{1-6}$alkyloxy; preferably R$^{10}$ is selected from the group consisting of hydrogen, $C_{1-6}$alkyl, hydroxyl; preferably R$^{10}$ is selected from the group consisting of hydrogen, $C_{1-4}$alkyl, and hydroxyl;

R$^{11}$ is selected from the group consisting of hydrogen, $C_{1-6}$alkyl, hydroxyl, haloC$_{1-6}$alkyl, and haloC$_{1-6}$alkyloxy; preferably R$^{11}$ is selected from the group consisting of hydrogen, $C_{1-6}$alkyl, hydroxyl; preferably R$^{11}$ is selected from the group consisting of hydrogen, $C_{1-4}$alkyl, and hydroxyl;

or R$^{10}$ and R$^{11}$ together with the carbon atom to which they are attached from a saturated 3-, 4-, 5-, or 6-membered ring; preferably R$^{10}$ and R$^{11}$ together with the carbon atom to which they are attached from a $C_{3-6}$cycloalkyl ring; preferably R$^{10}$ and R$^{11}$ together with the carbon atom to which they are attached from a $C_{3-5}$cycloalkyl ring;

L$^3$ is selected from the group consisting of —SO$_2$—, and —PO$_4$—; preferably L$^3$ is —SO$_2$—;

$L^4$ is a single bond or is —$(CR^{15}R^{16})_t$—; preferably $L^4$ is a single bond or is $C_{1-6}$alkylene; preferably $L^4$ is a single bond or is $C_{1-6}$alkylene; preferably $L^4$ is a single bond or is $C_{1-2}$alkylene; wherein, t is 1 or 2;

$R^{15}$ is hydrogen, or $C_{1-6}$alkyl; preferably $R^{15}$ is hydrogen, or $C_{1-6}$alkyl; preferably $R^{15}$ is hydrogen, or $C_{1-2}$alkyl;

$R^{16}$ is hydrogen, or $C_{1-6}$alkyl; preferably $R^{16}$ is hydrogen, or $C_{1-4}$alkyl; preferably $R^{16}$ is hydrogen, or $C_{1-2}$alkyl;

or $R^{15}$ and $R^{16}$ together with the carbon atom to which they are attached from a saturated 3-, 4-, 5-, or 6-membered ring; preferably $R^{15}$ and $R^{16}$ together with the carbon atom to which they are attached from a $C_{3-6}$cycloalkyl ring; preferably $R^{15}$ and $R^{16}$ together with the carbon atom to which they are attached from a $C_{3-5}$cycloalkyl ring;

wherein at least one of $L^3$, $L^4$ is not a single bond; and wherein when $L^4$ is a single bond, $R^4$ is not methyl;

each $R^{18}$ is independently selected from the group consisting of $C_{1-6}$alkyl, $C_{6-12}$aryl, $C_{3-8}$cycloalkyl, heterocyclyl, heteroaryl; wherein at least one carbon atom or heteroatom of said $C_{1-6}$alkyl, $C_{6-12}$aryl, $C_{3-8}$cycloalkyl, heterocyclyl, heteroaryl can be oxidized to form at least one C=O, C=S, N=O, N=S, S=O or S(O)$_2$; preferably each $R^{18}$ is independently selected from the group consisting of $C_{1-6}$alkyl, $C_{6-12}$aryl, $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O, C=S, N=O, N=S, S=O or S(O)$_2$; preferably each $R^{18}$ is independently selected from $C_{1-6}$alkyl or $C_{6-12}$aryl; preferably each $R^{18}$ is independently $C_{1-6}$alkyl;

each $R^{19}$ is independently selected from the group consisting of hydrogen, $C_{1-6}$alkyl, $C_{6-12}$aryl, $C_{3-8}$cycloalkyl, heterocyclyl, heteroaryl; wherein at least one carbon atom or heteroatom of said $C_{1-6}$alkyl, $C_{6-12}$aryl, $C_{3-8}$cycloalkyl, heterocyclyl, heteroaryl can be oxidized to form at least one C=O; preferably each $R^{19}$ is independently selected from the group consisting of hydrogen, $C_{1-6}$alkyl, $C_{6-12}$aryl, $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{19}$ is independently hydrogen, or $C_{1-6}$alkyl;

each $R^{20}$ is independently selected from the group consisting of hydrogen, $C_{1-6}$alkyl, $C_{6-12}$aryl, $C_{3-8}$cycloalkyl, heterocyclyl, heteroaryl; wherein at last one carbon atom or heteroatom of said $C_{1-6}$alkyl, $C_{6-12}$aryl, $C_{3-8}$cycloalkyl, heterocyclyl, heteroaryl can be oxidized to form at least one C=O; preferably each $R^{20}$ is independently selected from the group consisting of hydrogen, $C_{1-6}$alkyl, $C_{6-12}$aryl, $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{20}$ is independently hydrogen, or $C_{1-6}$alkyl;

each $R^{21}$ is independently selected from the group consisting of hydrogen, $C_{1-6}$alkyl, $C_{6-12}$aryl, $C_{3-8}$cycloalkyl, heterocyclyl, hetetoaryl; wherein at least one carbon atom or heteroatom of said $C_{1-6}$alkyl, $C_{6-12}$aryl, $C_{3-8}$cycloalkyl, heterocyclyl, heteroaryl can be oxidized to form at least one C=O; preferably each $R^{20}$ is independently selected from the group consisting of hydrogen, $C_{1-6}$alkyl, $C_{6-12}$aryl, $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{20}$ is independently hydrogen, or $C_{1-6}$alkyl;

or $R^{20}$ and $R^{21}$ together with the nitrogen atom to which they are attached form a 5-, or 6-membered heterocyclyl; and wherein at least one carbon atom or heteroatom of said heterocyclyl can be oxidized to form at least one C=O.

each $R^{22}$ is independently selected from the group consisting of hydrogen, hydroxyl, $C_{1-6}$alkyl, $C_{6-12}$aryl, $C_{3-8}$cycloalkyl, heterocyclyl, heteroaryl; wherein at least one carbon atom or heteroatom of said $C_{1-6}$alkyl, $C_{6-12}$aryl, $C_{3-8}$cycloalkyl, heterocyclyl, heteroaryl can be oxidized to form at least one C=O; preferably each $R^{22}$ is independently selected from the group consisting of hydrogen, hydroxyl, $C_{1-6}$alkyl, $C_{6-12}$aryl, $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{22}$ is independently selected from the group consisting of hydrogen, hydroxyl, and $C_{1-6}$alkyl;

each $R^{23}$ is independently selected from the group consisting of hydrogen, $C_{1-6}$alkyl, $C_{6-12}$aryl, $C_{3-8}$cycloalkyl, heterocyclyl, heteroaryl; wherein at least one carbon atom or heteroatom of said $C_{1-6}$alkyl, $C_{6-12}$aryl, $C_{3-8}$cycloalkyl, heterocyclyl, heteroaryl, can be oxidized to form at least one C=O; preferably each $R^{23}$ is independently selected from the group consisting of hydrogen, $C_{1-6}$alkyl, $C_{6-12}$aryl, $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{23}$ is independently hydrogen, or $C_{1-6}$alkyl;

each $R^{24}$ is independently selected from the group consisting of $C_{1-6}$alkylene, $C_{6-12}$arylene, $C_{3-8}$cycloalkylene, heterocyclylene, heteroarylene; wherein at least one carbon atom or heteroatom of said $C_{1-6}$alkylene, $C_{6-12}$arylene, $C_{3-8}$cycloalkylene, heterocyclylene, heteroarylene can be oxidized to form at least one C=O; preferably each $R^{24}$ is independently selected from the group consisting of $C_{1-6}$alkylene, $C_{6-12}$arylene, $C_{3-8}$cycloalkylene; wherein at least one carbon atom or heteroatom of said $C_{1-6}$alkylene, $C_{6-12}$arylene, $C_{3-8}$cycloalkylene, can be oxidized to form at least one C=O; preferably each $R^{24}$ is independently $C_{1-6}$alkylene;

each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —$SR^{19}$, cyano, amino, —$NR^{20}R^{21}$, —$CO_2R^{22}$, —$C(O)NR^{20}R^{21}$, —$S(O)_2R^{22}$, —$SO_2NR^{20}R^{21}$, nitro, —$NR^{23}C(O)R^{22}$, —$NR^{23}S(O)_2R^{22}$, and —$NR^{23}C(O)NR^{20}R^{21}$; wherein two $Z^1$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O; preferably each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, hydroxyl, —$SR^{19}$, cyano, amino; preferably each $Z^1$ is independently selected from the group consisting of halo$C_{1-6}$alkyloxy, halo, hydrogen, $C_{1-6}$alkyl, halo$C_{1-6}$alkyl, hydroxyl, cyano, amino;

each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2^{20}R^{21}$, —$SO_2NR^{20}R^{21}$, nitro, —$NR^{23}C(O)R^{22}$, —$R^{24}C(O)NR^{20}R^{21}$, —$NR^{23}S(O)_2R^{22}$, and $NR^{23}C(O)$ $NR^{20}R^{21}$; wherein two $Z^2$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O; preferably each $Z^2$ is independently selected from the group consisting of halo $C_{1-6}$alkyloxy, —$OR^{18}$, halo, hydrogen, $C_{1-6}$alkyl, halo $C_{1-6}$alkyl, $C_{3-12}$cycloalkyl, $C_{6-12}$aryl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$; preferably each $Z^2$ is independently selected from the group consisting of halo $C_{1-6}$alkyloxy, —$OR^{18}$, halo, hydrogen, $C_{1-6}$alkyl, halo $C_{1-6}$alkyl, $C_{3-12}$cycloalkyl, $C_{6-12}$aryl, hydroxyl, —$SR^{19}$, cyano, amino, —$CO_2R^{22}$, —$S(O)_2R^{22}$, —$NR^{23}C(O)R^{22}$; preferably each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, hydroxyl, —$SR^{19}$, cyano, —$CO_2R^{22}$, —$S(O)_2R^{22}$, —$NR^{23}C(O)R^{22}$.

According to an embodiment, the present invention encompasses compounds of formula (I), and any subgroup thereof such as (IA), (IB), (IC), (ID), (IE), (IF), wherein, n is 0 or 1; yet more preferably n is 0;

$R^1$ is $C_{1-6}$alkyl, or halo; preferably $R^1$ is $C_{1-6}$alkyl, $R^3$ is selected from the group consisting of $C_{6-12}$aryl, hydrogen, $C_{1-6}$alkyl, $C_{3-12}$cycloalkyl, heterocyclyl, heteroaryl, halo, hydroxyl, —$OR^{18}$, —$SR^{19}$, halo$C_{1-6}$alkyl, halo halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, can be unsubstituted or substituted with one or more $Z^1$; preferably $R^3$ is selected from the group consisting of $C_{6-12}$aryl, $C_{1-6}$alkyl, $C_{3-12}$cycloalkyl, heterocyclyl, heteroaryl, halo, hydroxyl, —$OR^{18}$, halo$C_{1-6}$alkyl, halo$C_{1-6}$alkyloxy, and cyano; wherein said $C_{6-12}$aryl, $C_{1-6}$alkyl, $C_{3-12}$cycloalkyl, heterocyclyl, heteroaryl, can be unsubstituted or substituted with one, two or three $Z^1$; preferably $R^3$ is selected from the group consisting of $C_{6-12}$aryl, $C_{1-6}$alkyl, $C_{3-12}$cycloalkyl, heterocyclyl, heteroaryl, halo, —$OR^{18}$, halo$C_{1-6}$alkyl, and halo$C_{1-6}$alkyloxy; wherein said $C_{6-12}$aryl, $C_{1-6}$alkyl, $C_{3-12}$cycloalkyl, heterocyclyl, heteroaryl, can be unsubstituted or substituted with one, two or three $Z^1$; preferably $R^3$ is selected from the group consisting of $C_{6-12}$aryl, $C_{1-6}$alkyl, $C_{3-6}$cycloalkyl, heterocyclyl, heteroaryl, halo, halo$C_{1-6}$alkyl; wherein said $C_{6-12}$aryl, $C_{1-6}$alkyl, $C_{3-12}$cycloalkyl, heterocyclyl, heteroaryl can be unsubstituted or substituted with one, two or three $Z^1$;

$L^1$ is selected from the group consisting of —$SO_2$—, —CO—,

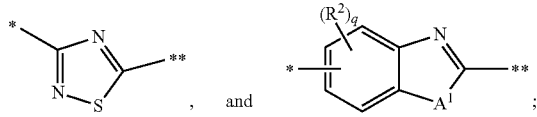

wherein * represents where $L^1$ is bound to $L^2$; and ** represents where $L^1$ is bound to the azetidine ring; and wherein, $A^1$ is S;

q is selected from 0, or 1; preferably q is 0;

each $R^2$ is independently selected from the group consisting of halo, hydrogen, $C_{1-6}$alkyl, halo$C_{1-6}$alkyl; preferably each $R^2$ is independently hydrogen, or $C_{1-6}$alkyl; preferably each $R^2$ is independently hydrogen;

$R^4$ is selected from the group consisting $C_{6-12}$aryl, $C_{1-6}$alkyl, $C_{3-12}$cycloalkyl heterocyclyl, heteroaryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, can be unsubstituted or substituted with one or more $Z^2$; preferably $R^4$ is selected from the group consisting $C_{6-12}$aryl, $C_{1-6}$alkyl, $C_{3-12}$cycloalkyl, heterocyclyl, heteroaryl, halo, hydroxyl, halo$C_{1-6}$alkyl, halo$C_{1-6}$alkyloxy; and wherein said $C_{6-12}$aryl, $C_{1-6}$alkyl, $C_{3-12}$cycloalkyl, heterocyclyl, heteroaryl, can be unsubstituted or substituted with one, two or three $Z^2$;

preferably $R^4$ is selected from the group consisting $C_{6-12}$aryl, $C_{1-6}$alkyl, $C_{3-12}$cycloalkyl, heterocyclyl, heteroaryl; and wherein said $C_{6-12}$aryl, $C_{1-6}$alkyl, $C_{3-12}$cycloalkyl, heterocyclyl, heteroaryl, can be unsubstituted or substituted with one, two or three $Z^2$;

$L^2$ is a single bond or a group of formula (i);

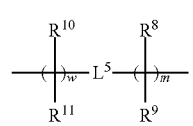

(i)

wherein the left side of the group of formula (i) is attached to $R^3$ and the right side thereof is attached to the nitrogen atom of the azetidine ring; and wherein, m is an integer selected from 0, or 1;

n is selected from 0, or 1;

$L^5$ is a single bond, or is —O—;

$R^8$ is selected from the group consisting of hydrogen, $C_{1-6}$alkyl, and hydroxyl; preferably $R^8$ is selected from the group consisting of hydrogen, $C_{1-4}$alkyl, and hydroxyl;

$R^9$ is selected from the group consisting of hydrogen, $C_{1-6}$alkyl, and hydroxyl; preferably $R^9$ is selected from the group consisting of hydrogen, $C_{1-4}$alkyl, and hydroxyl;

or $R^8$ and $R^9$ together with the carbon atom to which they are attached from a $C_{3-6}$cycloalkyl ring; preferably $R^8$ and $R^9$ together with the carbon atom to which they are attached from a $C_{3-5}$cycloalkyl ring;

$R^{10}$ is selected from the group consisting of hydrogen, $C_{1-6}$alkyl, and hydroxyl; preferably $R^{10}$ is selected from the group consisting of hydrogen, $C_{1-4}$alkyl, and hydroxyl;

$R^{11}$ is selected from the group consisting of hydrogen, $C_{1-6}$alkyl, and hydroxyl; preferably $R^{11}$ is selected from the group consisting of hydrogen, $C_{1-4}$alkyl, and hydroxyl;

or $R^{10}$ and $R^{11}$ together with the carbon atom to which they are attached from a $C_{3-6}$cycloalkyl ring; preferably $R^{10}$ and $R^{11}$ together with the carbon atom to which they are attached from a $C_{3-5}$cycloalkyl ring;

$L^3$ is —$SO_2$—;

$L^4$ is a single bond or is $C_{1-6}$alkylene; preferably $L^4$ is a single bond or is $C_{1-4}$alkylene; preferably $L^4$ is a single bond or is $C_{1-2}$alkylene; wherein, wherein at least one of $L^3$, $L^4$ is not a single bond; and wherein when $L^4$ is a single bond, $R^4$ is not methyl;

each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —$SR^{19}$, cyano, amino, —$NR^{20}R^{21}$, —$CO_2R^{22}$, —$C(O)NR^{20}R^{21}$, —$S(O)_2R^{22}$, —$SO_2NR^{20}R^{21}$, nitro, —$NR^{23}C(O)R^{22}$, —$NR^{23}S(O)_2R^{22}$, and —$NR^{23}C(O)NR^{20}R^{21}$; wherein two $Z^1$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O; preferably each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, hydroxyl, —$SR^{19}$, cyano, and amino; preferably each $Z^1$ is independently selected from the group consisting of halo$C_{1-6}$alkyloxy, halo, hydrogen, $C_{1-6}$alkyl, halo$C_{1-6}$alkyl, hydroxyl, cyano, and amino;

each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, heterocyclyl, heteroaryl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$NR^{24}C(O)NR^{20}R^{21}$, —$NR^{23}S(O)_2R^{22}$, and $NR^{23}C(O)NR^{20}R^{21}$; wherein two $Z^2$ together with the atom to which they are attached can form a saturated or unsaturated 5-, or 6-membered ring; and wherein at least one carbon atom or heteroatom of said $C_{1-6}$alkyl, $C_{3-12}$cycloalkyl, $C_{6-12}$aryl, heterocyclyl, heteroaryl can be oxidized to form at least one C=O; preferably each $Z^2$ is independently selected from the group consisting of halo $C_{1-6}$alkyloxy, —$OR^{18}$, halo, hydrogen, $C_{1-6}$alkyl, halo $C_{1-6}$alkyl, $C_{3-12}$cycloalkyl, $C_{6-12}$aryl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, and —$NR^{23}C(O)R^{22}$; preferably each $Z^2$ is independently selected from the group consisting of halo $C_{1-6}$alkyloxy, —$OR^{18}$, halo, hydrogen, $C_{1-6}$alkyl, halo $C_{1-6}$alkyl, $C_{3-12}$cycloalkyl, $C_{6-12}$aryl, hydroxyl, —$SR^{19}$, cyano, amino, —$CO_2R^{22}$, —$S(O)R^{22}$, and —$NR^{23}C(O)R^{22}$; preferably each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, hydroxyl, —$SR^{19}$, cyano, —$CO_2R^{22}$, —$S(O)_2R^{22}$, and —$NR^{23}C(O)R^{22}$;

each $R^{18}$ is independently selected from the group consisting of $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O, C=S, N=O, N=S, S=O or $S(O)_2$; preferably each $R^{18}$ is independently selected from $C_{1-6}$alkyl or $C_{6-12}$aryl; preferably each $R^{18}$ is independently $C_{1-6}$alkyl;

each $R^{19}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{19}$ is independently hydrogen, or $C_{1-6}$alkyl;

each $R^{20}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{20}$ is independently hydrogen, or $C_{1-6}$alkyl;

each $R^{21}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{21}$ is independently hydrogen, or $C_{1-6}$alkyl;

or $R^{20}$ and $R^{21}$ together with the nitrogen atom to which they are attached form a 5-, or 6-membered heterocyclyl; and wherein at least one carbon atom or heteroatom of said heterocyclyl can be oxidized to form at least one C=O, each $R^{22}$ is independently selected from the group consisting of hydrogen, hydroxyl, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{22}$ is independently selected from the group consisting of hydrogen, hydroxyl, and $C_{1-6}$alkyl;

each $R^{23}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{23}$ is independently hydrogen, or $C_{1-6}$alkyl;

each $R^{24}$ is independently selected from the group consisting of $C_{1-6}$alkylene, $C_{6-12}$arylene, and $C_{3-8}$cycloalkylene; wherein at least one carbon atom or heteroatom of said $C_{1-6}$alkylene, $C_{6-12}$arylene, $C_{3-8}$cycloalkylene, can be oxidized to form at least one C=O; preferably each $R^{24}$ is independently $C_{1-6}$alkylene.

According to an embodiment, the present invention encompasses compounds of formula (I), and any subgroup thereof such as (IA), (IB), (IC), (ID), (IE), (IF), wherein, n is 0 or 1; yet more preferably n is 0;

$R^1$ is $C_{1-6}$alkyl, or halo; preferably $R^1$ is $C_{1-6}$alkyl;

$R^3$ is selected from the group consisting of $C_{6-12}$aryl, hydrogen, $C_{1-6}$alkyl, $C_{3-12}$cycloalkyl, heterocyclyl, heteroaryl, halo, hydroxyl, —$OR^{18}$, —$SR^{19}$, halo$C_{1-6}$alkyl, halo $C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, can be unsubstituted or substituted with one or more $Z^1$; preferably $R^3$ is selected from the group consisting of $C_{6-12}$aryl, $C_{1-6}$alkyl, $C_{3-12}$cycloalkyl, heterocyclyl, heteroaryl, halo, hydroxyl, —$OR^{18}$, halo$C_{1-6}$alkyl, halo$C_{1-6}$alkyloxy, and cyano; wherein said $C_{6-12}$aryl, $C_{1-6}$alkyl, $C_{3-12}$cycloalkyl, heterocyclyl, heteroaryl, can be unsubstituted or substituted with one, two or three $Z^1$; preferably $R^3$ is selected from the group consisting of $C_{6-12}$aryl, $C_{1-6}$alkyl, $C_{3-12}$cycloalkyl, heterocyclyl, heteroaryl, halo, —$OR^{18}$, halo$C_{1-6}$alkyl, and halo$C_{1-6}$alkyloxy; wherein said $C_{6-12}$aryl, $C_{1-6}$alkyl, $C_{3-12}$cycloalkyl, heterocyclyl, heteroaryl, can be unsubstituted or substituted with one, two or three $Z^1$; preferably $R^3$ is selected from the group consisting of $C_{6-12}$aryl, $C_{1-6}$alkyl, $C_{3-8}$cycloalkyl, heterocyclyl, heteroaryl, halo, halo$C_{1-6}$alkyl; wherein said $C_{6-12}$aryl, $C_{1-6}$alkyl, $C_{3-12}$cycloalkyl, heterocyclyl, heteroaryl, can be unsubstituted or substituted with one, two or three $Z^1$;

$L^1$ is selected from the group consisting of —$SO_2$—, —CO—,

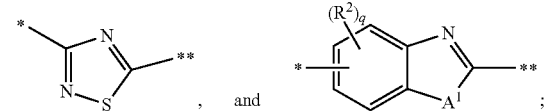

wherein * represents where $L^1$ is bound to $L^2$; and ** represents where $L^1$ is bound to the azetidine ring; and wherein, $A^1$ is S;

q is selected from 0, or 1; preferably q is 0;

each $R^2$ is independently selected from the group consisting of halo, hydrogen, $C_{1-6}$alkyl, and halo$C_{1-6}$alkyl; preferably each $R^2$ is independently hydrogen, or $C_{1-6}$alkyl; preferably each $R^2$ is independently hydrogen;

R is selected from the group consisting $C_{6-12}$aryl, $C_{1-6}$alkyl, $C_{3-12}$cycloalkyl, heterocyclyl, heteroaryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, can be unsubstituted or substituted with one or more $Z^2$; preferably $R^4$ is selected from the group consisting $C_{6-12}$aryl, $C_{1-6}$alkyl, $C_{6-12}$cycloalkyl, heterocyclyl, heteroaryl, halo, hydroxyl, halo$C_{1-6}$alkyl, and halo$C_{1-6}$alkyloxy; and wherein said $C_{6-12}$aryl, $C_{1-6}$alkyl, $C_{3-12}$cycloalkyl, heterocyclyl, heteroaryl, can be unsubstituted or substituted with one, two or three $Z^2$;

preferably $R^4$ is selected from the group consisting $C_{6-12}$aryl, $C_{1-6}$alkyl, $C_{3-12}$cycloalkyl, heterocyclyl, and heteroaryl; and wherein said $C_{6-12}$aryl, $C_{1-6}$alkyl, $C_{3-12}$cycloalkyl, heterocyclyl, heteroaryl can be unsubstituted or substituted with one, two or three $Z^2$;

$L^2$ is a single bond or a group of formula (i);

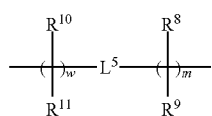

(i)

wherein the left side of the group of formula (i) is attached to $R^3$ and the right side thereof is attached to the nitrogen atom of the azetidine ring; and wherein, m is an integer selected from 0, or 1;
n is selected from 0, or 1;
$L^5$ is a single bond, or is —O—;
$R^8$ is selected from the group consisting of hydrogen, $C_{1-6}$alkyl, and hydroxyl; preferably $R^8$ is selected from the group consisting of hydrogen, $C_{1-4}$alkyl, and hydroxyl;
$R^9$ is selected from the group consisting of hydrogen, $C_{1-6}$alkyl, and hydroxyl; preferably $R^9$ is selected from the group consisting of hydrogen, $C_{1-4}$alkyl, and hydroxyl;
or $R^8$ and $R^9$ together with the carbon atom to which they are attached from a $C_{3-6}$cycloalkyl ring; preferably $R^8$ and $R^9$ together with the carbon atom to which they are attached from a $C_{3-5}$cycloalkyl ring;
$R^{10}$ is selected from the group consisting of hydrogen, $C_{1-6}$alkyl, and hydroxyl; preferably $R^{10}$ is selected from the group consisting of hydrogen, $C_{1-4}$alkyl, and hydroxyl;
$R^{11}$ is selected from the group consisting of hydrogen, $C_{1-6}$alkyl, and hydroxyl; preferably $R^{11}$ is selected from the group consisting of hydrogen, $C_{1-4}$alkyl, and hydroxyl;
or $R^{10}$ and $R^{11}$ together with the carbon atom to which they are attached from a $C_{3-6}$cycloalkyl ring; preferably $R^{10}$ and $R^{11}$ together with the carbon atom to which they are attached from a $C_{3-5}$cycloalkyl ring;
$L^3$ is —$SO_2$—;
$L^4$ is a single bond or is $C_{1-6}$alkylene; preferably $L^4$ is a single bond or is $C_{1-6}$alkylene; preferably $L^4$ is a single bond or is $C_{1-2}$alkylene; wherein,
wherein at least one of $L^3$, $L^4$ is not a single bond; and wherein when $L^4$ is a single bond, $R^4$ is not methyl;

each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$ aryl, hydroxyl, —$SR^{19}$, cyano, and amino; preferably each $Z^1$ is independently selected from the group consisting of halo $C_{1-6}$alkyloxy, halo, hydrogen, $C_{1-6}$alkyl, halo$C_{1-6}$alkyl, hydroxyl, cyano, and amino;

each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl $C_{6-12}$aryl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, and —$NR^{23}C(O)R^{22}$; preferably each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, hydroxyl, —$SR^{19}$, cyano, amino, —$CO_2R^{22}$, —$S(O)_2R^{22}$, and —$NR^{23}C(O)R^{22}$; preferably each $Z^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, hydroxyl, —$SR^{19}$, cyano, —$CO_2R^{22}$, —$S(O)_2R^{22}$, and —$NR^{23}C(O)R^{22}$;

each $R^{18}$ is independently selected from the group consisting of $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl can be oxidized to form at least one C=O, C=S, N=O, N=S, S=O or $S(O)_2$; preferably each $R^{18}$ is independently selected from $C_{1-6}$alkyl or $C_{6-12}$aryl; preferably each $R^{18}$ is independently $C_{1-6}$alkyl;

each $R^{19}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{20}$ is independently hydrogen, or $C_{1-6}$alkyl;

each $R^{20}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{20}$ is independently hydrogen, or $C_{1-6}$alkyl;

each $R^{21}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{21}$ is independently hydrogen, or $C_{1-6}$alkyl;

or $R^{20}$ and $R^{21}$ together with the nitrogen atom to which they are attached form a 5-, or 6-membered heterocyclyl; and wherein at least one carbon atom or heteroatom of said heterocyclyl can be oxidized to form at least one C=O, each $R^{22}$ is independently selected from the group consisting of hydrogen, hydroxyl, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{23}$ is independently selected from the group consisting of hydrogen, hydroxyl, and $C_{1-6}$alkyl;

each $R^{23}$ is independently selected from the group consisting of hydrogen, $C_{1-6}$alkyl, $C_{6-12}$aryl, and $C_{3-8}$cycloalkyl; wherein at least one carbon atom or heteroatom of said $C_{1-6}$alkyl, $C_{6-12}$aryl, $C_{3-8}$cycloalkyl, can be oxidized to form at least one C=O; preferably each $R^{23}$ is independently hydrogen, or $C_{1-6}$alkyl.

According to an embodiment, the present invention encompasses compounds of formula (I), and any subgroup thereof such as (IA), (IB), (IC), (ID), (IE), (IF), wherein, n is 0;
R$^3$ is selected from the group consisting of C$_{6-12}$aryl, C$_{1-6}$alkyl, C$_{3-12}$cycloalkyl, heterocyclyl, heteroaryl, halo, hydroxyl, —OR$^{18}$, haloC$_{1-6}$alkyl, haloC$_{1-6}$alkyloxy, and cyano; wherein said C$_{6-12}$aryl, C$_{1-6}$alkyl, C$_{3-12}$cycloalkyl, heterocyclyl, heteroaryl, can be unsubstituted or substituted with one, two or three Z$^1$; preferably R$^3$ is selected from the group consisting of C$_{6-12}$aryl, C$_{1-6}$alkyl, C$_{3-12}$cycloalkyl, heterocyclyl, heteroaryl, halo, —OR$^{18}$, haloC$_{1-6}$alkyl, and haloC$_{1-6}$alkyloxy; wherein said C$_{6-12}$aryl, C$_{1-6}$alkyl, C$_{3-12}$cycloalkyl, heterocyclyl, heteroaryl, can be unsubstituted or substituted with one, two or three Z$^1$; preferably R$^3$ is selected from the group consisting of C$_{6-12}$aryl, C$_{1-6}$alkyl, C$_{3-6}$cycloalkyl, heterocyclyl, heteroaryl, halo, haloC$_{1-6}$alkyl; wherein said C$_{6-12}$aryl, C$_{1-6}$alkyl, C$_{3-12}$cycloalkyl, heterocyclyl, heteroaryl can be unsubstituted or substituted with one, two or three Z$^1$;
L$^1$ is selected from the group consisting of —SO$_2$—, —CO—,

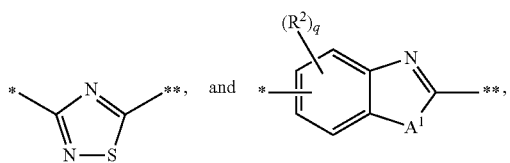

wherein * represents where L$^1$ is bound to L$^2$; and ** represents where L$^1$ is bound to the azetidine ring; and wherein,
A$^1$ is S;
q is 0;
R$^4$ is selected from the group consisting C$_{6-12}$aryl, C$_{1-6}$alkyl, C$_{3-12}$cycloalkyl, heterocyclyl, heteroaryl, halo, hydroxyl, haloC$_{1-6}$alkyl, and haloC$_{1-6}$alkyloxy; and wherein said C$_{6-12}$aryl, C$_{1-6}$alkyl, C$_{3-12}$cycloalkyl, heterocyclyl, heteroaryl, can be unsubstituted or substituted with one, two or three Z$^2$; preferably R$^4$ is selected from the group consisting C$_{6-12}$aryl C$_{1-6}$alkyl, C$_{3-12}$cycloalkyl, heterocyclyl, and heteroaryl; and wherein said C$_{6-12}$aryl, C$_{1-6}$alkyl, C$_{3-12}$cycloalkyl, heterocyclyl, heteroaryl can be unsubstituted or substituted with one, two or three Z$^2$;
L$^2$ is a single bond or a group of formula (i);

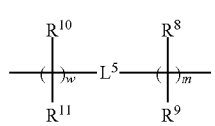
(i)

wherein the left side of the group of formula (i) is attached to R$^3$ and the right side thereof is attached to the nitrogen atom of the azetidine ring; and wherein,
m is an integer selected from 0, or 1;
n is selected from 0, or 1;
L$^5$ is a single bond, or is —O—;
R$^8$ is selected from the group consisting of hydrogen, C$_{1-4}$alkyl, and hydroxyl;
R$^9$ is selected from the group consisting of hydrogen, C$_{1-4}$alkyl, and hydroxyl;
or R$^8$ and R$^9$ together with the carbon atom to which they are attached from a C$_{3-5}$cycloalkyl ring;

R$^{10}$ is selected from the group consisting of hydrogen, C$_{1-4}$alkyl, and hydroxyl;
R$^{11}$ is selected from the group consisting of hydrogen, C$_{1-4}$alkyl, and hydroxyl;
or R$^{10}$ and R$^{11}$ together with the carbon atom to which they are attached from a C$_{3-5}$cycloalkyl ring;
L$^3$ is —SO$_2$—;
L$^4$ is a single bond or is C$_{1-4}$alkylene; preferably L$^4$ is a single bond or is C$_{1-2}$alkylene;
wherein at least one of L$^3$, L$^4$ is not a single bond; and wherein when L$^4$ is a single bond, R$^4$ is not methyl;
each Z$^1$ is independently selected from the group consisting of haloC$_{1-6}$alkyloxy, halo, hydrogen, C$_{1-6}$alkyl, halo C$_{1-6}$alkyl, hydroxyl, cyano, and amino;
each Z$^2$ is independently selected from the group consisting of haloC$_{1-6}$alkyloxy, —OR$^{18}$, halo, hydrogen, C$_{1-6}$alkyl, haloC$_{1-6}$alkyl, C$_{3-12}$cycloalkyl, C$_{6-12}$aryl, hydroxyl, —SR$^{19}$, cyano, amino, —CO$_2$R$^{22}$, —S(O)$_2$R$^{22}$, and —NR$^{23}$C(O)R$^{22}$; preferably each Z$^2$ is independently selected from the group consisting of haloC$_{1-6}$alkyloxy, —OR$^{18}$, halo, hydrogen, C$_{1-6}$alkyl, haloC$_{1-6}$alkyl, C$_{3-12}$cycloalkyl, hydroxyl, —SR$^{19}$, cyano, —CO$_2$R$^{22}$, —S(O)$_2$R$^{22}$, and —NR$^{23}$C(O)R$^{22}$;
each R$^{18}$ is independently selected from C$_{1-6}$alkyl or C$_{6-12}$aryl; preferably each R$^{18}$ is independently C$_{1-6}$alkyl;
each R$^{19}$ is independently hydrogen, or C$_{1-6}$alkyl;
each R$^{22}$ is independently selected from the group consisting of hydrogen, hydroxyl, and C$_{1-6}$alkyl;
each R$^{23}$ is independently hydrogen, or C$_{1-6}$alkyl.

According to an embodiment, the present invention encompasses compounds of formula (I), and any subgroup thereof such as (IA), (IB), (IC, (ID), (IE) (IF), wherein, n is 0;
R$^3$ is selected from the group consisting of C$_{6-12}$aryl, C$_{1-6}$alkyl, C$_{3-12}$cycloalkyl, heterocyclyl, heteroaryl, halo, —OR$^{18}$, haloC$_{1-6}$alkyl, and haloC$_{1-6}$alkyloxy; wherein said C$_{6-12}$aryl, C$_{1-6}$alkyl, C$_{3-12}$cycloalkyl, heterocyclyl, heteroaryl, can be unsubstituted or substituted with one, two or three Z$^1$; preferably R$^3$ is selected from the group consisting of C$_{6-12}$aryl, C$_{1-6}$alkyl, C$_{3-6}$cycloalkyl, heterocyclyl, heteroaryl, halo, haloC$_{1-6}$alkyl; wherein said C$_{6-12}$aryl, C$_{1-6}$alkyl, C$_{3-12}$cycloalkyl, heterocyclyl, heteroaryl, can be unsubstituted or substituted with one, two or three Z$^1$;
L$^1$ is selected from the group consisting of —SO$_2$—, —CO—,

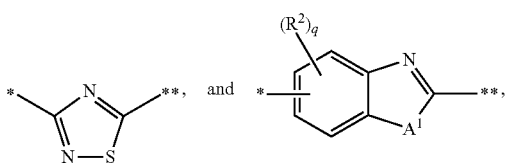

wherein * represents where L$^1$ is bound to L$^2$; and ** represents where L$^1$ is bound to the azetidine ring; and wherein,
A$^1$ is S;
q is 0;
R$^4$ is selected from the group consisting C$_{6-12}$aryl, C$_{1-6}$alkyl, C$_{3-12}$cycloalkyl, heterocyclyl, and heteroaryl; and wherein said C$_{6-12}$aryl, C$_{1-6}$alkyl, C$_{3-12}$cycloalkyl, heterocyclyl, heteroaryl can be unsubstituted or substituted with one, two or three Z$^2$;

$L^2$ is a single bond or a group of formula (i);

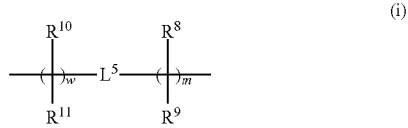

wherein the left side of the group of formula (i) is attached to $R^3$ and the right side thereof is attached to the nitrogen atom of the azetidine ring; and wherein,
m is an integer selected from 0, or 1;
n is selected from 0, or 1;
$L^5$ is a single bond, or is —O—;
$R^8$ is selected from the group consisting of hydrogen, $C_{1-4}$alkyl, and hydroxyl;
$R^9$ is selected from the group consisting of hydrogen, $C_{1-4}$alkyl, and hydroxyl;
or $R^8$ and $R^9$ together with the carbon atom to which they are attached from a $C_{3-5}$cycloalkyl ring;
$R^{10}$ is selected from the group consisting of hydrogen, $C_{1-4}$alkyl, and hydroxyl;
$R^{11}$ is selected from the group consisting of hydrogen, $C_{1-4}$alkyl, and hydroxyl;
or $R^{10}$ and $R^{11}$ together with the carbon atom to which they are attached from a $C_{3-5}$cycloalkyl ring;
$L^3$ is —SO$_2$—;
$L^4$ is a single bond or is $C_{1-4}$alkylene; preferably $L^4$ is a single bond or is $C_{1-2}$alkylene;
wherein at least one of $L^3$, $L^4$ is not a single bond; and wherein when $L^4$ is a single bond, $R^4$ is not methyl;
each $Z^1$ is independently selected from the group consisting of haloC$_{1-6}$alkyloxy, halo, hydrogen, C$_{1-6}$alkyl, halo C$_{1-6}$alkyl, hydroxyl, cyano, and amino;
each $Z^2$ is independently selected from the group consisting of haloC$_{1-6}$alkyloxy, —OR$^{18}$, halo, hydrogen, C$_{1-6}$alkyl, haloC$_{1-6}$alkyl, C$_{3-12}$cycloalkyl, hydroxyl, —SR$^{19}$, cyano, —CO$_2$R$^{22}$, —S(O)$_2$R$^{22}$, and —NR$^{23}$C(O)R$^{22}$;
each $R^{18}$ is independently C$_{1-6}$alkyl;
each $R^{19}$ is independently hydrogen, or C$_{1-6}$alkyl;
each $R^{22}$ is independently selected from the group consisting of hydrogen, hydroxyl, and C$_{1-6}$alkyl;
each $R^{23}$ is independently hydrogen, or C$_{1-6}$alkyl.

The present invention includes all possible stereoisomers compounds of formula (I) and any subgroup thereof and includes not only racemic compounds but the individual enantiomers as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L Eliel, S. H. Wilen, and L. N. Mander (Wiley-Interscience, 1994), incorporated by reference with regard to stereochemistry.

The compounds of the invention may be in the form of pharmaceutically acceptable salts, as generally described below. Some preferred, but non-limiting examples of suitable pharmaceutically acceptable organic and/or inorganic acids are as hydrochloric acid, hydrobromic acid, sulfuric acid, nitric acid, acetic acid and citric acid, as well as other pharmaceutically acceptable acids known per se (for which reference is made to the prior art referred to below).

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of the compounds of formula (I) and any subgroup thereof include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermth (Wiley-VCH, 2002), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Pharmaceutically acceptable salts of compounds of formula (I) may be prepared by one or more of these methods:
(i) by reacting the compound of formula (I) with the desired acid;
(ii) by reacting the compound of formula (I) with the desired base;
(iii) by removing an acid- or base-labile protecting group from a suitable precursor of the compound of formula (I) or by ring-opening a suitable cyclic precursor, for example, a lactone or lactam, using the desired acid; or
(iv) by converting one salt of the compound of formula (I) to another by reaction with an appropriate acid or by means of a suitable ion exchange column.

All these reactions are typically carried out in solution. The salt, may precipitate from solution and be collected by filtration or may be recovered by evaporation of the solvent.

The degree of ionization in the salt may vary from completely ionized to almost non-ionized.

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Britain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)$ polar head group. For more information, see Crystals and the Polarizing Microscope by N. H. Hartshorne and A. Stuart, $4^{th}$ Edition (Edward Arnold, 1970), incorporated herein by reference.

All references to compounds of formula (I) or any subgroups thereof include references to salts, solvates, multi-component complexes and liquid crystals thereof and to solvates, multi-component complexes and liquid crystals of salts thereof.

The compounds of the invention include compounds of formula (I) or any subgroups thereof as hereinbefore defined, including all polymorphs and crystal habits thereof, prodrugs and isomers thereof (including optical, geometric and tautomeric isomers) as hereinafter defined and isotopically-labeled compounds of formula (I).

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of formula (I) above.

The invention also generally covers all pharmaceutically acceptable prodrugs or "pre-drugs" of the compounds of formula (I) or any subgroups thereof for which general reference is made to the prior art cited hereinbelow.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active inhibitors in vivo. The term "pre-drug", as used herein, means any compound that will be modified to form a drug species, wherein the modification may take place either inside or outside of the body, and either before or after the pre-drug reaches the area of the body where administration of the drug is indicated.

Where a compound of formula (I) or any subgroup thereof contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, diastereomers, geometric isomers and tautomeric forms of the compounds of formula (I) or any subgroups thereof, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC).

The compounds of formula (I) or any subgroups thereof may be prepared as described in the experimental section below using methods and chemistries with which those skilled in the art shall be familiar.

Generally, the compounds of the invention are prepared from the intermediates described hereinafter which may be reacted with complementary reactive molecules so as to form the desired compound.

The present invention also encompasses a compound selected from the group comprising:

2,7-Bis((4-methoxyphenyl)sulfonyl)-2,7-diazaspiro[3.5]nonane;
2-((4-Fluorophenyl)sulfonyl)-7-((4-methoxyphenyl)sulfonyl)-2,7-diazaspiro[3.5]nonane;
2-((4-(Difluoromethoxy)phenyl)sulfonyl)-7-((4-methoxyphenyl)sulfonyl)-2,7-diazaspiro[3.5]nonane;
7-((4-Methoxyphenyl)sulfonyl)-2-((4-propoxyphenyl)sulfonyl)-2,7-diazaspiro[3.5]nonane;
2-((4-Chlorophenyl)sulfonyl)-7-((4-methoxyphenyl)sulfonyl)-2,7-diazaspiro[3.5]nonane;
2-(4-Fluorophenyl)-1-(7-((4-methoxyphenyl)sulfonyl)-2,7-diazaspiro[3.5]nonane-2-yl)ethanone;
(4-Chlorophenyl)(7-((4-methoxyphenyl)sulfonyl)-2,7-diazaspiro[3.5]nonan-2-yl)methanone;
(3,4-Difluorophenyl)(7-((4-methoxyphenyl)sulfonyl)-2,7-diazaspiro[3.5]nonan-2-yl)methanone;
(4-Fluorophenyl)7-((4-methoxyphenyl)sulfonyl)-2,7-diazaspiro[3.5]nonan-2-yl)methanone;
1-(7-((4-Methoxyphenyl)sulfonyl)-2,7-diazaspiro[3.5]nonane-2-yl)-2-phenylethanone;
1-(7-((4-Methoxyphenyl)sulfonyl)-2,7-diazaspiro[3.5]nonan-2-yl)-2-phenylbutan-1-one;
4,4,4-Trifluoro-1-(7-((4-methoxyphenyl)sulfonyl)-2,7-diazaspiro[3.5]nonan-2-yl)butan-1-one;
1-(7-((4-Methoxyphenyl)sulfonyl)-2,7-diazaspiro[3.5]nonan-2-yl)-2-methyl-2-phenylpropan-1-one,
(7-((4-Methoxyphenyl)sulfonyl)-2,7-diazaspiro[3.5]nonan-2-yl)(1-phenylcyclopropyl)methanone;
3-(4-Fluorophenyl)-1-(7-((4-methoxyphenyl)sulfonyl)-2,7-diazaspiro[3.5]nonan-2-yl)propan-1-one;
2-(3-Methoxyphenyl)-1-(7-((4-methoxyphenyl)sulfonyl)-2,7-diazaspiro[3.5]nonan-2-yl)-2-methylpropan-1-one;
1-(7-((4-Methoxyphenyl)sulfonyl)-2,7-diazaspiro[3.5]nonan-2-yl)-2-methyl-2-(pyridin-3-ylmethoxy)propan-1-one;
2-Hydroxy-1-(7-((4-methoxyphenyl)sulfonyl)-2,7-diazaspiro[3.5]nonan-2-yl)-2-(pyridin-2-yl)propan-1-one;
2-(4-Methoxyphenyl)-1-(7-((4-methoxyphenyl)sulfonyl)-2,7-diazaspiro[3.5]nonan-2-yl)propan-1-one;
1-(7-((4-Methoxyphenyl)sulfonyl)-2,7-diazaspiro[3.5]nonan-2-yl)-2-methyl-2-(o-tolyl)propan-1-one;
Chroman-4-yl(7-((4-methoxyphenyl)sulfonyl)-2,7-diazaspiro[3.5]nonan-2-yl)methanone;
(S)-2-(4-Fluorophenyl)-1-(7-((4-methoxyphenyl)sulfonyl)-2,7-diazaspiro[3.5]nonan-2-yl)-3-methylbutan-1-one;
2-(2-Methoxyphenyl)-1-(7-((4-methoxyphenyl)sulfonyl)-2,7-diazaspiro[3.5]nonan-2-yl)propan-1-one;
2-(2-Methoxyphenyl)-1-(7-((4-methoxyphenyl)sulfonyl)-2,7-diazaspiro[3.5]nonan-2-yl)-2-methylpropan-1-one;
(7-((4-Methoxyphenyl)sulfonyl)-2,7-diazaspiro[3.5]nonane-2-yl)(1,2,3,4-tetrahydronaphthalen-1-yl)methanone;
2-(4-Chlorophenyl)-1-(7-((4-methoxyphenyl)sulfonyl)-2,7-diazaspiro[3.5]nonan-2-yl)propan-1-one;
2-(4-Chlorophenyl)-1-(7-((4-methoxyphenyl)sulfonyl)-2,7-diazaspiro[3.5]nonan-2-yl)-2-methylpropan-1-one;
(7-((4-Methoxyphenyl)sulfonyl)-2,7-diazaspiro[3.5]nonan-2-yl)(1-phenylcyclopentyl)methanone;
2-(3,5-Difluorophenyl)-1-(7-((4-methoxyphenyl)sulfonyl)-2,7-diazaspiro[3.5]nonan-2-yl)propan-1-one;
2-(3-Chlorophenyl)-1-(7-((4-methoxyphenyl)sulfonyl)-2,7-diazaspiro[3.5]nonan-2-yl)-2-methylpropan-1-one;
5-(7-((4-Methoxyphenyl)sulfonyl)-2,7-diazaspiro[3.5]nonan-2-yl)-3-2,2,2-trifluoromethyl)-1,2,4-thiadiazole;
3-(4-Chlorophenyl)-5-(7-((4-methoxyphenyl)sulfonyl)-2,7-diazaspiro[3.5]nonan-2-yl)-1,2,4-thiadiazole;
3-(3,4-Difluorobenzyl)-5-(7-((4-methoxyphenyl)sulfonyl)-2,7-diazaspiro[3.5]nonan-2-yl)-1,2,4-thiadiazole;
3-Cyclopropyl-5-(7-((4-methoxyphenyl)sulfonyl)-2,7-diazaspiro[3.5]nonan-2-yl)-1,2,4-thiadiazole;
3-Butyl-5-(7-((4-methoxyphenyl)sulfonyl)-2,7-diazaspiro[3.5]nonan-2-yl)-1,2,4-thiadiazole;
5-(7-((4-Methoxyphenyl)sulfonyl)-2,7-diazaspiro[3.5]nonan-2-yl)-3-(3-trifluoromethyl)benzyl)-1,2,4-thiadiazole;
3-(4-Methoxyphenyl)-5-(7-((4-methoxyphenyl)sulfonyl)-2,7-diazaspiro[3.5]nonan-2-yl)-1,2,4-thiadiazole;
5-(7-((4-Methoxyphenyl)sulfonyl)-2,7-diazaspiro[3.5]nonan-2-yl)-3-(pyrazin-2-yl)-1,2,4-thiadiazole;
3-(4-Chlorophenyl)-5-(7-((4-methoxyphenyl)sulfonyl)-2,7-diazaspiro[3.5]nonan-2-yl)-1,2,4-thiadiazole;
3-(1-(4-Fluorophenyl)cyclopropyl)-5-(7-((4-methoxyphenyl)sulfonyl)-2,7-diazaspiro[3.5]nonan-2-yl)-1,2,4-thiadiazole;
3-(4-Fluorobenzyl)-5-(7-((4-(methylthio)phenyl)sulfonyl)-2,7-diazaspiro[3.5]nonan-2-yl)-1,2,4-thiadiazole;
7-((4-(Difluoromethoxy)phenyl)sulfonyl)-2-((4-ethoxyphenyl)sulfonyl)-2,7-diazaspiro[3.5]nonane;
2-((4-Chlorophenyl)sulfonyl)-7-((4-difluoromethoxyphenyl)sulfonyl)-2,7-diazaspiro[3.5]nonane;
7-((4-(Difluoromethoxy)phenyl)sulfonyl)-2-((4-fluorophenyl)sulfonyl)-2,7-diazaspiro[3.5]nonane;
7-((4-(Difluoromethoxy)phenyl)sulfonyl)-2-((4-methoxyphenyl)sulfonyl)-2,7-diazaspiro[3.5]nonane;
7-((4-Ethoxyphenyl)sulfonyl)-2-((4-methoxyphenyl)sulfonyl)-2,7-diazaspiro[3.5]nonane;
7-((4-Chlorophenyl)sulfonyl)-2-((4-methoxyphenyl)sulfonyl)-2,7-diazaspiro[3.5]nonane;
2,7-Bis((4-(difluoromethoxy)phenyl)sulfonyl)-2,7-diazaspiro[3.5]nonane;
2-((4-(Difluoromethoxy)phenyl)sulfonyl)-7-((4-ethoxyphenyl)sulfonyl)-2,7-diazaspiro[3.5]nonane;
7-((4-Chlorophenyl)sulfonyl)-2-((4-(difluoromethoxy)phenyl)sulfonyl)-2,7-diazaspiro[3.5]nonane;
2-((4-(Difluoromethoxy)phenyl)sulfonyl)-7-((4-fluorophenyl)sulfonyl)-2,7-diazaspiro[3.5]nonane;
6-Chloro-2-(7-((4-methoxyphenyl)sulfonyl)-2,7-diazaspiro[3.5]nonan-2-yl)benzo[d]thiazole;
6-Chloro-2-(7-((4-ethoxyphenyl)sulfonyl)-2,7-diazaspiro[3.5]nonan-2-yl)benzo[d]thiazole;
6-Chloro-2-(7-((4-(difluoromethoxy)phenyl)sulfonyl)-2,7-diazaspiro[3.5]nonan-2-yl)benzo[d]thiazole;
6-Chloro-2-(7-((4-(methylthio)phenyl)sulfonyl)-2,7-diazaspiro[3.5]nonan-2-yl)benzo[d]thiazole;
3-(1-(4-Fluorophenyl)ethyl)-5-(7-((4-methoxyphenyl)sulfonyl)-2,7-diazaspiro[3.5]nonan-2-yl)-1,2,4-thiadiazole;
3-(4-Fluorobenzyl)-5-(7-((4-methoxyphenyl)sulfonyl)-2,7-diazaspiro[3.5]nonan-2-yl)-1,2,4-thiadiazole;
N-(4-((2-(3-(4-fluorobenzyl)-1,2,4-thiadiazol-5-yl)-2,7-diazaspiro[3.5]nonan-7-yl)sulfonyl)phenyl)acetamide;
3-(4-Fluorophenyl)-5-(7-((4-(methylsulfonyl)phenyl)sulfonyl)-2,7-diazaspiro[3.5]nonan-2-yl)-1,2,4-thiadiazole;
5-(7-((2,4-Difluorophenyl)sulfonyl)-2,7-diazaspiro[3.5]nonan-2-yl)-3-(4-fluorobenzyl)-1,2,4-thiadiazole;

5-(7-((3,4-Dimethoxyphenyl)sulfonyl)-2,7-diazaspiro[3.5]nonan-2-yl)-3-(4-fluorobenzyl)-1,2,4-thiadiazole;
3-(4-Fluorobenzyl)-5-(7-((2-methoxy-5-methylphenyl)sulfonyl)-2,7-diazaspiro[3.5]nonan-2-yl)-1,2,4-thiadiazole;
5-(7-((5-Chloro-2-methoxyphenyl)sulfonyl)-2,7-diazaspiro[3.5]nonan-2-yl)-3-(4-fluorobenzyl)-1,2,4-thiadiazole;
3-(4-Fluorobenzyl)-5-(7-((3-(trifluoromethyl)phenyl)sulfonyl)-2,7-diazaspiro[3.5]nonan-2-yl)-1,2,4-thiadiazole;
3-(4-Fluorobenzyl)-5-(7-((4-trifluoromethyl)phenyl)sulfonyl)-2,7-diazaspiro[3.5]nonan-2-yl)-1,2,4-thiadiazole;
3-(4-Fluorobenzyl)-5-(7-(m-tolylsulfonyl)-2,7-diazaspiro[3.5]nonan-2-yl)-1,2,4-thiadiazole;
3-(4-Fluorobenzyl)-5-(7-((2-fluorophenyl)sulfonyl)-2,7-diazaspiro[3.5]nonan-2-yl)-1,2,4-thiadiazole;
5-(7-((4-Ethylphenyl)sulfonyl)-2,7-diazaspiro[3.5]nonan-2-yl)-3-(4-fluorobenzyl)-1,2,4-thiadiazole;
3-(4-fluorobenzyl)-5-(7-(o-tolylsulfonyl)-2,7-diazaspiro[3.5]nonan-2-yl)-1,2,4-thiadiazole;
5-(7-((4-(Tert-butyl)phenyl)sulfonyl)-2,7-diazaspiro[3.5]nonan-2-yl)-3-(4-fluorobenzyl)-1,2,4-thiadiazole;
3-(4-Fluorobenzyl)-5-(7-((3-fluorophenyl)sulfonyl)-2,7-diazaspiro[3.5]nonan-2-yl)-1,2,4-thiadiazole;
5-(7-(2,5-Dimethoxyphenyl)sulfonyl)-2,7-diazaspiro[3.5]nonan-2-yl)-3-(4-fluorobenzyl)-1,2,4-thiadiazole;
5-(7-((2,5-Difluorophenyl)sulfonyl)-2,7-diazaspiro[3.5]nonan-2-yl)-3-(4-fluorobenzyl)-1,2,4-thiadiazole;
5-(7-((3,4-Difluorophenyl)sulfonyl)-2,7-diazaspiro[3.5]nonan-2-yl)-3-(4-fluorobenzyl)-1,2,4-thiadiazole;
3-(4-Fluorobenzyl)-5-(7-((3-methoxyphenyl)sulfonyl)-2,7-diazaspiro[3.5]nonan-2-yl)-1,2,4-thiadiazole;
5-(7-((5-Fluoro-2-methylphenyl)sulfonyl)-2,7-diazaspiro[3.5]nonan-2-yl)-3-(4-fluorobenzyl)-1,2,4-thiadiazole;
2-Ethoxy-5-((2-(3-(4-fluorobenzyl)-1,2,4-thiadiazol-5-yl)-2,7-diazaspiro[3.5]nonan-7-yl)sulfonyl)benzonitrile;
3-(4-Fluorobenzyl)-5-(7-((4-methoxy-3-(trifluoromethyl)phenyl)sulfonyl)-2,7-diazaspiro[3.5]nonan-2-yl)-1,2,4-thiadiazole;
3-(4-Fluorobenzyl)-5-(7-((2-methoxyphenyl)sulfonyl)-2,7-diazaspiro[3.5]nonan-2-yl)-1,2,4-thiadiazole;
5-(7-((3-Chloro-4-methoxyphenyl)sulfonyl)-2,7-diazaspiro[3.5]nonan-2-yl)-(4-fluorobenzyl)-1,2,4-thiadiazole;
3-(4-Fluorobenzyl)-5-(7-((3-(methylsulfonyl)phenyl)sulfonyl)-2,7-diazaspiro[3.5]nonan-2-yl)-1,2,4-thiadiazole;
5-(7-((3,5-Difluorophenyl)sulfonyl)-2,7-diazaspiro[3.5]nonan-2-yl)-3-(4-fluorobenzyl)-1,2,4-thiadiazole;
Methyl 3-((2-(3-(4-fluorobenzyl)-1,2,4-thiadiazol-5-yl)-2,7-diazaspiro[3.5]nonan-7-yl)sulfonyl)benzoate;
5-(7-((4-(Difluoromethoxy)phenyl)sulfonyl)-2,7-diazaspiro[3.5]nonan-2-yl)-3-(4-fluorobenzyl)-1,2,4-thiadiazole;
5-(7-((5-Fluoro-2-methoxyphenyl)sulfonyl)-2,7-diazaspiro[3.5]nonan-2-yl)-3-(4-fluorobenzyl)-1,2,4-thiadiazole;
5-(7-((4-Ethoxy-3-methylphenyl)sulfonyl)-2,7-diazaspiro[3.5]nonan-2-yl)-3-(4-fluorobenzyl)-1,2,4-thiadiazole;
3-(4-Fluorobenzyl)-5-(7-((4-methoxy-3-methylphenyl)sulfonyl)-2,7-diazaspiro[3.5]nonan-2-yl)-1,2,4-thiadiazole;
3-(4-Fluorobenzyl)-5-(7-(pyridin-3-ylsulfonyl)-2,7-diazaspiro[3.5]nonan-2-yl)-1,2,4-thiadiazol;
3-(4-Fluorobenzyl)-5-(7-((1-methyl-1H-pyrazol-4-yl)sulfonyl)-2,7-diazaspiro[3.5]nonan-2-yl)-1,2,4-thiadiazole;
4-((2-(3-(4-Fluorobenzyl)-1,2,4-thiadiazol-5-yl)-2,7-diazaspiro[3.5]nonan-7-yl)sulfonyl)-3,5-dimethylisoxazole;
3-(4-Fluorobenzyl)-5-(7-(thiophen-2-ylsulfonyl)-2,7-diazaspiro[3.5]nonan-2-yl)-1,2,4-thiadiazole;
5-(7-((5-Chlorothiophen-2-yl)sulfonyl)-2,7-diazaspiro[3.5]nonan-2-yl)-3-(4-fluorobenzyl)-1,2,4-thiadiazole;
3-(4-Fluorobenzyl)-5-(7-(thiophen-3-ylsulfonyl)-2,7-diazaspiro[3.5]nonan-2-yl)-1,2,4-thiadiazole;
3-(4-Fluorobenzyl)-5-(7-((5-methylthiophen-2-yl)sulfonyl)-2,7-diazaspiro[3.5]nonan-2-yl)-1,2,4-thiadiazole;
3-(4-Fluorobenzyl)-5-(7-((3,3,3-trifluoropropyl)sulfonyl)-2,7-diazaspiro[3.5]nonan-2-yl)-1,2,4-thiadiazole;
5-(7-((Cyclohexylmethyl)sulfonyl)-2,7-diazaspiro[3.5]nonan-2-yl)-3-(4-fluorobenzyl)-1,2,4-thiadiazole;
4-((2-(3-(4-Fluorobenzyl)-1,2,4-thiadiazol-5-yl)-2,7-diazaspiro[3.5]nonan-7-yl)sulfonyl)morpholine; and a solvate, hydrate, pharmaceutically acceptable salt thereof The present invention also encompasses processes for the preparation of compounds of formula (I) and any subgroup thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999. Protected forms of the inventive compounds are included within the scope of the present invention. It will also be clear to the skilled person that compounds of the invention in which one or more functional groups have been protected with suitable functional groups can find use as intermediates in the production and/or synthesis of the compounds of the invention, and as such form a further aspect of the invention.

The compounds formula (I), the subgroups thereof and their pharmaceutically acceptable salts can be prepared as described hereunder.

In the general schemes described below, all substituents are defined as in the general formula (I), (IA), (IB), (IC), (ID), (IE), (IF), or any subgroups thereof unless otherwise mentioned or indicated.

The present compounds of formula (I) and their pharmaceutically acceptable salts can be prepared by methods known in the art, for example, by processes described below, which process comprises:

coupling a compound of formula II:

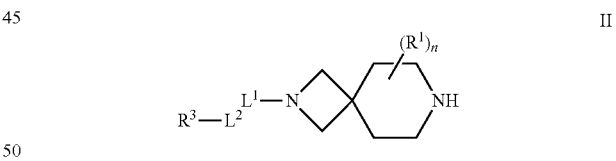

II with a derivative of formula III, for example a sulfonyl chloride of formula (IIIA):

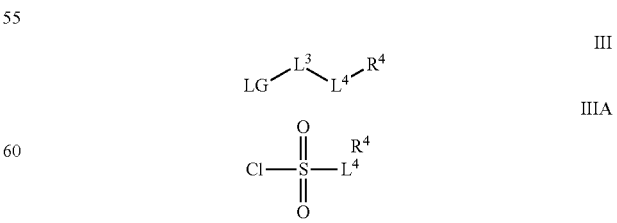

III

IIIA wherein LG is a leaving group (for example an halogen atom); to give a compound of formula (I), such as for example a compound of formula IVA

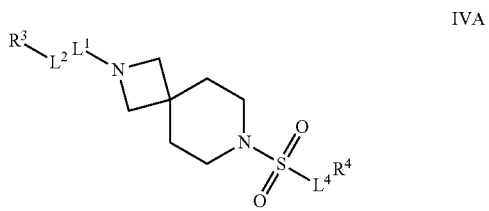

IVA or if desired, converting the compounds obtained into pharmaceutically acceptable acid addition salts.

The preparation of compounds of formula (I) of the present invention may be carried out in sequential or convergent synthetic routes. In some embodiments, syntheses of the compounds of the invention are shown in the following general schemes 1 to 6. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. The reaction sequence is not limited to the one displayed in schemes 1 to 7, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The invention includes all stereoisomeric forms, including individual diastereoisomers and enantiomers of the compound of formula (I) as well as racemic and non-racemic mixtures thereof.

Wherein $L^1$ is a thiadiazole ring, the intermediate of formula II can be prepared according to General Scheme 1:

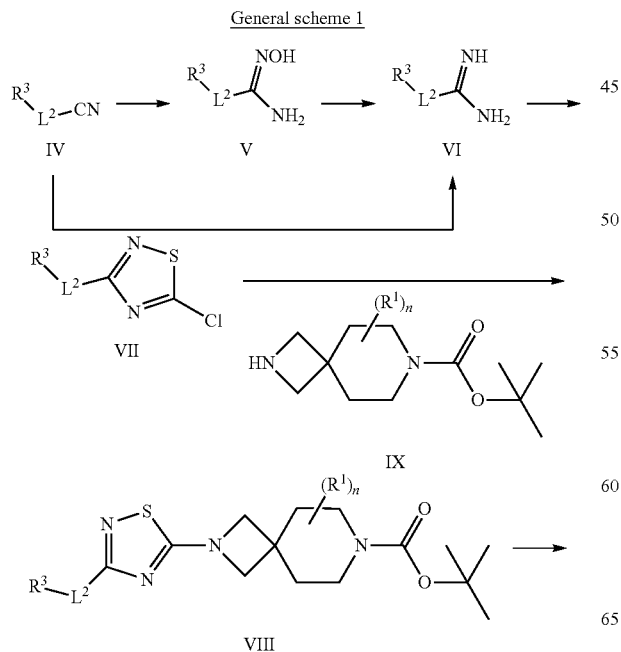

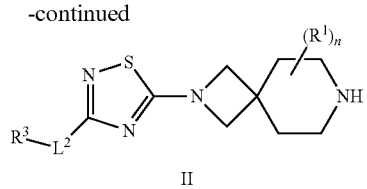

II

The nitrile moiety of compounds of formula IV (commercially available of prepared according to procedures available in the literature) is converted into the amidine intermediate VI in a one step procedure upon addition of methylchloroaluminium amides (MeClAlNH$_2$). Alternatively, amidines VI are prepared in a two steps sequence from IV, by addition of hydroxyl amine to afford intermediate V, followed by hydrogenolysis (for instance using Pd in presence of ammonium formate). 5-Chloro-[1,2,4]-thiadiazoles VII are then prepared by reacting the amidine VI with perchloromethyl mercaptan. A nucleophilic aromatic substitution of VII with commercially available tert-butyl 2,7-diazaspiro[3.5]nonane-7-carboxylate IX afford VII. Removal of the protecting group (e.g. with trifluoroacetic acid (TFA)) affords derivatives of formula II wherein $L^1$ is a thiadiazole ring.

Wherein $L^1$ is a group of formula

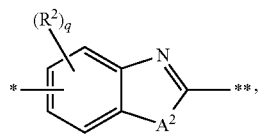

the intermediate of formula II can be prepared according to General Scheme 2:

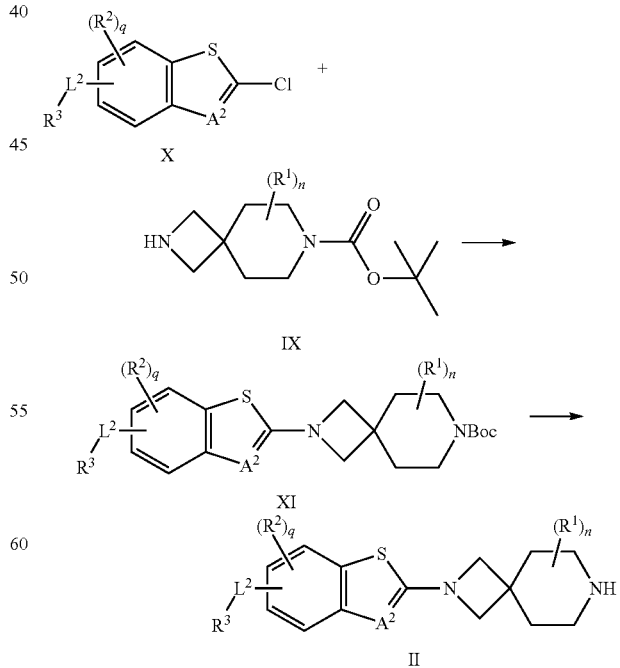

The commercially available amine derivative IX is coupled to a substituted 2-chlor-benzothiazole derivative X upon heating at high temperature to give intermediate X. After removal of the protecting group (e.g. with trifluoroacetic acid (TFA)), the benzothiazole intermediate II wherein $L^1$ a group of formula

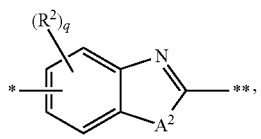

is obtained.

Wherein $L^1$ is an $SO_2$ group, intermediates of formula II can be prepared according to General Scheme 3:

General scheme 3

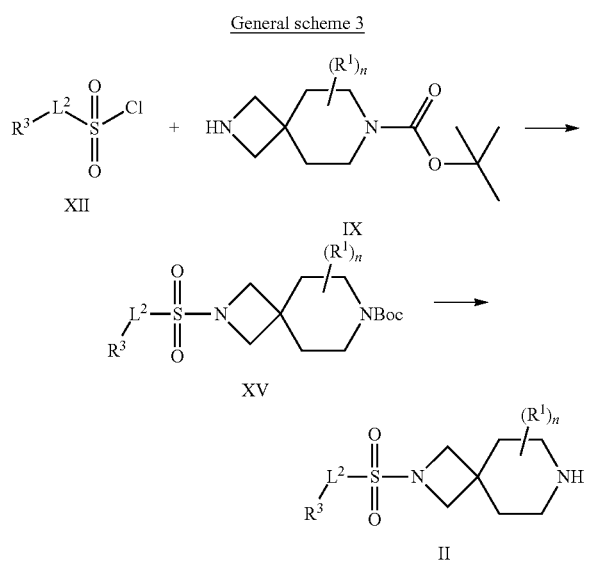

The sulfonyl chlorides XII, commercially available or prepared according to methods described in the literature, are coupled with the commercially available tert-butyl 2,7-diazaspiro[3.5]nonane-7-carboxylate IX to give intermediate XIII. After removal of the protecting group (e.g. with trifluoroacetic acid (TFA)), the sulfonamide intermediate II wherein $L^1$ is an $SO_2$ group, is obtained.

Wherein $L^1$ is a CO group, intermediates of formula II can be prepared according to General Scheme 4.

General scheme 4

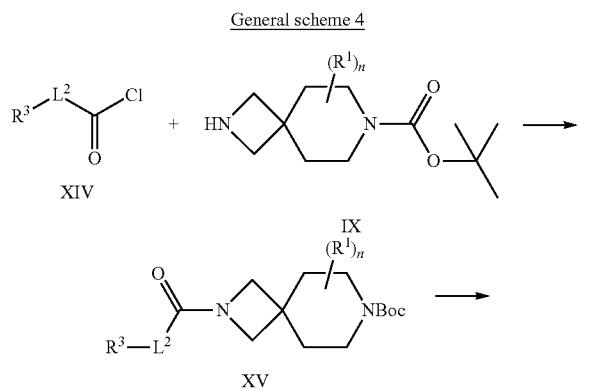

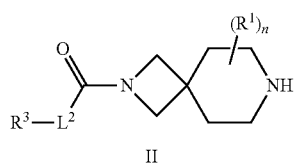

The acyl chloride XIV (commercially available or prepared following methods described in the literature) is coupled with the commercially available tert-butyl 2,7-diazaspiro[3.5]nonane-7-carboxylate IX to give intermediate XV. After removal of the protecting group (e.g. with trifluoroacetic acid (TFA)), the sulfonamide intermediate II wherein $L^1$ is a CO group, is obtained.

Wherein $L^1$ is a single bond, intermediates of formula II can be prepared according to General Scheme 5.

General scheme 5

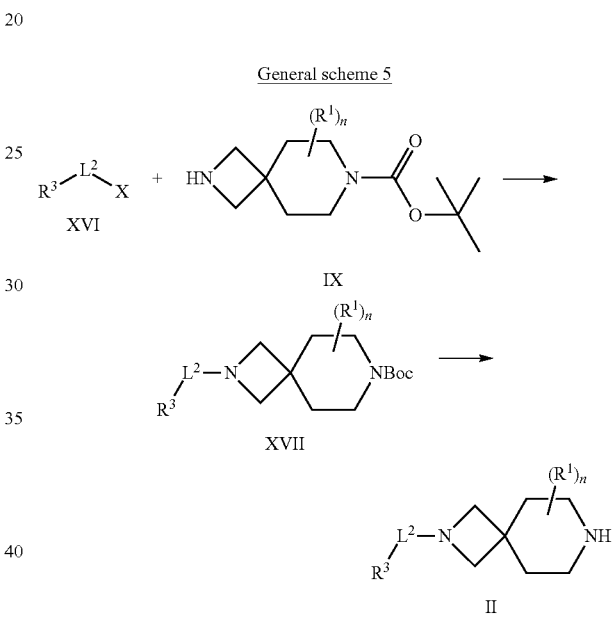

The halogen derivative XVI, commercially available or prepared according to procedures available in the literature, is coupled with the commercially available tat-butyl 2,7-diazaspiro[3.5]nonane-7-carboxylate IX to give intermediate XVII. After removal of the protecting group (e.g. with trifluoroacetic acid (TFA)), the sulfonamide intermediate II wherein $L^1$ is a single bond, is obtained.

Final compounds of formula (I) are obtained by coupling II with intermediate of formula III such as an aryl sulfonyl chloride (scheme 7), commercially available or prepared following procedures described in the literature according to General Scheme 6.

General scheme 6

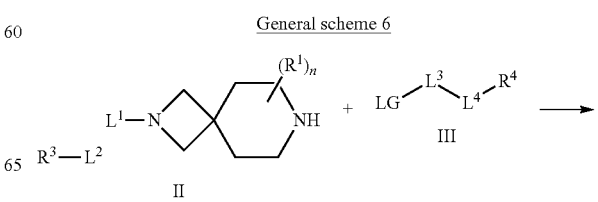

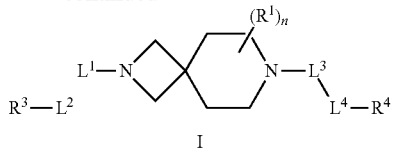

wherein LG is a leaving group (for example a halogen atom).

General scheme 7

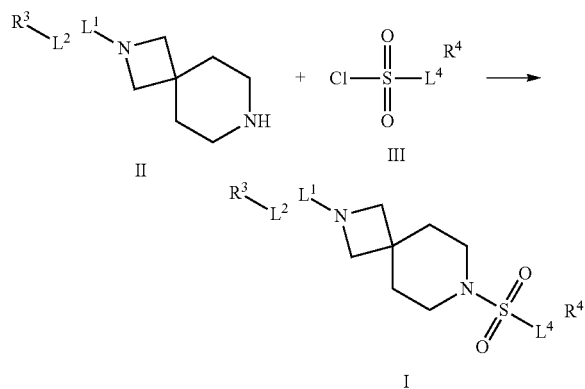

The present invention encompasses compounds according to the invention, as well as the compounds obtained by the methods of the invention. The present invention also encompasses pharmaceutical composition comprising at least one compound of the present invention. The present invention also encompasses pharmaceutical composition comprising at least one compound of the invention and at least one carrier, excipient or diluent acceptable for pharmaceutical purposes.

In some embodiments, the present invention relates to the use of at least one compound of formula (I), or any subgroups thereof; in (the preparation of a composition for) the prevention and/or treatment of metabolic disorders and/or neurodegenerative diseases, and/or protein misfolding disorders.

In some embodiments, the present invention relates to a method of prevention and/or of treatment of metabolic disorders and/or neurodegenerative diseases, and/or protein misfolding disorders, comprising administering to a subject in need thereof an effective amount of at least one compound of formula (I), or any subgroups thereof, or a pharmaceutical composition comprising said at least one compound of formula (I) or any subgroups thereof.

In some embodiments, the present invention relates to the use of at least one compound of formula (I), or any subgroups thereof; in (the preparation of a composition for) the prevention and/or treatment of neurodegenerative disorders and/or protein misfolding disorders, preferably neurodegenerative disorders and/or protein misfolding disorders related to aryloidosis; more preferably neurodegenerative disorders and/or protein misfolding disorders related to synucleinopathies comprising Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease; yet more preferably for the prevention and/or treatment of Parkinson's disease and/or Alzheimer's disease.

In some embodiments, the present invention relates to the use of at least one compound of formula (I), or any subgroups thereof, in (the preparation of a composition for) the prevention and/or treatment of metabolic disorders, preferably metabolic disorders related to aryloidosis, yet more preferably Metabolic disorders such as diabetes mellitus, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases, hypertension; yet more preferably diabetes mellitus such as diabetes mellitus type 1 or type 2, more preferably diabetes mellitus type 2.

The term "subject" as used herein refers to a mammal. The subject will preferably be a human, but may also be a domestic livestock, laboratory or pet animals.

In some embodiments, at least one compound of formula (I) is used (for the preparation of a medicament) for preventing and/or treating a disease selected from the group comprising diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis. Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension and/or for preventing, treating and/or alleviating complications and/or symptoms associated therewith.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as stereoisomers, tautomers, racemics, salts, hydrates or solvates thereof, may be administered as the raw chemical. Additionally, the active ingredient may be presented as a pharmaceutical composition.

Accordingly, the invention further provides pharmaceutical compositions that include effective amounts of compounds of formula (I), or stereoisomers, tautomers, racemics, salts, hydrates or solvates thereof and one or more pharmaceutically acceptable carriers, diluents, or excipients. The compounds of formula (I) or stereoisomers, tautomers, racemics, salts, hydrates or solvates thereof, are as herein described.

The compounds according to the invention may be administered as the sole active ingredient or together, i.e. in a fixed or free combination, with other therapeutic agents used in clinical practice for the treatment of those diseases listed above.

The compounds according to the invention and the other pharmaceutical active agent(s) may be administered together or separately and, when administered separately, administration may occur simultaneously or sequentially, in any order. The amounts of the compounds according to the invention and the other pharmaceutically active agent (s) and the relative timings of administration will be selected in order to achieve the desired combined therapeutic effect. The administration in combination of a compound of formula (I) or a stereoisomer, tautomer, racemic, salt, hydrate or solvate thereof, with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, gluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diaryl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gun acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, disintegrates, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention can be more suitable due to their increased water solubility.

Appropriate cyclodextrins are α-, β- or γ-cyclodextrins (CDs) or ethers and mixed ethers thereof wherein one or more of the hydroxyl groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkoxycarbonylalkyl or carboxyalkoxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated βCD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxyl groups are etherified with different groups such as, for example, hydroxypropyl and hydroxyethyl. An interesting way of formulating the compounds in combination with a cyclodextrin or a derivative thereof has been described in EP-A-721,331. Although the formulations described therein are with antifungal active ingredients, they are equally interesting for formulating the compounds. Said formulations may also be rendered more palatable by adding pharmaceutically acceptable sweeteners and/or flavors. In particular, the present invention encompasses a pharmaceutical composition comprising an effective amount of a compound according to the invention with a pharmaceutically acceptable cyclodextrin. The present invention also encompasses cyclodextrin complexes consisting of a compound according to the invention and a cyclodextrin.

Particular reference is made to the compositions, formulations (and carriers, excipients, diluents, etc. for use therein), routes of administration etc., which are known per se such as those described in U.S. Pat. No. 4,997,834 and EP-A-0 370 498.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa·s when dissolved in a 2% aqueous solution at 20° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products, and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded, or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides, and derivatives thereof.

The preparations may be prepared in a manner known per se, which usually involves mixing the at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the formula (I) above that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

The compositions are of value in the veterinary field, which for the purposes heroin not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a (pharmaceutical) composition for veterinary use that contains at least one compound of the invention and at least one suitable carrier (i.e. a carrier suitable for veterinary use). The invention also relates to the use of a compound of the invention in the preparation of such a composition.

The following examples are provided for the purpose of illustrating the present invention and by no means should be interpreted to limit the scope of the present invention.

EXAMPLES

The synthesis of the compounds of table 1 is described in this experimental part.

TABLE 1

| COMPOUND | STRUCTURE | NAME | EXAMPLE |
|---|---|---|---|
| Cmpd001 | (structure) | 2,7-Bis((4-methoxyphenyl)sulfonyl)-2,7-diazaspiro[3.5]nonane | 1 |
| Cmpd002 | (structure) | 2-((4-Fluorophenyl)sulfonyl)-7-((4-methoxyphenyl)sulfonyl)-2,7-diazaspiro[3.5]nonane | 2 |

TABLE 1-continued

| COMPOUND | STRUCTURE | NAME | EXAMPLE |
|---|---|---|---|
| Cmpd003 | 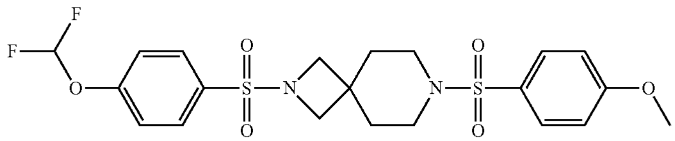 [SMILES: COc1ccc(S(=O)(=O)N2CCC3(CC2)CN(S(=O)(=O)c2ccc(OC(F)F)cc2)C3)cc1] | 2-((4-Difluoromethoxy)phenyl)sulfonyl)-7-((4-methoxyphenyl)sulfonyl)-2,7-diazaspiro[3.5]nonane | 3 |
| Cmpd004 | 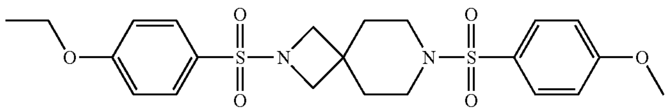 [SMILES: CCOc1ccc(S(=O)(=O)N2CC3(CCN(S(=O)(=O)c4ccc(OC)cc4)CC3)C2)cc1] | 7-((4-Methoxyphenyl)sulfonyl)-2-((4-propoxyphenyl)sulfonyl)-2,7-diazaspiro[3.5]nonane | 4 |
| Cmpd005 | 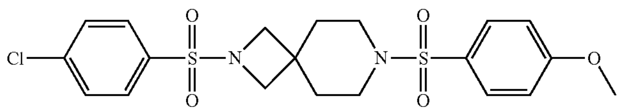 [SMILES: COc1ccc(S(=O)(=O)N2CCC3(CC2)CN(S(=O)(=O)c2ccc(Cl)cc2)C3)cc1] | 2-((4-Chlorophenyl)sulfonyl)-7-((4-methoxyphenyl)sulfonyl)-2,7-diazaspiro[3.5]nonane | 5 |
| Cmpd006 | 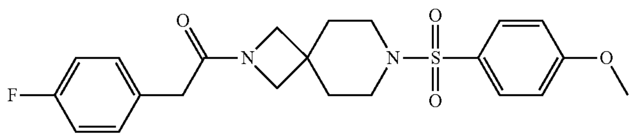 [SMILES: COc1ccc(S(=O)(=O)N2CCC3(CC2)CN(C(=O)Cc2ccc(F)cc2)C3)cc1] | 2-(4-Fluorophenyl)-1-(7-((4-methoxyphenyl)sulfonyl)-2,7-diazaspiro[3.5]nonan-2-yl)ethanone | 6 |
| Cmpd007 | 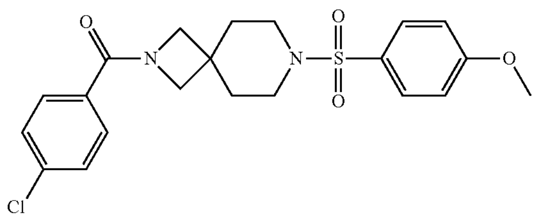 [SMILES: COc1ccc(S(=O)(=O)N2CCC3(CC2)CN(C(=O)c2ccc(Cl)cc2)C3)cc1] | (4-Chlorophenyl)(7-((4-methoxyphenyl)sulfonyl)-2,7-diazaspiro[3.5]nonan-2-yl)methanone | 7 |
| Cmpd008 | 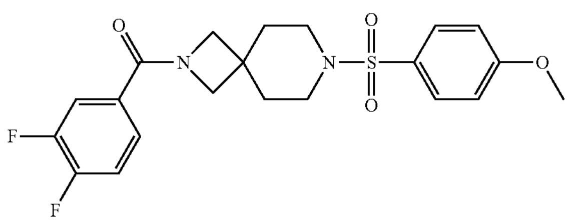 [SMILES: COc1ccc(S(=O)(=O)N2CCC3(CC2)CN(C(=O)c2ccc(F)c(F)c2)C3)cc1] | (3,4-Difluorophenyl)(7-((4-methoxyphenyl)sulfonyl)-2,7-diazaspiro[3.5]nonan-2-yl)methanone | 8 |
| Cmpd009 | 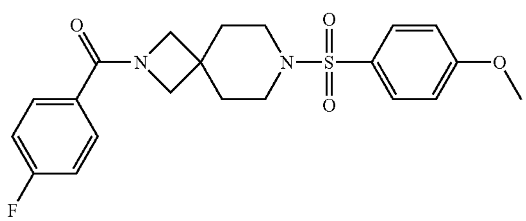 [SMILES: COc1ccc(S(=O)(=O)N2CCC3(CC2)CN(C(=O)c2ccc(F)cc2)C3)cc1] | (4-Fluorophenyl)(7-((4-methoxyphenyl)sulfonyl)-2,7-diazaspiro[3.5]nonan-2-yl)methanone | 9 |
| Cmpd010 | 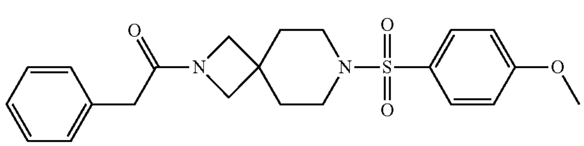 [SMILES: COc1ccc(S(=O)(=O)N2CCC3(CC2)CN(C(=O)Cc2ccccc2)C3)cc1] | 1-(7-((4-Methoxyphenyl)sulfonyl)-2,7-diazaspiro[3.5]nonan-2-yl)-2-phenylethanone | 10 |
| Cmpd011 | 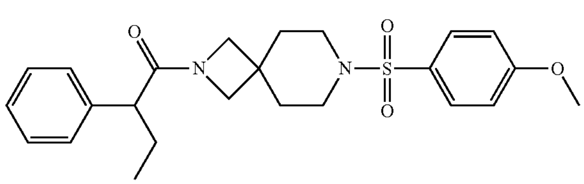 [SMILES: CCC(C(=O)N1CC2(CCN(S(=O)(=O)c3ccc(OC)cc3)CC2)C1)c1ccccc1] | 1-(7-((4-Methoxypehnyl)sulfonyl)-2,7-diazaspiro[3.5]nonan-2-yl)-2-phenylbutan-1-one | 11 |

TABLE 1-continued

| COMPOUND | STRUCTURE | NAME | EXAMPLE |
|---|---|---|---|
| Cmpd012 | 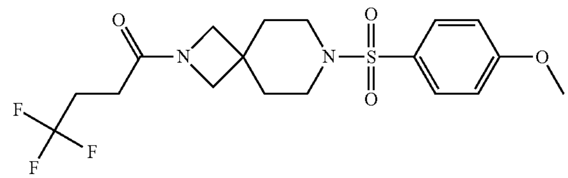 [SMILES: COc1ccc(S(=O)(=O)N2CCC3(CC2)CN(C(=O)CCC(F)(F)F)C3)cc1] | 4,4,4-Trifluoro-1-(7-((4-methoxyphenyl)sulfonyl)-2,7-diazaspiro[3.5]nonan-2-yl)butan-1-one | 12 |
| Cmpd013 | 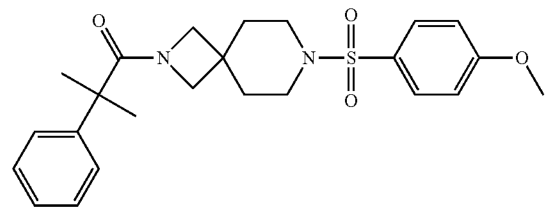 [SMILES: COc1ccc(S(=O)(=O)N2CCC3(CC2)CN(C(=O)C(C)(C)c2ccccc2)C3)cc1] | 1-(7-((4-Methoxyphenyl)sulfonyl)-2,7-diazaspiro[3.5]nonan-2-yl)-2-methyl-2-phenylpropan-1-one | 13 |
| Cmpd014 | 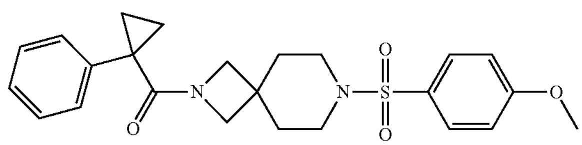 [SMILES: COc1ccc(S(=O)(=O)N2CCC3(CC2)CN(C(=O)C2(c4ccccc4)CC2)C3)cc1] | (7-((4-Methoxyphenyl)sulfonyl)-2,7-diazaspiro[3.5]nonan-2-yl)(1-phenylcyclopropyl)methanone | 14 |
| Cmpd015 | 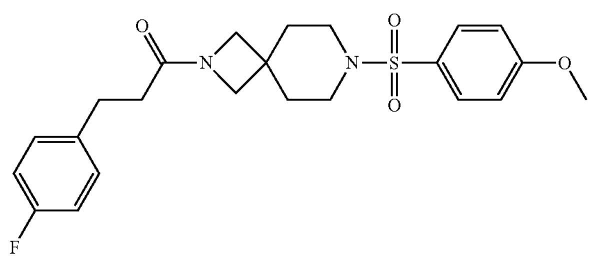 [SMILES: COc1ccc(S(=O)(=O)N2CCC3(CC2)CN(C(=O)CCc2ccc(F)cc2)C3)cc1] | 3-(5-Fluorophenyl)-1-(7-((4-methoxyphenyl)sulfonyl)-2,7-diazaspiro[3.5]nonan-2-yl)propan-1-one | 15 |
| Cmpd016 | 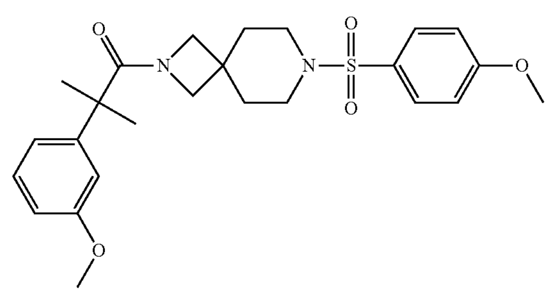 [SMILES: COc1ccc(S(=O)(=O)N2CCC3(CC2)CN(C(=O)C(C)(C)c2cccc(OC)c2)C3)cc1] | 2-(3-Methoxyphenyl)-1-(7-((4-methoxyphenyl)sulfonyl)-2,7-diazaspiro[3.5]nonan-2-yl)-2-methylpropan-1-one | 16 |
| Cmpd017 | 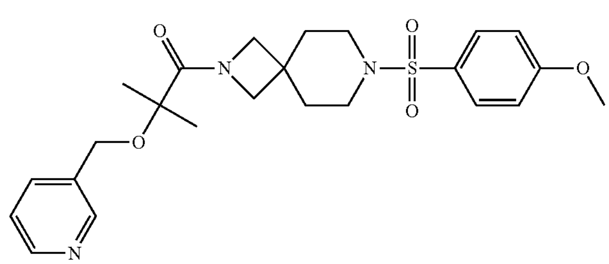 [SMILES: COc1ccc(S(=O)(=O)N2CCC3(CC2)CN(C(=O)C(C)(C)OCc2cccnc2)C3)cc1] | 1-(7-((4-Methoxyphenyl)sulfonyl)-2,7-diazaspiro[3.5]nonan-2-yl)-2-methyl-2-(pyridin-3-ylmethoxy)propan-1-one | 17 |
| Cmpd018 | 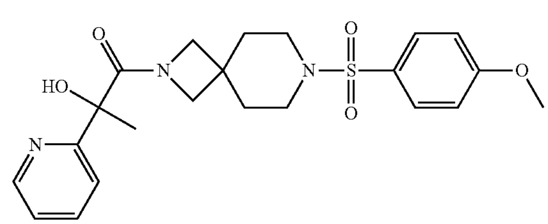 [SMILES: COc1ccc(S(=O)(=O)N2CCC3(CC2)CN(C(=O)C(C)(O)c2ccccn2)C3)cc1] | 2-Hydroxy-1-(7-((4-methoxyphenyl)sulfonyl)-2,7-diazaspiro[3.5]nonan-2-yl)-2-(pyridin-2-yl)propan-1-one | 18 |

TABLE 1-continued

| COMPOUND | STRUCTURE | NAME | EXAMPLE |
|---|---|---|---|
| Cmpd019 | 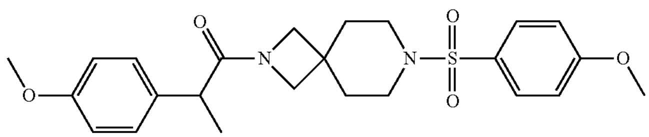 | 2-(4-Methoxyphenyl)-1-(7-((4-methoxyphenyl)sulfonyl)-2,7-diazaspiro[3.5]nonan-2-yl)propan-1-one | 19 |
| Cmpd020 | 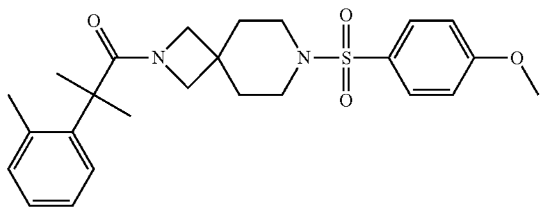 [SMILES: COc1ccc(S(=O)(=O)N2CCC3(CC2)CN(C(=O)C(C)(C)c2ccccc2C)C3)cc1] | 1-(7-((4-Methoxyphenyl)sulfonyl)-2,7-diazaspiro[3.5]nonan-2-yl)-2-methyl-2-(o-tolyl)propan-1-one | 20 |
| Cmpd021 | 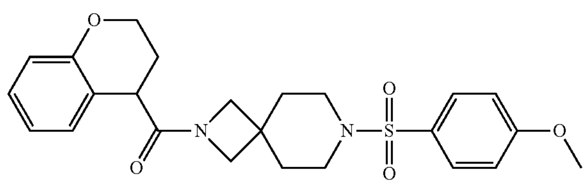 [SMILES: COc1ccc(S(=O)(=O)N2CCC3(CC2)CN(C(=O)C2CCOc4ccccc42)C3)cc1] | Chroman-4-yl(7-((4-methoxyphenyl)sulfonyl)-2,7-diazaspiro[3.5]nonan-2-yl)methanone | 21 |
| Cmpd022 | 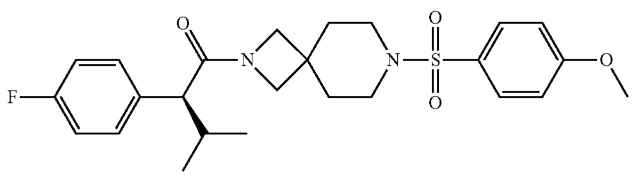 [SMILES: COc1ccc(S(=O)(=O)N2CCC3(CC2)CN(C(=O)[C@H](c2ccc(F)cc2)C(C)C)C3)cc1] | (S)-2-(4-fluorophenyl)-1-(7-((4-methoxyphenyl)sulfonyl)-2,7-diazaspiro[3.5]nonan-2-yl)-3-methylbutan-1-one | 22 |
| Cmpd023 | 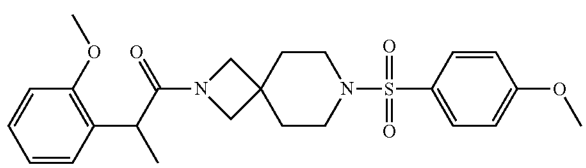 [SMILES: COc1ccc(S(=O)(=O)N2CCC3(CC2)CN(C(=O)C(C)c2ccccc2OC)C3)cc1] | 2-(2-Methoxyphenyl)-1-(7-((4-methoxyphenyl)sulfonyl)-2,7-diazaspiro[3.5]nonan-2-yl)propan-1-one | 23 |
| Cmpd024 | 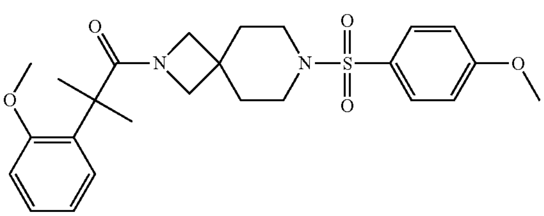 [SMILES: COc1ccc(S(=O)(=O)N2CCC3(CC2)CN(C(=O)C(C)(C)c2ccccc2OC)C3)cc1] | 2-(2-Methoxypehnyl)-1-(7-((4-methoxyphenyl)sulfonyl)-2,7-diazaspiro[3.5]nonan-2-yl)-2-methyl propan-1-one | 24 |
| Cmpd025 | 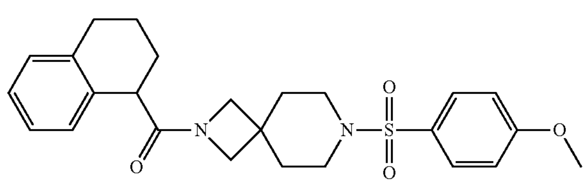 [SMILES: COc1ccc(S(=O)(=O)N2CCC3(CC2)CN(C(=O)C2CCCc4ccccc42)C3)cc1] | (7-((4-Methoxyphenyl)sulfonyl)-2,7-diazaspiro[3.5]nonan-2-yl)(1,2,3,4-tetrahydronaphthalen-1-yl)methanone | 25 |
| Cmpd026 | 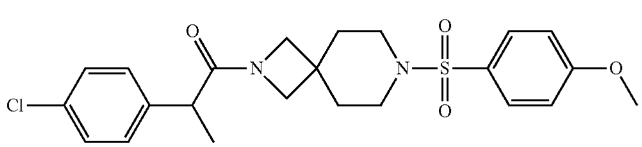 [SMILES: COc1ccc(S(=O)(=O)N2CCC3(CC2)CN(C(=O)C(C)c2ccc(Cl)cc2)C3)cc1] | 2-(4-Chlorophenyl)-1-(7-((4-methoxyphenyl)sulfonyl)-2,7-diazaspiro[3.5]nonan-2-yl)propan-1-one | 26 |

TABLE 1-continued

| COMPOUND | STRUCTURE | NAME | EXAMPLE |
|---|---|---|---|
| Cmpd027 | 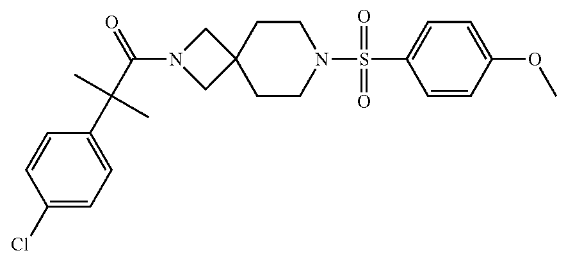 [SMILES: COc1ccc(S(=O)(=O)N2CCC3(CC2)CN(C(=O)C(C)(C)c2ccc(Cl)cc2)C3)cc1] | 2-(4-Chlorophenyl)-1-(7-((4-methoxyphenyl)sulfonyl)-2,7-diazaspiro[3.5]nonan-2-yl)-2-methylpropan-1-one | 27 |
| Cmpd028 | 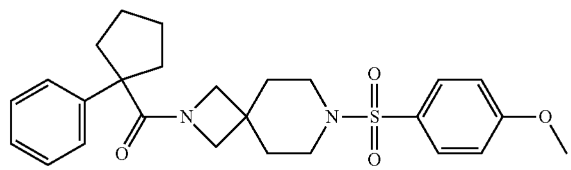 [SMILES: COc1ccc(S(=O)(=O)N2CCC3(CC2)CN(C(=O)C2(c4ccccc4)CCCC2)C3)cc1] | (7-((4-Methoxyphenyl)sulfonyl)-2,7-diazaspiro[3.5]nonan-2-yl)(1-phenylcyclopentyl)methanone | 28 |
| Cmpd029 | 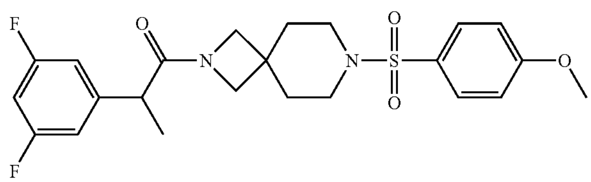 [SMILES: COc1ccc(S(=O)(=O)N2CCC3(CC2)CN(C(=O)C(C)c2cc(F)cc(F)c2)C3)cc1] | 2-(3,5-Difluorophenyl)-1-(7-((4-methoxyphenyl)sulfonyl)-2,7-diazaspiro[3.5]nonan-2-yl)propan-1-one | 29 |
| Cmpd030 | 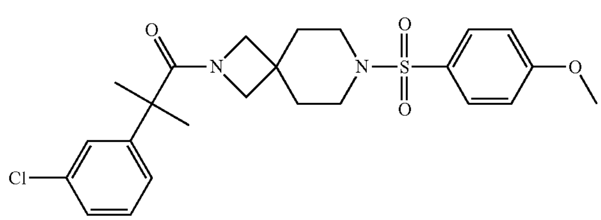 [SMILES: COc1ccc(S(=O)(=O)N2CCC3(CC2)CN(C(=O)C(C)(C)c2cccc(Cl)c2)C3)cc1] | 2-(3-Chlorophenyl)-1-(7-((4-methoxyphenyl)sulfonyl)-2,7-diazaspiro[3.5]nonan-2-yl)-2-methylpropan-1-one | 30 |
| Cmpd031 | 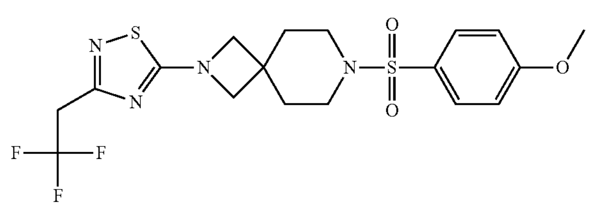 [SMILES: COc1ccc(S(=O)(=O)N2CCC3(CC2)CN(c2nc(CC(F)(F)F)ns2)C3)cc1] | 5-(7-((4-Methoxyphenyl)sulfonyl)-2,7-diazaspiro[3.5]nonan-2-yl)-3-(2,2,2-trifluoroethyl)-1,2,4-thiadiazole | 31 |
| Cmpd032 | 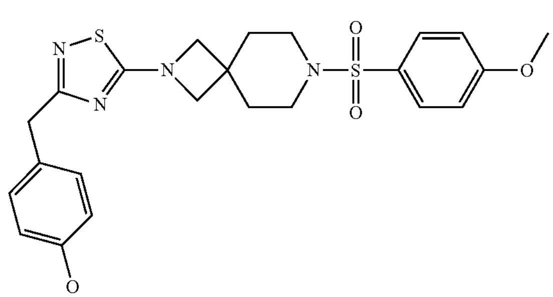 [SMILES: COc1ccc(S(=O)(=O)N2CCC3(CC2)CN(c2nc(Cc4ccc(O)cc4)ns2)C3)cc1] | 3-(4-Chlorobenzyl)-5-(7-((4-methoxyphenyl)sulfonyl)-2,7-diazaspiro[3.5]nonan-2-yl)-1,2,4-thiadiazole | 32 |

TABLE 1-continued

| COMPOUND | STRUCTURE | NAME | EXAMPLE |
|---|---|---|---|
| Cmpd033 | 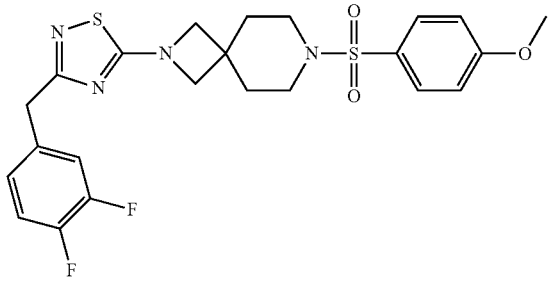 [SMILES: COc1ccc(S(=O)(=O)N2CCC3(CC2)CN(c2nc(Cc4ccc(F)c(F)c4)ns2)C3)cc1] | 3-(3,4-Difluorobenzyl)-5-(7-((4-methoxyphenyl)sulfonyl)-2,7-diazaspiro[3.5]nonan-2-yl)-1,2,4-thiadiazole | 33 |
| Cmpd034 | 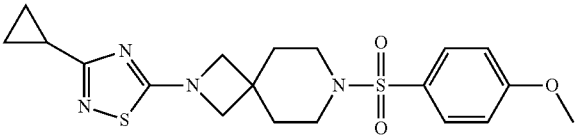 [SMILES: COc1ccc(S(=O)(=O)N2CCC3(CC2)CN(c2nc(C4CC4)ns2)C3)cc1] | 3-Cyclopropyl-5-(7-((4-methoxyphenyl)sulfonyl)-2,7-diazaspiro[3.5]nonan-2-yl)-1,2,4-thiadiazole | 34 |
| Cmpd035 | 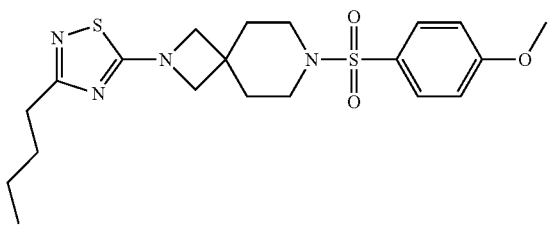 [SMILES: CCCCc1nsc(N2CC3(CCN(S(=O)(=O)c4ccc(OC)cc4)CC3)C2)n1] | 3-Butyl-5-(7-((4-methoxyphenyl)sulfonyl)-2,7-diazaspiro[3.5]nonan-2-yl)-1,2,4-thiadiazole | 35 |
| Cmpd036 | 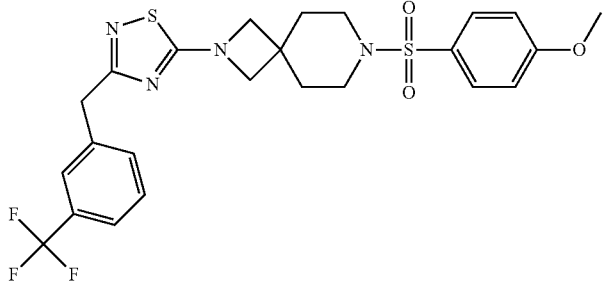 [SMILES: COc1ccc(S(=O)(=O)N2CCC3(CC2)CN(c2nc(Cc4cccc(C(F)(F)F)c4)ns2)C3)cc1] | 5-(7-((4-Methoxyphenyl)sulfonyl)-2,7-diazaspiro[3.5]nonan-2-yl)-3-(3-(trifluoromethyl)benzyl)-1,2,4-thiadiazole | 36 |
| Cmpd037 | 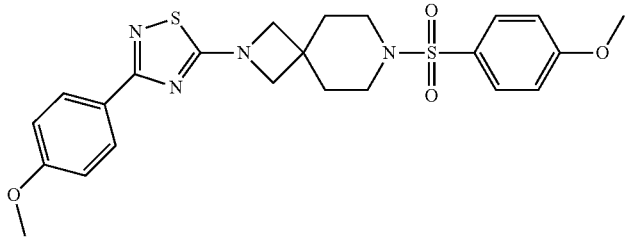 [SMILES: COc1ccc(-c2nsc(N3CC4(CCN(S(=O)(=O)c5ccc(OC)cc5)CC4)C3)n2)cc1] | 3-(4-Methoxyphenyl)-5-(7-((4-methoxyphenyl)sulfonyl)-2,7-diazaspiro[3.5]nonan-2-yl)-1,2,4-thiadiazole | 37 |
| Cmpd038 | 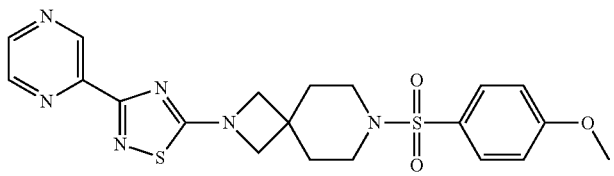 [SMILES: COc1ccc(S(=O)(=O)N2CCC3(CC2)CN(c2nc(-c4cnccn4)ns2)C3)cc1] | 5-(7-((4-Methoxyphenyl)sulfonyl)-2,7-diazaspiro[3.5]nonan-2-yl)-3-(pyrazin-2-yl)-1,2,4-thiadiazole | 38 |

TABLE 1-continued

| COMPOUND | STRUCTURE | NAME | EXAMPLE |
|---|---|---|---|
| Cmpd039 | 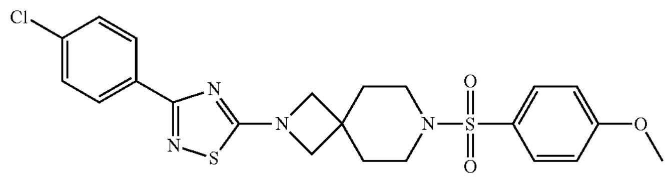 [SMILES: COc1ccc(S(=O)(=O)N2CCC3(CC2)CN(c2nc(-c4ccc(Cl)cc4)ns2)C3)cc1] | 3-(4-Chlorophenyl)-5-(7-((4-methoxyphenyl)sulfonyl)-2,7-diazaspiro[3.5]nonan-2-yl)-1,2,4-thiadiazole | 39 |
| Cmpd040 | 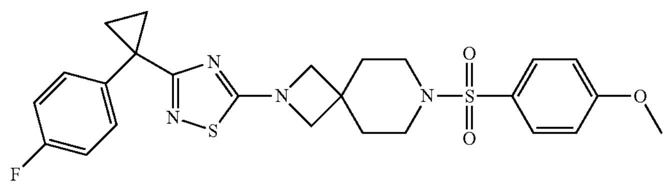 [SMILES: COc1ccc(S(=O)(=O)N2CCC3(CC2)CN(c2nc(C4(c5ccc(F)cc5)CC4)ns2)C3)cc1] | 3-(1-(4-Fluorophenyl)cyclopropyl)-5-(7-((4-methoxyphenyl)sulfonyl)-2,7-diazaspiro[3.5]nonan-2-yl)-1,2,4-thiadiazole | 40 |
| Cmpd041 | 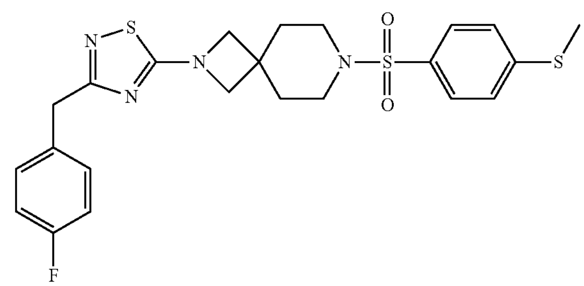 | 3-(4-Fluorobenzyl)-5-(7-((4-(methylthio)phenyl)sulfonyl)-2,7-diazaspiro[3.5]nonan-2-yl)-1,2,4-thiadiazole | 41 |
| Cmpd042 | 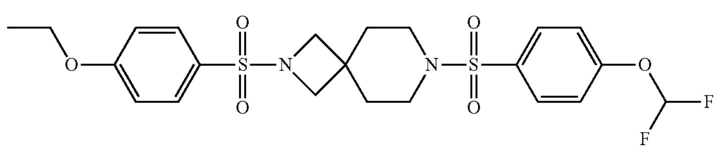 [SMILES: CCOc1ccc(S(=O)(=O)N2CC3(CCN(S(=O)(=O)c4ccc(OC(F)F)cc4)CC3)C2)cc1] | 7-((4-(Difluoromethoxy)phenyl)sulfonyl)-2-((4-ethoxyphenyl)sulfonyl)-2,7-diazaspiro[3.5]nonane | 42 |
| Cmpd043 | 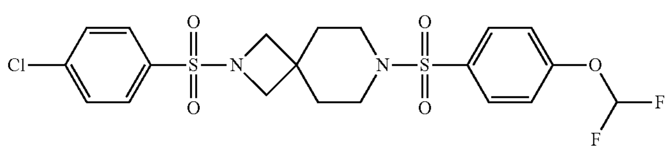 [SMILES: O=S(=O)(c1ccc(OC(F)F)cc1)N1CCC2(CC1)CN(S(=O)(=O)c1ccc(Cl)cc1)C2] | 2-((4-Chlorophenyl)sulfonyl)-7-((4-(difluoromethoxy)phenyl)sulfonyl)-2,7-diazaspiro[3.5]nonane | 43 |
| Cmpd044 | 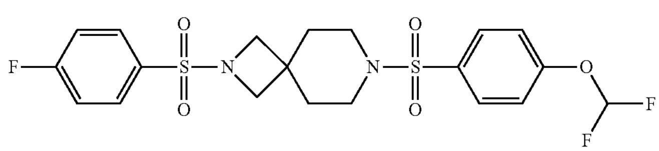 [SMILES: O=S(=O)(c1ccc(OC(F)F)cc1)N1CCC2(CC1)CN(S(=O)(=O)c1ccc(F)cc1)C2] | 7-((4-(Difluromethoxy)phenyl)sulfonyl)-2-((4-fluorophenyl)sulfonyl)-2,7-diazaspiro[3.5]nonane | 44 |
| Cmpd045 | 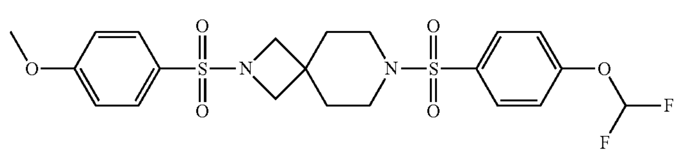 [SMILES: COc1ccc(S(=O)(=O)N2CC3(CCN(S(=O)(=O)c4ccc(OC(F)F)cc4)CC3)C2)cc1] | 7-((4-(Difluoromethoxy)phenyl)sulfonyl)-2-((4-methoxypehnyl)sulfonyl)-2,7-diazaspiro[3.5]nonane | 45 |
| Cmpd046 | 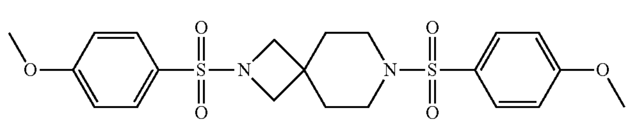 | 7-((4-Ethoxyphenyl)sulfonyl)-2-((4-methoxyphenyl)sulfonyl)-2,7-diazaspiro[3.5]nonane | 46 |
| Cmpd047 | 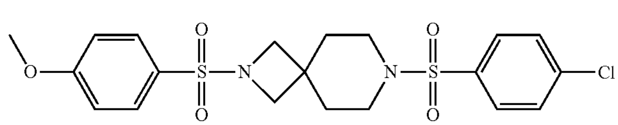 [SMILES: COc1ccc(S(=O)(=O)N2CC3(CCN(S(=O)(=O)c4ccc(Cl)cc4)CC3)C2)cc1] | 7-((4-Chlorophenyl)sulfonyl)-2-((4-methoxyphenyl)sulfonyl)-2,7-diazaspiro[3.5]nonane | 47 |

TABLE 1-continued

| COMPOUND | STRUCTURE | NAME | EXAMPLE |
|---|---|---|---|
| Cmpd048 | 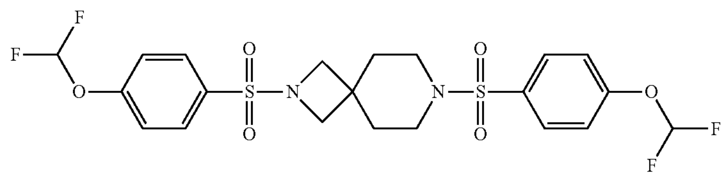 [SMILES: O=S(=O)(c1ccc(OC(F)F)cc1)N1CCC2(CC1)CN(S(=O)(=O)c1ccc(OC(F)F)cc1)C2] | 2,7-Bis((4-(difluoromethoxy)phenyl)sulfonyl)-2,7-diazaspiro[3.5]nonane | 48 |
| Cmpd049 | 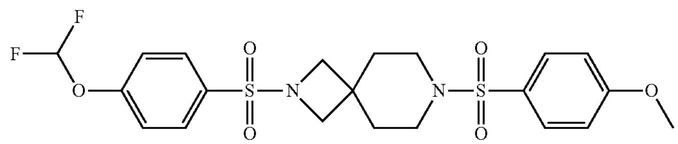 [SMILES: COc1ccc(S(=O)(=O)N2CCC3(CC2)CN(S(=O)(=O)c2ccc(OC(F)F)cc2)C3)cc1] | 2-((4-(Difluoromethoxy)phenyl)sulfonyl)-7-((4-ethoxyphenyl)sulfonyl)-2,7-diazaspiro[3.5]nonane | 49 |
| Cmpd050 | 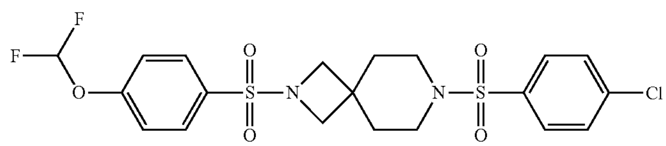 [SMILES: O=S(=O)(c1ccc(Cl)cc1)N1CCC2(CC1)CN(S(=O)(=O)c1ccc(OC(F)F)cc1)C2] | 7-((4-Chlorophenyl)sulfonyl)-2-((4-(difluoromethoxy)phenyl)sulfonyl)-2,7-diazaspiro[3.5]nonane | 50 |
| Cmpd051 | 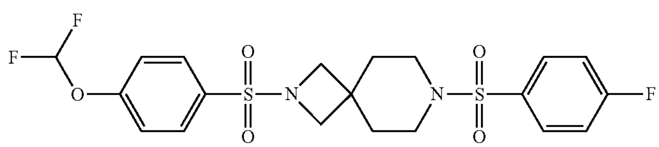 [SMILES: O=S(=O)(c1ccc(F)cc1)N1CCC2(CC1)CN(S(=O)(=O)c1ccc(OC(F)F)cc1)C2] | 2-((4-(Difluoromethoxy)phenyl)sulfonyl)-7-((4-fluorophenyl)sulfonyl)-2,7-diazaspiro[3.5]nonane | 51 |
| Cmpd052 | 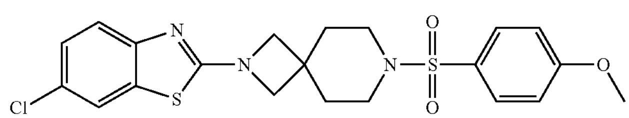 [SMILES: COc1ccc(S(=O)(=O)N2CCC3(CC2)CN(c2nc4ccc(Cl)cc4s2)C3)cc1] | 6-Chloro-2-(7-((4-methoxyphenyl)sulfonyl)-2,7-diazaspiro[3.5]nonan-2-yl)benzo[d]thiazole | 52 |
| Cmpd053 | 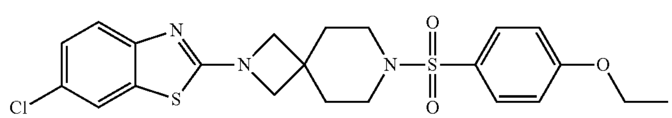 [SMILES: CCOc1ccc(S(=O)(=O)N2CCC3(CC2)CN(c2nc4ccc(Cl)cc4s2)C3)cc1] | 6-Chloro-2-(7-((4-ethoxyphenyl)sulfonyl)-2,7-diazaspiro[3.5]nonan-2-yl)benzo[d]thiazole | 53 |
| Cmpd054 | 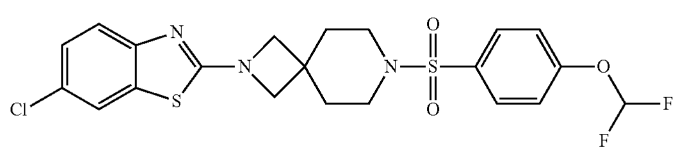 [SMILES: O=S(=O)(c1ccc(OC(F)F)cc1)N1CCC2(CC1)CN(c1nc3ccc(Cl)cc3s1)C2] | 6-Chloro-2-(7-((4-(difluoromethoxy)phenyl)sulfonyl)-2,7-diazaspiro[3.5]nonan-2-yl)benzo[d]thiazole | 54 |
| Cmpd055 | 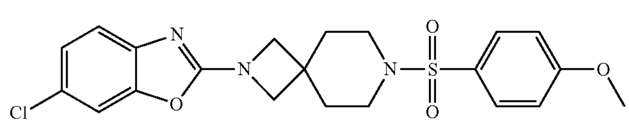 | 6-Chloro-2-(7-((4-(methylthio)phenyl)sulfonyl)-2,7-diazaspiro[3.5]nonan-2-yl)benzo[d]thiazole | 55 |
| Cmpd056 | 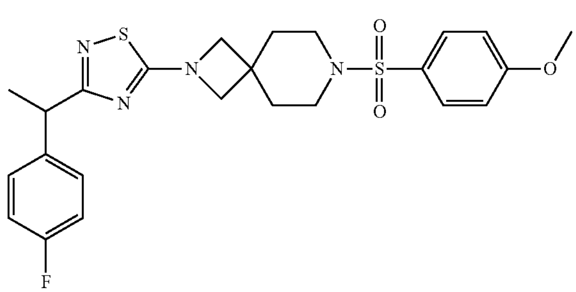 [SMILES: COc1ccc(S(=O)(=O)N2CCC3(CC2)CN(c2nc(C(C)c4ccc(F)cc4)ns2)C3)cc1] | 3-(1-(4-Fluorophenyl)ethyl)-5-(7-((4-methoxyphenyl)sulfonyl)-2,7-diazaspiro[3.5]nonan-2-yl)-1,2,4-thiadiazole | 56 |

TABLE 1-continued

| COMPOUND | STRUCTURE | NAME | EXAMPLE |
|---|---|---|---|
| Cmpd057 | 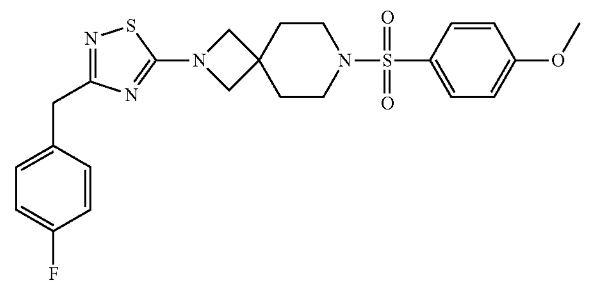 [SMILES: COc1ccc(S(=O)(=O)N2CCC3(CC2)CN(c2nc(Cc4ccc(F)cc4)ns2)C3)cc1] | 3-(4-Fluorobenzyl)-5-(7-((4-methoxyphenyl)sulfonyl)-2,7-diazaspiro[3.5]nonan-2-yl)-1,2,4-thiadiazole | 57 |
| Cmpd058 | 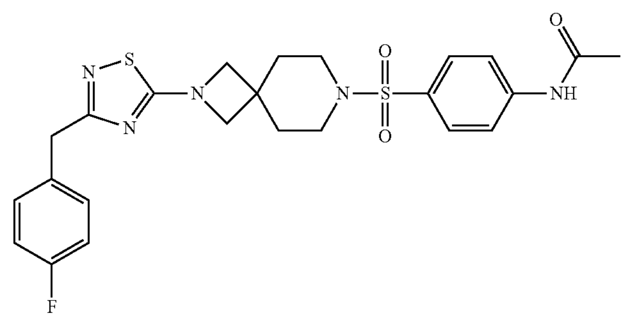 [SMILES: CC(=O)Nc1ccc(S(=O)(=O)N2CCC3(CC2)CN(c2nc(Cc4ccc(F)cc4)ns2)C3)cc1] | N-(4-((2-(3-(4-fluorobenzyl)-1,2,4-thiadiazol-5-yl)-2,7-diazaspiro[3.5]nonan-7-yl)sulfonyl)phenyl)acetamide | 58 |
| Cmpd059 | 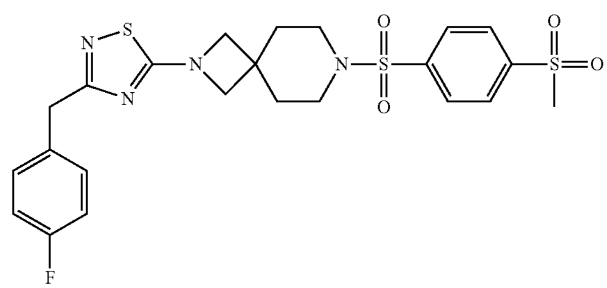 [SMILES: CS(=O)(=O)c1ccc(S(=O)(=O)N2CCC3(CC2)CN(c2nc(Cc4ccc(F)cc4)ns2)C3)cc1] | 3-(4-Fluorobenzyl)-5-(7-((4-(methylsulfonyl)phenyl)sulfonyl)-2,7-diazaspiro[3.5]nonan-2-yl)-1,2,4-thiadiazole | 59 |
| Cmpd060 | 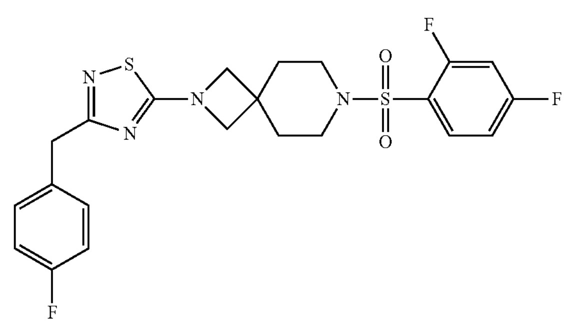 [SMILES: O=S(=O)(c1ccc(F)cc1F)N1CCC2(CC1)CN(c1nc(Cc3ccc(F)cc3)ns1)C2] | 5-(7-((2,4-Difluorophenyl)sulfonyl)-2,7-diazaspiro[3.5]nonan-2-yl)-3-(4-fluorobenzyl)-1,2,4-thiadiazole | 60 |
| Cmpd061 | 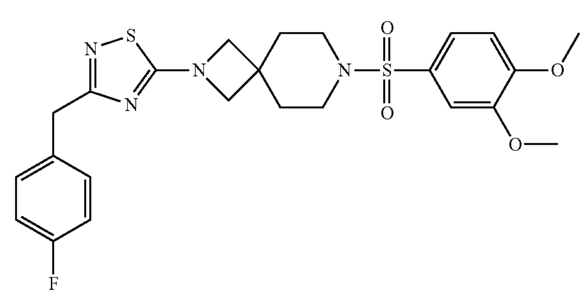 [SMILES: COc1ccc(S(=O)(=O)N2CCC3(CC2)CN(c2nc(Cc4ccc(F)cc4)ns2)C3)cc1OC] | 5-(7-((3,4-Dimethoxyphenyl)sulfonyl)-2,7-diazaspiro[3.5]nonan-2-yl)-3-(4-fluorobenzyl)-1,2,4-thiadiazole | 61 |

| COMPOUND | STRUCTURE | NAME | EXAMPLE |
|---|---|---|---|
| Cmpd062 | 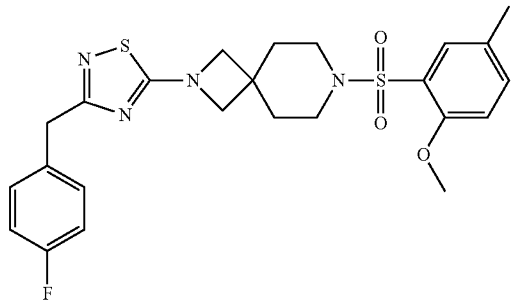 [SMILES: COc1ccc(C)cc1S(=O)(=O)N1CCC2(CC1)CN(c1nc(Cc3ccc(F)cc3)ns1)C2] | 3-(4-Fluorobenzyl)-5-(7-((2-methoxy-5-methylphenyl)sulfonyl)-2,7-diazaspiro[3.5]nonan-2-yl)-1,2,4-thiadiazole | 62 |
| Cmpd063 | 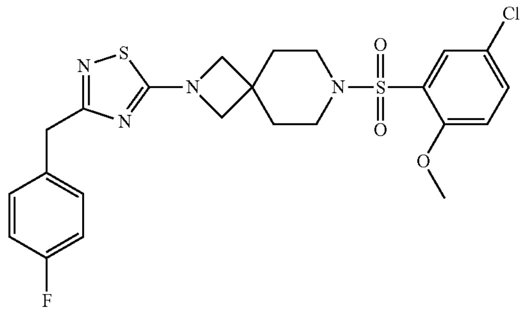 [SMILES: COc1ccc(Cl)cc1S(=O)(=O)N1CCC2(CC1)CN(c1nc(Cc3ccc(F)cc3)ns1)C2] | 5-(7-((5-Chloro-2-methoxyphenyl)sulfonyl)-2,7-diazaspiro[3.5]nonan-2-yl)-3-(4-fluorobenzyl)-1,2,4-thiadiazole | 63 |
| Cmpd064 | 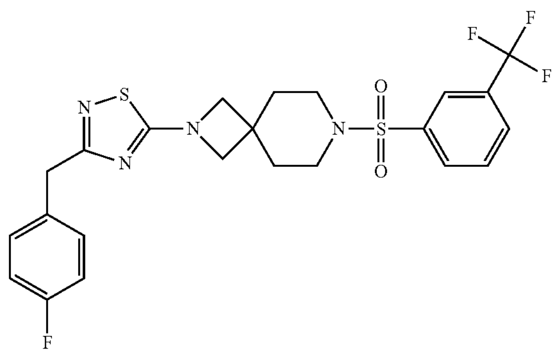 [SMILES: O=S(=O)(c1cccc(C(F)(F)F)c1)N1CCC2(CC1)CN(c1nc(Cc3ccc(F)cc3)ns1)C2] | 3-(4-Fluorobenzyl)-5-(7-((3-(trifluoromethyl)phenyl)sulfonyl)-2,7-diazaspiro[3.5]nonan-2-yl)-1,2,4-thiadiazole | 64 |
| Cmpd065 | 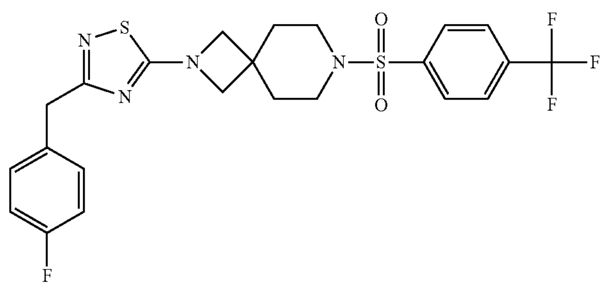 [SMILES: O=S(=O)(c1ccc(C(F)(F)F)cc1)N1CCC2(CC1)CN(c1nc(Cc3ccc(F)cc3)ns1)C2] | 3-(4-Fluorobenzyl)-5-(7-((4-(trifluoromethyl)phenyl)sulfonyl)-2,7-diazaspiro[3.5]nonan-2-yl)-1,2,4-thiadiazole | 65 |
| Cmpd066 | 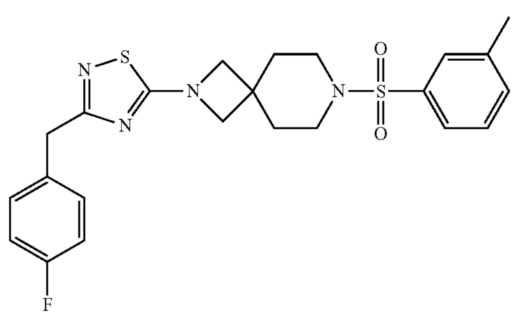 [SMILES: Cc1cccc(S(=O)(=O)N2CCC3(CC2)CN(c2nc(Cc4ccc(F)cc4)ns2)C3)c1] | 3-(4-Fluorobenzyl)-5-(7-(m-tolylsulfonyl)-2,7-diazaspiro[3.5]nonan-2-yl)-1,2,4-thiadiazole | 66 |

TABLE 1-continued

| COMPOUND | STRUCTURE | NAME | EXAMPLE |
|---|---|---|---|
| Cmpd067 | 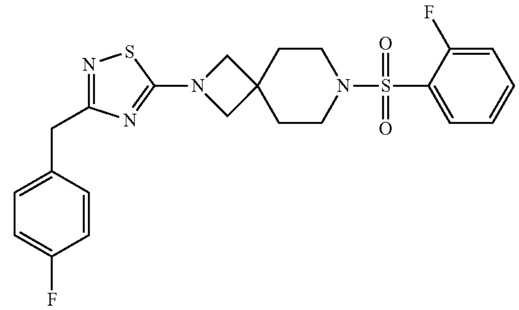 [SMILES: O=S(=O)(c1ccccc1F)N1CCC2(CC1)CN(c1nc(Cc3ccc(F)cc3)ns1)C2] | 3-(4-Fluorobenzyl)-5-(7-((2-fluorophenyl)sulfonyl)-2,7-diazaspiro[3.5]nonan-2-yl)-1,2,4-thiadiazole | 67 |
| Cmpd068 | 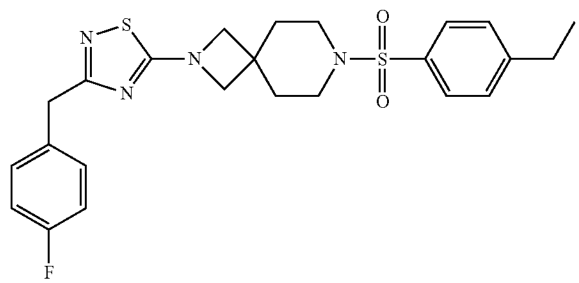 [SMILES: CCc1ccc(S(=O)(=O)N2CCC3(CC2)CN(c2nc(Cc4ccc(F)cc4)ns2)C3)cc1] | 5-(7-((4-Ethylphenyl)sulfonyl)-2,7-diazaspiro[3.5]nonan-2-yl)-3-(4-fluorobenzyl)-1,2,4-thiadiazole | 68 |
| Cmpd069 | 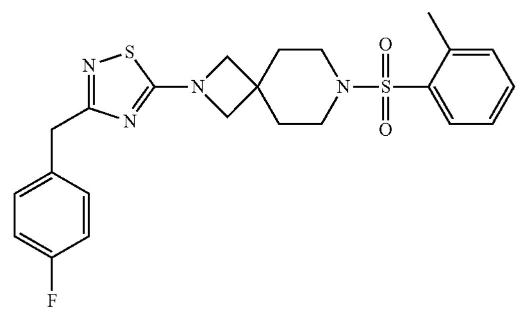 [SMILES: Cc1ccccc1S(=O)(=O)N1CCC2(CC1)CN(c1nc(Cc3ccc(F)cc3)ns1)C2] | 3-(4-Fluorobenzyl)-5-(7-(o-tolylsulfonyl)-2,7-diazaspiro[3.5]nonan-2-yl)-1,2,4-thiadiazole | 69 |
| Cmpd070 | 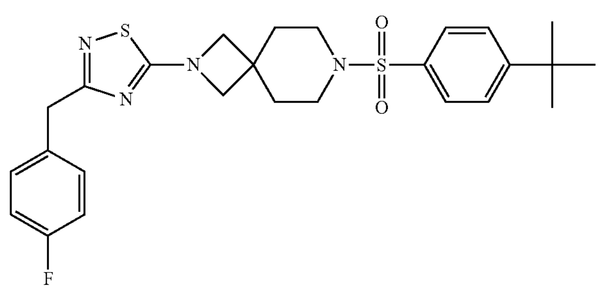 [SMILES: CC(C)(C)c1ccc(S(=O)(=O)N2CCC3(CC2)CN(c2nc(Cc4ccc(F)cc4)ns2)C3)cc1] | 5-(7-((4-(Tert-butyl)phenyl)sulfonyl)-2,7-diazaspiro[3.5]nonan-2-yl)-3-(4-fluorobenzyl)-1,2,4-thiadiazole | 70 |
| Cmpd071 | 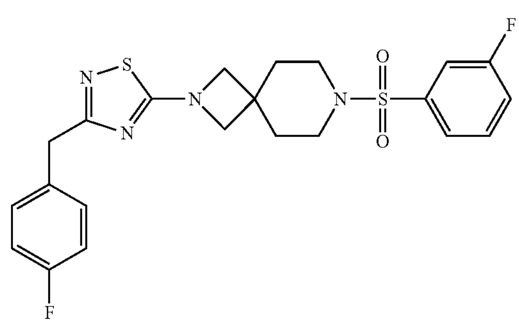 [SMILES: O=S(=O)(c1cccc(F)c1)N1CCC2(CC1)CN(c1nc(Cc3ccc(F)cc3)ns1)C2] | 3-(4-Fluorobenzyl)-5-(7-((3-fluorophenyl)sulfonyl)-2,7-diazaspiro[3.5]nonan-2-yl)-1,2,4-thiadiazole | 71 |

TABLE 1-continued

| COMPOUND | STRUCTURE | NAME | EXAMPLE |
|---|---|---|---|
| Cmpd072 | 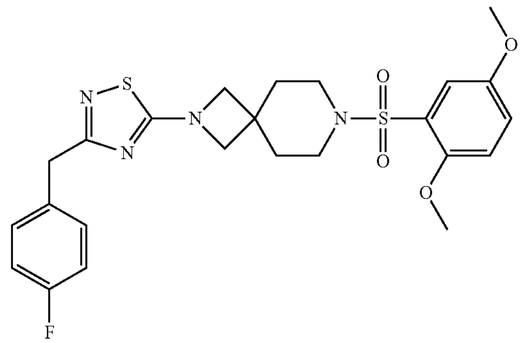 [SMILES: COc1ccc(OC)c(S(=O)(=O)N2CCC3(CC2)CN(c2nc(Cc4ccc(F)cc4)ns2)C3)c1] | 5-(7-((2,5-Dimethoxyphenyl)sulfonyl)-2,7-diazaspiro[3.5]nonan-2-yl)-3-(4-fluorobenzyl)-1,2,4-thiadiazole | 72 |
| Cmpd073 | 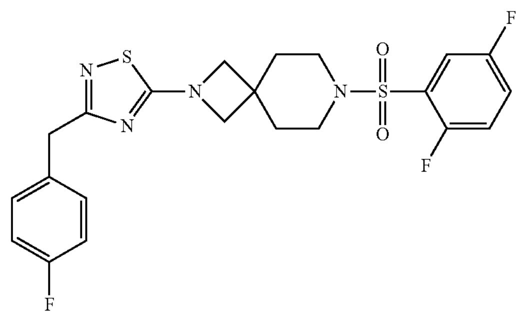 [SMILES: O=S(=O)(c1cc(F)ccc1F)N1CCC2(CC1)CN(c1nc(Cc3ccc(F)cc3)ns1)C2] | 5-(7-((2,5-Difluorophenyl)sulfonyl)-2,7-diazaspiro[3.5]nonan-2-yl)-3-(4-fluorobenzyl)-1,2,4-thiadiazole | 73 |
| Cmpd074 | 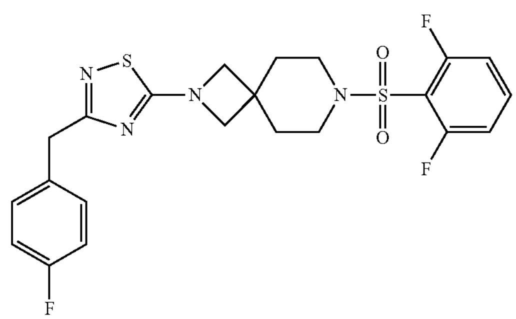 [SMILES: O=S(=O)(c1c(F)cccc1F)N1CCC2(CC1)CN(c1nc(Cc3ccc(F)cc3)ns1)C2] | 5-(7-((2,6-Difluorophenyl)sulfonyl)-2,7-diazaspiro[3.5]nonan-2-yl)-3-(4-fluorobenzyl)-1,2,4-thiadiazole | 74 |
| Cmpd075 | 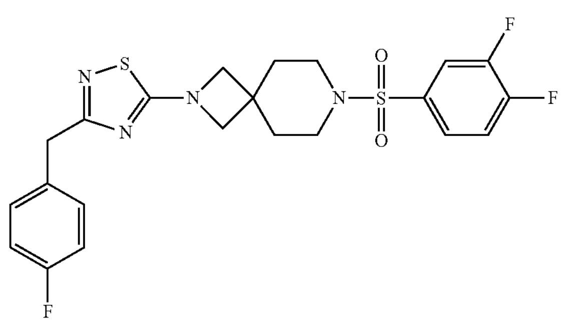 [SMILES: O=S(=O)(c1ccc(F)c(F)c1)N1CCC2(CC1)CN(c1nc(Cc3ccc(F)cc3)ns1)C2] | 5-(7-((3,4-Difluroophenyl)sulfonyl)-2,7-diazaspiro[3.5]nonan-2-yl)-3-(4-fluorobenzyl)-1,2,4-thiadiazole | 75 |

TABLE 1-continued

| COMPOUND | STRUCTURE | NAME | EXAMPLE |
|---|---|---|---|
| Cmpd076 | 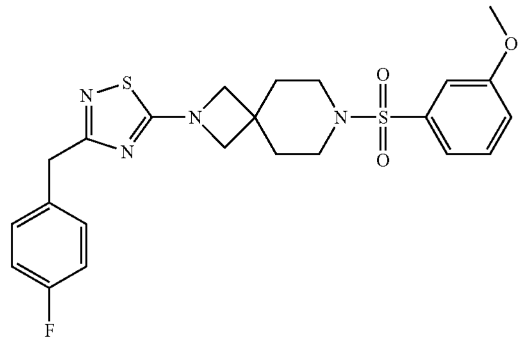 [SMILES: COc1cccc(S(=O)(=O)N2CCC3(CC2)CN(c2nc(Cc4ccc(F)cc4)ns2)C3)c1] | 3-(4-Fluorobenzyl)-5-(7-((3-methoxyphenyl)sulfonyl)-2,7-diazaspiro[3.5]nonan-2-yl)-1,2,4-thiadiazole | 76 |
| Cmpd077 | 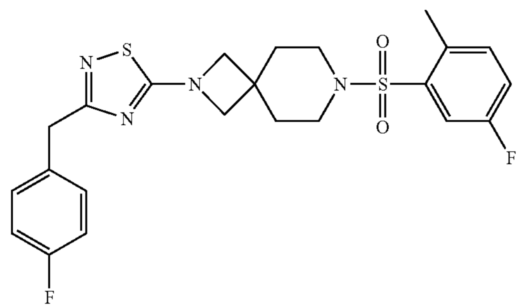 [SMILES: Cc1ccc(F)cc1S(=O)(=O)N1CCC2(CC1)CN(c1nc(Cc3ccc(F)cc3)ns1)C2] | 5-(7-((5-Fluoro-2-methylphenyl)sulfonyl)-2,7-diazaspiro[3.5]nonan-2-yl)-3-(4-fluorobenzyl)-1,2,4-thiadiazole | 77 |
| Cmpd078 | 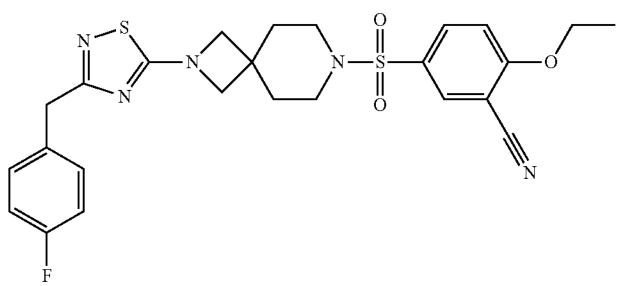 [SMILES: CCOc1ccc(S(=O)(=O)N2CCC3(CC2)CN(c2nc(Cc4ccc(F)cc4)ns2)C3)cc1C#N] | 2-Ethoxy-5-((2-(3-(4-fluorobenzyl)-1,2,4-thiadiazol-5-yl)-2,7-diazaspiro[3.5]nonan-7-yl)sulfonyl)benzonitrile | 78 |
| Cmpd079 | 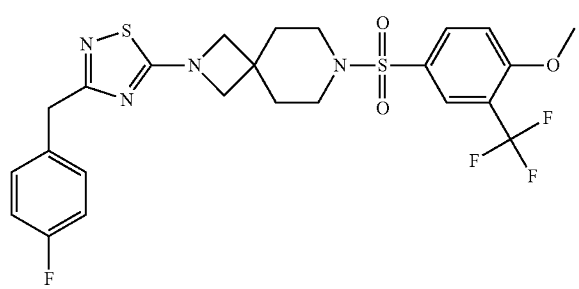 [SMILES: COc1ccc(S(=O)(=O)N2CCC3(CC2)CN(c2nc(Cc4ccc(F)cc4)ns2)C3)cc1C(F)(F)F] | 3-(4-Fluorobenzyl)-5-(7-((4-methoxy-3-(trifluoromethyl)phenyl)sulfonyl)-2,7-diazaspiro[3.5]nonan-2-yl)-1,2,4-thiadiazole | 79 |
| Cmpd080 | 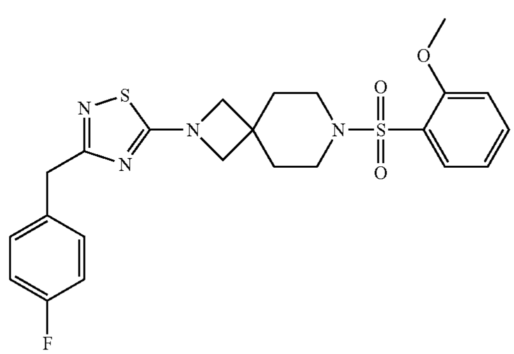 [SMILES: COc1ccccc1S(=O)(=O)N1CCC2(CC1)CN(c1nc(Cc3ccc(F)cc3)ns1)C2] | 3-(4-Fluorobenzyl)-5-(7-((2-methoxyphenyl)sulfonyl)-2,7-diazaspiro[3.5]nonan-2-yl)-1,2,4-thiadiazole | 80 |

TABLE 1-continued

| COMPOUND | STRUCTURE | NAME | EXAMPLE |
|---|---|---|---|
| Cmpd081 | 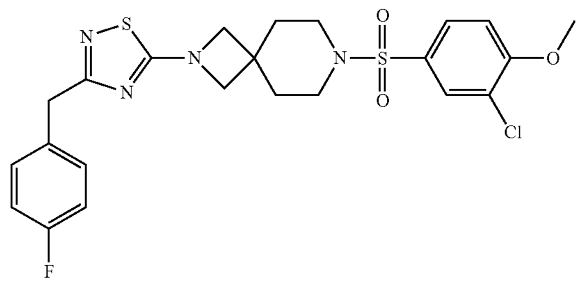 [SMILES: COc1ccc(S(=O)(=O)N2CCC3(CC2)CN(c2nc(Cc4ccc(F)cc4)ns2)C3)cc1Cl] | 5-(7-((3-Chloro-4-methoxyphenyl)sulfonyl)-2,7-diazaspiro[3.5]nonan-2-yl)-3-(4-fluorobenzyl)-1,2,4-thiadiazole | 81 |
| Cmpd082 | 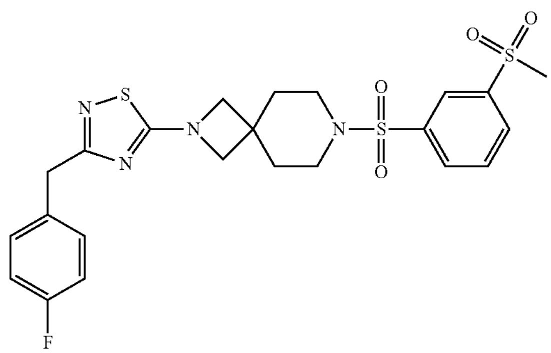 [SMILES: CS(=O)(=O)c1cccc(S(=O)(=O)N2CCC3(CC2)CN(c2nc(Cc4ccc(F)cc4)ns2)C3)c1] | 3-(4-Fluorobenzyl)-5-(7-((3-(methylsulfonyl)phenyl)sulfonyl)-2,7-diazaspiro[3.5]nonan-2-yl)-1,2,4-thiadiazole | 82 |
| Cmpd083 | 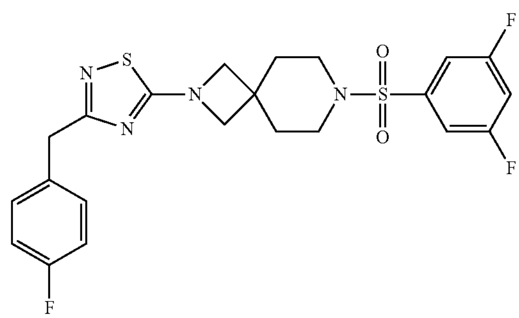 [SMILES: O=S(=O)(c1cc(F)cc(F)c1)N1CCC2(CC1)CN(c1nc(Cc3ccc(F)cc3)ns1)C2] | 5-(7-((3,5-Difluorophenyl)sulfonyl)-2,7-diazaspiro[3.5]nonan-2-yl)-3-(4-fluorobenzyl)-1,2,4-thiadiazole | 83 |
| Cmpd084 | 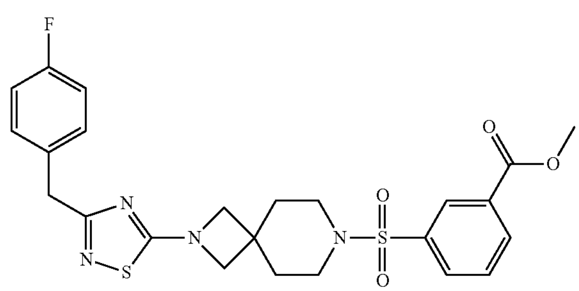 [SMILES: COC(=O)c1cccc(S(=O)(=O)N2CCC3(CC2)CN(c2nc(Cc4ccc(F)cc4)ns2)C3)c1] | Methyl 3-((2-(3-(4-fluorobenzyl)-1,2,4-thiadiazol-5-yl)-2,7-diazaspiro[3.5]nonan-7-yl)sulfonyl)benzoate | 84 |
| Cmpd085 | 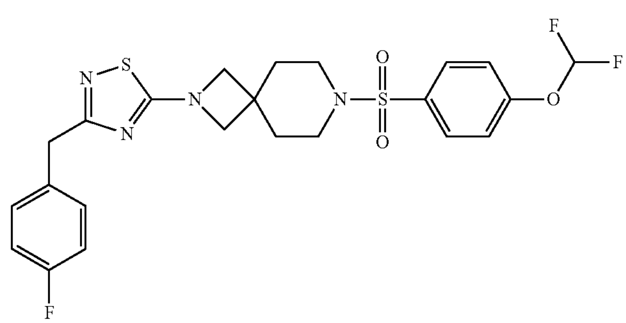 [SMILES: O=S(=O)(c1ccc(OC(F)F)cc1)N1CCC2(CC1)CN(c1nc(Cc3ccc(F)cc3)ns1)C2] | 5-(7-((4-(Difluoromethoxy)phenyl)sulfonyl)-2,7-diazaspiro[3.5]nonan-2-yl)-3-(4-fluorobenzyl)-1,2,4-thiadiazole | 85 |

TABLE 1-continued

| COMPOUND | STRUCTURE | NAME | EXAMPLE |
|---|---|---|---|
| Cmpd086 | 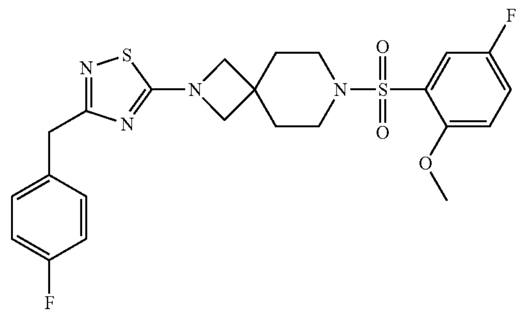 [SMILES: COc1ccc(F)cc1S(=O)(=O)N1CCC2(CC1)CN(c1nc(Cc3ccc(F)cc3)ns1)C2] | 5-(7-((5-Fluoro-2-methoxyphenyl)sulfonyl)-2,7-diazaspiro[3.5]nonan-2-yl)-3-(4-fluorobenzyl)-1,2,4-thiadiazole | 86 |
| Cmpd087 | 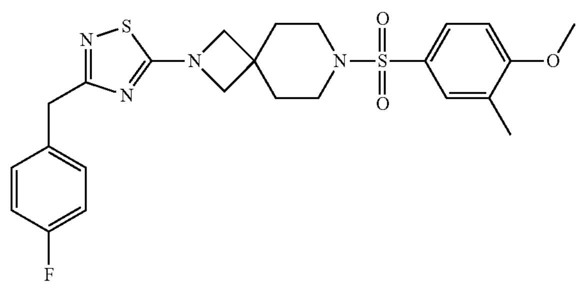 [SMILES: COc1ccc(S(=O)(=O)N2CCC3(CC2)CN(c2nc(Cc4ccc(F)cc4)ns2)C3)cc1C] | 5-(7-((4-Ethoxy-3-methylphenyl)sulfonyl)-2,7-diazaspiro[3.5]nonan-2-yl)-3-(4-fluorobenzyl)-1,2,4-thiadiazole | 87 |
| Cmpd088 | 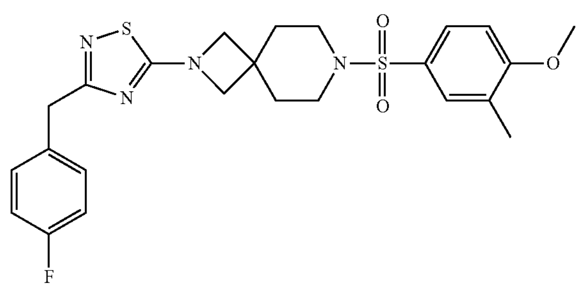 [SMILES: COc1ccc(S(=O)(=O)N2CCC3(CC2)CN(c2nc(Cc4ccc(F)cc4)ns2)C3)cc1C] | 3-(4-Fluorobenzyl)-5-(7-((4-methoxy-3-methylphenyl)sulfonyl)-2,7-diazaspiro[3.5]nonan-2-yl)-1,2,4-thiadiazole | 88 |
| Cmpd089 | 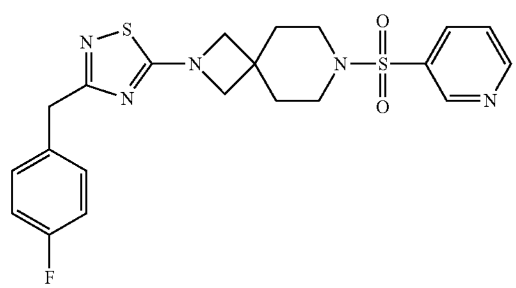 [SMILES: O=S(=O)(c1cccnc1)N1CCC2(CC1)CN(c1nc(Cc3ccc(F)cc3)ns1)C2] | 3-(4-Fluorobenzyl)-5-(7-(pyridin-3-ylsulfonyl)-2,7-diazaspiro[3.5]nonan-2-yl)-1,2,4-thiadiazole | 89 |
| Cmpd090 | 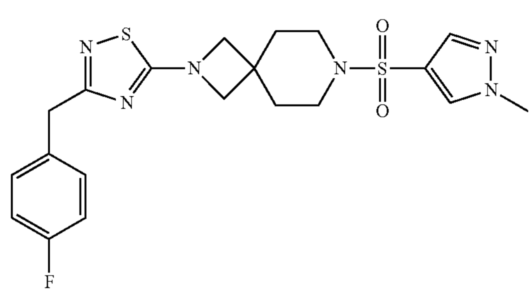 [SMILES: Cn1cc(S(=O)(=O)N2CCC3(CC2)CN(c2nc(Cc4ccc(F)cc4)ns2)C3)cn1] | 3-(4-Fluorobenzyl)-5-(7-((1-methyl-1H-pyrazol-4-yl)sulfonyl)-2,7-diazaspiro[3.5]nonan-2-yl)-1,2,4-thiadiazole | 90 |

TABLE 1-continued

| COMPOUND | STRUCTURE | NAME | EXAMPLE |
|---|---|---|---|
| Cmpd091 | 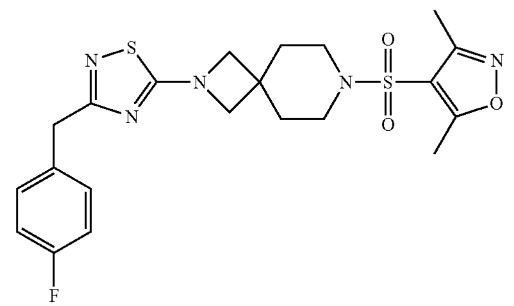 [SMILES: Cc1noc(C)c1S(=O)(=O)N1CCC2(CC1)CN(c1nc(Cc3ccc(F)cc3)ns1)C2] | 4-((2-(3-(4-Fluorobenzyl)-1,2,4-thiadiazol-5-yl)-2,7-diazaspiro[3.5]nonan-7-yl)sulfonyl)-3,5-dimethylisoxazole | 91 |
| Cmpd092 | 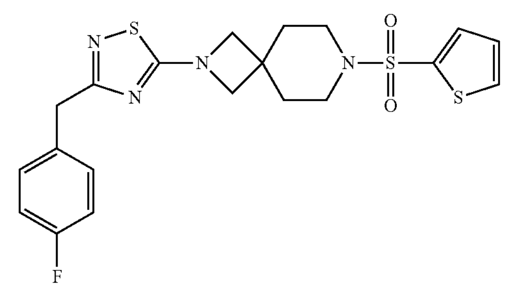 [SMILES: O=S(=O)(c1cccs1)N1CCC2(CC1)CN(c1nc(Cc3ccc(F)cc3)ns1)C2] | 3-(4-Fluorobenzyl)-5-(7-(thiophen-2-ylsulfonyl)-2,7-diazaspiro[3.5]nonan-2-yl)-1,2,4-thiadiazole | 92 |
| Cmpd093 | 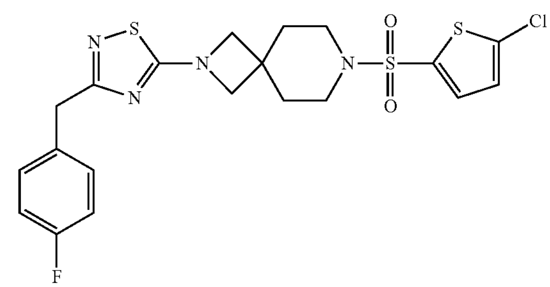 [SMILES: O=S(=O)(c1ccc(Cl)s1)N1CCC2(CC1)CN(c1nc(Cc3ccc(F)cc3)ns1)C2] | 5-(7-((5-Chlorothiophen-2-yl)sulfonyl)-2,7-diazaspiro[3.5]nonan-2-yl)-3-(4-fluorobenzyl)-1,2,4-thiadiazole | 93 |
| Cmpd094 | 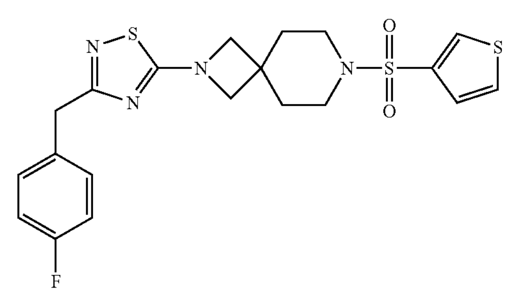 [SMILES: O=S(=O)(c1ccsc1)N1CCC2(CC1)CN(c1nc(Cc3ccc(F)cc3)ns1)C2] | 3-(4-Fluorobenzyl)-5-(7-(thiophen-3-ylsulfonyl)-2,7-diazaspiro[3.5]nonan-2-yl)-1,2,4-thiadiazole | 94 |
| Cmpd095 | 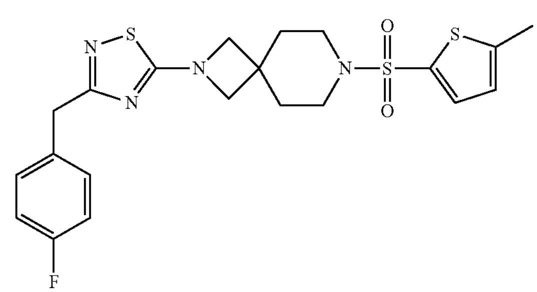 [SMILES: Cc1ccc(S(=O)(=O)N2CCC3(CC2)CN(c2nc(Cc4ccc(F)cc4)ns2)C3)s1] | 3-(4-Fluorobenzyl)-5-(7-((5-methylthiophen-2-yl)sulfonyl)-2,7-diazaspiro[3.5]nonan-2-yl)-1,2,4-thiadiazole | 95 |

TABLE 1-continued

| COMPOUND | STRUCTURE | NAME | EXAMPLE |
|---|---|---|---|
| Cmpd096 | 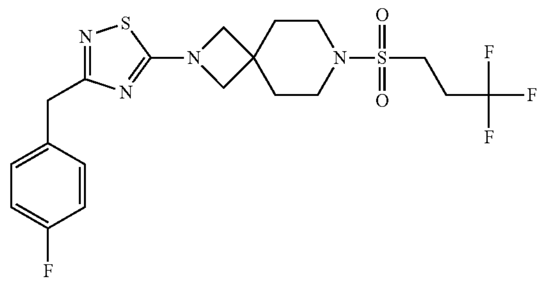 [SMILES: O=S(=O)(CCC(F)(F)F)N1CCC2(CC1)CN(c1nc(Cc3ccc(F)cc3)ns1)C2] | 3-(4-Fluorobenzyl)-5-(7-((3,3,3-trifluoropropyl)sulfonyl)-2,7-diazaspiro[3.5]nonan-2-yl)-1,2,4-thiadiazole | 96 |
| Cmpd097 | 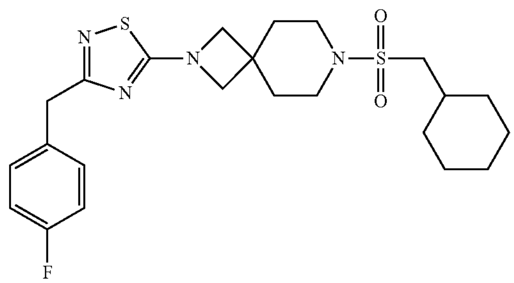 [SMILES: O=S(=O)(CC1CCCCC1)N1CCC2(CC1)CN(c1nc(Cc3ccc(F)cc3)ns1)C2] | 5-(7-((Cyclohexylmethyl)sulfonyl)-2,7-diazaspiro[3.5]nonan-2-yl)-3-(4-fluorobenzyl)-1,2,4-thiadiazole | 97 |
| Cmpd098 | 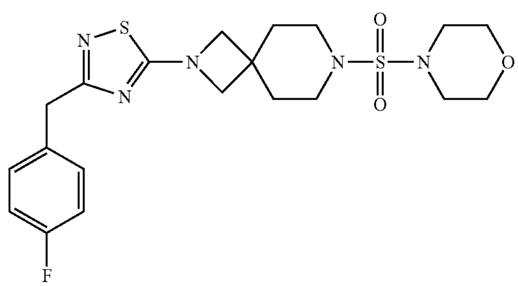 [SMILES: O=S(=O)(N1CCOCC1)N1CCC2(CC1)CN(c1nc(Cc3ccc(F)cc3)ns1)C2] | 4-((2-(3-(4-Fluorobenzyl)-1,2,4-thiadiazol-5-yl)-2,7-diazaspiro[3.5]nonan-7-yl)sulfonyl)morpholine | 98 |

ABBREVIATIONS

BOP=(Benzotriazol-1-yloxy)tris(dimethylamino)phosphonium hexaflurophosphate;
CH₂Cl₂=dichloromethane;
DMAP=dimethylaminopyridine;
DMF=dimethylformamide;
DIPEA=N,N-Diisopropylethylamine;
EDC=1-(3-dimethylaminopropyl)-3-ethylcarbodiimide hydrochloride;
EE/H=Ethyl acetate/Heptane;
eq=equivalents;
EtOH=ethanol;
EtOAc=ethyl acetate;
Et₃N=triethylamine;
h=hour;
HPLC=high performance liquid chromatography;
HATU=1-[Bis(dimethylamino)methylene]-1H-1,2,3-triazolo[4,5-b]pyridinium 3-oxid hexafluorophosphate;
HOBt=1-hydroxy-benzotriazol hydrate;
iPr₂NEt=Ethyl-diisopropyl-amine;
min=minutes:
MeOH=methanol;
o/n=overnight;
RT=room temperature;
THF=tetrahydrofuran;
TFA=trifluoroacetic acid.

PROCESS FOR THE PREPARATION OF INTERMEDIATES

Intermediate 1

2,7-Diazaspiro[3.5]nonane

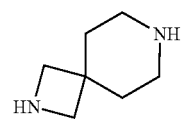

In a 10 mL round-bottomed flask, tert-butyl 2,7-diazaspiro[3.5]nonane-2-carboxylate (100 mg, 442 μmol) and trifluoroacetic acid (353 mg, 238 μl, 3.09 mmol) were combined with CH₂Cl₂ (1 mL) to give a colorless solution which was stirred 3 h at RT. The mixture was then evaporated to dryness to give quantitatively the tide product as a TFA salt.

Intermediate 2

7-((4-Methoxyphenyl)sulfonyl)-2,7-diazaspiro[3.5]nonane

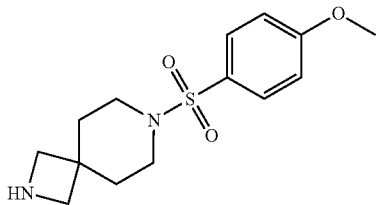 [SMILES: COc1ccc(S(=O)(=O)N2CCC3(CC2)CNC3)cc1]

In a 50 mL pear-shaped flask, tert-butyl 2,7-diazaspiro[3.5]nonane-2-carboxylate (700 mg, 3.09 mmol), 4-methoxybenzene-1-sulfonyl chloride (639 mg, 3.09 mmol) and DIPEA (600 mg, 794 μl, 4.64 mmol) were stirred in CH$_2$Cl$_2$ (20.6 ml) for 90 min. The reaction mixture was poured into CH$_2$Cl$_2$ and extracted with water. The organic layers were dried over Na$_2$SO$_4$ and concentrated in vacuo. The crude material was purified by flash chromatography (silica gel, 20 g, 0% to 30% EtOAc in heptane) to give 950 mg (77%) of tert-butyl 7-((4-methoxyphenyl)sulfonyl)-2,7-diazaspiro[3.5]nonane-2-carboxylate. ES-MS m/e: 397.3, 341.3 (M+H$^+$).

This compound (950 mg, 2.4 mmol) was combined with CH$_2$Cl$_2$ (4.36 mL) and TFA (2.73 g, 1.83 mL, 24.0 mmol). The reaction mixture was stirred for 30 min. The crude reaction mixture was concentrated in vacuo. Diethyl other was added and evaporated to give a white solid. Reaction medium was diluted with more CH$_2$Cl$_2$, extracted with aq. sol. NaOH 1M, organic phase separated, dried over sodium sulfate, filtered and evaporated down to dryness to give quantitatively the tide compound. ES-MS m/e: 297.4 (M+H$^+$).

Intermediate 3

7-((4-Methylthio)phenyl)sulfonyl)-2,7-diazaspiro[3.5]nonane

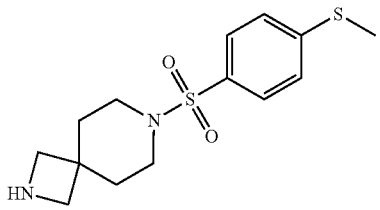 [SMILES: CSc1ccc(S(=O)(=O)N2CCC3(CC2)CNC3)cc1]

In a 25 mL pear-shaped flask, tert-butyl 2,7-diazaspiro[3.5]nonane-2-carboxylate (200 mg, 884 μmol), 4-(methylthio)benzene-1-sulfonyl chloride (256 mg, 1.15 mmol) and DIPEA (171 mg, 227 μL, 1.33 mmol) were combined with CH$_2$Cl$_2$ (5.89 mL). The reaction mixture was stirred for 90 min at room temperature. The reaction mixture was poured onto CH$_2$C$_2$ and extracted with water. The organic layers were dried over sodium sulfate and concentrated in vacuo. The crude material was purified by flash chromatography (silica gel, 20 g, 0% to 30% EtOAc in heptane) to give 281 mg (73%) of 7-((4-(methylthio)phenylsulfonyl)-2,7-diazaspiro[3.5]nonane-2-carboxylate. ES-MS m/e: 413.3 (M+H$^+$).

All of this compound was dissolved in CH$_2$Cl$_2$ (1.29 mL) and TFA (777 mg, 522 μL, 6.81 mmol) was added. The reaction mixture was stirred for 40 min at room temperature. The crude reaction mixture was concentrated in vacuo. Diethyl ether was added and evaporated to give quantitatively the tide compound as a white solid.

ES-MS m/e: 313.2 (M+H$^+$).

Intermediate 4

7-((4-(Difluoromethoxy)phenyl)sulfonyl)-2,7-diazaspiro[3.5]nonane

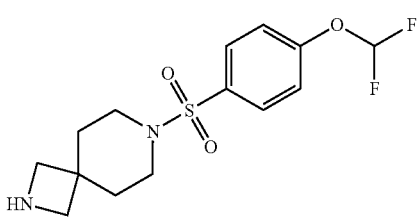 [SMILES: O=S(=O)(c1ccc(OC(F)F)cc1)N1CCC2(CC1)CNC2]

7-((4-(Difluoromethoxy)phenyl)sulfonyl)-2,7-diazaspiro[3.5]nonane was prepared following the same procedure as for Intermediate 3, starting from 4-(difluoromethoxy)benzene-1-sulfonyl chloride. ES-MS m/e: 333.2 (M+H$^+$).

Intermediate 5

2-((4-Methoxyphenyl)sulfonyl)-2,7-diazaspiro[3.5]nonane

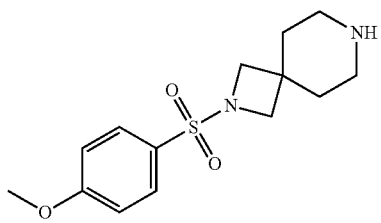 [SMILES: COc1ccc(S(=O)(=O)N2CC3(CCNCC3)C2)cc1]

In a 150 mL pear-shaped flask, tert-butyl 2,7-diazaspiro[3.5]nonane-7-carboxylate (1.5 g, 6.63 mmol) and DIPEA (1.71 g, 2.32 mL, 13.3 mmol) were combined with CH$_2$Cl$_2$ (44.2 mL) to give a light yellow solution. 4-Methoxybenzene-1-sulfonyl chloride (1.64 g, 7.95 mmol,) was added and the reaction mixture was stirred for at RT overnight. The reaction mixture was poured into 300 mL CH$_2$Cl$_2$ and extracted with water (1×75 mL). The organic layers were dried over sodium sulfate and concentrated in vacuo. The crude material was purified by flash chromatography (silica gel, 120 g, 0% to 50% EtOAc in heptane) to give 942 mg (36% yield) of tert-butyl 2-(4-methoxyphenylsulfonyl)-2,7-diazaspiro[3.5]nonane-7-carboxylate. ES-MS m/e: 397.4 (M+H$^+$).

All of this compound and TFA (1.9 g, 1.28 ml, 16.6 mmol) were combined with CH$_2$C$_2$ to give a colorless solution. The reaction mixture was stirred at RT overnight. The crude reaction mixture was concentrated in vacuo. Diethyl ether was added and evaporated, to give quantitatively title compound as a bisTFA salt. ES-MS m/e: 297.3 (M+H$^+$).

Intermediate 6

2-((4-(Difluoromethoxy)phenyl)sulfonyl)-2,7-diazaspiro[3.5]nonane

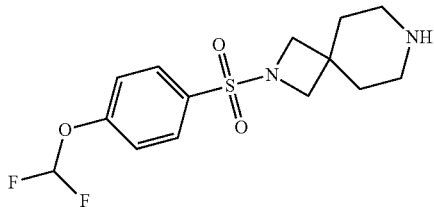 [SMILES: O=S(=O)(c1ccc(OC(F)F)cc1)N1CC2(CCNCC2)C1]

2-((4-(Difluoromethoxy)phenyl)sulfonyl)-2,7-diazaspiro[3.5]nonane was prepared in 85% yield following the same procedure as for Intermediate 5, starting from 4-(difluoromethoxy)benzene-1-sulfonyl chloride. ES-MS m/e: 333.2 (M+H$^+$).

Intermediate 7

6-Chloro-2-(2,7-diazaspiro[3.5]nonan-2-yl)benzo[d]thiazole

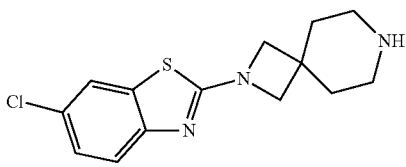 [SMILES: Clc1ccc2nc(N3CC4(CCNCC4)C3)sc2c1]

In a 10 mL scaled reactor were introduced 2,6-dichlorobenzo[d]thiazole (0.2 g, 980 μmol), tert-butyl 2,7-diazaspiro[3.5]nonane-7-carboxylate (222 mg, 980 μmol) and DIPEA (190 mg, 257 μL, 1.47 mmol) with DMF (4.5 mL). The reaction mixture was heated to 80° C. for 8 hours. The solvent was evaporated under vacuo. The crude material was purified by chromatography (silica gel, factor 50, EtOAc/Heptane-1/2) to give 230 mg of tert-butyl 2-(6-chlorobenzo[d]thiazol-2-yl)-2,7-diazaspiro[3.5]nonane-7-carboxylat.

All of the above was stirred in CH$_2$Cl$_2$/TFA (8/2 ratio) (5 mL) at RT for 20 minutes. The solvents were evaporated under high vacuum to give quantitatively the title compound as a TFA salt. ES-MS m/e: 294.2 (M+H$^+$).

Intermediate 8

3-(1-(4-Fluorophenyl)ethyl)-5-(2,7-diazaspiro[3.5]nonan-2-yl)-1,2,4-thiadiazole

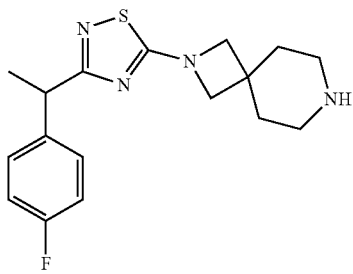 [SMILES: CC(c1ccc(F)cc1)c1nsc(N2CC3(CCNCC3)C2)n1]

In a 25 mL pear-shaped flask, tert-butyl 2,7-diazaspiro[3.5]nonane-7-carboxylate (300 mg, 1.33 mmol) and DIPEA (428 mg, 579 μL, 3.31 mmol) were combined with DMF (8.84 mL) to give a colorless solution. 5-chloro-3-(4-fluorobenzyl)-1,2,4-thiadiazole (333 mg, 1.46 mmol) was added and the reaction mixture was stirred for 45 min at RT. The reaction mixture was poured into 50 mL EtOAc and washed with water (1×15 mL). The organic layers was dried over sodium sulfate and concentrated in vacuo. The crude material was purified by flash chromatography (silica gel, 30 g, 30% to 50% EtOAc in heptane). To give 432 mg (78%) of tert-butyl 2-(3-(4-fluorobenzyl)-1,2,4-thiadiazol-5-yl)-2,7-diazaspiro[3.5]nonane-7-carboxylate. ES-MS m/e: 419.2 (M+H$^+$).

All of the above compound (432 mg, 1.03 mmol) was combined with DMF (20.6 ml) to give a colorless solution. Sodium hydride (99.1 mg, 2.06 mmol) was added to give a pink suspension, which became purple then pale brown then yellow over the course of 20 min. After 20 minutes, methyl iodide (440 mg, 194 μL, 3.1 mmol) was added and the reaction mixture was stirred at room temperature for 23 h. A further 0.5 eq sodium hydride and methyl iodide were added and the solution turned firm dark brown to yellow suspension. The reaction mixture was poured into 50 mL ammonium chloride saturated solution and extracted with EtOAc (2×125 mL). The organic layers were dried over sodium sulfate and concentrated in vacuo. The crude material was purified by flash chromatography (silica gel, 25 g, 0% to 50% EtOAc in heptane) to give tert-butyl 2-(3-(1-(4-fluorophenyl)ethyl)-1,2,4-thiadiazol-5-yl)-2,7-diazaspiro[3.5]nonane-7-carboxylate.

This compound and TFA (349 mg, 236 μL, 3.06 mmol) were combined with CH$_2$Cl$_2$ (1 mL) and the reaction mixture was stirred for 15 h at RT. The crude reaction mixture was concentrated in vacuo. Diethyl ether was added and evaporated to give 189 mg (42%) of the title compound as a TFA salt, which remained an oil. ES-MS m/e: 333.2 (M+H$^+$).

Intermediate 9

3-(4-Fluorobenzyl)-5-(2,7-diazaspiro[3.5]nonan-2-yl)-1,2,4-thiadiazole

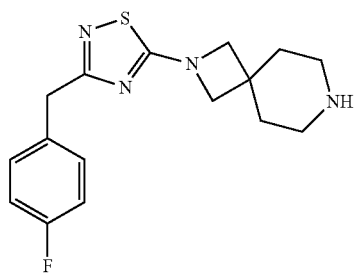 [SMILES: Fc1ccc(Cc2nsc(N3CC4(CCNCC4)C3)n2)cc1]

In a 250 mL pear-shaped flask, tert-butyl 2-(3-(4-fluorobenzyl)-1,2,4-thiadiazol-5-yl)-2,7-diazaspiro[3.5]nonane-7-carboxylate (as described in the synthesis of Intermediate 8; 3.302 & 7.89 mmol) and TFA (7.2 g, 4.86 mL, 63.1 mmol) were combined with $CH_2Cl_2$ (15 mL) and the reaction mixture was stirred for 2 h. The crude reaction mixture was concentrated in vacuo. Diethyl ether was added and evaporated, repeated several times resulting in white solid to give quantitatively title compound. ES-MS m/e: 319.1 (M+H$^+$).

Intermediate 10

5-Chloro-3-(1-(4-fluorophenyl)cyclopropyl)-1,2,4-thiadiazole

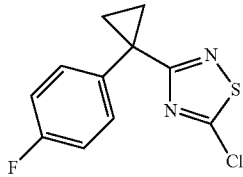 [SMILES: Fc1ccc(C2(c3nsc(Cl)n3)CC2)cc1]

In a 150 mL round-bottomed flask, 1-(4-fluorophenyl)cyclopropanecarbonitrile (3 g, 18.6 mmol), $Na_2CO_3$ (3.95 g, 37.2 mmol) and hydroxylamine hydrochloride (2.59 g, 37.2 mmol) were combined with ethanol (37 mL) and water (12.3 mL). The reaction mixture was heated to 80° C. and stirred over the night. The reaction mixture was poured into 150 mL EtOAc and washed with water (1×100 mL). The crude material was purified by flash chromatography on silica gel to give 3.54 g (98%) of 1-(4-fluorophenyl)-N'-hydroxycyclopropanecarboximidamide.

In a 20 mL scaled reactor, 1-(4-fluorophenyl)-N'-hydroxycyclopropanecarboximidamide (750 mg, 3.86 mmol) and ammonium formate (1.22 g, 19.3 mmol) were combined with acetic acid (10 mL) to give a colorless solution. Then, Pd/C (100 mg, 3.86 mmol) was added. The reaction mixture was heated to 120° C. and stirred over the night. The reaction mixture was filtered on decalite and extracted with EtOAc. The solvents were evaporated. The crude material was purified by chromatography on silica gel to give 1-(4-fluorophenyl)cyclopropanecarboximidamide acetate quantitatively.

In a 50 mL four necked flask, 1-(4-fluorophenyl)cyclopropanecarboximidamide acetate (900 mg, 3.78 mmol) was combined with $CH_2Cl_2$ (10 mL) to give a white suspension. The resulting suspension was cooled down to −10° C. Trichloromethyl hypochlorothioite (632 mg, 372 μL, 3.4 mmol) was slowly added, followed by a solution of sodium hydroxide (755 mg, 18.9 mmol) in water (2.5 mL). The resulting slurry was stirred at −10° C. for 30 min, then at 0° C. for 30 min, then at RT for 30 min. Salts were filtered off on decalite. The remaining filtrate was extracted with $CH_2Cl_2$ (80 mL) and organic layers were washed with water (40 mL). The organic layers were dried over $Na_2SO_4$ and concentrated in vacuo. The crude material was purified by chromatography (silica gel, factor 50, Heptane 100% to Heptane/EtOAc=9/1) to give 300 mg (31%) of title compound.

General Procedure A 2,7-Diazaspiro[3.5]nonane intermediate (91.4 μmol), DIPEA (47.2 ng, 63.8 μl, 365 μmol) and a sulfonyl chloride (110 μmol), were combined with DMF. The reaction mixture was stirred until completion (typically a few hours). The DMF was evaporated and the crude material was purified by preparative HPLC or flash chromatography on silica gel.

General Procedure B 2,7-Diazaspiro[3.5]nonane intermediate (552 μmol) was dissolved $CH_2Cl_2$ (4 mL) and a chloride (552 μmol) was added followed by DIPEA (286 mg, 386 μl, 2.21 mmol). The resulting reaction mixture was stirred at RT until completion. The volatiles were evaporated in vacuo, the residue was purified by preparative HPLC or flash chromatography on silica gel.

General Procedure C

A carboxylic acid (133 μmol, Eq: 1) was dissolved in DMF (1.33 mL) with DIPEA (Eq: 4). HATU (Eq: 1.2) was added and the mixture was stirred 15 min. 2,7-Diazaspiro[3.5]nonane intermediate was then added, and the mixture was stirred until completion. The crude material was purified by flash chromatography on silica gel or preparative HPLC.

General Procedure D

In a 25 mL three-necked flask, 2,7-diazaspiro[3.5]nonane intermediate (329 μmol) and DIPEA (102 mg, 138 μL, 789 μmol) were combined with DMF (2.19 mL) to give a colorless solution. A 5-halo-1,2,4-thiadiazole (329 μmol) was added and the reaction mixture was stirred until completion. The reaction mixture was poured into EtOAc and washed with water. The organic layers were dried over sodium sulfate and concentrated in vacuo. The crude material was purified by flash chromatography or by preparative HPLC.

Example 1

2,7-Bis((4-methoxyphenyl)sulfonyl)-2,7-diazaspiro[3.5]nonane

The crude Intermediate 1 (442 μmol) was mixed with 4-methoxybenzene-1-sulfonyl chloride (192 mg, 928 μmol) and DIPEA (228 mg, 309 μL, 1.77 mmol) in $CH_2Cl_2$ (2.95 mL) to give a colorless suspension. The reaction was stirred overnight at room temperature. The mixture was washed 3 times with $NaHCO_3$ and the combined organic layers were concentrated in vacuo. The crude material was purified by flash chromatography (silica gel, 10 g, 25% to 80% EtOAc in heptane) to give 87 mg (42%) of title compound. ES-MS m/e: 467.2 (M+H$^+$).

Example 2

2-((4-Fluorophenyl)sulfonyl)-7-((4-methoxyphenyl)sulfonyl)-2,7-diazaspiro[3.5]nonane 2-((4-Fluorphenyl)sulfonyl)-7-((4-methoxyphenyl)sulfonyl)-2,7-diazaspiro[3.5]nonane was prepared in 19% yield following general procedure A, using intermediate 2 and 4-fluorobenzene-1-sulfonyl chloride. ES-MS m/e: 455.3 (M+H$^+$).

Example 3

2-((4-(Difluoromethoxy)phenyl)sulfonyl)-7-((4-methoxylphenyl)sulfonyl)-2,7-diazaspiro[3.5]nonane 2-((4-(Difluoromethoxy)phenyl)sulfonyl)-7-((4-methoxyphenyl)sulfonyl)-2,7-diazaspiro[3.5]nonane was prepared in 26% yield following general procedure A, using intermediate 2 and 4-(difluoromethoxy)benzene-1-sulfonyl chloride. ES-MS m/e: 503.23 (M+H$^+$).

Example 4

7-((4-Methoxyphenyl)sulfonyl)-2-((4-propoxyphenyl)sulfonyl)-2,7-diazaspiro[3.5]nonane 7-((4-Methoxyphenyl)sulfonyl)-2-((4-propoxyphenyl)sulfonyl)-2,7-diazaspiro[3.5]nonane was prepared in 30% yield following general procedure A, using intermediate 2 and 4-ethoxybenzene-1-sulfonyl chloride. ES-MS m/e: 481.3 (M+H$^+$).

Example 5

2-((4-Chlorophenyl)sulfonyl)-7-((4-methoxyphenyl)sulfonyl)-2,7-diazaspiro[3.5]nonane 2-((4-Chlorophenyl)sulfonyl)-7-((4-methoxyphenyl)sulfonyl)-2,7-diazaspiro[3.5]nonane was prepared in 11% yield following general procedure A, using intermediate 2 and 4-chlorobenzene-1-sulfonyl chloride. ES-MS m/e: 471.2 (M+H$^+$).

Example 6

2-(4-Fluorophenyl)-1-(7-((4-methoxyphenyl)sulfonyl)-2,7-diazaspiro[3.5]nonan-2-yl)ethanone 2-(4-Fluorophenyl)-1-(7-((4-methoxyphenyl)sulfonyl)-2,7-diazaspiro[3.5]nonan-2-yl)ethanone was prepared in 49% yield following general procedure B, using intermediate 2 and 2-(4-fluorophenyl)acetyl chloride. ES-MS m/e: 433.3 (M+H$^+$).

Example 7

(4-Chlorophenyl)(7-((4-methoxyphenyl)sulfonyl)-2,7-diazaspiro[3.5]nonan-2-yl)methanone (4-Chlorophenyl)(7-((4-methoxyphenyl)sulfonyl)-2,7-diazaspiro[3.5]nonan-2-yl)methanone was prepared in 10% yield following general procedure B, using intermediate 2 and 4-chlorobenzoyl chloride. ES-MS m/e: 435.0 (M+H$^+$).

Example 8

(3,4-Difluorophenyl)(7-((4-methoxyphenyl)sulfonyl)-2,7-diazaspiro[3.5]nonan-2-yl)methanone (3,4-difluorophenyl)(7-((4-methoxyphenyl)sulfonyl)-2,7-diazaspiro[3.5]nonan-2-yl)methanone was prepared in 29% yield following general procedure B, using intermediate 2 and 3,4-difluorobenzoyl chloride. ES-MS m/e: 437.1 (M+H$^+$).

Example 9

(4-Fluorophenyl)(7-((4-methoxyphenyl)sulfonyl)-2,7-diazaspiro[3.5]nonan-2-yl)methanone (4-Fluorophenyl)(7-((4-methoxyphenyl)sulfonyl)-2,7-diazaspiro[3.5]nonan-2-yl)methanone was prepared in 20% yield following general procedure B, using intermediate 2 and 4-fluorobenzoyl chloride. ES-MS m/e: 419.4 (M+H$^+$).

Example 10

1-(7-((4-Methoxyphenyl)sulfonyl)-2,7-diazaspiro[3.5]nonan-2-yl-2-phenylethanone 1-(7-((4-Methoxyphenyl)sulfonyl)-2,7-diazaspiro[3.5]nonan-2-yl)-2-phenylethanone was prepared in 36% yield following general procedure B, using intermediate 2 and 2-phenylacetyl chloride. ES-MS m/e: 419.4 (M+H$^+$).

Example 11

1-(7-((4-Methoyphenyl)sulfonyl)-2,7-diazaspiro[3.5]nonan-2-yl)-2-phenylbutan-1-one 1-(7-((4-Methoxyphenyl)sulfonyl)-2,7-diazaspiro[3.5]nonan-2-yl)-2-phenylbutan-1-one was prepared in 35% yield following general procedure B, using intermediate 2 and 2-phenylbutanoyl chloride. ES-MS m/e: 443.3 (M+H$^+$).

Example 12

4,4,4-Trifluoro-1-(7-((4-methoxyphenyl)sulfonyl)-2,7-diazaspiro[3.5]nonan-2-yl)butan-1-one 4,4,4-Trifluoro-1-(7-((4-methoxyphenyl)sulfonyl)-2,7-diazaspiro[3.5]nonan-2-yl)butan-1-one was prepared in 17% yield following general procedure C, using intermediate 2 and 4,4,4-trifluorobutanoic acid and conducting the reaction at 40° C. ES-MS m/e: 421.1 (M+H$^+$).

Example 13

1-(7-((4-methoxyphenyl)sulfonyl)-2,7-diazaspiro[3.5]nonan-2-yl)-2-methyl-2-phenylpropan-1-one 1-(7-((4-methoxyphenyl)sulfonyl)-2,7-diazaspiro[3.5]nonan-2-yl)-2-methyl-2-phenylpropan-1-one was prepared in 19% yield following general procedure C, using intermediate 2 and 2-methyl-2-phenylpropanoic acid and conducting the reaction at 40° C. ES-MS m/e: 443.4 (M+H$^+$).

Example 14

(7-((4-Methoxyphenyl)sulfonyl)-2,7-diazaspiro[3.5]nonan-2-yl)(1-phenylcyclopropyl)methanone (7-((4-Methoxyphenyl)sulfonyl)-2,7-diazaspiro[3.5]nonan-2-yl)(1-phenylcyclopropyl)methanone was prepared in 13% yield following general procedure C, using intermediate 2 and 1-phenylcyclopropanecarboxylic acid and conducting the reaction at 40° C. ES-MS m/e: 441.3 (M+H$^+$).

Example 15

3-(4-Fluorophenyl)-1-(7-((4-methoxyphenyl)sulfonyl)-2,7-diazaspiro[3.5]nonan-2-yl)propan-1-one 3-(4-Fluorophenyl)-1-(7-((4-methoxylphenyl)sulfonyl)-2,7-diazaspiro[3.5]nonan-2-yl)propan-1-one was prepared in 25% yield following general procedure C, using intermediate 2 and 3-(4-fluorophenyl)propanoic acid. ES-MS m/e: 447.2 (M+H$^+$).

Example 16

2-(3-Methoxyphenyl)-1-(7-((4-methoxyphenyl)sulfonyl)-2,7-diazaspiro[3.5]nonan-2-yl-2-methylpropan-1-one 2-(3-Methoxyphenyl)-1-(7-((4-methoxyphenyl)sulfonyl)-2,7-diazaspiro[3.5]nonan-2-yl)-2-methylpropan-1-one was prepared in 47% yield following general procedure C, using intermediate 2 and 2-(3-methoxyphenyl)-2-methylpropanoic acid. ES-MS m/e: 473.2 (M+H$^+$).

Example 17

1-(7-((4-Methoxyphenyl)sulfonyl)-2,7-diazaspiro[3.5]nonan-2-yl)-2-methyl-2-(pyridin-3-ylmethoxy)propan-1-one 1-(7-((4-Methoxyphenyl)sulfonyl)-2,7-diazaspiro[3.5]nonan-2-yl)-2-methyl-2-(pyridin-3-ylmethoxy)propan-1-one was prepared in 61% yield following general procedure C, using intermediate 2 and 2-methyl-2-(pyridin-3-ylmethoxy)propanoic acid. ES-MS m/e: 473.3 (M+H$^+$).

Example 18

2-Hydroxy-1-(7-((4-methoxyphenyl)sulfonyl)-2,7-diazaspiro[3.5]nonan-2-yl)-2-(pyridin-2-yl)propan-1-one 2-Hydroxy-1-(7-((4-methoxyphenyl)sulfonyl)-2,7-diazaspiro[3.5]nonan-2-yl)-2-(pyridin-2-yl)propan-1-one was prepared in 27% yield following general procedure C, using intermediate 2 and 2-hydroxy-2-(pyridin-2-yl)propanoic acid hydrochloride. ES-MS m/e: 446.4 (M+H$^+$).

Example 19

2-(4-Methoxyphenyl)-1-(7-((4-methoxyphenyl)sulfonyl)-2,7-diazaspiro[3.5]nonan-2-yl)propan-1-one 2-(4-Methoxyphenyl)-1-(7-((4-Methoxyphenyl)sulfonyl-2,7-diazaspiro[3.5]nonan-2-yl)propan-1-one was prepared in 18% yield following general procedure C, using intermediate 2 and 2-(4-methoxyphenyl)propanoic acid. ES-MS m/e: 459.4 (M+H$^+$).

Example 20

1-(7-((4-Methoxyphenyl)sulfonyl)-2,7-diazaspiro[3.5]nonan-2-yl)-2-methyl-2-(o-tolyl)propan-1-one 1-(7-((4-Methoxyphenyl)sulfonyl)-2,7-diazaspiro[3.5]nonan-2-yl)-2-methyl-2-(o-tolyl)propan-1-one was prepared in 48% yield following general procedure C, using intermediate 2 and 2-methyl-2-o-tolylpropanoic acid. ES-MS m/e: 457.5 (M+H$^+$).

Example 21

Chroma-4-yl(7-((4-methoxyphenyl)sulfonyl)-2,7-diazaspiro[3.5]nonan-2-yl)methanone Chroman-4-yl(7-((4-methoxyphenyl)sulfonyl)-2,7-diazaspiro[3.5]nonan-2-yl)methanone was prepared in 13% yield following general procedure C, using intermediate 2 and chroman-4-carboxylic acid. ES-MS m/e: 457.4 (M+H$^+$).

Example 22

(S)-2-(4-Fluorophenyl)-1-(7-((4-methoxyphenyl)sulfonyl)-2,7-diazaspiro[3.5]nonan-2-yl)-3-methylbutan-1-one (S)-2-(4-Fluorophenyl)-1-(7-((4-methoxyphenyl)sulfonyl)-2,7-diazaspiro[3.5]nonan-2-yl)-3-methylbutan-1-one was prepared in 15% yield following general procedure C, using intermediate 2 and (S)-2-(4-fluorophenyl)-3-methylbutanoic acid. ES-MS m/e: 475.5 (M+H$^+$).

Example 23

2-(2-Methoxyphenyl)-1-(7-((4-methoxyphenyl)sulfonyl)-2,7-diazaspiro[3.5]nonan-2-yl)propan-1-one 2-(2-Methoxyphenyl)-1-(7-((4-methoxyphenyl)sulfonyl)-2,7-diazaspiro[3.5]nonan-2-yl)propan-1-one was prepared in 34% yield following general procedure C, using intermediate 2 and 2-(2-methoxyphenyl)propanoic acid. ES-MS m/e: 459.4 (M+H$^+$).

Example 24

2-(2-Methoxyphenyl)-1-(7-((4-methoxyphenyl)sulfonyl)-2,7-diazaspiro[3.5]nonan-2-yl)-2-methylpropan-1-one 2-(2-Methoxyphenyl)-1-(7-((4-methoxyphenyl)sulfonyl)-2,7-diazaspiro[3.5]nonan-2-yl)-2-methylpropan-1-one was prepared in 38% yield following general procedure C, using intermediate 2 and 2-(2-methoxyphenyl)-2-methylpropanoic acid. ES-MS m/e: 473.5 (M+H$^+$).

Example 25

(7-((4-Methoxyphenyl)sulfonyl)-2,7-diazaspiro[3.5]nonan-2-yl)(1,2,3,4-tetrahydronaphthalen-1-yl)methanone (7-((4-Methoxyphenyl)sulfonyl)-2,7-diazaspiro[3.5]nonan-2-yl)(1,2,3,4-tetrahydronaphthalen-1-yl)methanone was prepared in 30% yield following general procedure C, using intermediate 2 and 1,2,3,4-tetrahydronaphthalene-1-carboxylic acid. ES-MS m/e: 455.5 (M+H$^+$).

Example 26

2-(4-Chlorphenyl)-1-(7-((4-methoxyphenyl)sulfonyl)-2,7-diazaspiro[3.5]nonan-2-yl)propan-1-one 2-(4-Chlorphenyl)-1-(7-((4-melhoxyphenyl)sulfonyl)-2,7-diazaspiro[3.5]nonan-2-yl)propan-1-one was prepared in

Example 27

2-(4-Chlorophenyl-1-(7-((4-methoxyphenyl)sulfonyl)-2,7-diazaspiro[3.5]nonan-2-yl)-2-methylpropan-1-one 2-(4-Chlorophenyl)-1-(7-((4-methoxyphenyl)sulfonyl)-2,7-diazaspiro[3.5]nonan-2-yl)-2-methylpropan-1-one was prepared in 20% yield following general procedure C, using intermediate 2 and 2-(4-chlorophenyl)-2-methylpropanoic acid. ES-MS m/e: 477.4 (M+H$^+$).

Example 28

(7-((4-Methoxyphenyl)sulfonyl)-2,7-diazaspiro[3.5]nonan-2-yl)(1-phenylcyclopentyl)methanone (7-((4-Methoxyphenyl)sulfonyl)-2,7-diazaspiro[3.5]nonan-2-yl)(1-phenylcyclopentyl)methanone was prepared in 30% yield following general procedure C, using intermediate 2 and 1-phenylcyclopentanecarboxylic acid. ES-MS m/e: 469.5 (M+H$^+$).

Example 29

2-(3,5-Difluorophenyl)-1-(7-((4-methoxyphenyl)sulfonyl)-2,7-diazaspiro[3.5]nonan-2-yl)propan-1-one 2-(3,5-Difluorophenyl)-1-(7-((4-methoxyphenyl)sulfonyl)-2,7-diazaspiro[3.5]nonan-2-yl)propan-1-one was prepared in 38% yield following general procedure C, using intermediate 2 and 2-(3,5-difluorophenyl)propanoic acid. ES-MS m/e: 465.4 (M+H$^+$).

Example 30

2-(3-Chlorophenyl)-1-(7-((4-methoxyphenyl)sulfonyl)-2,7-diazaspiro[3.5]nonan-2-yl)-2-methylpropan-1-one 2-(3-Chlorophenyl)-1-(7-((4-methoxyphenyl)sulfonyl)-2,7-diazaspiro[3.5]nonan-2-yl)-2-methylpropan-1-one was prepared in 26% yield following general procedure C, using intermediate 2 and 2-(3-chlorophenyl)-2-methylpropanoic acid. ES-MS m/e: 477.4 (M+H$^+$).

Example 31

5-(7-((4-Methoxyphenyl)sulfonyl)-2,7-diazaspiro[3.5]nonan-2-yl)-3-(2,2,2-trifluoroethyl)-1,2,4-thiadiazole In a 5 mL round-bottomed flask, 3-(2,2,2-trifluoroethyl)-1,2,4-thiadiazol-5-(4H)-one (60 mg, 326 µmol), Intermediate 2 (Eq: 1.0) and DIPEA (168 mg, 228 µL, 1.3 mmol) were combined with DMF (1.38 mL) to give a colorless solution. After 5 min stirring at RT, BOP (159 mg, 358 µmol) was added. The reaction mixture was heated to 45° C. and stirred for 2 h. The reaction mixture was then poured into 50 mL EtOAc and washed with sat. NaHCO$_3$ (1×15 mL) and sat NH$_4$Cl (1×10 mL). The organic layers were dried over sodium sulfate and concentrated in vacuo. The crude material was purified by chromatography (silica gel, factor 60, EtOAc/Heptane=1/2) to give 54 mg (36%) of title compound. ES-MS m/e: 463.2 (M+H$^+$).

Example 32

3-(4-Chlorobenzyl)-5-(7-((4-methoxyphenyl)sulfonyl)-2,7-diazaspiro[3.5]nonan-2-yl)-1,2,4-thiadiazole 3-(4-Chlorobenzyl)-5-(7-((4-methoxyphenyl)sulfonyl)-2,7-diazaspiro[3.5]nonan-2-yl)-1,2,4-thiadiazole was prepared in 44% yield following general procedure D, using intermediate 2 and 5-chloro-3-(4-chlorobenzyl)-1,2,4-thiadiazole. ES-MS m/e: 505.0 (M+H$^+$).

Example 33

3-(3,4-Difluorobenzyl)-5-(7-((4-methoxyphenyl)sulfonyl)-2,7-diazaspiro[3.5]nonan-2-yl)-1,2,4-thiadiazole 3-(3,4-Difluorobenzyl)-5-(7-((4-methoxyphenyl)sulfonyl)-2,7-diazaspiro[3.5]nonan-2-yl)-1,2,4-thiadiazole was prepared in 35% yield following general procedure D, using intermediate 2 and 5-chloro-3-(3,4-difluorobenzyl)-1,2,4-thiadiazole. ES-MS m/e: 507.2 (M+H$^+$).

Example 34

3-Cyclopropyl-5-(7-((4-methoxyphenyl)sulfonyl)-2,7-diazaspiro[3.5]nonan-2-yl)-1,2,4-thiadiazole 3-Cyclopropyl-5-(7-((4-methoxyphenyl)sulfonyl)-2,7-diazaspiro[3.5]nonan-2-yl)-1,2,4-thiadiazole was prepared in 6% yield following general procedure D, using intermediate 2 and 5-chloro-3-cyclopropyl-1,2,4-thiadiazole. ES-MS m/e: 421.1 (M+H$^+$).

Example 35

3-Butyl-5-(7-((4-methoxyphenyl)sulfonyl)-2,7-diazaspiro[3.5]nonan-2-yl)-1,2,4-thiadiazole 3-Butyl-5-(7-((4-methoxyphenyl)sulfonyl)-2,7-diazaspiro[3.5]nonan-2-yl)-1,2,4-thiadiazole was prepared in 54% yield following general procedure D, using intermediate 2 and 3-butyl-5-chloro-1,2,4-thiadiazole. ES-MS m/e: 437.2 (M+H$^+$).

Example 36

5-(7-((4-Methoxyphenyl)sulfonyl)-2,7-diazaspiro[3.5]nonan-2-yl)-3-(3-(trifluoromethyl)benzyl)-1,2,4-thiadiazole 5-(7-((4-Methoxyphenyl)sulfonyl)-2,7-diazaspiro[3.5]nonan-2-yl)-3-(3-(trifluoromethyl)benzyl)-1,2,4-thiadiazole was prepared in 51% yield following general procedure D, using intermediate 2 and 5-chloro-3-(3-(trifluoromethyl)benzyl)-1,2,4-thiadiazole. ES-MS m/e: 539.2 (M+H$^+$).

Example 37

3-(4-Methoxyphenyl(7-((4-methoxyphenyl)sulfonyl)-2,7-diazaspiro[3.5]nonan-2-yl)-1,2,4-thiadiazole 3-(4-Methoxyphenyl)-5-(7-((4-methoxyphenyl)sulfonyl)-2,7-diazaspiro[3.5]nonan-2-yl)-1,2,4-thiadiazole was pre- (Previous page continuation: 31% yield following general procedure C, using intermediate 2 and 2-(4-chlorophenyl)propanoic acid. ES-MS m/e: 463.4 (M+H$^+$).)

pared in 70% yield following general procedure D, using intermediate 2 and 5-chloro-3-(4-methoxyphenyl)-1,2,4-thiadiazole. ES-MS m/e: 487.1 (M+H$^+$).

Example 38

5-(7-((4-Methoxyphenyl)sulfonyl)-2,7-diazaspiro[3.5]nonan-2-yl)-3-(pyrazin-2-yl)-1,2,4-thiadiazole 5-(7-((4-Methoxyphenyl)sulfonyl)-2,7-diazaspiro[3.5]nonan-2-yl)-3-pyrazin-2-yl)-1,2,4-thiadiazole was prepared in 71% yield following general procedure D, using intermediate 2 and 5-chloro-3-(pyrazin-2-yl)-1,2,4-thiadiazole. ES-MS m/e: 459.3 (M+H$^+$).

Example 39

3-(4-Chlorophenyl)-5-(7-((4-methoxyphenyl)sulfonyl-2,7-diazaspiro[3.5]nonan-2-yl)-1,2,4-thiadiazole 3-(4-Chlorophenyl)-5-(7-((4-methoxyphenyl)sulfonyl)-2,7-diazaspiro[3.5]nonan-2-yl)-1,2,4-thiadiazole was prepared in 49% yield following general procedure D, using intermediate 2 and 5-chloro-3-(4-chlorophenyl)-1,2,4-thiadiazole. ES-MS m/e: 491.0 (M+H$^+$).

Example 40

3-(1-(4-Fluorophenyl)cyclopropyl)-5-(7-((4-methoxyphenyl)sulfonyl)-2,7-diazaspiro[3.5]nonan-2-yl)-1,2,4-thiadiazole In a 5 mL screw cap reactor, 5-chloro-3-(1-(4-fluorophenyl)cyclopropyl)-1, 2,4-thiadiazole (30 mg, 112 µmol), Intermediate 2 (134 µmol) and DIPEA (43.4 mg, 58.6 µL, 336 µmol) were combined with DMF (1 mL). The reaction mixture was heated to 50° C. and stirred for 15 h. The crude material was purified by preparative HPLC to give 20 mg (35%) of title compound.

Example 41

3-(4-Fluorobenzyl-5-(7-((4-(methylthio)phenyl)sulfonyl)-2,7-diazaspiro[3.5]nonan-2-yl)-1,2,4-thiadiazole 3-(4-Fluorobenzyl)-5-(7-((4-(methylthio)phenyl)sulfonyl)-2,7-diazaspiro[3.5]nonan-2-yl)-1,2,4-thiadiazole was prepared in 23% yield following general procedure D, using intermediate 3 and 5-chloro-3-(4-fluorobenzyl)-1,2,4-thiadiazole. ES-MS m/e: 505.1 (M+H$^+$).

Example 42

7-((4-(Difluoromethoxy)phenyl)sulfonyl)-2-((4-ethoxyphenyl)sulfonyl)-2,7-diazaspiro[3.5]nonane 7-((4-(Difluoromethoxy)phenyl)sulfonyl)-2-((4-ethoxyphenyl)sulfonyl)-2,7-diazaspiro[3.5]nonane was prepared following general procedure B, using intermediate 4 and 4-ethoxybenzene-1-sulfonylchloride. ES-MS m/e: 517.2 (M+H$^+$)

Example 43

2-((4-Chlorophenyl)sulfonyl)-7-((4-(difluoromethoxy)phenyl)sulfonyl)-2,7-diazaspiro[3.5]nonan 2-((4-Chlorophenyl)sulfonyl)-7-((4-(difluoromethoxy)phenyl)sulfonyl)-2,7-diazaspiro[3.5]nonane was prepared following general procedure B, using intermediate 4 and 4-chlorobenzene-1-sulfonyl chloride.

Example 44

7-((4-(Difluoromethoxy)phenyl)sulfonyl)-2-((4-fluorophenyl)sulfonyl)-2,7-diazaspiro[3.5]nonane 7-((4-(Difluoromethoxy)phenyl)sulfonyl)-2-((4-fluorophenyl)sulfonyl)-2,7-diazaspiro[3.5]nonane was prepared following general procedure B, using intermediate 4 and 4-fluorobenzene-1-sulfonyl chloride.

Example 45

7-((4-(Difluoromethoxy)phenyl)sulfonyl)-2-((4-methoxyphenyl)sulfonyl)-2,7-diazaspiro[3.5]nonane 7-((4-(Difluoromethoxy)phenyl)sulfonyl)-2-((4-methoxyphenyl)sulfonyl)-2,7-diazaspiro[3.5]nonane was prepared in 15% yield following general procedure A, using intermediate 5 and 4-(difluoromethoxy)benzene-1-sulfonyl chloride. ES-MS m/e: 503.2 (M+H$^+$).

Example 46

7-((4-Ethoxyphenyl)sulfonyl)-2-((4-methoxyphenyl)sulfonyl)-2,7-diazaspiro[3.5]nonane 7-((4-Ethoxyphenyl)sulfonyl)-2-((4-methoxyphenyl)sulfonyl)-2,7-diazaspiro[3.5]nonane was prepared in 16% yield following general procedure A, using intermediate 5 and 4-ethoxybenzene-1-sulfonyl chloride. ES-MS m/e: 481.3 (M+H$^+$).

Example 47

7-((4-Chlorophenyl)sulfonyl)-2-((4-methoxyphenyl)sulfonyl)-2,7-diazaspiro[3.5]nonane 7-((4-Chlorophenyl)sulfonyl)-2-((4-methoxyphenyl)sulfonyl)-2,7-diazaspiro[3.5]nonane was prepared in 32% yield following general procedure A, using intermediate 5 and 4-chlorobenzene-1-sulfonyl chloride. ES-MS m/e: 471.2 (M+H$^+$).

Example 48

2,7-Bis((4-(difluoromethoxy)phenyl)sulfonyl)-2,7-diazaspiro[3.5]nonane 2,7-Bis((4-(difluoromethoxy)phenyl)sulfonyl)-2,7-diazaspiro[3.5]nonane was prepared following general procedure B, using intermediate 6 and 4-(difluoromethoxy)benzene-1-sulfonyl chloride. ES-MS m/e: 539.0 (M+H$^+$).

Example 49

2-((4-(Difluoromethoxy)phenyl)sulfonyl)-7-((4-ethoxyphenyl)sulfonyl)-2,7-diazaspiro[3.5]nonane 2-((4-(Difluoromethoxy)phenyl)sulfonyl)-7-((4-ethoxyphenyl)sulfonyl)-2,7-diazaspiro[3.5]nonane was prepared following general procedure B, using intermediate 6 and 4-ethoxybenzene-1-sulfonyl chloride.

Example 50

7-((4-Chlorophenyl)sulfonyl)-2-((4-(difluoromethoxy)phenyl)sulfonyl)-2,7-diazaspiro[3.5]nonane 7-((4-Chlorophenyl)sulfonyl)-2-((4-(difluoromethoxy)phenyl)sulfonyl)-2,7-diazaspiro[3.5]nonane was prepared following general procedure B, using intermediate 6 and 4-chlorobenzene-1-sulfonyl chloride.

Example 51

2-((4-(Difluoromethoxy)phenyl)sulfonyl-7-((4-fluorophenol)sulfonyl)-2,7-diazaspiro[3.5]nonane 2-((4-(Difluoromethoxy)phenyl)sulfonyl)-7-((4-fluorophenyl)sulfonyl)-2,7-diazaspiro[3.5]nonane was prepared following general procedure B, using intermediate 6 and 4-fluorobenzene-1-sulfonyl chloride.

Example 52

6-Chloro-2-(7-((4-methoxyphenyl)sulfonyl)-2,7-diazaspiro[3.5]nonan-2-yl)benzo[d]thiazole 6-Chloro-2-(7-((4-methoxyphenyl)sulfonyl)-2,7-diazaspiro[3.5]nonan-2-yl)benzo[d]thiazole was prepared following general procedure B, using intermediate 7 and 4-methoxybenzene-1-sulfonyl chloride.

Example 53

6-Chloro-2-(7-((4-ethoxyphenyl)sulfonyl)-2,7-diazaspiro[3.5]nonan-2-yl)benzo[d]thiazole 6-Chloro-2-(7-((4-ethoxyphenyl)sulfonyl)-2,7-diazaspiro[3.5]nonan-2-yl)benzo[d]thiazole was prepared following general procedure B, using intermediate 7 and 4-methoxybenzene-1-sulfonyl chloride.

Example 54

6-Chloro-2-(7-((4-(difluoromethoxy)phenyl)sulfonyl)-2,7-diazaspiro[3.5]nonan-2-yl)benzo[d]thiazole 6-Chloro-2-(7-((4-(difluoromethoxy)phenyl)sulfonyl)-2,7-diazaspiro[3.5]nonan-2-yl)benzo[d]thiazole was prepared following general procedure B, using intermediate 7 and 4-(difluoromethoxy)benzene-1-sulfonyl chloride.

Example 55

6-Chloro-2-(7-((4-(methylthio)phenyl)sulfonyl)-2,7-diazaspiro[3.5]nonan-2-yl)benzo[d]thiazole 6-Chloro-2-(7-((4-(methylthio)phenyl)sulfonyl)-2,7-diazaspiro[3.5]nonan-2-yl)benzo[d]thiazole was prepared following general procedure B, using intermediate 7 and 4-(methylthio)benzene-1-sulfonyl chloride.

Example 56

3-(1-(4-Fluorophenyl)ethyl)-5-(7-((4-methoxyphenyl)sulfonyl)-2,7-diazaspiro[3.5]nonan-2-yl)-1,2,4-thiadiazole 3-(1-(4-Fluorophenyl)ethyl)-5-(7-((4-methoxyphenyl)sulfonyl)-2,7-diazaspiro[3.5]nonan-2-yl)-1,2,4-thiadiazole was prepared in 38% yield following general procedure B, using intermediate 8 and 4-methoxybenzene-1-sulfonyl chloride. ES-MS m/e: 503.2 (M+H$^+$).

Example 57

3-(4-Fluorobenzyl)-5-(4-methoxyphenyl)sulfonyl)-2,7-diazaspiro[3.5]nonan-2-yl)-1,2,4-thiadiazole 3-(4-Fluorobenzyl)-5-(7-((4-methoxyphenyl)sulfonyl)-2,7-diazaspiro[3.5]nonan-2-yl)-1,2,4-thiadiazole was prepared in 32% yield following general procedure B, using intermediate 9 and 4-methoxybenzene-1-sulfonyl chloride. ES-MS m/e: 489.4 (M+H$^+$).

Example 58

N-(4-((2-(3-(4-fluorobenzyl)-1,2,4-thiadiazol-5-yl)-2,7-diazaspiro[3.5]nonan-7-yl)sulfonyl)phenyl)acetamide N-(4-((2-(3-(4-fluorobenzyl)-1,2,4-thiadiazol-5-yl)-2,7-diazaspiro[3.5]nonan-7-yl)sulfonyl)phenyl)acetamide was prepared in 26% yield following general procedure B, using intermediate 9 and 4-acetamidobenzene-1-sulfonyl chloride. ES-MS m/e: 516.5 (M+H$^+$).

Example 59

3-(4-Fluorobenzyl)-5-(7-((4-(methylsulfonyl)phenyl)sulfonyl)-2,7-diazaspiro[3.5]nonan-2-yl)-1,2,4-thiadiazole 3-(4-Fluorobenzyl)-5-(7-((4-(methylsulfonyl)phenyl)sulfonyl)-2,7-diazaspiro[3.5]nonan-2-yl)-1,2,4-thiadiazole was prepared in 18% yield following general procedure B, using intermediate 9 and 4-(methylsulfonyl)benzene-11-sulfonyl chloride. ES-MS m/e: 537.5 (M+H$^+$).

Example 60

5-(7-((2,4-Difluorophenyl)sulfonyl)-2,7-diazaspiro[3.5]nonan-2-yl)-3-(4-fluorobenzyl)-1,2,4-thiadiazole 5-(7-((2,4-Difluorophenyl)sulfonyl)-2,7-diazaspiro[3.5]nonan-2-yl)-3-(4-fluorobenzyl)-1,2,4-thiadiazole was prepared in 12% yield following general procedure B, using intermediate 9 and 2,4-difluorobenzene-1-sulfonyl chloride. ES-MS m/e: 495.5 (M+H$^+$).

Example 61

5-(7-((3,4-Dimethoxyphenyl)sulfonyl)-2,7-diazaspiro[3.5]nonan-2-yl)-3-(4-fluorobenzyl)-1,2,4-thiadiazole 5-(7-((3,4-Dimethoxyphenyl)sulfonyl)-2,7-diazaspiro[3.5]nonan-2-yl)-3-(4-fluorobenzyl)-1,2,4-thiadiazole was prepared in 33% yield following general procedure B, using intermediate 9 and 3,4-dimethoxybenzene-1-sulfonyl chloride. ES-MS m/e: 519.5 (M+H$^+$).

Example 62

3-(4-Fluorobenzyl)-5-(2-methoxy-5-methylphenyl)sulfonyl)-2,7-diazaspiro[3.5]nonan-2-yl)-1,2,4-thiadiazole 3-(4-Fluorobenzyl)-5-(7-((2-methoxy-5-methylphenyl)sulfonyl)-2,7-diazaspiro[3.5]nonan-2-yl)-1,2,4-thiadiazole was prepared in 35% yield following general procedure B, using intermediate 9 and 2-methoxy-5-methylbenzene-1-sulfonyl chloride. ES-MS m/e: 503.4 (M+H$^+$).

Example 63

5-(7-((5-Chloro-2-methoxyphenyl)sulfonyl)-2,7-diazaspiro[3.5]nonan-2-yl)-3-(4-fluorobenzyl)-1,2,4-thiadiazole 5-(7-((5-Chloro-2-methoxyphenyl)sulfonyl)-2,7-diazaspiro[3.5]nonan-2-yl)-3-(4-fluorobenzyl)-1,2,4-thiadiazole was prepared in 57% yield following general procedure B, using intermediate 9 and 5-chloro-2-methoxybenzene-1-sulfonyl chloride. ES-MS m/e: 523.4 (M+H$^+$).

Example 64

3-(4-Fluorobenzyl)-5-(7-((3-(trifluoromethyl)phenyl)sulfonyl)-2,7-diazaspiro[3.5]nonan-2-yl)-1,2,4-thiadiazole 3-(4-Fluorobenzyl)-5-(7-((3-(trifluoroethyl)phenyl)sulfonyl)-2,7-diazaspiro[3.5]nonan-2-yl)-1,2,4-thiadiazole was prepared in 19% yield following general procedure B, using intermediate 9 and 3-(trifluoromethyl)benzene-1-sulfonyl chloride. ES-MS m/e: 527.5 (M+H$^+$).

Example 65

3-(4-Fluorobenzyl)-5-(7-((4-(trifluoromethyl)phenyl)sulfonyl)-2,7-diazaspiro[3.5]nonan-2-yl)-1,2,4-thiadiazole 3-(4-Fluorobenzyl)-5-(7-((4-(trifluromethyl)phenyl)sulfonyl)-2,7-diazaspiro[3.5]nonan-2-yl)-1,2,4-thiadiazole was prepared in 60% yield following general procedure B, using intermediate 9 and 4-(trifluoromethyl)benzene-1-sulfonyl chloride. ES-MS m/e: 527.4 (M+H$^+$).

Example 66

3-(4-Fluorobenzyl)-5-(7-(m-tolylsulfonyl)-2,7-diazaspiro[3.5]nonan-2-yl)-1,2,4-thiadiazole 3-(4-Fluorobenzyl)-5-(7-(m-tolylsulfonyl)-2,7-diazaspiro[3.5]nonan-2-yl)-1,2,4-thiadiazole was prepared in 4% yield following general procedure B, using intermediate 9 and 3-methylbenzene-1-sulfonyl chloride. ES-MS m/e: 473.4 (M+H$^+$).

Example 67

3-(4-Fluorobenzyl)-5-(7-((2-fluorophenyl)sulfonyl)-2,7-diazaspiro[3.5]nonan-2-yl)-1,2,4-thiadiazole 3-(4-Fluorobenzyl)-5-(7-((2-fluorophenyl)sulfonyl)-2,7-diazaspiro[3.5]nonan-2-yl)-1,2,4-thiadiazole was prepared in 31% yield following general procedure B, using intermediate 9 and 2-fluorobenzene-1-sulfonyl chloride. ES-MS m/e: 477.4 (M+H$^+$).

Example 68

5-(7-((4-Ethylphenyl)sulfonyl)-2,7-diazaspiro[3.5]nonan-2-yl)-3-(4-fluorobenzyl)-1,2,4-thiadiazole 5-(7-((4-Ethylphenyl)sulfonyl)-2,7-diazaspiro[3.5]nonan-2-yl)-3-(4-fluorobenzyl)-1,2,4-thiadiazole was prepared in 55% yield following general procedure B, using intermediate 9 and 4-ethylbenzene-1-sulfonyl chloride. ES-MS m/e: 487.4 (M+H$^+$).

Example 69

3-(4-Fluorobenzyl)-5-(7-(o-tolylsulfonyl)-2,7-diazaspiro[3.5]nonan-2-yl)-1,2,4-thiadiazole 3-(4-Fluorobenzyl)-5-(7-(o-tolylsulfonyl)-2,7-diazaspiro[3.5]nonan-2-yl)-1,2,4-thiadiazole was prepared in 28% yield following general procedure B, using intermediate 9 and 2-methylbenzene-1-sulfonyl chloride. ES-MS m/e: 473.4 (M+H$^+$).

Example 70

5-(7-((4-(Tert-butyl)phenyl)sulfonyl)-2,7-diazaspiro[3.5]nonan-2-yl)-3-(4-fluorobenzyl)-1,2,4-thiadiazole 5-(7-((4-(Tert-butyl)phenyl)sulfonyl)-2,7-diazaspiro[3.5]nonan-2-yl)-3-(4-fluorobenzyl)-1,2,4-thiadiazole was prepared in 17% yield following general procedure B, using intermediate 9 and 4-tert-butylbenzene-1-sulfonyl chloride. ES-MS m/e: 515.5 (M+H$^+$).

Example 71

3-(4-Fluorobenzyl)-5-(7-((3-fluorophenyl)sulfonyl)-2,7-diazaspiro[3.5]nonan-2-yl)-1,2,4-thiadiazole 3-(4-Fluorobenzyl)-5-(7-((3-fluorophenyl)sulfonyl)-2,7-diazaspiro[3.5]nonan-2-yl)-1,2,4-thiadiazole was prepared in 12% yield following general procedure B, using intermediate 9 and 3-fluorobenzene-1-sulfonyl chloride. ES-MS m/e: 477.4 (M+H$^+$).

Example 72

5-(7-((2,5-Dimethoxyphenyl)sulfonyl)-2,7-diazaspiro[3.5]nonan-2-yl)-3-(4-fluorobenzyl)-1,2,4-thiadiazole 5-(7-((2,5-Dimethoxyphenyl)sulfonyl)-2,7-diazaspiro[3.5]nonan-2-yl)-3-(4-fluorobenzyl)-1,2,4-thiadiazole was prepared in 44% yield following general procedure B, using intermediate 9 and 2,5-dimethoxybenzene-1-sulfonyl chloride. ES-MS m/e: 519.4 (M+H$^+$).

Example 73

5-(7-(2,5-Difluorophenyl)sulfonyl)-2,7-diazaspiro[3.5]nonan-2-yl-3-(4-fluorobenzyl)-1,2,4-thiadiazole 5-(7-((2,5-Difluorophenyl)sulfonyl)-2,7-diazaspiro[3.5]nonan-2-yl)-3-(4-fluorobenzyl)-1,2,4-thiadiazole was prepared in 20% yield following general procedure B, using intermediate 9 and 2,5-difluorobenzene-1-sulfonyl chloride. ES-MS m/e: 495.4 (M+H$^+$).

Example 74

5-(7-((2,6-Difluorophenyl)sulfonyl)-2,7-diazaspiro[3.5]nonan-2-yl)-3-(4-fluorobenzyl)-1,2,4-thiadiazole 5-(7-((2,6-Difluorophenyl)sulfonyl-2,7-diazaspiro[3.5]nonan-2-yl)-3-(4-fluorobenzyl)-1,2,4-thiadiazole was prepared in 35% yield following general procedure B, using intermediate 9 and 2,6-difluorobenzene-1-sulfonyl chloride. ES-MS m/e: 495.5 (M+H$^+$).

Example 75

5-(3,4-Difluorophenyl)sulfonyl)-2,7-diazaspiro[3.5]nonan-2-yl-3-(4-fluorobenzyl)-1,2,4-thiadiazole 5-(7-((3,4-Difluorophenyl)sulfonyl)-2,7-diazaspiro[3.5]nonan-2-yl)-3-(4-fluorobenzyl)-1,2,4-thiadiazole was prepared in 34% yield following general procedure B, using intermediate 9 and 3,4-difluorobenzene-1-sulfonyl chloride. ES-MS m/e: 495.4 (M+H$^+$).

Example 76

3-(4-Fluorobenzyl)-5-(7-((3-methoxyphenyl)sulfonyl)-2,7-diazaspiro[3.5]nonan-2-yl)-1,2,4-thiadiazole 3-(4-Fluorobenzyl)-5-(7-((3-methoxyphenyl)sulfonyl)-2,7-diazaspiro[3.5]nonan-2-yl)-1,2,4-thiadiazole was prepared in 20% yield following general procedure B, using intermediate 9 and 3-methoxybenzene-1-sulfonyl chloride. ES-MS m/e: 489.5 (M+H$^+$).

Example 77

5-(7-((5-Fluoro-2-methylphenyl)sulfonyl)-2,7-diazaspiro[3.5]nonan-2-yl)-3-(4-fluorobenzyl)-1,2,4-thiadiazole 5-(7-((5-Fluoro-2-methylphenyl)sulfonyl)-2,7-diazaspiro[3.5]nonan-2-yl)-3-(4-fluorobenzyl)-1,2,4-thiadiazole was prepared in 25% yield following general procedure B, using intermediate 9 and 5-fluoro-2-methylbenzene-1-sulfonyl chloride. ES-MS m/e: 491.4 (M+H$^+$).

Example 78

2-Ethoxy-5-((2-(3-(4-fluorobenzyl-1,2,4)-thiadiazol-5-yl)-2,7-diazaspiro[3.5]nonan-7-yl)sulfonyl)benzonitrile 2-Ethoxy-5-((2-(3-(4-fluorobenzyl)-1,2,4-thiadiazol-5-yl)-2,7-diazaspiro[3.5]nonan-7-yl)sulfonyl)benzonitrile was prepared in 5% yield following general procedure B, using intermediate 9 and 3-cyano-4-ethoxybenzene-1-sulfonyl chloride. ES-MS m/e: 528.5 (M+H$^+$).

Example 79

3-(4-Fluorobenzyl)-5-(7-((4-methoxy-3-(trifluoromethyl)phenyl)sulfonyl)-2,7-diazaspiro[3.5]nonan-2-yl) 1,2,4-thiadiazole 3-(4-Fluorobenzyl)-5-(7-((4-methoxy-3-(trifluoromethyl)phenyl)sulfonyl)-2,7-diazaspiro[3.5]nonan-2-yl)-1,2,4-thiadiazole was prepared in 25% yield following general procedure B, using intermediate 9 and 4-methoxy-3-(trifluoromethyl)benzene-1-sulfonylchloride. ES-MS m/e: 557.6 (M+H$^+$).

Example 80

3-(4-Fluorobenzyl)-5-(7-((2-methoxyphenyl)sulfonyl)-2,7-diazaspiro[3.5]nonan-2-yl)-1,2,4-thiadiazole 3-(4-Fluorobenzyl)-5-(7-((2-methoxyphenyl)sulfonyl)-2,7-diazaspiro[3.5]nonan-2-yl)-1,2,4-thiadiazole was prepared in 44% yield following general procedure B, using intermediate 9 and 2-methoxybenzene-1-sulfonyl chloride. ES-MS m/e: 489.4 (M+H$^+$).

Example 81

5-(7-((3-Chloro-4-methoxyphenyl)sulfonyl)-2,7-diazaspiro[3.5]nonan-2-yl-3-(4-fluorobenzyl)-1,2,4-thiadiazole 5-(7-((3-Chloro-4-methoxyphenyl)sulfonyl)-2,7-diazaspiro[3.5]nonan-2-yl)-3-(4-fluorobenzyl)-1,2,4-thiadiazole was prepared in 16% yield following general procedure B, using intermediate 9 and 3-chloro-4-methoxybenzene-1-sulfonyl chloride. ES-MS m/e: 523.4 (M+H$^+$).

Example 82

3-(4-Fluorobenzyl)-5-(7-((3-(methylsulfonyl)phenyl)sulfonyl)-2,7-diazaspiro[3.5]nonan-2-yl)-1,2,4-thiadiazole 3-(4-Fluorobenzyl)-5-(7-(3-(methylsulfonyl)phenyl)sulfonyl)-2,7-diazaspiro[3.5]nonan-2-yl)-1,2,4-thiadiazole was prepared in 28% yield following general procedure B, using intermediate 9 and 3-(methylsulfonyl)benzene-1-sulfonyl chloride. ES-MS m/e: 537.5 (M+H$^+$).

Example 83

5-(7-(3,5-Difluorophenyl)sulfonyl)-2,7-diazaspiro[3.5]nonan-2-yl)-3-(4-fluorobenzyl)-1,2,4-thiadiazole 5-(7-((3,5-Difluorophenyl)sulfonyl)-2,7-diazaspiro[3.5]nonan-2-yl-3-(4-fluorobenzyl)-1,2,4-thiadiazole was prepared in 7% yield following general procedure B, using intermediate 9 and 3,5-difluorobenzene-1-sulfonyl chloride. ES-MS m/e: 495.4 (M+H$^+$).

Example 84

Methyl 3-((2-(3-(4-fluorobenzyl)-1,2,4-thiadiazol-5-yl)-2,7-diazaspiro[3.5]nonan-7-yl)sulfonyl)benzoate Methyl 3-((2-(3-(4-fluorobenzyl)-1,2,4-thiadiazol-5-yl)-2,7-diazaspiro[3.5]nonan-7-yl)sulfonyl)benzoate was prepared in 26% yield following general procedure B, using intermediate 9 and methyl 3-(chlorosulfonyl)benzoate. ES-MS m/e: 517.4 (M+H$^+$).

Example 85

5-(7-((4-(Difluoromethoxy)phenyl)sulfonyl)-2,7-diazaspiro[3.5]nonan-2-yl)-3-(4-fluorobenzyl)-1,2,4-thiadiazole 5-(7-((4-(Difluoromethoxy)phenyl)sulfonyl)-2,7-diazaspiro[3.5]nonan-2-yl)-3-(4-fluorobenzyl)-1,2,4-thiadiazole was prepared in 38% yield following general procedure B, using intermediate 9 and 4-(difluoromethoxy)benzene-1-sulfonyl chloride. ES-MS m/e: 525.4 (M+H$^+$).

Example 86

5-(7-((5-Fluoro-2-methoxyphenyl)sulfonyl)-2,7-diazaspiro[3.5]nonan-2-yl)-3-(4-fluorobenzyl)-1,2,4-thiadiazole 5-(7-((5-Fluoro-2-methoxyphenyl)sulfonyl)-2,7-diazaspiro[3.5]nonan-2-yl)-3-(4-fluorobenzyl)-1,2,4-thiadiazole was prepared in 52% yield following general procedure B, using intermediate 9 and 5-fluoro-2-methoxybenzene-1-sulfonyl chloride. ES-MS m/e: 507.4 (M+H$^+$).

Example 87

5-(7-((4-Ethoxy-3-methylphenyl)sulfonyl)-2,7-[3.5]nonan-2-yl)-3-(4-fluorobenzyl)-1,2,4-thiadiazole 5-(7-((4-Ethoxy-3-methylphenyl)sulfonyl)-2,7-diazaspiro[3.5]nonan-2-yl)-3-(4-fluorobenzyl)-1,2,4-thiadiazole was prepared in 31% yield following general procedure B, using intermediate 9 and 4-ethoxy-3-methylbenzene-1-sulfonyl chloride. ES-MS m/e: 517.5 (M+H$^+$).

Example 88

3-(4-Fluorobenzyl)-5-(7-((4-methoxy-3-methylphenyl)sulfonyl)-2,7-diazaspiro[3.5]nonan-2-yl)-1,2,4-thiadiazole 3-(4-Fluorobenzyl)-5-(7-((4-methoxy-3-methylphenyl)sulfonyl)-2,7-diazaspiro[3.5]nonan-2-yl)-1,2,4-thiadiazole was prepared in 9% yield following general procedure B, using intermediate 9 and 4-methoxy-3-methylbenzene-1-sulfonyl chloride. ES-MS m/e: 503.4 (M+H$^+$).

Example 89

3-(4-Fluorobenzyl)-5-(7-(pyridin-3-ylsulfonyl)-2,7-diazaspiro[3.5]nonan-2-yl)-1,2,4 thiadiazole 3-(4-Fluorobenzyl)-5-(7-(pyridin-3-ylsulfonyl)-2,7-diazaspiro[3.5]nonan-2-yl)-1,2,4-thiadiazole was prepared in 4% yield following general procedure B, using intermediate 9 and pyridin-3-sulfonyl chloride. ES-MS m/e: 460.4 (M+H$^+$).

Example 90

3-(4-Fluorobenzyl-5-(7-((1-methyl-1H-pyrazol-4-yl)sulfonyl)-2,7-diazaspiro[3.5]nonan-2-yl)-1,2,4-thiadiazole 3-(4-Fluorobenzyl)-5-(7-((1-methyl-1H-pyrazol-4-yl)sulfonyl)-2,7-diazaspiro[3.5]nonan-2-yl)-1,2,4-thiadiazole was prepared in 4% yield following general procedure B, using intermediate 9 and 1-methyl-1H-pyrazole-4-sulfonyl chloride. ES-MS m/e: 505.4 (M+H$^+$).

Example 91

4-((2-(3-(4-Fluorobenzyl-1,2,4-thiadiazol-5-yl)-2,7-diazaspiro[3.5]nonan-7-yl)sulfonyl)-3,5-dimethylisoxazole 4-((2-(3-(4-Fluorobenzyl)-1,2,4-thiadiazol-5-yl)-2,7-diazaspiro[3.5]nonan-7-yl)sulfonyl)-3,5-dimethylisoxazole was prepared in 28% yield following general procedure B, using intermediate 9 and 3,5-dimethylisoxazole-4-sulfonyl chloride. ES-MS m/e: 478.4 (M+H$^+$).

Example 92

3-(4-Fluorobenzyl)-5-(7-(thiophen-2-ylsulfonyl)-2,7-diazaspiro[3.5]nonan-2-yl)-1,2,4-thiadiazole 3-(4-Fluorobenzyl)-5-(7-thiophen-2-ylsulfonyl)-2,7-diazaspiro[3.5]nonan-2-yl)-1,2,4-thiadiazole was prepared in 6% yield following general procedure B, using intermediate 9 and thiophene-2-sulfonyl chloride. ES-MS m/e: 465.3 (M+H$^+$).

Example 93

5-(7-((5-Chlorothiophen-2-yl)sulfonyl)-2,7-diazaspiro[3.5]nonan-2-yl)-3-(4-fluorobenzyl)-1,2,4-thiadiazole 5-(7-((5-Chlorothiophen-2-yl)sulfonyl)-2,7-diazaspiro[3.5]nonan-2-yl)-3-(4-fluorobenzyl)-1,2,4-thiadiazole was prepared in 23% yield following general procedure B, using intermediate 9 and 5-chlorothiophene-2-sulfonyl chloride. ES-MS m/e: 500.4 (M+H$^+$).

Example 94

3-(4-Fluorobenzyl)-5-(7-(thiophen-3-ylsulfonyl)-2,7-diazaspiro[3.5]nonan-2-yl)-1,2,4-thiadiazole 3-(4-Fluorobenzyl)-5-(7-(thiophen-3-ylsulfonyl)-2,7-diazaspiro[3.5]nonan-2-yl)-1,2,4-thiadiazole was prepared in 27% yield following general procedure B, using intermediate 9 and thiophene-3-sulfonyl chloride. ES-MS m/e: 465.3 (M+H$^+$).

Example 95

3-(4-Fluorobenzyl-5-(7-((5-methylthiophenyl-2-yl)sulfonyl)-2,7-diazaspiro[3.5]nonan-2-yl)-1,2,4-thiadiazole 3-(4-Fluorobenzyl)-5-(7-((5-methylthiophen-2-yl)sulfonyl)-2,7-diazaspiro[3.5]nonan-2-yl)-1,2,4-thiadiazole was prepared in 15% yield following general procedure B, using intermediate 9 and 5-methylthiophene-2-sulfonyl chloride. ES-MS m/e: 479.4 (M+H$^+$).

Example 96

3-(4-Fluorobenzyl)-5-(7-((3,3,3-trifluoropropyl)sulfonyl)-2,7-diazaspiro[3.5]nonan-2-yl)-1,2,4-thiadiazole 3-(4-Fluorobenzyl)-5-(7-((3,3,3-trifluoropropyl)sulfonyl)-2,7-diazaspiro[3.5]nonan-2-yl)-1,2,4-thiadiazole was prepared in 64% yield following general procedure B, using intermediate 9 and 3,3,3-trifluoropropane-1-sulfonyl chloride. ES-MS m/e: 479.4 (M+H$^+$).

Example 97

5-(7-((Cyclohexylmethyl)sulfonyl)-2,7-diazaspiro[3.5]nonan-2-yl)-3-(4-fluorobenzyl)-1,2,4-thiadiazole 5-(7-((Cyclohexylmethyl)sulfonyl)-2,7-diazaspiro[3.5]nonan-2-yl)-3-(4-fluorobenzyl)-1,2,4-thiadiazole was prepared in 56% yield following general procedure B, using intermediate 9 and cyclohexylmethanesulfonyl chloride. ES-MS m/e: 479.4 (M+H$^+$).

Example 98

4-((2-(3-(4-Fluorobenzyl)-1,2,4-thiadiazol-5-yl)-2,7-diazaspiro[3.5]nonan-7-yl)sulfonyl)morpholine 4-((2-(3-(4-Fluorobenzyl)-1,2,4-thiadiazol-5-yl)-2,7-diazaspiro[3.5]nonan-7-yl)sulfonyl)morpholine was prepared in 58% yield following general procedure B, using intermediate 9 and morpholine-4-sulfonyl chloride. ES-MS m/e: 468.4 (M+H$^+$).

Example 99

Use of a Rat Insulinoma Cell Line Exposed to Extracellular Stressors as a Model for Beta Cell Stress/Apoptosis The INS-1E cell line, a rat insulinoma cell line, has been characterized extensively. INS-1E cells respond to glucose by secreting insulin and, unlike most other immortalized β-cell lines, they do this in a consistent manner over time. The cells are sensitive to hyperglycemia-, free fatty acid (FFA)-, and cytokine-induced stress. Prolonged stress ultimately leads to induction of apoptotic pathways and, if stress is not counter-acted, to apoptosis. Caspase-3 and -7 play a central role downstream where various apoptotic pathways merge. As such, activation (i.e. cleavage) of these caspases forms a relevant primary read-out to evaluate protective activity of compounds against stress-induced apoptosis.

To evaluate the efficacy of different compounds to prevent induction of apoptosis, an in vitro screen was developed in which INS-1E cells were exposed to a cytokine mix (IFN-γ, 5 ng/ml; IL-1β, 20 pg/ml; TNF-α, 0.25 ng/ml). The degree of induction of apoptosis was evaluated using a substrate for cleaved caspase-3 and -7, i.e. a proluminescent caspase-3/7 DEVD aminoluciferin substrate with a thermostable luciferase (Caspase-Glo® 3/7 assay; Promega, cat. G8092). Experimental Procedure: On day 0, INS-1E cells were plated in a white-walled 96-well microplate (Greiner, cat. 655098) at 20,000 cells per well in 100 μl complete medium (RPMI containing 11 mM glucose supplemented with 5% FCS, 100 IU/ml penicillin, 100 μg/ml streptomycin, 10 mM HEPES, 1 mM Sodium Pyruvate and 50 μM 2-Mercapto-ethanol). On day 2, 100 μl medium containing cytokines and compound dissolved in DMSO was added to the cells. Wells without cytokines containing DMSO and wells with cytokines and DMSO were included to evaluate the degree of caspase 3/7 activation by the cytokine mix. After 24 hours exposure to cytokines and/or compound, Caspase-Glo® 3/7 reagent was added to the cells and caspase activity was determined by measuring luminescence.

To evaluate compound efficacy, the "toxicity window" was calculated by subtracting caspase activity of wells without stressor from activity of wells with stressor but without compound. The amount of caspase activity in the latter wells was normalized to 1 and used as reference. Subsequently, caspase activity in the wells with stressor and varying concentrations of compound was calculated relative to the wells without compound. Plotting caspase activity vs the log 10 of the concentration of compound permitted calculation of the EC$_{50}$ values for the compounds which typically lied between 0.0001 and 10 μM. Compounds with an EC$_{50}$<10 μM were considered active.

The EC$_{50}$ values of compounds of the invention on the stress induced beta cells apoptosis model are shown in Table 2 as "CYT EC$_{50}$".

TABLE 2

| COMPOUND | CYT EC$_{50}$ (μM) |
|---|---|
| Cmpd001 | 0.201 |
| Cmpd003 | 0.040 |
| Cmpd005 | 0.020 |
| Cmpd006 | 0.178 |
| Cmpd010 | 0.178 |
| Cmpd011 | 0.248 |
| Cmpd014 | 0.034 |
| Cmpd015 | 0.031 |
| Cmpd018 | 0.058 |
| Cmpd019 | 0.054 |
| Cmpd020 | 0.043 |
| Cmpd021 | 0.503 |
| Cmpd022 | 0.108 |
| Cmpd023 | 0.019 |
| Cmpd024 | 0.063 |
| Cmpd025 | 0.616 |
| Cmpd026 | 0.088 |
| Cmpd027 | 0.181 |
| Cmpd028 | 0.029 |
| Cmpd029 | 0.057 |
| Cmpd030 | 0.134 |
| Cmpd031 | 0.149 |
| Cmpd038 | 0.317 |
| Cmpd039 | 0.100 |
| Cmpd042 | 0.041 |
| Cmpd043 | 0.086 |
| Cmpd044 | 0.188 |
| Cmpd045 | 0.012 |

TABLE 2-continued

| COMPOUND | CYT EC$_{50}$ (µM) |
|---|---|
| Cmpd047 | 0.014 |
| Cmpd048 | 0.061 |
| Cmpd049 | 0.090 |
| Cmpd050 | 0.103 |
| Cmpd051 | 0.033 |
| Cmpd058 | 0.022 |
| Cmpd082 | 0.034 |
| Cmpd092 | 0.018 |

Example 100

Use of α-Synuclein Expressing Cells as a Model for Neuronal Degeneration

Construction of an α-Synuclein Over-Expressing Cell Line
A α-synuclein expression plasmid was constructed by subcloning the NcoI/XhoI fragment from 212T-SYN(WT) (Griffioen et al., Biochem Biophys Acta (2006) 1762(3): 312-318) containing the cDNA of human wild type α-synuclein correspondingly into a standard mammalian expression vector pcDNA3.1 resulting in plasmid pcDNA3.1-SYNwt. Plasmids pcDNA3.1 and pcDNA3.1-SYNwt were transfected into human neuroblastoma cells (BE-M17; ATCC No. CRL-2267™) using lipofectamine reagent and subsequently, independent clonal cell lines with the plasmids stably integrated into the genome were selected by antibiotic resistance selection (Geneticin (G418)), resulting in cell lines M7.pcDNA3 and M17_3SYN. Overexpression of α-synuclein in the M17_3SYN cell line was confirmed by Western blot analysis.

Use of α-Synuclein Expressing Cells as a Model for Neuronal Degeneration
Due to the high levels of α-synuclein, M17_3SYN cells were sensitive to paraquat, a well-known risk factor Parkinson's disease and of synuclcin-dependent neuronal degeneration. Cytotoxicity of cells was measured by quantification of lactate dehydrogenase (LDH) levels. In dead cells, LDH leaked out of the cells into the medium due to a loss of plasma-membrane integrity.

Experimental Procedure: Three days preceding the experiment, primary pre-cultures of M17.pcDNA3 (as possible control) and M17_3SYN cells were prepared, starting from a stock culture, at a density of 20,000-40,000 cells/cm2 in culture medium (Opti-MEM® Reduced Serum Medium with Phenol Red (Invitrogen, Cat. 31985-047) supplemented with 10% FCS, 1 mM sodium pyruvate, 1×NEAA, 500 µg/ml G418 and 0.5× antibiotic/antimycotic (ABAM)). 3 days later these primary pre-cultures were used as a starting point to make secondary pre-cultures at a density of 50,000-100,000 cells/cm$^2$. At the day of the experiment these secondary precultures were diluted to ~0.5.106 cells/ml in detection medium (Opti-MEM® Reduced-Serum Medium without Phenol Red (Invitrogen, Cat. 11085-021) supplemented with 10% FCS, 1 mM sodium pyruvate, 1×NEAA, 500 µg/ml G418 and 0.5×ABAM) and 60 µL of this suspension was dispensed per well into a 96-well microtiter plate. After 3 hours of incubation at 37° C./5% CO$_2$ an equal volume of detection medium containing a final concentration of 6 mM Paraquat was added and subsequently incubated for 2 days at 37° C./5% CO$_2$. Then LDH activity was determined using the Promega Cytotox 96 Non-Radioactive cytotoxicity assay (Promega. Cat. 01780), according to the manufacturer's instructions. Cytotoxicity was defined as the ratio of LDH relative to the total LDH in the cells and supernatant.

Use of the Neuroblastoma α-Synucleinopathy Model to Screen Compounds

The assay described above using the M17_3SYN cell line allowed screening compounds for their ability to decrease cytotoxicity in PQ-challenged cells. Compounds of the invention were tested for their ability to decrease toxicity at different concentrations, ranging from low non-effective concentrations to high effective concentrations. Afterwards, a dose-dependent inhibition curve was used to calculate the EC$_{50}$. A compound was considered to be active in this test when it inhibited toxicity by more than 20% relative to untreated M17_3SYN cells at a concentration of 10 µM or lower.

The EC$_{50}$ values of toxicity inhibition of the compounds of the invention using the M17_3SYN cells are shown in Table 3 as "SYN EC$_{50}$".

TABLE 3

| COMPOUND | SYN EC$_{50}$ (µM) |
|---|---|
| Cmpd001 | 0.0013 |
| Cmpd002 | 0.0258 |
| Cmpd005 | 0.0064 |
| Cmpd011 | 0.0664 |
| Cmpd013 | 0.0444 |
| Cmpd014 | 0.0568 |
| Cmpd015 | 0.5346 |
| Cmpd016 | 0.0293 |
| Cmpd018 | 0.2409 |
| Cmpd019 | 0.0953 |
| Cmpd020 | 0.0143 |
| Cmpd022 | 0.0287 |
| Cmpd023 | 0.0390 |
| Cmpd024 | 0.0815 |
| Cmpd025 | 0.0653 |
| Cmpd026 | 0.1311 |
| Cmpd027 | 0.0148 |
| Cmpd028 | 0.0220 |
| Cmpd029 | 0.1890 |
| Cmpd030 | 0.0050 |
| Cmpd031 | 0.1212 |
| Cmpd032 | 0.1695 |
| Cmpd033 | 0.3317 |
| Cmpd035 | 0.3258 |
| Cmpd036 | 0.4990 |
| Cmpd041 | 0.1770 |
| Cmpd045 | 0.0020 |
| Cmpd046 | 0.0033 |
| Cmpd052 | 0.4632 |
| Cmpd054 | 0.4063 |
| Cmpd055 | 0.3341 |
| Cmpd057 | 0.0019 |
| Cmpd058 | 0.2902 |
| Cmpd061 | 0.3205 |
| Cmpd062 | 0.3420 |
| Cmpd064 | 1.0690 |
| Cmpd066 | 0.3991 |
| Cmpd068 | 0.3990 |
| Cmpd069 | 0.1816 |
| Cmpd071 | 0.4408 |
| Cmpd072 | 0.2119 |
| Cmpd073 | 0.2167 |
| Cmpd074 | 0.2595 |
| Cmpd076 | 0.3939 |
| Cmpd077 | 0.2347 |
| Cmpd080 | 0.5010 |
| Cmpd082 | 0.4768 |
| Cmpd083 | 0.3746 |
| Cmpd084 | 0.3830 |
| Cmpd085 | 0.5411 |
| Cmpd086 | 0.3005 |
| Cmpd090 | 0.2849 |
| Cmpd092 | 0.6147 |
| Cmpd095 | 0.3772 |
| Cmpd097 | 0.1902 |
| Cmpd098 | 1.1902 |

Example 101

In Vivo Evaluation of Compounds

For in vivo evaluation of compound efficacy, male BKS.Cg-+Leprd/Leprdb/OlaHsd mice (db/db mice—Harlan) were used. The db/db phenotype results from a mutation in the leptin receptor gene, leading to a splice variant (Chen, Charlat et al. 1996; Lee, Proenca et al. 1996). The development of type 2 diabetes in db/db mice is associated with reduced insulin levels due to progressive β-cell failure following an initial period of hypersecretion of insulin. Since these mice develop type 2 diabetes in a manner related to pathology development in humans, and the model is accepted as in vivo model for evaluation of novel antidiabetic treatments by the Food and Drug Administration (FDA, US), it is a highly relevant model for testing candidate drugs for efficacy.

Compounds were administered intraperitoneal (IP) or oral (PO) at a dose of maximally 50 mg/kg. Mice were subjected to metabolic analysis weekly or bi-weekly. These tests included but were not limited to determination of fasting (5 hrs) and non-fasting blood glucose levels, plasma insulin levels, % glycated hemoglobin (HbA1c) levels, glucose tolerance test and insulin sensitivity test.

Treatment with Cmpd045 at 15 mg/kg PO decreased body weight (FIG. 1A). Fasted blood glucose levels were significantly lower in animals treated with cmpd045 (FIG. 1B), which was reflected in reduced % HbA1c levels (FIG. 1C).

The invention claimed is:

1. A method of treating a disease in a subject comprising administering to the subject a therapeutically effective amount of a compound of formula (I), or a stereoisomer, enantiomer, racemic, tautomer, solvent, hydrate or pharmaceutically acceptable salt thereof, wherein the disease is selected from the group consisting of diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, and hypertension;

wherein the compound of formula (I) has the structure

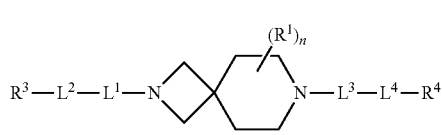

(I)

wherein,
n is an integer selected from 0, 1, 2 or 3;
$R^1$ is selected from the group consisting of $C_{1-6}$alkyl, halo, halo$C_{1-6}$alkyl, and halo$C_{1-6}$alkyloxy;
$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{18}$, —$SR^{19}$, halo$C_{1-6}$alkyl, halo$C_{1-6}$alkyloxy, amino, —$NR^{20}R^{21}$, and cyano; wherein said $C_{6-12}$aryl, $C_{1-6}$alkyl, $C_{3-12}$cycloalkyl, heterocyclyl, heteroaryl, $C_{6-12}$aiyl$C_{1-6}$alkyl, or $C_{6-12}$aryl$C_{1-6}$alkyl$C_{6-12}$aryl can be unsubstituted or substituted with one or more $Z^1$;

$L^1$ is selected from the group consisting of —$SO_2$—, —CO—,

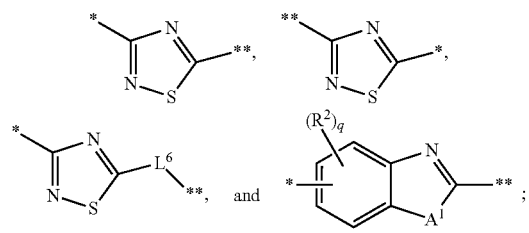

wherein * represents where $L^1$ is bound to $L^2$; and ** represents where $L^1$ is bound to the azetidine ring; and wherein,
$A^1$ is S or O;
q is an integer selected from 0, 1, 2, or 3;
$L^6$ is —CO— or —$SO_2$—,
each $R^2$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heteroaryl, hydroxyl, $SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$, wherein two $R^2$ together with the atom to which they are attached can form a saturated or unsaturated 5-, 6-, or 7-membered ring; and wherein at least one carbon atom or heteroatom of said ring, $C_{6-12}$aryl, $C_{3-8}$cycloalkyl, heterocyclyl, heteroaryl can be oxidized to form at least one C=O, C=S, N=O, N=S, S=O or $S(O)_2$;
$R^4$ is selected from the group consisting $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl $C_{6-12}$aryl, halo, hydroxyl, —$OR^{18}$, —$SR^{19}$, halo $C_{1-6}$alkyl, halo$C_{1-6}$alkyloxy, amino, —$NR^{20}R^{21}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$;
$L^2$ is a single bond or a group of formula (i);

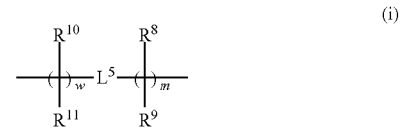

(i)

wherein the left side of the group of formula (i) is attached to $R^3$ and the right side thereof is attached to the nitrogen atom of the azetidine ring; and wherein,
m is an integer selected from 0, 1, 2, or 3;
w is an integer selected from 0, 1, 2, or 3;
$L^5$ is a single bond, or is selected from the group consisting of —O—, and —$NR^{12}$—;

$R^8$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy;

$R^9$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy;

or $R^8$ and $R^9$ together with the carbon atom to which they are attached from a saturated or unsaturated 3-, 4-, 5-, 6- or 7-membered ring;

$R^{10}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy;

$R^{11}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy;

or $R^{10}$ and $R^{11}$ together with the carbon atom to which they are attached from a saturated or unsaturated 3-, 4-, 5-, 6- or 7-membered ring;

$R^{12}$ is selected from the group consisting of hydrogen, and $C_{1-6}$alkyl;

$L^3$ is selected from the group consisting of —$SO_2$—, —$PO_4$—, and —$PO_3$—;

$L^4$ is a single bond or is selected from the group consisting of —$(CR^{15}R^{16})_t$—, —O—, and —$NR^{17}$—; wherein, t is an integer selected from 1, 2 or 3;

$R^{15}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy;

$R^{16}$ is selected from the group consisting of hydrogen, $C_{1-6}$alkyl, halo, hydroxyl, —$OR^{18}$, —$SR^{19}$, halo $C_{1-6}$alkyl, and halo$C_{1-6}$alkyloxy;

or $R^{15}$ and $R^{16}$ together with the carbon atom to which they are attached form a saturated or unsaturated 3-, 4-, 5-, 6- or 7-membered ring;

$R^{17}$ is selected from the group consisting of hydrogen, and $C_{1-6}$alkyl;

wherein at least one of $L^3$, $L^4$ is not a single bond; and wherein when $L^4$ is a single bond, $R^4$ is not methyl;

each $R^{18}$ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{19}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one CO,=C=S, N=O, N=S, S=O or $S(O)_2$;

each $R^{21}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one CO,=C=S, N=O, N=S, S=O or $S(O)_2$;

or wherein $R^{20}$ and $R^{21}$ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or $S(O)_2$;

each $R^{22}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one CO,=C=S, N=O, N=S, S=O or $S(O)_2$;

each $R^{23}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{642}$aryl$C_{1-6}$alkyl, heterocyclyl, heteroaryl, heterocyclyl$C_{1-6}$alkyl, and heteroaryl$C_{1-6}$alkyl can be oxidized to form at least one CO,=C=S, N=O, N=S, S=O or $S(O)_2$;

each $R^{24}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene $C_{1-6}$alkylene*; wherein * represents where $R^{24}$ is bound to CO;

wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, C=S, N=O, N=S, S=O or $S(O)_2$;

each $Z^1$ is independently selected from the group consisting of halo$C_{1-6}$alkyloxy, —$OR^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heterocyclyl $C_{1-6}$alkyl, heteroaryl, heteroaryl$C_{1-6}$alkyl, hydroxyl, —$SR^{19}$, cyano, amino, —$NR^{20}R^{21}$, —$CO_2R^{22}$, —$C(O)NR^{20}R^{21}$, —$C(O)R^{22}$, —$S(O)R^{22}$, —$S(O)_2R^{22}$, —$SO_2NR^{20}R^{21}$, nitro, —$NR^{23}C(O)R^{22}$, —$R^{24}$—$C(O)NR^{20}R^{21}$, —$NR^{23}S(O)_2R^{22}$, and —$NR^{23}C(O)NR^{20}R^{21}$; wherein two $Z^1$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized to form at least one C=O, C=S, N=O, N=S, S=O or S(O)$_2$; and each $Z^2$ is independently selected from the group consisting of halo$C_{1-6}$alkyloxy, —OR$^{18}$, halo, hydrogen, $C_{1-6}$alkyl, halo$C_{1-6}$alkyl, $C_{3-12}$cycloalkyl, $C_{6-12}$aryl, $C_{6-12}$aryl$C_{1-6}$alkyl, heterocyclyl, heterocyclyl $C_{1-6}$alkyl, heteroaryl, heteroaryl$C_{1-6}$alkyl, hydroxyl, —SR$^{19}$, cyano, amino, —NR$^{20}$R$^{21}$, —CO$_2$R$^{22}$, —C(O)NR$^{20}$R$^{21}$, —C(O)R$^{22}$, —S(O)R$^{22}$, —S(O)$_2$R$^{22}$, —SO$_2$NR$^{20}$R$^{21}$, nitro, —NR$^{23}$C(O)R$^{22}$, —R$^{24}$C(O) NR$^{20}$R$^{21}$, —NR$^{23}$S(O)$_2$R$^{22}$, and NR$^{23}$C(O)NR$^{20}$R$^{21}$; wherein two $Z^2$ together with the atom to which they are attached can form a saturated or unsaturated 5-, 6-, or 7-membered ring; and wherein at least one carbon atom or heteroatom of said $C_{1-6}$alkyl, $C_{3-12}$cycloalkyl, $C_{6-12}$aryl, $C_{6-12}$aryl$C_{1-6}$alkyl, heterocyclyl, heterocyclyl$C_{1-6}$alkyl, heteroaryl or heteroaryl$C_{1-6}$alkyl can be oxidized to form at least one C=O, C=S, N=O, N=S, S=O or S(O)$_2$;

with the proviso that said compound is not
N-(1-methylethyl)-7-(phenylsulfonyl)-2,7-diazaspiro [3.5]nonane-2-carboxamide,
N-(3-fluorophenyl)-7-(phenylsulfonyl)-2,7-diazaspiro [3.5]nonane-2-carboxamide,
N-phenyl-7-(phenylsulfonyl)-2,7-diazaspiro[3.5]nonane-2-carboxamide,
N-(4-methoxyphenyl)-7-(phenylsulfonyl)-2,7-diazaspiro [3.5]nonane-2-carboxamide,
(1H-benzotriazol-5-yl)-{7-[2-(3-chloro-phenyl)-ethanesulfonyl]-2,7-diaza-spiro[3.5]non-2-yl}-methanone,
N-(4-methoxyphenyl)-7-(methylsulfonyl)-2,7-diazaspiro [3.5]nonane-2-carboxamide,
N-(3-cyanophenyl)-7-(methylsulfonyl)-2,7-diazaspiro [3.5]nonane-2-carboxamide,
7-(methylsulfonyl)-N-phenyl-2,7-diazaspiro[3.5]nonane-2-carboxamide,
N-(3-fluorophenyl)-7-(methylsulfonyl)-2,7-diazaspiro [3.5]nonane-2-carboxamide,
or a solvate, hydrate, pharmaceutically acceptable salt or prodrug thereof.

2. The method according to claim 1, wherein the compound has structural formula (IA)

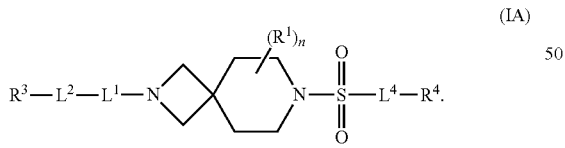

(IA)

3. The method according to claim 1, wherein L$^1$ is —SO$_2$—.

4. The method according to claim 1, wherein the compound has structural formula (IB)

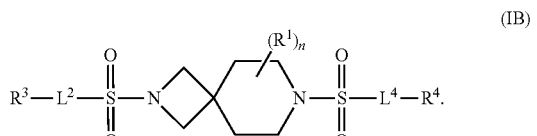

(IB)

5. The method according to claim 1, wherein the compound has structural formula (ID)

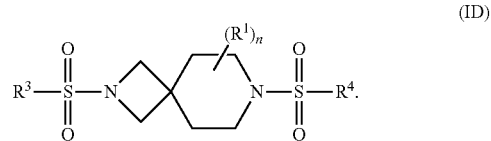

(ID)

6. The method according to claim 1, wherein the compound has structural formula (IC)

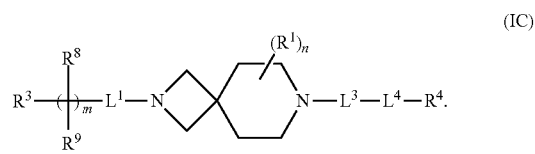

(IC)

7. The method according to claim 1, wherein the compound has structural formula (IE)

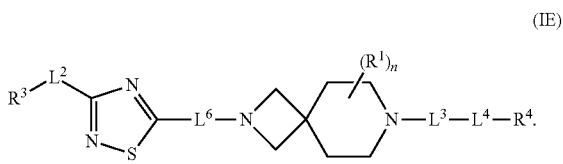

(IE)

8. The method according to claim 1, wherein the compound has structural formula (IF)

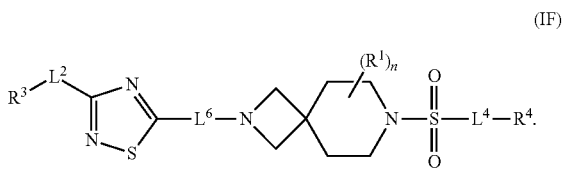

(IF)

9. The method according to claim 1, wherein L$^6$ is a single bond.

10. The method according to claim 1, wherein L$^1$ is

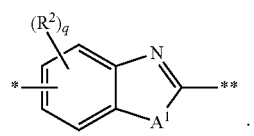

11. The method according to claim 1, wherein the compound is selected from the group consisting of 2,7-Bis((4-methoxyphenyl)sulfonyl)-2,7-diazaspiro[3.5]nonane; 2-((4-Fluorophenyl)sulfonyl)-7-((4-methoxyphenyl)sulfonyl)-2,7-diazaspiro[3.5]nonane; 2-((4-(Difluoromethoxy)phenyl) sulfonyl)-7-((4-methoxyphenyl)sulfonyl)-2,7-diazaspiro [3.5]nonane; 7-((4-Methoxyphenyl)sulfonyl)-2-((4-propoxyphenyl)sulfonyl)-2,7-diazaspiro[3.5]nonane; 2-((4-Chlorophenyl)sulfonyl)-7-((4-methoxyphenyl)sulfonyl)-2,7-diazaspiro[3.5]nonane; 2-(4-Fluorophenyl)-1-(7-((4-methoxyphenyl)sulfonyl)-2,7-diazaspiro[3.5]nonan-2-yl)

ethanone; (4-Chlorophenyl)(7-((4-methoxyphenyl)sulfonyl)-2,7-diazaspiro[3.5]nonan-2-yl)methanone; (3,4-Difluorophenyl)(7-(4-methoxyphenyl)sulfonyl)-2,7-diazaspiro[3.5]nonan-2-yl)methanone; (4-Fluorophenyl)(7-((4-methoxyphenyl)sulfonyl)-2,7-diazaspiro[3.5]nonan-2-yl)methanone; 1-(7-((4-Methoxyphenyl)sulfonyl)-2,7-diazaspiro[3.5]nonan-2-yl)-2-phenylethanone; 1-(7-((4-Methoxyphenyl)sulfonyl)-2,7-diazaspiro[3.5]nonan-2-yl)-2-phenylbutan-1-one; 4,4,4-Trifluoro-1-(7-((4-methoxyphenyl)sulfonyl)-2,7-diazaspiro[3.5]nonan-2-yl)butan-1-one; 1-(7-((4-Methoxyphenyl)sulfonyl)-2,7-diazaspiro[3.5]nonan-2-yl)-2-methyl-2-phenylpropan-1-one; (7-((4-Methoxyphenyl)sulfonyl)-2,7-diazaspiro[3.5]nonan-2-yl)(1-phenylcyclopropyl)methanone; 3-(4-Fluorophenyl)-1-(7-((4-methoxyphenyl)sulfonyl)-2,7-diazaspiro[3.5]nonan-2-yl)propan-1-one; 2-(3-Methoxyphenyl)-1-(7-((4-methoxyphenyl)sulfonyl)-2,7-diazaspiro[3.5]nonan-2-yl)-2-methylpropan-1-one; 1-(7-((4-Methoxyphenyl)sulfonyl)-2,7-diazaspiro[3.5]nonan-2-yl)-2-methyl-2-(pyridin-3-ylmethoxy)propan-1-one; 2-Hydroxy-1-(7-((4-methoxyphenyl)sulfonyl)-2,7-diazaspiro[3.5]nonan-2-yl)-2-(pyridin-2-yl)propan-1-one; 2-(4-Methoxyphenyl)-1-(7-((4-methoxyphenyl)sulfonyl)-2,7-diazaspiro[3.5]nonan-2-yl)propan-1-one; 1-(7-((4-Methoxyphenyl)sulfonyl)-2,7-diazaspiro[3.5]nonan-2-yl)-2-methyl-2-(o-tolyl)propan-1-one; Chroman-4-yl(7-((4-methoxyphenyl)sulfonyl)-2,7-diazaspiro[3.5]nonan-2-yl)methanone; (S)-2-(4-Fluorophenyl)-1-(7-((4-methoxyphenyl)sulfonyl)-2,7-diazaspiro[3.5]nonan-2-yl)-3-methylbutan-1-one; 2-(2-Methoxyphenyl)-1-(7-((4-methoxyphenyl)sulfonyl)-2,7-diazaspiro[3.5]nonan-2-yl)propan-1-one; 2-(2-Methoxyphenyl)-1-(7-((4-methoxyphenyl)sulfonyl)-2,7-diazaspiro[3.5]nonan-2-yl)-2-methylpropan-1-one; (7-((4-Methoxyphenyl)sulfonyl)-2,7-diazaspiro[3.5]nonan-2-yl)(1,2,3,4-tetrahydronaphthalen-1-yl)methanone; 2-(4-Chlorophenyl)-1-(7-((4-methoxyphenyl)sulfonyl)-2,7-diazaspiro[3.5]nonan-2-yl)propan-1-one; 2-(4-Chlorophenyl)-1-(7-((4-methoxyphenyl)sulfonyl)-2,7-diazaspiro[3.5]nonan-2-yl)-2-methylpropan-1-one; (7-((4-Methoxyphenyl)sulfonyl)-2,7-diazaspiro[3.5]nonan-2-yl)(1-phenylcyclopentyl)methanone; 2-(3,5-Difluorophenyl)-1-(7-((4-methoxyphenyl)sulfonyl)-2,7-diazaspiro[3.5]nonan-2-yl)propan-1-one; 2-(3-Chlorophenyl)-1-(7-((4-methoxyphenyl)sulfonyl)-2,7-diazaspiro[3.5]nonan-2-yl)-2-methylpropan-1-one; 5-(7-((4-Methoxyphenyl)sulfonyl)-2,7-diazaspiro[3.5]nonan-2-yl)-3-(2,2,2-trifluoroethyl)-1,2,4-thiadiazole; 3-(4-Chlorobenzyl)-5-(7-((4-methoxyphenyl)sulfonyl)-2,7-diazaspiro[3.5]nonan-2-yl)-1,2,4-thiadiazole; 3-(3,4-Difluorobenzyl)-5-(7-((4-methoxyphenyl)sulfonyl)-2,7-diazaspiro[3.5]nonan-2-yl)-1,2,4-thiadiazole; 3-Cyclopropyl-5-(7-((4-methoxyphenyl)sulfonyl)-2,7-diazaspiro[3.5]nonan-2-yl)-1,2,4-thiadiazole; 3-Butyl-5-(7-((4-methoxyphenyl)sulfonyl)-2,7-diazaspiro[3.5]nonan-2-yl)-1,2,4-thiadiazole; 5-(7-((4-Methoxyphenyl)sulfonyl)-2,7-diazaspiro[3.5]nonan-2-yl)-3-(3-(trifluoromethyl)benzyl)-1,2,4-thiadiazole; 3-(4-Methoxyphenyl)-5-(7-((4-methoxyphenyl)sulfonyl)-2,7-diazaspiro[3.5]nonan-2-yl)-1,2,4-thiadiazole; 5-(7-((4-Methoxyphenyl)sulfonyl)-2,7-diazaspiro[3.5]nonan-2-yl)-3-(pyrazin-2-yl)-1,2,4-thiadiazole; 3-(4-Chlorophenyl)-5-(7-((4-methoxyphenyl)sulfonyl)-2,7-diazaspiro[3.5]nonan-2-yl)-1,2,4-thiadiazole; 3-(1-(4-Fluorophenyl)cyclopropyl)-5-(7-((4-methoxyphenyl)sulfonyl)-2,7-diazaspiro[3.5]nonan-2-yl)-1,2,4-thiadiazole; 3-(4-Fluorobenzyl)-5-(7-((4-(methylthio)phenyl)sulfonyl)-2,7-diazaspiro[3.5]nonan-2-yl)-1,2,4-thiadiazole; 7-((4-(Difluoromethoxy)phenyl)sulfonyl)-2-((4-ethoxyphenyl)sulfonyl)-2,7-diazaspiro[3.5]nonane; 2-((4-Chlorophenyl)sulfonyl)-7-((4-(difluoromethoxy)phenyl)sulfonyl)-2,7-diazaspiro[3.5]nonane; 7-((4-(Difluoromethoxy)phenyl)sulfonyl)-2-((4-fluorophenyl)sulfonyl)-2,7-diazaspiro[3.5]nonane; 7-((4-(Difluoromethoxy)phenyl)sulfonyl)-2-((4-methoxyphenyl)sulfonyl)-2,7-diazaspiro[3.5]nonane; 7-((4-Ethoxyphenyl)sulfonyl)-2-((4-methoxyphenyl)sulfonyl)-2,7-diazaspiro[3.5]nonane; 7-((4-Chlorophenyl)sulfonyl)-2-((4-methoxyphenyl)sulfonyl)-2,7-diazaspiro[3.5]nonane; 2,7-Bis((4-(difluoromethoxy)phenyl)sulfonyl)-2,7-diazaspiro[3.5]nonane; 2-((4-(Difluoromethoxy)phenyl)sulfonyl)-7-((4-ethoxyphenyl)sulfonyl)-2,7-diazaspiro[3.5]nonane; 7-((4-Chlorophenyl)sulfonyl)-2-((4-(difluoromethoxy)phenyl)sulfonyl)-2,7-diazaspiro[3.5]nonane; 2-((4-(Difluoromethoxy)phenyl)sulfonyl)-7-((4-fluorophenyl)sulfonyl)-2,7-diazaspiro[3.5]nonane; 6-Chloro-2-(7-((4-methoxyphenyl)sulfonyl)-2,7-diazaspiro[3.5]nonan-2-yl)benzo[d]thiazole; 6-Chloro-2-(7-((4-ethoxyphenyl)sulfonyl)-2,7-diazaspiro[3.5]nonan-2-yl)benzo[d]thiazole; 6-Chloro-2-(7-((4-(difluoromethoxy)phenyl)sulfonyl)-2,7-diazaspiro[3.5]nonan-2-yl)benzo[d]thiazole; 6-Chloro-2-(7-((4-(methylthio)phenyl)sulfonyl)-2,7-diazaspiro[3.5]nonan-2-yl)benzo[d]thiazole; 3-(1-(4-Fluorophenyl)ethyl)-5-(7-((4-methoxyphenyl)sulfonyl)-2,7-diazaspiro[3.5]nonan-2-yl)-1,2,4-thiadiazole; 3-(4-Fluorobenzyl)-5-(7-((4-methoxyphenyl)sulfonyl)-2,7-diazaspiro[3.5]nonan-2-yl)-1,2,4-thiadiazole; N-(4-((2-(3-(4-fluorobenzyl)-1,2,4-thiadiazol-5-yl)-2,7-diazaspiro[3.5]nonan-7-yl)sulfonyl)phenyl)acetamide; 3-(4-Fluorobenzyl)-5-(7-((4-(methylsulfonyl)phenyl)sulfonyl)-2,7-diazaspiro[3.5]nonan-2-yl)-1,2,4-thiadiazole; 5-(7-((2,4-Difluorophenyl)sulfonyl)-2,7-diazaspiro[3.5]nonan-2-yl)-3-(4-fluorobenzyl)-1,2,4-thiadiazole; 5-(7-((3,4-Dimethoxyphenyl)sulfonyl)-2,7-diazaspiro[3.5]nonan-2-yl)-3-(4-fluorobenzyl)-1,2,4-thiadiazole; 3-(4-Fluorobenzyl)-5-(7-((2-methoxy-5-methylphenyl)sulfonyl)-2,7-diazaspiro[3.5]nonan-2-yl)-1,2,4-thiadiazole; 5-(7-((5-Chloro-2-methoxyphenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-(trifluoromethyl)phenyl)sulfonyl)-2,7-diazaspiro[3.5]nonan-2-yl)-1,2,4-thiadiazole; 3-(4-Fluorobenzyl)-5-(7-((4-(trifluoromethyl)phenyl)sulfonyl)-2,7-diazaspiro[3.5]nonan-2-yl)-1,2,4-thiadiazole; 3-(4-Fluorobenzyl)-5-(7-(m-tolylsulfonyl)-2,7-diazaspiro[3.5]nonan-2-yl)-1,2,4-thiadiazole; 3-(4-Fluorobenzyl)-5-(7-((2-fluorophenyl)sulfonyl)-2,7-diazaspiro[3.5]nonan-2-yl)-1,2,4-thiadiazole; 5-(7-((4-Ethylphenyl)sulfonyl)-2,7-diazaspiro[3.5]nonan-2-yl)-3-(4-fluorobenzyl)-1,2,4-thiadiazole; 3-(4-Fluorobenzyl)-5-(7-(o-tolylsulfonyl)-2,7-diazaspiro[3.5]nonan-2-yl)-1,2,4-thiadiazole; 5-(7-((4-(Tert-butyl)phenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-fluorophenyl)sulfonyl)-2,7-diazaspiro[3.5]nonan-2-yl)-1,2,4-thiadiazole; 5-(7-((2,5-Dimethoxyphenyl)sulfonyl)-2,7-diazaspiro[3.5]nonan-2-yl)-3-(4-fluorobenzyl)-1,2,4-thiadiazole; 5-(7-((2,5-Difluorophenyl)sulfonyl)-2,7-diazaspiro[3.5]nonan-2-yl)-3-(4-fluorobenzyl)-1,2,4-thiadiazole; 5-(7-((2,6-Difluorophenyl)sulfonyl)-2,7-diazaspiro[3.5]nonan-2-yl)-3-(4-fluorobenzyl)-1,2,4-thiadiazole; 5-(7-((3,4-Difluorophenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-methoxyphenyl)sulfonyl)-2,7-diazaspiro[3.5]nonan-2-yl)-1,2,4-thiadiazole; 5-(7-((5-Fluoro-2-methylphenyl)sulfonyl)-2,7-diazaspiro[3.5]nonan-2-yl)-3-(4-fluorobenzyl)-1,2,4-thiadiazole; 2-Ethoxy-5-((2-(3-(4-fluorobenzyl)-1,2,4-thiadiazol-5-yl)-2,7-diazaspiro[3.5]

nonan-7-yl)sulfonyl)benzonitrile; 3-(4-Fluorobenzyl)-5-(7-((4-methoxy-3-(trifluoromethyl)phenyl)sulfonyl)-2,7-diazaspiro[3.5]nonan-2-yl)-1,2,4-thiadiazole; 3-(4-Fluorobenzyl)-5-(7-((2-methoxyphenyl)sulfonyl)-2,7-diazaspiro[3.5]nonan-2-yl)-1,2,4-thiadiazole; 5-(7-((3-Chloro-4-methoxyphenyl)sulfonyl)-2,7-diazaspiro[3.5]nonan-2-yl)-3-(4-fluorobenzyl)-1,2,4-thiadiazole; 3-(4-Fluorobenzyl)-5-(7-((3-(methylsulfonyl)phenyl)sulfonyl)-2,7-diazaspiro[3.5]nonan-2-yl)-1,2,4-thiadiazole; 5-(7-((3,5-Difluorophenyl)sulfonyl)-2,7-diazaspiro[3.5]nonan-2-yl)-3-(4-fluorobenzyl)-1,2,4-thiadiazole; Methyl 3-((2-(3-(4-fluorobenzyl)-1,2,4-thiadiazol-5-yl)-2,7-diazaspiro[3.5]nonan-7-yl)sulfonyl)benzoate; 5-(7-((4-(Difluoromethoxy)phenyl)sulfonyl)-2,7-diazaspiro[3.5]nonan-2-yl)-3-(4-fluorobenzyl)-1,2,4-thiadiazole; 5-(7-((5-Fluoro-2-methoxyphenyl)sulfonyl)-2,7-diazaspiro[3.5]nonan-2-yl)-3-(4-fluorobenzyl)-1,2,4-thiadiazole; 5-(7-((4-Ethoxy-3-methylphenyl)sulfonyl)-2,7-diazaspiro[3.5]nonan-2-yl)-3-(4-fluorobenzyl)-1,2,4-thiadiazole; 3-(4-Fluorobenzyl)-5-(7-((4-methoxy-3-methylphenyl)sulfonyl)-2,7-diazaspiro[3.5]nonan-2-yl)-1,2,4-thiadiazole; 3-(4-Fluorobenzyl)-5-(7-(pyridin-3-ylsulfonyl)-2,7-diazaspiro[3.5]nonan-2-yl)-1,2,4-thiadiazole; 3-(4-Fluorobenzyl)-5-(7-((1-methyl-1H-pyrazol-4-yl)sulfonyl)-2,7-diazaspiro[3.5]nonan-2-yl)-1,2,4-thiadiazole; 4-((2-(3-(4-Fluorobenzyl)-1,2,4-thiadiazol-5-yl)-2,7-diazaspiro[3.5]nonan-7-yl)sulfonyl-3,5-dimethylisoxazole; 3-(4-Fluorobenzyl)-5-(7(thiophen-2-ylsulfonyl)-2,7-diazaspiro[3.5]nonan-2-yl)-1,2,4-thiadiazole; 5-(7-((5-Chlorothiophen-2-yl)sulfonyl)-2,7-diazaspiro[3.5]nonan-2-yl)-3-(4-fluorobenzyl)-1,2,4-thiadiazole; 3-(4-Fluorobenzyl)-5-(7-(thiophen-3-ylsulfonyl)-2,7-diazaspiro[3.5]nonan-2-yl)-1,2,4-thiadiazole; 3-(4-Fluorobenzyl)-5-(7-((5-methylthiophen-2-yl)sulfonyl)-2,7-diazaspiro[3.5]nonan-2-yl)-1,2,4-thiadiazole; 3-(4-Fluorobenzyl)-5-(7-((3,3,3-trifluoropropyl)sulfonyl)-2,7-diazaspiro[3.5]nonan-2-yl)-1,2,4-thiadiazole; 5-(7-((Cyclohexylmethyl)sulfonyl)-2,7-diazaspiro[3.5]nonan-2-yl)-3-(4-fluorobenzyl)-1,2,4-thiadiazole; and 4-((2-(3-(4-Fluorobenzyl)-1,2,4-thiadiazol-5-yl)-2,7-diazaspiro[3.5]nonan-7-yl)sulfonyl)morpholine; or a solvate, hydrate, or pharmaceutically acceptable salt thereof, or a pharmaceutical composition thereof.

12. The method according to claim 1, wherein the compound is selected from the group consisting of N-(1-methylethyl)-7-(phenylsulfonyl)-2,7-diazaspiro[3.5]nonane-2-carboxamide; N-(3-fluorophenyl)-7-(phenylsulfonyl)-2,7-diazaspiro[3.5]nonane-2-carboxamide; N-phenyl-7-(phenylsulfonyl)-2,7-diazaspiro[3.5]nonane-2-carboxamide; N-(4-methoxyphenyl)-7-(phenylsulfonyl)-2,7-diazaspiro[3.5]nonane-2-carboxamide, N-(4-methoxyphenyl)-7-(methylsulfonyl)-2,7-diazaspiro[3.5]nonane-2-carboxamide, N-(3-cyanophenyl)-7-(methylsulfonyl)-2,7-diazaspiro[3.5]nonane-2-carboxamide, 7-(methylsulfonyl)-N-phenyl-2,7-diazaspiro[3.5]nonane-2-carboxamide, N-(3-fluorophenyl)-7-(methylsulfonyl)-2,7-diazaspiro[3.5]nonane-2-carboxamide, and (1H-benzotriazol-5-yl)-{7-[2-(3-chlorophenyl)-ethanesulfonyl]-2,7-diaza-spiro[3.5]non-2-yl}-methanone; or a solvate, hydrate, or pharmaceutically acceptable salt thereof, or a pharmaceutical composition thereof.

* * * * *